(12) United States Patent
Macdonald et al.

(10) Patent No.: US 12,207,628 B2
(45) Date of Patent: *Jan. 28, 2025

(54) ADAM6 MICE

(71) Applicant: Regeneron Pharmaceuticals, Inc., Tarrytown, NY (US)

(72) Inventors: Lynn Macdonald, Harrison, NY (US); Sean Stevens, Del Mar, CA (US); Andrew J. Murphy, Croton-on-Hudson, NY (US); Margaret Karow, Santa Rosa Valley, CA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 1056 days.

This patent is subject to a terminal disclaimer.

(21) Appl. No.: 17/129,706

(22) Filed: Dec. 21, 2020

(65) Prior Publication Data

US 2021/0105984 A1 Apr. 15, 2021

Related U.S. Application Data

(60) Division of application No. 16/059,821, filed on Aug. 9, 2018, now Pat. No. 10,905,108, which is a continuation of application No. 14/600,829, filed on Jan. 20, 2015, now Pat. No. 10,072,095, which is a continuation of application No. 14/192,051, filed on Feb. 27, 2014, now Pat. No. 9,932,408, which is a continuation of application No. 13/890,519, filed on May 9, 2013, now Pat. No. 8,697,940, which is a continuation of application No. 13/404,075, filed on Feb. 24, 2012, now Pat. No. 8,642,835.

(60) Provisional application No. 61/595,200, filed on Feb. 6, 2012, provisional application No. 61/497,650, filed on Jun. 16, 2011, provisional application No. 61/446,895, filed on Feb. 25, 2011.

(51) Int. Cl.

| | |
|---|---|
| A01K 67/00 | (2006.01) |
| A01K 67/0275 | (2024.01) |
| A01K 67/0278 | (2024.01) |
| B60H 1/32 | (2006.01) |
| C07K 16/22 | (2006.01) |
| C07K 16/28 | (2006.01) |
| C07K 16/40 | (2006.01) |
| C07K 16/46 | (2006.01) |
| C12N 9/64 | (2006.01) |
| C12N 15/85 | (2006.01) |

(52) U.S. Cl.
CPC ...... *A01K 67/0278* (2013.01); *A01K 67/0275* (2013.01); *B60H 1/32281* (2019.05); *C07K 16/22* (2013.01); *C07K 16/28* (2013.01); *C07K 16/2866* (2013.01); *C07K 16/40* (2013.01); *C07K 16/461* (2013.01); *C07K 16/462* (2013.01); *C12N 9/6489* (2013.01); *C12N 15/8509* (2013.01); *A01K 2207/15* (2013.01); *A01K 2217/072* (2013.01); *A01K 2217/15* (2013.01); *A01K 2227/105* (2013.01); *A01K 2267/01* (2013.01); *C07K 2317/21* (2013.01); *C07K 2317/92* (2013.01); *C12N 2800/204* (2013.01); *C12N 2800/30* (2013.01)

(58) Field of Classification Search
CPC ............ A01K 67/0278; A01K 67/0275; A01K 2207/15; A01K 2217/072; A01K 2217/15; A01K 2227/105; B60H 1/32281; C07K 16/22; C07K 16/28; C07K 16/2866; C07K 16/40; C07K 16/461; C07K 16/462; C12N 9/6489; C12N 15/8509

See application file for complete search history.

(56) References Cited

U.S. PATENT DOCUMENTS

| | | | |
|---|---|---|---|
| 5,545,807 | A | 8/1996 | Surani et al. |
| 6,162,963 | A | 12/2000 | Kucherlapati et al. |
| 6,586,251 | B2 | 7/2003 | Economides et al. |
| 6,596,541 | B2 | 7/2003 | Murphy et al. |
| 6,657,103 | B1 | 12/2003 | Kucherlapati et al. |
| 6,673,986 | B1 | 1/2004 | Kucherlapati et al. |
| 7,105,348 | B2 | 9/2006 | Murphy et al. |
| 7,183,076 | B2 | 2/2007 | Arathoon et al. |

(Continued)

FOREIGN PATENT DOCUMENTS

| | | |
|---|---|---|
| CN | 1203922 A | 1/1999 |
| CN | 1484707 A | 3/2004 |

(Continued)

OTHER PUBLICATIONS

Adderson, E.E. et al., Restricted Ig H Chain V Gene Usage in the Human Antibody Response to Haemophilus influenzae Type b Capsular Polysaccharide, The Journal of Immunology, 147:1667-1674 (1991).

(Continued)

*Primary Examiner* — Titilayo Moloye
(74) *Attorney, Agent, or Firm* — Choate, Hall & Stewart LLP

(57) ABSTRACT

Mice are provided that comprise a reduction or deletion of ADAM6 activity from an endogenous ADAM6 locus, or that lack an endogenous locus encoding a mouse ADAM6 protein, wherein the mice comprise a sequence encoding an ADAM6 or ortholog or homolog or fragment thereof that is functional in a male mouse. In one embodiment, the sequence is an ectopic ADAM6 sequence or a sequence that confers upon a male mouse the ability to generate offspring by mating. Mice and cells with genetically modified immunoglobulin heavy chain loci that comprise an ectopic nucleotide sequence encoding a mouse ADAM6 or functional fragment or homolog or ortholog thereof are also provided.

13 Claims, 41 Drawing Sheets

Specification includes a Sequence Listing.

(56) References Cited

U.S. PATENT DOCUMENTS

| | | |
|---|---|---|
| 7,501,552 B2 | 3/2009 | Lonberg et al. |
| 7,582,298 B2 | 9/2009 | Stevens et al. |
| 7,910,798 B2 | 3/2011 | Tanamachi et al. |
| 8,158,419 B2 | 4/2012 | Lonberg et al. |
| 8,502,018 B2 | 8/2013 | Murphy et al. |
| 8,697,940 B2 | 4/2014 | Macdonald et al. |
| 9,932,408 B2 | 4/2018 | Macdonald et al. |
| 9,944,716 B2 | 4/2018 | Macdonald et al. |
| 10,072,095 B2 | 9/2018 | Macdonald et al. |
| 10,577,430 B2 | 3/2020 | Macdonald et al. |
| 10,694,725 B2 | 6/2020 | Macdonald et al. |
| 10,905,108 B2 | 2/2021 | Macdonald et al. |
| 10,905,109 B2 | 2/2021 | Macdonald et al. |
| 11,559,050 B2 | 1/2023 | Macdonald et al. |
| 11,950,578 B2 | 4/2024 | Macdonald et al. |
| 2002/0106628 A1 | 8/2002 | Economides et al. |
| 2002/0106629 A1 | 8/2002 | Murphy et al. |
| 2003/0108925 A1 | 6/2003 | Dix et al. |
| 2003/0109021 A1 | 6/2003 | Wu et al. |
| 2004/0018626 A1 | 1/2004 | Murphy et al. |
| 2006/0015957 A1 | 1/2006 | Lonberg et al. |
| 2006/0015958 A1 | 1/2006 | Kuroiwa et al. |
| 2006/0199204 A1 | 9/2006 | Dix et al. |
| 2008/0196922 A1 | 8/2008 | Van Marion et al. |
| 2008/0267982 A1 | 10/2008 | Kiselev et al. |
| 2011/0145937 A1 | 6/2011 | MacDonald et al. |
| 2011/0195454 A1 | 8/2011 | Mcwhirter et al. |
| 2011/0236378 A1 | 9/2011 | Green et al. |
| 2011/0314563 A1 | 12/2011 | Craig et al. |
| 2012/0021409 A1 | 1/2012 | McWhirter et al. |
| 2012/0047585 A1 | 2/2012 | Rohrer et al. |
| 2012/0167237 A1 | 6/2012 | Bradley et al. |
| 2012/0204278 A1 | 8/2012 | Bradley et al. |
| 2012/0272344 A1 | 10/2012 | Tanamachi et al. |
| 2012/0322108 A1 | 12/2012 | Macdonald et al. |
| 2013/0096287 A1 | 4/2013 | Macdonald et al. |
| 2013/0198879 A1 | 8/2013 | McWhirter et al. |
| 2013/0243759 A1 | 9/2013 | Friedrich et al. |
| 2013/0243773 A1 | 9/2013 | Van Berkel et al. |
| 2013/0263292 A1 | 10/2013 | Liang et al. |
| 2013/0323235 A1 | 12/2013 | Craig et al. |
| 2014/0213773 A1 | 7/2014 | Macdonald et al. |
| 2015/0201589 A1 | 7/2015 | Macdonald et al. |
| 2015/0210776 A1 | 7/2015 | Macdonald et al. |
| 2015/0250152 A1 | 9/2015 | Jakobovits et al. |
| 2018/0345760 A1 | 12/2018 | Macdonald et al. |
| 2018/0346598 A1 | 12/2018 | Macdonald et al. |
| 2018/0346599 A1 | 12/2018 | Macdonald et al. |
| 2018/0362663 A1 | 12/2018 | Macdonald et al. |
| 2021/0105985 A1 | 4/2021 | Macdonald et al. |

FOREIGN PATENT DOCUMENTS

| | | |
|---|---|---|
| CN | 1668636 A | 9/2005 |
| CN | 102791866 A | 11/2012 |
| CN | 103429746 A | 12/2013 |
| EA | 010469 | 8/2008 |
| EA | 010506 B1 | 10/2008 |
| JP | 2005-230020 A | 9/2005 |
| KR | 10-2005-0042792 A | 5/2005 |
| RU | 2151612 C1 | 6/2000 |
| RU | 2264413 C2 | 11/2005 |
| RU | 010506 U1 | 10/2008 |
| WO | WO-90/04036 A1 | 4/1990 |
| WO | WO-91/00906 A1 | 1/1991 |
| WO | WO-98/24893 A2 | 6/1998 |
| WO | WO-00/073323 A2 | 12/2000 |
| WO | WO-02/46237 A2 | 6/2002 |
| WO | WO-02/066630 A1 | 8/2002 |
| WO | WO-2005/028510 A2 | 3/2005 |
| WO | WO-2007/003323 A1 | 1/2007 |
| WO | WO-2007/117410 A2 | 10/2007 |
| WO | WO-2009/097006 A2 | 8/2009 |
| WO | WO-2010/039900 A2 | 4/2010 |
| WO | WO-2011/004192 A1 | 1/2011 |
| WO | WO-2011/072204 A1 | 6/2011 |
| WO | WO-2011/158009 A1 | 12/2011 |
| WO | WO-2012/141798 A1 | 10/2012 |
| WO | WO-2013/022782 A1 | 2/2013 |
| WO | WO-2013/061098 A2 | 5/2013 |
| WO | WO-2013/079953 A1 | 6/2013 |

OTHER PUBLICATIONS

Adderson, E.E. et al., Restricted Immunoglobulin VH Usage and VDJ Combinations in the Human Response to Haemophilus influenzae Type b Capsular Polysaccharide, Journal of Clinical Investigation, 91:2734-2743 (1993).

Alfandari, D. et al., Xenopus ADAM 13 is a metalloprotease required for cranial neural crest-cell migration, Current Biology, 11:918-930 (2001).

Amit, M. and Itskovitz-Eldor, J., Embryonic Stem Cells: Isolation, Characterization and Culture, Adv Biochem Engin/Biotechnol, 114:173-184 (2009).

Appeal by Opponent for EP 12716101.6, 14 pages (Jun. 20, 2016).

Astellas Negotiates $295M License Extension to Regeneron's VelocImmune mAb Platform, GEN News Highlights, Jul. 28, 2010.

Austin, C. et al., The Knockout Mouse Project, Nat. Genet., 36(9): 921-924 (2004).

Bando, Y. et al., Characterization of VH gene expressed in PBL from children with atopic diseases: detection of homologous VH1-69 derived transcripts from three unrelated patients, Immunology Letters, 94:99-106 (2004).

Baseggio, L. et al., CD5 expression identifies a subset of splenic marginal zone lymphomas with higher lymphocytosis: a clinicopathological, cytogenetic and molecular study of 24 cases, Haematologica, 95(4):604-612 (2010).

Berberian, L. et al., A VH Clonal Deficit in Human Immunodeficiency Virus-Positive Individuals Reflects a B-Cell Maturational Arrest, Blood, 78(1):175-179 (1991).

Blobel, Carl P., ADAMS: Key Components in EGFR Signalling and Development, Nature Reviews, Molecular Cell Biology, 6:32-43 (2005).

Borghei, A. et al., Targeted Disruption of Tyrosylprotein Sulfotransferase-2, an Enzyme That Catalyzes Post-translational Protein Tyrosine O-Sulfation, Causes Male Infertility, The Journal of Biological Chemistry, 281(14):9423-9431 (2006).

Brezinschek, H.P. et al., Analysis of the Heavy Chain Repertoire of Human Peripheral B Cells Using Single-Cell Polymerase Chain Reaction, Journal of Immunology, 155:190-202 (1995).

Brouwers, B. et al., Unexpected Phenotypes in Mouse Models Carrying the Human Growth Hormone Minigene to Enhance Transgene Expression, Journal of Steroids & Hormonal Science, 6(2): 2 pages (2015).

Bruggemann, M. and Neuberger, M., Strategies for expressing human antibody repertoires in transgenic mice, Review Immunology Today, 192(17):391-397 (1996).

Bruggemann, M. et al., A repertoire of monoclonal antibodies with human heavy chains from transgenic mice, Proceedings of the National of Academy of Science USA, 86:6709-6713 (1989).

Bruggemann, M., Human Antibody Expression in Transgenic Mice, Archivum Immunologiae et Therapiae Experimentalis, 49:203-208 (2001).

Butler, J.E., Immunoglobulin diversity, B-cell and antibody repertoire development in large farm animals, Rev. Sci. Tech. Off. Int. Epiz., 17(1):43-70 (1998).

Canadian Office Action for Application No. 2,820,824, 3 pages, Aug. 5, 2014.

Carbonari, M, et al., Hepatitis C Virus Drives the Unconstrained Monoclonal Expansion of VH1-69-Expressing Memory B Cells in Type II Cryoglobulinemia: A Model of Infection-Driven Lymphomagenesis, The Journal of Immunology, 174:6532-6539 (2005).

Chan, C.H. et al., VH1-69 gene is preferentially used by hepatitis C virus-associated B cell lymphomas and by normal B cells responding to the E2 viral antigen, Blood, 97(4):1023-1026 (2001).

(56) References Cited

OTHER PUBLICATIONS

Charles, E.D. et al., A flow cytometry-based strategy to identify and express IgM from VH1-69+ clonal peripheral B cells, Journal of Immunological Methods, 363:210-220 (2011).
Cheval, L. et al., Of Mice and Men: Divergence of Gene Expression Patterns in Kidney, PLoS One, 7(10): e46876—12 pages (2012).
Cho, C. et al., Analysis of Mouse Fertilin in Wild-Type and Fertilin β−/− Sperm: Evidence for C-terminal Modification, αI β Dimerization, and Lack of Essential Role of Fertilin α in Sperm-Egg Fusion, Developmental Biology, 222:289-295 (2000).
Cho, C. et al., Fertilization Defects in Sperm from Mice Lacking Fertilin β, Science, 281:1857-1859 (1998).
Cho, Chunghee, Mammalian ADAMS with Testis-Specific or -Predominant Expression, The ADAM Family of Proteases, 239-259 (2005).
Cho, Chunghee, Testicular and epididymal ADAMS: expression and function during fertilization, Nat. Rev. Urol., 9:550-560 (2012).
Choi, H. et al., Identification and characterization of promoter and regulatory regions for mouse Adam2 gene expression, Mol Biol Rep, 40:787-796 (2013).
Choi, I. et al., Characterization and comparative genomic analysis of intronless Adams with testicular gene expression, Genomics, 83(4):636-46 (2004).
Choi, K. et al., Expression of the metabotropic glutamate receptor 5 (mGluR5) induces melanoma in transgenic mice, PNAS, 108(37):15219-15224 (2011).
Communication in Cases for which No Other Form is Applicable for PCT/US2012/026416, 9 pages (Jun. 7, 2013).
Communication In Cases For Which No Other Form Is Applicable for PCT/US2012/069981, 18 pages (Jul. 3, 2013).
Communication pursuant to Article 114(2) EPC, dated Jun. 21, 2013.
Communication Relating to the Results of the Partial International Search for PCT/US2013/029624 (9 pages), mailed May 17, 2013.
Davidkova, G. et al., Selective Usage of VH Genes in Adult Human B Lymphocyte Repertoires, Scandinavian Journal of Immunology, 45:62-73 (1997).
De Wildt, R. et al., Analysis of heavy and light chain pairings indicates that receptor editing shapes the human antibody repertoire, J. Mol. Biol., 285(3):895-901 (1999).
Declaration of Dr. Glenn Friedrich, 4 page (Mar. 3, 2016).
Declaration of Dr. Jürgen Roes, Ph.D., 14 pages (Jul. 19, 2014).
Declaration of Dr. Kosuke Yusa and associated Annexes, 7 pages (Oct. 2, 2017).
Declaration of Dr. Liang in EP 2550363, 9 pages (Feb. 1, 2018).
Declaration of E-Chiang Lee, Ph.D., 8 pages (Jun. 20, 2016).
Declaration of Hui Liu, Ph.D., 4 pages (Jun. 20, 2016).
Declaration of Meng (Amy) Li, Ph.D., 4 pages (Jun. 20, 2016).
Declaration of Prof. Allan Bradley, Ph.D., 37 pages (Jun. 20, 2016).
Declaration of Wei Wang, Ph.D., 8 pages (Jun. 20, 2016).
Edwards D.R. et al., The ADAM metalloproteinases, Molecular Aspects of Medicine, 29(5):258-89 (2008).
Ensembl database entries for the heavy and light chain immunoglobulin loci, as submitted in EP 2550363 on Oct. 16, 2017, 3 pages.
European Examination Report for EP 14154967.5, Sep. 9, 2014, 4 pages.
European Office Action for 12 716 101.6-1410, 5 pages, Jun. 17, 2014.
Extended European Search Report for 12192727.1, 8 pages (Mar. 7, 2013).
Extended European Search Report for 14154918.8, 8 pages (Aug. 27, 2014).
Extended European Search Report for 14176593.3, 10 pages (Nov. 19, 2014).
Featherstone, K. et al., The mouse immunoglobulin heavy chain V-D intergenic sequence contains insulators that may regulate ordered V(D)J recombination, J. Biol. Chem. 285(13): 9327-9338 (2010).
Gaultier, A. et al., ADAM13 Disintegrin and Cysteine-rich Domains Bind to the Second Heparin-binding Domain of Fibronectin, The Journal of Biological Chemistry, 277(26):23336-23344 (2002).
Giallourakis, C.C. et al., Elements between the IgH variable (V) and diversity (D) clusters influence antisense transcription and lineage-specific V(D)K recombination, PNAS, 107(51):22207-22212 (2010).
Glassey, B. and Civetta, A., Positive Selection at Reproductive ADAM Genes with Potential Intercellular Binding Activity, Molecular Biology and Evolution, 21(5):851-859 (2004).
Gorman, et al., The LGK 3' Enhancer Influences the Ratio of LGK Versus LGL B Lymphocytes, Immunity, 5(3): 241-252(1996).
Hagaman, J. et al., Angiotensin-covering enzyme and male fertility, Proc. Natl. Acad. Sci. USA, 95:2552-2557 (1998).
Han, C. et al., Comprehensive analysis of reproductive ADAMs: relationship of ADAM4 and ADAM6; with an ADAM complex required for fertilization in mice, Biology of Reproduction, 80(5):1001-8 (2009).
Han, C. et al., Impaired sperm aggregation in Adam2 and Adam3 null mice, Fertility and Sterility, 93(8):2754-2756 (2010).
Hendricks J. et al., Organization of the variable region of the immunoglobulin heavy-chain gene locus of the rat, Immunogenetics, 62(7):479-86 (2010).
Hirohata, S. et al., Chromosomal Assignment of Two ADAM Genes, TACE (ADAM17) and MLTNB (Adam 19), to Human Chromosomes 2 and 5, Respectively, and of Mitnb to Mouse Chromosome 11, Genomics, 54:178-179 (1998).
Hoiruchi, K. and Blobel, C., Studies From ADAM Knockout Mice, The ADAM Family of Proteases, 29-64 (2005).
Huang, C. and Stoller, B.D., A Majority of Ig H Chain cDNA of Normal Human Adult Blood Lymphocytes Resembles cDNA for Fegal Ig and Natural Autoantibodies, The Journal of Immunology, 151(10):5290-5300 (1993).
Huovila, A. et al., ADAMs and cell fusion, Current Opinion in Cell Biology, 8:692-699 (1996).
Ikawa, M. et al., Calsperin Is a Testis-specific Chaperone Required for Sperm Fertility, The Journal of Biological Chemistry, 286(7):5639-5646 (2011).
Immler, S. et al., By Hook or by Crook? Morphometry, Competition and Cooperation in Rodent Sperm, PLoS ONE, Issue 1(e170) 5 pages (2007).
Immler, Simone, Sperm competition and sperm cooperation: the potential role of diploid and haploid expression, Reproduction, 135:275-283 (2008).
Interlocutory decision in Opposition proceedings (Art. 101(3)(a) and 106(2) EPC) for EP12716101.6, 36 pages (May 26, 2017).
International Search Report for PCT/US2011/041366, 5 pages (Sep. 22, 2011).
International Search Report for PCT/US2012/026416, 4 pages (Jun. 25, 2012).
International Search Report for PCT/US2012/060487, 7 pages (Feb. 1, 2013).
International Search Report for PCT/US2013/029624, 9 pages (Aug. 2, 2013).
Johnson, T.A. et al., Ig VH1 Genes Expressed in B Cell Chronic Lymphocytic Leukemia Exhibit Distinctive Molecular Features, The Journal of Immunology, 158:235-246 (1997).
Johnston, C. et al., Complete Sequence Assembly and Characterization of the C57BL/6 Mouse Ig Heavy Chain V Region, The Journal of Immunology, 176:4221-4234 (2006).
Kantor, A.B. et al., An Unbiased Analysis of VH-D-JH Sequences from B-1a, B-1b, and Conventional B Cells, The Journal of Immunology, 158:1175-1186 (1997).
Kim T. et al., Expression and relationship of male reproductive ADAMs in mouse, Biology of Reproduction, 74(4):744-50 (2006).
Kim, E. et al., Differential localization of ADAM1a and ADAM1b in the endoplasmic reticulum of testicular germ cells and on the surface of epididymal sperm, Biochemical and Biophysical Research Communications, 304:313-309 (2003).
Kim, E. et al., Mouse Sperm Lacking ADAM1b/ADAM2 Fertilin Can Fuse with the Egg Plasma Membrane and Effect Fertilization, The Journal of Biological Chemistry, 281(9):5634-5639 (2006).

(56) References Cited

OTHER PUBLICATIONS

Kim, E. et al., Synthesis, Processing, and Subcellular Localization of Mouse ADAM3 during Spermatogenesis and Epididymal Sperm Transport, Journal of Reproduction and Development, 50(5):571-578 (2004).
Kong et al., Transgene expression is associated with copy number and cytomegalovirus promoter methylation in transgenic pigs, PLoS One 4(8):1-10 (2009).
Krutskikh, A. et al., Epididymal protein Rnase10 is required for post-testicular sperm maturation and male fertility, The FASEB Journal, 26(10):4198-4209 (2012).
Kunert, R. et al., Characterization of Molecular Features, Antigen-Binding, and in Vitro Properties of IgG and IgM Variants of 4E10, an Anti-HIV Type 1 Neutralizing Monoclonal Antibody, Aids Research and Human Retroviruses, 20(7):755-762 (2004).
Kuroiwa, Y. et al., Sequential targeting of the genes encoding immunoglobulin-μ and prion protein in cattle, Nature Genetics, 36:775-780 (2004).
Lee, E. et al., Complete humanization of the mouse immunoglobulin loci enables efficient therapeutic antibody discovery, Nature Biotechnology, 32:4:356, 12 pages (2014).
Lefranc, M.P., Nomenclature of the Human Immunoglobulin Genes Current Protocols in Immunology, Supplement 40:A.1P.1-A.1P.37 (2000).
Lin, P. et al., Research of Immune Globulin in Mice, Guangzhou Medical Journal, 01:49-50 (1990).
Linder, B. et al., Delayed Translation and Posttranslational Processing of Cyritestin, an Integral Transmembrane Protein of the Mouse Acrosome, Experimental Cell Research, 221:66-72 (1995).
Liu, Y. et al., Primary Genetic Investigation of a Hyperlipidemia Model: Molecular Characteristics and Variants of the Apolipoprotein E Gene in Mongolian Gerbil, Biomed Research International, 2014: 9 pages (2014).
Lonberg, N., Human antibodies from transgenic animals, Nature Biotechnology, 23(9):1117-1125 (2005).
Long, J. et al., Phylogenetic and molecular evolution of the ADAM (A Disintegrin And Metalloprotease) gene family from Xenopus tropicalis, to Mus musculus, Rattus norvegicus, and *Homo sapiens*, Gene, 507:36-43 (2012).
Lovell-Badge, Robin, Many ways to pluripotency, Nature Biotechnology, 25:1114-1116 (2007).
Macdonald, L. et al., Precise and in situ genetic humanization of 6 Mb of mouse immunoglobulin genes, PNAS, 10(1073), 6 pages (2014).
Macdonald, L. et al., Velocigene Technology Extended to Humanization of Several Megabases of Complex Gene Loci, First International MUGEN Conference of Animal Models for Human Immunological Disease, Sep. 10-13, 2006—Athens, Greece, Abstract 21 and Poster, 2 pages (2006).
Mageed, R.A. et al., Rearrangement of the human heavy chain variable region gene V3-23 in transgenic mice generates antibodies reactive with a range of antigens on the basis of VHCDR3 and residues intrinsic to the heavy chain variable region, Clinical and Experimental Immunology, 123(1):1-8 (2001).
Mahmoud, T.L. et al., Limiting CDR-H3 Diversity Abrogates the Antibody Response to the Bacterial Polysaccharide x 1→3 Dextran, The Journal of Immunology, 187:879-886 (2011).
Mahmoudi, M. et al., V region gene analysis of human IgM hybridoma monoclonal anti-Sm antibodies, Lupus, 6:578-589 (1997).
Manis, J. P. et al., Mechanism and control of Icass-switch recombination, Trends in immunology, 23:1:31-39 (2002).
Marasca, R. et al., Immunoglobulin Gene Mutations and Frequent Use of VH1-69 and VH4-34 Segments in Hepatitis C Virus-Positive and Hepatitis C Virus-Negative Nodal Marginal Zone B-Cell Lymphoma, American Journal of Pathology, 159(1):253-261 (2001).
Marcello, M. et al., Lack of tyrosylprotein sulfotransferase-2 activity results in altered sperm-egg interactions and loss of ADAM3 and ADAM6 in epididymal sperm, J Biol Chem, 286(15):13060-13070 (2011).

Mar. 3, 2016 Letter from H. Van Der Hoff, Opposition against EP 2550363 (2 pages).
Mcgoldrick, P. et al., Roden models of amyotrophic lateral sclerosis, Biochimica et Biophysica Acta, 1832:1421-1436 (2013).
Melton, David W., Chapter 8: Gene-Targeting Strategies, Methods in Molecular Biology, Transgenesis Techniques, 2nd Edition, Principles and Protocols, 180:19 pages (2002).
Miklos, J.A. et al., Salivary gland mucosa-associated lymphoid tissue lymphoma immunoglobulin VH genes show frequent use of V1-69 with distinctive CDR3 features, Blood, 95:3878-3884 (2000).
Minutes of the taking of evidence by hearing of witnesses recorded in the oral proceedings before the Opposition Division for EP12716101. 6, 25 pages (May 26, 2017).
Moore, H. et al., Exceptional sperm cooperation in the wood mouse, Nature, 418:174-177 (2002).
Moran N., Mouse platforms jostle for slice of humanized antibody market, Nature Biotechnology, 31(4): 267-268, (2013).
Mortari, F. et al., Human Cord Blood Antibody Repertoire, The Journal of Immunology, 150(4):1348-1357 (1993).
Muller, S. et al., B-Cell Abnormalities in AIDS: Stable and Clonally-Restricted Antibody Response in HIV-1 Infection, Scandinavian Journal of Immunology, 38:327-334 (1993).
Murphy, A., Declaration Under 37 C.F.R. §1.132, 4 pages (2014).
Murphy, Andrew, Chapter 8: VelocImmune: Immunoglobulin Variable Region Humanized Mice, Recombinant Antibodies for Immunotherapy, Part III, 14 pages (2009).
Murphy, D., BAC-based Modifications of the Mouse Genome: The Big and the Backward, Wellcome Trust Advanced Course: Genetic Manipulation of ES Cells, 58 pages (2009).
Murphy, L. and Silha, J., Unexpected and unexplained phenotypes in transgenic models, Growth Horm IGF Res., 10(5):233-235 (2000).
Nagle, Mike, Regeneron helps make Sanofi VelocImmune to its 'weak' pipeline, Breaking News on Contract Research, Manufacturing & Clinical Trials, 2 pages (2007).
Nakanishi, T. et al., Selective Passage Through the Uterotubal Junction of Sperm from a Mixed Population Produced by Chimeras of Calmegin-Knockout and Wild-Type Male Mice, Biology of Reproduction, 71:959-965 (2004).
Nishimura, H. et al., Analysis of Loss of Adhesive Function in Sperm Lacking Cyritestin or Fertilin ß, Developmental Biology, 233:204-213 (2001).
Nishimura, H. et al., Identification of an ADAM2-ADAM3 Complex on the Surface of Mouse Testicular Germ Cells and Cauda Epididymal Sperm, The Journal of Biological Chemistry, 282(24):17900-17907 (2007).
Nishimura, H. et al., Possible Function of the ADAM1a/ADAM2 Fertilin Complex in the Appearance of ADAM3 on the Sperm Surface, The Journal of Biological Chemistry, 279(33):34957-34962 (2004).
Notice of Opposition to a European Patent for EP2550363, 28 pages (Dec. 10, 2014).
Office Action for U.S. Appl. No. 13/716,238, 7 pages (Jan. 4, 2016).
Office Action for U.S. Appl. No. 13/951,996, 7 pages (Dec. 17, 2015).
Office Action for U.S. Appl. No. 14/137,902, 23 pages (Oct. 30, 2015).
Office Action for U.S. Appl. No. 14/818,162, 30 pages (Dec. 11, 2015).
Opinion & Order between Regeneron Pharmaceuticals, Inc. and Merus B.V., 114 pages (Nov. 2, 2015).
Opponent Final Submissions for EP2550363, 15 pages (Jan. 27, 2017).
Pasqualini, R. and Arap, W., Hybridoma-free generation of monoclonal antibodies, Proceedings of the National Academy of Sciences USA, 101(1):257-259 (2004).
Patentee Final Submissions for EP12716101.6, 4 pages (Jan. 27, 2017).
Perez, M. et al., Primary cutaneous B-cell Lymphoma is associated with somatically hypermutated immunoglobulin variable genes and frequent use of VH1-69 and VH4-59 segments, British Journal of Dermatopathology, 162:611-618 (2010).
Pizzari, T. and Foster, K., Sperm Sociality: Cooperation, Altruism, and Spite, PLoS Biology, 6(5)(e130):0925-0931 (2008).

(56) References Cited

OTHER PUBLICATIONS

Popov, et al., A Human Immunoglobulin I locus is Similarly Well Expressed in Mice and Humans, J. Exp. Med., 189(10):1611-1619(1999).
Pos, W. et al., VH1-69 germline encoded antibodies directed towards ADAMTS13 in patients with acquired thrombotic thrombocytopeniaurpura, Journal of Thrombosis and Haemostatis, 7:421-428 (2008).
Poueymirou, W. et al., F0 generation mice fully derived from gene-targeted embryonic stem cells allowing immediate phenotypic analyses, Nature Biotechnology, 25(1):91-99 (2007).
Preliminary Opinion of Opposition Division on EP 2550363, 24 pages, Jul. 29, 2016.
Primakoff, P. and Myles, D., The ADAM gene family: surface proteins with adhesion and protease activity, Trends Genet, 16(2):83-87 (2000).
Provision of the minutes in accordance with Rule 124(4) EPC for EP1276101.6, 62 pages (May 26, 2017).
Ray, P. et al., Ectopic expression of a c-kitW42 minigene in transgenic mice: recapitulation of phenotypes and evidence for c-kit function in melanoblast progenitors, Genes Development, 5(12A):2265-2273 (1991).
Reply to Third Party Observations on EP2501817, (May 20, 2013).
Response to Summons to attend Oral Proceedings for EP255036, 1 page (Feb. 28, 2017).
Rodríguez, C.I., et al., High-efficiency deleter mice show that FLPe is an alternative to Cre-loxP, Nat. Genet., 25(2):139-40 (2000).
Roebroek, A. et al., Chapter 10: Knockin Approaches, Methods in Molecular Biology, Transgenic Mouse Methods and Protocols, 209:16 pages (2003).
Roychaudhuri, R. et al., ADAM9 Is a Novel Product of Polymorphonuclear Neutrophils: Regulation of Expression and Contributions to Extracellular Matrix Protein Degradation during Acute Lung Injury, The Journal of Immunology, 193:2469-2482 (2014).
Rudikoff, S. et al., Single amino acid substitution altering antigen-binding specificity, Immunology, 79:1979-1983 (1982).
Sasso E.H. et al., A Fetally Expressed Immunoglobulin VH1 Gene Belongs to a Complex Set of Alleles, Journal of Clinical Investigation, 91:2358-2367 (1993).
Sasso E.H. et al., Expression of the Immunoglobulin VH Gene 51p1 is Proportional to its Germline Gene Copy Number, Journal of Clinical Investigation, 97(9):2074-2080 (1996).
Sasso, E.H. et al., Prevalence and Polymorphism of Human VH3 Genes, The Journal of Immunology, 145(8):2751-2757 (1990).
Schelonka, R.L. et al., A Single DH Gene Segment Creates Its Own Unique CDR-H3 Repertoire and Is Sufficient for B Cell Development and Immune Function, The Journal of Immunology, 175:6624-6632 (2005).
Schulze, M. et al., Derivation, Maintenance, and Characterization of Rat Embryonic Stem Cells In Vitro, Methods in Molecular Biology, 329:45-58 (2006).
Schwartz, D. and Cantor, C., Separation of Yeast Chromosome-Sized DNAs by Pulsed Field Gradient Gel Electrophoresis, Cell, 37:67-75 (1984).
Seals D.F. and Courtneidge S.A., The ADAMs family of metalloproteases: multidomain; proteins with multiple functions, Genes and Development, 17(1):7-30 (2003).
Second Declaration of Meng (Amy) Li, Ph.D., 14 pages (Sep. 15, 2016).
Shamsadin, R. et al., Male Mice Deficient for Germ-Cell Cyritestin Are Infertile, Biology of Reproduction, 61:1445-1451 (1999).
Shmerling et al., Strong and ubiquitous expression of transgenes targeted into the β-actin locus by Cre/lox cassette replacement, Genesis 42(5):229-235 (2005).
Sibilia, J. et al., Structural Analysis of Human Antibodies to Proteinase 3 from Patients with Wegener Granulomatosis, The Journal of Immunology, 159:712-719 (1997).
Sigmund, Curt D., Viewpoint: Are Studies in Genetically Altered Mice Out of Control?, Arterioscler Thromb Vasc Biol, 20(6):1425-1429 (2000).

Sorrell, D. and Kolb, A., Chapter XI: Targeted Modification of Mammalian Genomes, Focus on Genome Research, 6 pages (2004).
Souroujon, M.C. et al., Polymorphisms in Human H Chain V Region Genes from the VHIII Gene Family, The Journal fo Immunology, 143(2):706-711 (1989).
Stevens, S. et al., Velocimmune: Humanization of Immunoglobulin Loc Using Velocigene Technology, First International MUGEN Conference of Animal Models for Human Immunological Disease, Sep. 10-13, 2006—Athens, Greece, Abstract 4 and Poster, 2 pages (2006).
Storb, U. et al., Transgenic Mice with μ and k Genes Encoding Antiphosphorycholine Antibodies, J. Exp Med, 164:627-64 (1986).
Suarez, Susan S., Sperm Transport and Motility in the Mouse Oviduct: Observations in Situ, Biology of Reproduction, 36:203-210 (1987).
Sui, J. et al., Structural and functional bases for broad-spectrum neutralization of avian and human influenza A viruses, Nature Structural and Molecular Biology, 16(3):265-273 (2009).
Suzuki, I. et al., Representation of Rearranged VH Gene Segments in the Human Adult Antibody Repertoire, The Journal of Immunology, 154:3902-3911 (1995).
Swanson, W. and Vacquier, V., The Rapid Evolution of Reproductive Proteins, Nature Reviews, Genetics, 3:137-144 (2002).
Taki, S. et al., Targeted Insertion of a Variable Region Gene into the Immunoglobulin Heavy Chain Locus, Science, 262:1268-1271 (1993).
Taylor, L.D. et al., A Transgenic Mouse that Expresses a Diversity of Human Sequence Heavy and Light Chain Immunoglobulins, Nucleic Acid Research, 20(23):6287-6295 (1992).
Third Party Observations on EP2501817, (Feb. 28, 2013).
Third Party Observations on European Patent Application No. 12192727.1, 17 pages (Jun. 18, 2013).
Third Party Observations on European Patent Application No. 12192727.1, 3 pages (Feb. 25, 2014).
Third Party Observations on European Patent Application No. 12192727.1, 5 pages (Nov. 17, 2014).
Third Party Observations on European Patent Application No. 12192727.1, 7 pages (Apr. 8, 2015).
Third Party Observations on European Patent Application No. 12192727.1, 9 pages (Aug. 11, 2015).
Third Party Observations on European Patent Application No. 12716101.6, 4 pages (Feb. 25, 2014).
Third Party Observations on European Patent Application No. 12716101.6, 4 pages (Jul. 31, 2014).
Third Party Observations on European Patent Application No. 12716101.6, 4 pages (Sep. 4, 2013).
Third Party Observations on European Patent Application No. 12716101.6, 5 pages (Jun. 27, 2014).
Third Party Observations on European Patent Application No. 12809955.3, 3 pages (Aug. 6, 2015).
Third Party Observations on European Patent Application No. 12809955.3, 4 pages (Jun. 24, 2014).
Third Party Observations on European Patent Application No. 14154918.8, 5 pages (Nov. 26, 2014).
Third Party Observations on European Patent Application No. 14154918.8, 7 pages (Apr. 14, 2015).
Third Party Observations on European Patent Application No. 14154967.5, 5 pages (Nov. 18, 2014).
Third Party Observations on European Patent Application No. 14154967.5, 7 pages (Apr. 23, 2015).
Third Party Observations on European Patent Application Nos. 12192727.1, 14154918.8, 14154967.5, 14176593.3 and 12809955.3, 3 pages (Nov. 12, 2015).
Third Party Observations on U.S. Appl. No. 13/890,519, 27 pages (Oct. 23, 2013).
Timetable for Mouse ES Cells course at Wellcome Trust Sanger Institute Oct. 26, 2009-Nov. 8, 2009 (black and white).
Timetable for Mouse ES Cells course at Wellcome Trust Sanger Institute Oct. 26, 2009-Nov. 8, 2009 (greyscale).
Tokuhiro, K. et al., Protein disulfide isomerase homolog PDILT is required for quality control of sperm membrane protein ADAM3 and male fertility, PNAS, 109(10):3850-3855 (2012).

(56) References Cited

OTHER PUBLICATIONS

Tuaillon, N. et al., Human immunoglobulin heavy-chain minilocus recombination in transgenic mice: Gene-segment use in u and y transcripts, Proceeding of the National Academy of Science USA, 90:3720-3724 (1993).

Tuaillon, N., Repertoire analysis in human immunoglobulin heavy chain minilocus transgenic, [mu]MT/[mu]MT mice, Molecular Immunology, 37(5):221-231(2000).

Valenzuela, D. et al., High-throughput engineering of the mouse genome coupled with high-resolution expression analysis, Nature Biotechnology, 21(6):652-659 (2003).

Veronina, V. et al., Deletion of Adam6 in Mus musculus leads to male subfertility and deficits in sperm ascent intothe oviduct, Biology of Reproduction, 100(3):686-696 (2019).

Wagner S.D. et al., The diversity of antigen-specific monoclonal antibodies from transgenic mice bearing human immunoglobulin gene miniloci, Eur J Immunol. 24(11):2672-81 (1994).

Wagner, S.D. et al., Antibodies generated from human immunoglobulin miniloci in transgenic mice, Nucleic Acids Research, 22(8):1389-1393 (1994).

Wang, T.T. and Palese, P., Universal epitopes of influenza virus hemagglutinins?, Nature Structural & Molecular Biology, 16(3):233-234 (2009).

Watson, J. and Crick, F., Molekulyarnaya biotekhnologiya. Printsipy i primeneniye, Moscow Mir., 45-47 (2002).

White, Judith M., ADAMS: modulators of cell-cell and cell-matrix interactions, Current Opinion in Cell Biology, 15:598-606 (2003).

Wolfsberg, T. et al., ADAM, a Widely Distributed and Developmentally Regulated Gene Family Encoding Membrane Proteins with A Disintegrin And Metalloprotease Domain, Developmental Biology, 169:378-383 (1995).

Written Opinion for PCT/US2012/026416 (8 pages), mailed Jun. 25, 2012.

Written Opinion for PCT/US2012/060487, 5 pages (Feb. 1, 2013).

Written Opinion for PCT/US2013/029624, 12 pages (Aug. 2, 2013).

Written Opinion for PCT/US2014/026040 dated Jul. 29, 2014 (8 pages).

Xu, J.L. and Davis, M.M., Diversity in the CDR3 region of VH is sufficient for most antibody specificities, Immunity 13(1):37-45 (2000).

Yamada, M. et al., Preferential Utilization of Specific Immunoglobulin Heavy Chain Diversity and Joining Segments in Adult Human Peripheral Blood B Lymphocytes, Journal of Experimental Medicine, 173:395-407 (1991).

Yamaguchi, R. et al., Aberrant Distribution of ADAM3 in Sperm from Both Angiotensin-Converting Enzyme (Ace)- and Calmegin (Clgn)-Deficient Mice, Biology of Reproduction, 75:760-766 (2006).

Yamaguchi, R. et al., Disruption of ADAM3 Impairs the Migration of Sperm into Oviduct in Mouse, Biology of Reproduction, 81:142-146 (2009).

Yamaguchi, R. et al., Mice expressing aberrant sperm-specific protein PMIS2 produce normal-looking but fertilization-incompetent spermatozoa, MBoC, 23:2671-2679 (2012).

Yantha, J. et al., Unexpected Acceleration of Type 1 Diabetes by Transgenic Expression of B7-H1 in NOD Mouse Peri-Islet Glia, Diabetes, 59:2588-2596 (2010).

Zhang, Y. et al., A new logic for DNA engineering using recombination in *Escherichia coli*, Nature Genetics, 20:123-128 (1998).

Zhu, G. et al., Testase 1 (ADAM 24) a plasma membrane-anchored sperm protease implicated in sperm function during epididymal maturation or fertilization, Journal of Cell Science, 114:1787-1794 (2001).

Zou, Y. et al., Cre-loxP-mediated gene replacement: a mouse strain producing humanized antibodies, Current Biology, 4:1099-1103 (1994).

|  | A | B | C | D | E | F | G | H |
|---|---|---|---|---|---|---|---|---|
| Parental ES | Theoretical copy number | 2 | 2 | 2 | 2 | 2 | 2 | 0 | 0 |
| | Observed copy number | 1.9 | 1.8 | 2.1 | 1.8 | 1.9 | 1.8 | <0.01 | <0.04 |
| Modified ES | Theoretical copy number | 2 | 2 | 1 | 1 | 2 | 2 | 1 | 1 |
| | Observed copy number | 1.9 | 2.4 | 1.0 | 1.0 | 2.0 | 1.9 | + | + |

FIG. 3B

| copy number | D | H |
|---|---|---|
| WT Mice | | |
| Theoretical | 2 | 0 |
| Observed 1 | 1.71 | <0.01 |
| Observed 2 | 2.07 | <0.01 |
| Observed 3 | 2.16 | <0.01 |
| Observed 4 | 1.88 | <0.01 |
| Het Mice | | |
| Theoretical | 1 | 1 |
| Observed 1 | 1.22 | 1.04 |
| Observed 2 | 0.94 | 1.02 |
| Observed 3 | 0.85 | 0.95 |
| Observed 4 | 1.02 | 1.00 |
| Homo Mice | | |
| Theoretical | 0 | 2 |
| Observed 1 | <0.01 | 2.37 |
| Observed 2 | <0.01 | 2.22 |
| Observed 3 | <0.01 | 2.43 |
| Observed 4 | <0.01 | 1.93 |

FIG. 3C

| 3'V_H | | N | D_H | N | 5' J_H |
|---|---|---|---|---|---|
| | | | (D_H 1-26) GGTATAGTGGGAGCTACTAC | | |
| (3-72) | GCTAG | | TAGTGGGgcCTAC | AGGC | CTTTTGATATC(3) |
| (3-9) | GCAAAAG | CCCAGGGG | AGTGGGAGCTACTAC | ACCT | ATGCTTTTGATATC(3) |
| (3-7) | GCGAGAGA | G | GGTATAGTGGGAaCTACT | GAGG | ACTTTGAtTAC(4) |
| (4-59) | GCGAGAG | GGAC | AGTGGGAGC | CCT | CTTTGACTAC(4) |
| (3-23) | GCGAAA | CC | TAGTGGGAGCTACT | C | CTGGTTCGACCCC(5) |
| | | | (D_H 1-7) GGTATAACTGGAACTAC | | |
| (4-34) | GCGAGAGG | AGGAG | GGTATAACTGGAACT | CGA | ATGCTTTTGATATC(3) |
| (1-2) | GCGAGAG | GA | TATAACTGGA | | ACTACTTTGACTAC(4) |
| (3-23) | GCGAAAGA | | GTATAACTGGAACCAC | TGG | TACTTTGACTAC(4) |
| (3-7) | GCGAGAGA | G | ATAACTGGAAC | CCC | CTTTGACTAC(4) |
| (4-59) | GCGAG | GGGA | TATAACTGGAACT | TTTCTTTT | TTTGACTAC(4) |
| (4-39) | GCGAGA | GG | TAACTGGAACT | CTCTGGG | CTTTGACTAC(4) |
| | | | (D_H 3-10) GTATTACTATGGTTCGGGGAGTTATTATAAC | | |
| (3-30) | GCGA | AAAGGGC | TACTATGGTTCGGGGAG | CTC | TTGACTAC(4) |
| (1-2) | GCGAGAGA | | TATTACTATGGTTCGGGGAGTTATTATAAC | GAAGGT | CTACGGTATGGACGTC(6) |
| | | | (D_H 6-6) GAGTATAGCAGCTCGTCC | | |
| (1-2) | GCGAGAGA | | GTATAGCAG | | CTTTGACTAC(4) |
| (3-48) | GCGAGA | GA | GAGTATAGCAGCTCGT | TG | TGACTAC(4) |
| (3-13) | GCAAGAGA | GG | ATAGgAGCTCGCCC | CTCGGG | TACTTTGACTAC(4) |
| | | | (D_H 7-27) CTAACTGGGGA | | |
| (3-7) | GCGAGAGA | TCT | TGGGGA | AGG | CTAC(4) |
| (3-15) | ACCAC | CCA | TAACTGGGGA | GGG | TTTGACTAC(4) |
| (3-48) | GCGAGA | GATA | GGGGA | | CCg(5) |

FIG. 7A

| 3'Vκ | N | 5' Jκ |
|---|---|---|
| (1-6) CAACAGAGTTAtAGTACCCCCTCC | GGA | GACG(1) |
| (1-9) CAACAGCTTAATAGTTACCCTC | | GGACG(1) |
| (1-9) CAACAGCTTAATAGTTACC | | ATTCACT(3) |
| (1-9) CAACAttTTAATAGTTACCC | | GCTCACT(4) |
| (1-9) CAGCAGTATAATAGTTACCCTC | | TCACT(4) |
| (3-15) CTACAGCATAATAGTTACCC | | GTGGACG(1) |
| (1-17) CTACAGCATAATAGTTACCCTC | | GGACG(1) |
| (1-17) CAGCAGTATGGTAGCTCACCTC | | GGACG(1) |
| (3-20) ATGCAAGGTACACACTGGCC | | GTGGACG(1) |
| (2-30) ATGCAAGGTtCACACTGGCC | | GTACACT(2) |
| (2-30) ATGCAAGGTACACACTGGCC | | GCTCACT(4) |
| (2-30) CAACAGTATGATAATCTCCCTCC | | CACT(3) |
| (1-33) CAACAGTATGATAATCTCCC | CG | ATTCACT(3) |
| (1-33) CAACAGTATGATAATCTCCC | | TCACT(4) |
| (1-33) CAACAGTATGATAATCTCCC | | GATCACC(5) |
| (1-33) CAACGGAtTTACAATGCC | GA | CACC(5) |
| (1-37) CAACAGAGTTACAGTACCCCC | CA | TGTACACT(2) |
| (1-39) CAACAGAGTTACAGTACCCCCTC | | TCACT(4) |
| (1-39) CAACAGAGTTACAGTACtCCTCC | | CACT(4) |

FIG. 7B

SEQUENCE LISTING

<160> NUMBER OF SEQ ID NOS: 63

<210> SEQ ID NO 1
<211> LENGTH: 754
<212> TYPE: PRT
<213> ORGANISM: Mus musculus

<400> SEQUENCE: 1

```
Met Leu Ser Leu Thr Trp Gly Met Arg Leu Val Glu Arg Pro Val Val
1               5                   10                  15

Pro Arg Val Leu Leu Leu Leu Phe Ala Leu Trp Leu Leu Leu Leu Val
            20                  25                  30

Pro Val Trp Cys Ser Gln Gly His Pro Thr Trp Arg Tyr Ile Ser Ser
        35                  40                  45

Glu Val Val Ile Pro Arg Lys Glu Ile Tyr His Thr Lys Gly Leu Gln
    50                  55                  60

Ala Gln Arg Leu Leu Ser Tyr Ser Leu Arg Phe Arg Gly Gln Arg His
65                  70                  75                  80

Ile Ile His Leu Arg Arg Lys Thr Leu Ile Trp Pro Arg His Leu Leu
                85                  90                  95

Leu Thr Thr Gln Asp Asp Gln Gly Ala Leu Gln Met Glu Tyr Pro Phe
            100                 105                 110

Phe Pro Val Asp Cys Tyr Tyr Ile Gly Tyr Leu Glu Gly Ile Leu Gln
        115                 120                 125

Ser Met Val Thr Val Asp Thr Cys Tyr Gly Gly Leu Ser Gly Val Ile
    130                 135                 140

Lys Leu Asp Asn Leu Thr Tyr Glu Ile Lys Pro Leu Asn Asp Ser Gln
145                 150                 155                 160

Ser Phe Glu His Leu Val Ser Gln Ile Val Ser Glu Ser Asp Asp Thr
                165                 170                 175

Gly Pro Met Asn Ala Trp Lys His Trp Ser His Asn Thr Gly Ser Pro
            180                 185                 190

Ser Ser Arg Leu Glu Tyr Ala Asp Gly Ala Pro Arg Leu Ser Ser Lys
        195                 200                 205

Asn Tyr Ala Thr His Pro Ala Ala Ile Lys Gly His Phe Gln Ala Thr
    210                 215                 220

His Ser Val Tyr Ser Ala Ser Gly Gly Asp Lys Leu Ser Ser Thr Val
225                 230                 235                 240

Glu Tyr Leu Phe Lys Val Ile Ser Leu Met Asp Thr Tyr Leu Thr Asn
                245                 250                 255

Leu His Met Arg Tyr Tyr Val Phe Leu Met Thr Val Tyr Thr Glu Ala
            260                 265                 270

Asp Pro Phe Ser Gln Asp Phe Arg Val Pro Gly Gln Ala His Thr
        275                 280                 285

Phe Tyr Glu Arg Val Phe Tyr Ala His Phe Arg Pro Asp Ala Gly Ala
    290                 295                 300

Ile Ile Asn Lys Asn Ser Pro Gly Asp Asp Ala Val Asn Pro Ala Glu
305                 310                 315                 320

Arg Ser Ile Cys Ser Pro Ser Ala Leu Ile Cys Leu Gly Gln His Gly
```

```
                325                 330                 335
Arg Asn Pro Leu Phe Leu Ser Ile Ile Thr Asn Arg Val Gly Arg
            340                 345                 350

Ser Leu Gly Leu Lys His Asp Glu Gly Tyr Cys Ile Cys Gln Arg Arg
            355                 360                 365

Asn Thr Cys Ile Met Phe Lys Asn Pro Gln Leu Thr Asp Ala Phe Ser
370                 375                 380

Asn Cys Ser Leu Ala Glu Ile Ser Asn Ile Leu Asn Thr Pro Asp Leu
385                 390                 395                 400

Met Pro Cys Leu Phe Tyr Asp Arg His Val Tyr Tyr Asn Thr Ser Leu
                405                 410                 415

Thr Tyr Lys Phe Cys Gly Asn Phe Lys Val Asp Asn Asn Glu Gln Cys
            420                 425                 430

Asp Cys Gly Ser Gln Lys Ala Cys Tyr Ser Asp Pro Cys Cys Gly Asn
            435                 440                 445

Asp Cys Arg Leu Thr Pro Gly Ser Ile Cys Asp Lys Glu Leu Cys Cys
450                 455                 460

Ala Asn Cys Thr Tyr Ser Pro Ser Gly Thr Leu Cys Arg Pro Ile Gln
465                 470                 475                 480

Asn Ile Cys Asp Leu Pro Glu Tyr Cys Ser Gly Ser Lys Phe Ile Cys
                485                 490                 495

Pro Asp Asp Thr Tyr Leu Gln Asp Gly Thr Pro Cys Ser Glu Gly
            500                 505                 510

Tyr Cys Tyr Lys Gly Asn Cys Thr Asp Arg Asn Ile Gln Cys Met Glu
            515                 520                 525

Ile Phe Gly Val Ser Ala Lys Asn Ala Asn Ile Lys Cys Tyr Asp Ile
            530                 535                 540

Asn Lys Gln Arg Phe Arg Phe Gly His Cys Thr Arg Ala Glu Glu Ser
545                 550                 555                 560

Leu Thr Phe Asn Ala Cys Ala Asp Gln Asp Lys Leu Cys Gly Arg Leu
                565                 570                 575

Gln Cys Thr Asn Val Thr Asn Leu Pro Phe Leu Gln Glu His Val Ser
                580                 585                 590

Phe His Gln Ser Val Ile Ser Gly Val Thr Cys Phe Gly Leu Asp Glu
            595                 600                 605

His Arg Gly Thr Glu Thr Ala Asp Ala Gly Leu Val Arg His Gly Thr
            610                 615                 620

Pro Cys Ser Arg Gly Lys Phe Cys Asp Arg Gly Ala Cys Asn Gly Ser
625                 630                 635                 640

Leu Ser Arg Leu Gly Tyr Asp Cys Thr Pro Glu Lys Cys Asn Phe Arg
                645                 650                 655

Gly Val Cys Asn Asn Arg Arg Asn Cys His Cys His Phe Gly Trp Ser
                660                 665                 670

Pro Pro Lys Cys Lys Glu Glu Gly His Ser Gly Ser Ile Asp Ser Gly
            675                 680                 685

Ser Pro Pro Val Gln Arg Arg Ile Ile Lys Gln Asn Leu Glu Pro Val
            690                 695                 700

Val Tyr Leu Arg Ile Leu Phe Gly Arg Ile Tyr Phe Leu Phe Val Ala
705                 710                 715                 720

Leu Leu Phe Gly Ile Ala Thr Arg Val Gly Val Thr Lys Ile Phe Arg
                725                 730                 735

Phe Glu Asp Leu Gln Ala Ala Leu Arg Ser Trp Gln Glu Gln Ala Lys
            740                 745                 750
```

Asp Lys

<210> SEQ ID NO 2
<211> LENGTH: 756
<212> TYPE: PRT
<213> ORGANISM: Mus musculus

<400> SEQUENCE: 2

```
Met Leu Ser Leu Thr Trp Gly Met Arg Leu Val Glu Arg Pro Val Val
1               5                   10                  15

Pro Arg Val Leu Leu Leu Phe Ala Leu Trp Leu Leu Leu Val
            20                  25                  30

Pro Val Trp Cys Ser Gln Gly His Pro Thr Trp Arg Tyr Ile Ser Ser
        35                  40                  45

Glu Val Val Ile Pro Arg Lys Glu Ile Tyr His Thr Lys Gly Leu Gln
    50                  55                  60

Ala Gln Arg Leu Leu Ser Tyr Ser Leu His Phe Arg Gly Gln Arg His
65                  70                  75                  80

Ile Ile His Leu Arg Arg Lys Thr Leu Ile Trp Pro Arg His Leu Leu
                85                  90                  95

Leu Thr Thr Gln Asp Asp Gln Gly Ala Leu Gln Met Asp Tyr Pro Phe
            100                 105                 110

Phe Pro Val Asp Cys Tyr Tyr Ile Gly Tyr Leu Glu Gly Ile Pro Gln
        115                 120                 125

Ser Met Val Thr Val Asp Thr Cys Tyr Gly Gly Leu Ser Gly Val Met
    130                 135                 140

Lys Leu Asp Asp Leu Thr Tyr Glu Ile Lys Pro Leu Asn Asp Ser Gln
145                 150                 155                 160

Ser Phe Glu His Leu Val Ser Gln Ile Val Ser Glu Ser Asp Asp Thr
                165                 170                 175

Gly Pro Met Asn Ala Trp Lys His Trp Ser His Asn Thr Gly Ser Pro
            180                 185                 190

Ser Ser Arg Leu Glu Tyr Ala Asp Gly Ala Pro Arg Ile Ser Ser Lys
        195                 200                 205

Asn Tyr Ala Thr His Pro Ala Ala Ile Lys Gly His Phe Gln Ala Thr
    210                 215                 220

Asn Ser Val Tyr Asn Ser Ala Ala Gly Asp Lys Leu Ser Ser Thr Val
225                 230                 235                 240

Gly Tyr Leu Phe Gln Val Ile Ser Leu Met Asp Thr Tyr Leu Thr Asn
                245                 250                 255

Leu His Met Arg Tyr Tyr Val Phe Leu Met Thr Val Tyr Thr Asn Ser
            260                 265                 270

Asp Pro Phe Arg Leu Glu Phe Ala Val Pro Gly Gly Ser Ala Tyr Asn
        275                 280                 285

Tyr Tyr Val Ser Val Phe Tyr Asn Lys Phe Lys Pro Asp Ala Gly Val
    290                 295                 300

Leu Leu Asn Lys Tyr Gly Pro Gln Asp Asn Gln Val Asn Pro Ala Glu
305                 310                 315                 320

Arg Ser Ile Cys Ser Leu Ala Leu Ile Cys Ile Gly Lys Tyr Asp
                325                 330                 335

Arg Asn Pro Leu Phe Leu Ser Pro Ile Ile Thr Asn Arg Val Gly Arg
            340                 345                 350

Ser Leu Gly Leu Lys Tyr Asp Glu Gly Tyr Cys Val Cys Gln Arg Arg
        355                 360                 365
```

```
Asn Thr Cys Ile Met Phe Arg His Pro Gln Leu Thr Asp Ala Phe Ser
370                 375                 380

Asn Cys Ser Leu Ala Glu Ile Ser Asn Ile Leu Asn Thr Pro Gly Leu
385                 390                 395                 400

Met Pro Cys Leu Phe Tyr Asp Arg His Val Tyr Tyr Asn Thr Ser Leu
                405                 410                 415

Thr Tyr Lys Phe Cys Gly Asn Phe Lys Val Asp Asn Asp Glu Gln Cys
            420                 425                 430

Asp Cys Gly Ser Gln Lys Ala Cys Tyr Ser Asp Pro Cys Cys Gly Asn
        435                 440                 445

Asp Cys Arg Leu Thr Pro Gly Ser Ile Cys Asp Lys Glu Leu Cys Cys
450                 455                 460

Ala Asn Cys Thr Tyr Ser Pro Ser Gly Thr Leu Cys Arg Pro Ile Gln
465                 470                 475                 480

Asn Ile Cys Asp Leu Pro Glu Tyr Cys Asn Gly Thr Lys Tyr Ile Cys
            485                 490                 495

Pro Asp Asp Thr Tyr Leu Gln Asp Gly Thr Pro Cys Ser Glu Asp Gly
        500                 505                 510

Tyr Cys Tyr Lys Gly Asn Cys Thr Asp Arg Asn Ile Gln Cys Met Glu
    515                 520                 525

Ile Phe Gly Val Ser Ala Lys Asn Ala Asn Ile Lys Cys Tyr Asp Ile
530                 535                 540

Asn Lys Gln Arg Phe Arg Phe Gly His Cys Thr Arg Ala Glu Glu Ser
545                 550                 555                 560

Leu Thr Phe Asn Ala Cys Ala Asp Gln Asp Lys Leu Cys Gly Arg Leu
                565                 570                 575

Gln Cys Thr Asn Val Thr Asn Leu Pro Tyr Leu Gln Glu His Val Ser
            580                 585                 590

Phe His Gln Ser Ile Ile Ser Gly Phe Thr Cys Phe Gly Leu Asp Glu
        595                 600                 605

His Arg Gly Thr Glu Thr Thr Asp Ala Gly Met Val Arg His Gly Thr
610                 615                 620

Pro Cys Ser Lys Ser Lys Phe Cys Asp Gln Gly Ala Cys Ser Gly Ser
625                 630                 635                 640

Leu Ser His Leu Gly Tyr Asp Cys Thr Pro Glu Lys Cys Ser Phe Arg
                645                 650                 655

Gly Val Cys Asn Asn His Arg Asn Cys His Cys His Phe Gly Trp Lys
            660                 665                 670

Pro Pro Glu Cys Lys Glu Glu Gly Leu Ser Gly Ser Ile Asp Ser Gly
        675                 680                 685

Ser Pro Pro Val Gln Arg His Thr Ile Lys Gln Lys Gln Glu Pro Val
690                 695                 700

Val Tyr Leu Arg Ile Leu Phe Gly Arg Ile Tyr Phe Leu Phe Val Ala
705                 710                 715                 720

Leu Leu Phe Gly Ile Ala Thr Arg Val Gly Val Thr Lys Ile Phe Arg
                725                 730                 735

Phe Glu Asp Leu Gln Ala Thr Leu Arg Ser Gly Gln Gly Pro Ala Arg
            740                 745                 750

Asp Lys Pro Lys
            755

<210> SEQ ID NO 3
<211> LENGTH: 13894
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
gtcctaaggt agcgagggat gacagattct ctgttcagtg cactcagggt ctgcctccac      60
gagaatcacc atgcccttc tcaagactgt gttctgtgca gtgccctgtc agtggaaatc     120
tggagagcat gcttccatga gcttgtgagt agtatatcta gtaagccatg gctttgtgtt    180
aatggtgatg ttctacatac cagttctctg gcttaataat gaggtgatga ttctatgttc    240
ctgtaacgct tcctcaactg ggtcctaagt ctttcttcac tccatctatt cctctaagga    300
atgatcctga aaatcccatc acaaactata ggagatggga accatcaaaa aacacagtga    360
caaagaggtg ggaacgcatc agggttcagg aaccatattt taaaaagata tcgtaaataa    420
cttcttaaaa gagatataga caaatctcca ttaatacgga gaccagaggc ctaaggctaa    480
gaaccaatgg tggctcaagg tctcctgcta cccgaggagc aaacgtagag cagtttctaa    540
tgatttattt aaaatataga atcaaaagta ccagtttgca attttgaaag atttatttca    600
gcaatgcaac aacatcaggt ggtgccgagt ccaacacgtc ttatgtccca tgatataaac    660
aaaggccatc cagaactgtg gactggagtt ctaccttgtc ccctaatgac attcagattt    720
tttttccatt ctctttatct tagaggagac aggggggctaa ctcattttac ttgtcctttg    780
cttgttcttg ccaagaacgt aaagcagctt gcaagtcttc aaacctaaat atcttagtaa    840
ctcctacacg agtggcaatg ccaaagagca gtgcaacaaa gaggaagtaa atacgaccaa    900
agagtattct taaatacact actggctcta ggttctgttt tattatgcgc ctttgaaccg    960
gaggggaccc actgtctatg ctcccactgt gtccctcttc tttgcactt ggagggctcc    1020
aaccaaaatg gcaatggcaa ttccgacgat tgttacacac tcctctgaaa ttgcattttt    1080
ctggggtgca gtcataaccc aaacgagata aacttccatt gcaagctcct cgatcacaga    1140
acttacccct tgaacacggg gtaccatgtc tcaccaatcc agcatctgct gtttctgtcc    1200
cacgatgttc atcaagccca aagcaggtaa ccccagagat aaccgattga tggaatgaaa    1260
catgttcttg caaaaatgga agattggtga cattggtaca ctgcaacctt ccacacagct    1320
tgtcctgatc agcacaagca ttgaatgtga ggctttcttc tgctctagta caatgcccaa    1380
atcgaaaccg ttgtttgttg atgtcatagc acttaatatt agcattctta gcacttacac    1440
caaagatttc catgcattgt atgttgcgat cagtgcagtt acctttatag cagtaaccct    1500
cttctgagca tggtgtccca tcttgcagat aagtgtcatc tgggcaaatg aacttagagc    1560
cactacagta ctctggaaga tcacatatgt tctggatagg tctgcagagt gtcccagaag    1620
gactgtaagt gcaatttgca cagcataatt ctttatcaca aatgctacca ggtgttaacc    1680
tgcaatcatt tccacagcag ggatctgaat aacatgcctt tgggagcca cagtcacact     1740
gctcattgtt atctactttg aagtttccac aaaactata agtcaatgat gtattataat     1800
aaacatgacg gtcatagaaa agacatggca tcagatcagg agtattaagt atgttgctta    1860
tctctgcaag ggaacaattg ctgaaagcat ctgttaattg aggattttg aacatgatgc     1920
aggtgttcct tctctggcag atacagtacc cctcatcatg ttttaggcct aaactccttc    1980
caacacgatt ggttattata atagataaaa ataaggatt tcgaccatgt tgaccaagac     2040
aaattagggc tgagggagaa catatactcc tctcagctgg attaacagca tcatctcctg    2100
gcgaattctt gttaattata gctcctgcat caggcctaaa atgagcataa aatactctct    2160
```

```
catagaaagt atgagcctgc cctcctggaa ctcgaaaatc ttgtgaaaat ggatcagcct    2220
cggtatacac agtcatgaga aagacatagt accgcatatg aagattggtc agataggtgt    2280
ccattaaact aatgacttta aacaaatact caacagtaga tgaaagtttg tcacctccag    2340
aagcactata tacagaatgg gttgcttgaa agtggccttt tatagcagct ggatgtgtag    2400
cgtaattctt actagatagt ctgggagctc catctgcata ttccaatctg gaggagggag    2460
aacctgtatt atggctccag tgcttccatg cattcatagg ccctgtgtca tcagactcag    2520
atactatctg agaaacaagg tgttcaaagc tctgtgaatc attgagggt ttgatttcat     2580 aggtaaggtt atccaacttt atgacccctg acaggcccccc ataacaagta tccacagtga   2640
ccatggattg caggatcccc tccaggtagc caatatagta acaatctaca ggaaaaaagg    2700
ggtactccat ctgtaaggct ccttggtcat cttgagttgt cagcaacaag tgtctgggcc    2760
aaatgagtgt ctttctccgc aggtggatga tatgtctctg gccccgaaaa cgcaagctat    2820
acgagagcag tctttgtgct tgaagtcctt tggtatggta gatctccttc cgaggaataa    2880
ccacctccga tgagatgtaa cgccaagtgg gatggccttg agaacaccag actggaacca    2940
ggaggagcag ccagagtgca aatagcaaga ggaggaccct ggggaccaca ggtcttttcca   3000 ctagcctcat gccccaggtc agagataaca tcctgggtgg agctaactcc ctctgctgtg    3060
gccactgcct ggtctagaaa atactgacag aggactaaaa acctcctcag gctcccaacc    3120
taagtggtta cccagacaac tggagttagg taacagtcac tgggtgtggc aggaattgag    3180
tctgaatgtg ttagctgagg ttgaggttaa atattgtcaa aagggatgtc tataaatgtg    3240
cctggacaag aaaagtcaga agcagcaagg agtgtctctg acaggctcaa tcctttcttt    3300 tcttttttg aagttcaaaa tatcatttcc acgtgaatgt atttggttcc cagtgtgact     3360
ctgggtctct ttctaggagt caatatttct ttatatcttg gctcatgttt ttcacagttg    3420
ttctaacttc ttgttttgtt ttgtttgttt gtttgtttga agttagaag taaatactgt     3480 ctatattagc cttttagcta taaatgattg tttttatttc ttctaatcat gttttgtttg    3540
agttttggtt aaactattta caaatgagtt tttttttcc ttttgggtgt tgctcgaaag     3600
tttggagctt tctgttaata ttgtgttgtt gtttctccaa tattattaga cctgagaatt    3660
ctacctgggt acctgtgaac tccagaattt ttaaaaattc catctcttgg gaacattatc    3720
tctgaccccg tctgaggccg aagtggctgt ccccctccaa cctttagtat ctttctttcc    3780
tgactattgg gatttcttca agcaatcagg ctgatgggtt ctcagcagtg agaccagtag    3840
actgtcggta tgaacgtcga agagtctgcc acacactccg ggttcatcaa cagtgctttc    3900
gcgtctctta cttttgtaga aggaaatgca gcctctgagt tttctccaag aaatcattga    3960
tgaaagggtg aaaagatggg tatcacccgg agttcatgac aagccctggc tcagacacgt    4020
gagcaaggtc tacagccccca aagataggct gccctgcaac atgtatttat aagataggag    4080
aaaaaaatgg gtagttggag ggttgatcaa cttacttcct ctcaaacata tatatctcat    4140
ctaagtgtgc aggggaaaac tctgtagaac tactgggata cctgctcacc cccaggagcc    4200
tcatgaataa gtctctgctt ctgccttgta gccatgagca ttactgcacc tgataccccct   4260 gcagcttcct agggaagagg gaggaagtga cttggccccct gtctggttaa ggtaagagga   4320
gataaatccc ttctcattga ttagggtgag aggggtcatg tgctctatca ttggtgaccc    4380
agttgggaca tgggttttata ccaaagtcat cactctgagg ttctgtgtac caccaggctg   4440
aactcccata tcctacatgg acataggaca acaccaagca gaaggaggtt ttaggactaa    4500
```

-continued

```
actgaaggac agagatgcgg tttctaaaca actagggagt gccagggcca gcctctctaa    4560
ccactatagg acactgtgga gtctggttac aaagagagat tactcaaggt ccttagcact    4620
gattacagag catatctcag atgccttctg ctgaccagat gtatctttgc ataatctgcc    4680
tatccagatt cagaaaattg atgccacata gccaagtgga ctttcaggaa cagacgattt    4740
aaaaacaggc agagagatgt gagagaaagg agaaggagag agagaaggga gagggagaga    4800
agagagaggg agacggagaa ggaaagaggg agaaggagaa ggagagaagg ggcatggaca    4860
gagggaggga cagaaggaga gaggagatag agaggggat aaggaagaag ggagggaggg    4920
agagagagag aaggctaagt cttccatac ctgggtccca atacctctta taacccaagc    4980
acatggtttc acatatcaca atgcggttgg gatatagata actgtaaata cttgtgaaaa    5040
taatggggct gagatctggg gttttcatga tagtttcaaa gtcaccgtac tgactaaaac    5100
cttccactgg cccatctcca gcttcctaat ctgagggtat caaatttccc actaagtgtg    5160
tttagaaaga tctccacctt tttgcccttg tcttccagtg ccccacctac gttctggtct    5220
cccacatctg atgtcttctc agtgattctg gccctgcctg ctccacagct acaaacccct    5280
tcctataatg agctctgtgc tgagccatca tcctgaatca atccaccta agcagatgtt    5340 ttgcttattt ttcctgtgtc catactacag aggaaaggta ggcatgtaga agctgaagca    5400
tctcacctca ttccaagcac cctcagtctc taaatgtgcc cccttgtttc cagaagtgca    5460
acctcaagca tctttattc attcatctta gagggccaca tgtgctgtag tgttataaga    5520
tgaaatttaa agcattaatt attcctaaca agccaattaa acaagccaaa aacattcatc    5580
agtcattccc atggaacctc tgaagcatct tcctgctcta accttgggtt ttccagggct    5640
gctctgggat cacaggagct gtcctgtcta ccagccatat aaaggcagac ctatcagaat    5700 tacaccgac ttctcaccat agactataaa agccagaata tcctggacag atgttataca    5760
gaaactaaga gaacacaaat gccagcccag gctactatac ccagcaaaac tctcaattac    5820
catcgatgaa gaaccaaga tattccatta caagtccaaa tttacacaat atctttccat    5880
aaatccagcc ctacaaagga tagcagatgg aaaactccaa cacaggtagg aaaactacac    5940
cctagaaaga gcactaaagt aatcatcttt caacacactc aaaagaagat aaccacacaa    6000
acataattcc acctctaaca acaaaaataa agtaggcaac aatcactatt ccttaatatc    6060
tcttttaaca tcaatggact caattctcca ataaaagac atagactaac agactgaata    6120
cataaacagg acacagcatt tgctgcata aagcaaacac agcgttactt ttttttttct    6180
aaatgacatt ttttattaga tattgtcttt attgacattt caaatgttat ccccttcct    6240 ggtttaccct ctgaaatccc ctatctcctc cccctccccc tgctcaccaa tccacccact    6300
cccacttcca ggccctggca atcccctata tttgggcata gagccttcac aggaccaagg    6360
tactctcctt gcattgatga ccaactagtc cattctctgc tacaaatgca gctagatcta    6420
tgagtcccac catgttttct tttgttggtg gtttcatgcc agggagctct tggagtactg    6480
attggttcat attgttgttc tccctatggg gttacaaaac ccttcaactt cttgggtcct    6540
ttctctggct gcctcattgg ggaccttgtg cgaagtccaa tggatgactg tgagcatcca    6600
cttctgtatt tgccaggcac tggcagagcc tctcagaaga cagctatatc aagatcctgg    6660
cagcaagctc ttgttggtat ccacaaaagt gtctggtggt tgtctatggg atggatcccc    6720
aaaggggcag tctctggatg gtcattcctt cagtctctgt tccacacttt gtctctttaa    6780
ctccttccat gactatttta ttcctccctc taagaaggac cgaagtattc atactttggt    6840
cttccttctt gaaattcatg tgttttgtga attgtatctt tgatattccg aacttctggg    6900
```

```
ctaatatcca cttatcagtg agtgaatatc atgtgtgttc ttatgtgatt gagttacctc    6960
actcaggatg atatcctcca gaaccatcca tttgtctaag aatttaatga attcattgtt    7020
tttaatagct gaggagtact ccattgtgta aatgtaccac attttctgta cccattgttc    7080
tcttgaggga catctgggtt cttttaaagct tctggacatt aaatataagg ctgctatgga    7140
aatagtggag aatgtgtcct tattacatgt tggagcatct tctgggtata tgcccaggag    7200
tgctattgct ggatcctctg atagtactat gtccaattt  ctgaggaact gccaaactga    7260
tttacagagt ggttgtacca gcttgcaatt ccaccagcaa tggagaaatg ttccccttcc    7320
tccacatcct caccaacatc tgctgtcacc tcaatttgtt cttagtgatt cagacaggtg    7380
tgaggtggaa tatcagggtt gtttggcatt tccctgatga ctagtgatat tgaaaaaaat    7440
tttaagtgtt tctcagccat tcagtattct tcagttgaga attcactgtt tagctctgta    7500
ctcaggtttt tttaataggg ttatttggtt ttctggagtc taacgtcttg aattctttct    7560
atatattgga tattagccct ctgtcatatt taggattggt aaagatcttt cccaatatgt    7620
tggctgcctt tttgtgtcct ttgccttaca gaaccttttt aattttatga ggtcccattt    7680
gctaattctt cattttacag cacaagccat tggtgttctg ttcaaaaatc tttccccctg    7740
aaccctatct tcgaggatct tccccacttt ctcctctata agtttcagtg tctctattat    7800
tgtgctgagg ggtaccgaag ttcctattcc gaagttccta ttctctagaa agtataggaa    7860
cttccctagg gtttaaaccc gcggtggagc tctgatgtgg gaacgcttca gtgttcagga    7920
accatatgat ttatttaaaa tatagaatca aaagtaccaa tttgcagttt tgaaagattt    7980
attccagtgt aagcattagc aatgcaccaa catcaggtga tttctgaatc caacacgtct    8040
tatgtcctca tgatattaaa aaaaaaaaaa ggccatccag aactgtgaac ttgagttcta    8100
ccttgttccc tactgacatt cagattttct tttttgcatt ctctttatct tacaggagac    8160
aggaggggag ggctaactca ttttactttg gcttgtccct tgctggtcct tgcccagaac    8220
gtaaagtagc ttgcaagtct tcaaatctaa aaatcttagt aactcctaca cgagtggcaa    8280
tgccaaagag cagtgcaaca aagaggaagt aaatacgacc aaagagtatt cttaaataca    8340
ccactggctc ttgttttttgt tttattgtgt gcctttgaac tggaggggac ccactgtcta    8400
tgctcccact tagtccctct tctttgcact ctggaggctt ccaaccaaaa tgacaatggc    8460
aattccgatg attgttacac actcctctaa aactgcattt ttctggggtg cagtcataac    8520
ccaaatgaga taaacttcca ctgcaagctc cttgatcaca gaacttactt ttggagcagg    8580
gggtaccatg tctcaccatt ccagcatctg ttgtttctgt cccacgatgt tcatcaagcc    8640
caaagcaggt aaacccagag ataatcgatt gatggaatga acatgttct  tgcaaatatg    8700
gaagattggt gacattggta cactgcaacc ttccacacag cttgtcctga tcagcacaag    8760
cattgaatgt gaggctttct tctgctctag tacaatgccc aaatcgaaac cgttgtttgt    8820
tgatgtcata gcacttaata ttagcattct tagcacttac accaaagatt tccatgcatt    8880
gtatgttgcg atcagtgcag ttacctttat agcagtaacc atcttctgag catggtgtcc    8940
catcttgcag ataagtgtca tctgggcaaa tgtatttagt cccattacag tactctggaa    9000
gatcacatat gttctggata ggtctgcaga gtgtcccaga aggactgtaa gtgcaatttg    9060
cacagcataa ttctttatca caaatgctac caggtgttaa cctgcaatca tttccacagc    9120
agggatctga ataacatgcc ttttgggagc cacagtcaca ctgctcatcg ttatctactt    9180
tgaagtttcc acaaaactta taagtcaatg atgtattata ataaacatga cggtcataga    9240
```

-continued

```
aaagacatgg catcagacca ggagtattaa gtatgttgct tatctctgca agggaacaat   9300
tgctgaaagc atctgttaat tgaggatgtc tgaacataat gcaggtgttc cttctctggc   9360
agacacagta cccctcatca tattttaagc ctaaactcct tccaacacga ttggttatta   9420
taggagataa aaataaagga tttcgatcat atttaccaat acaaattagg gctaaggaag   9480
aacatatact cctctcagct ggattaacct ggttatcttg tgcccatac ttattaagta    9540
aaactcctgc atcaggctta aatttattat aaaagactga cacatagtaa ttataagccg   9600
accctcctgg aactgcaaac tcaagtcgaa atggatcaga attggtgtac acagtcatga   9660
gaaagacata gtaccgcata tgaagattgg tcagataggt gtccattaaa ctaatgactt   9720
gaaacaaata cccaacagta gatgaaagtt tgtcacctgc agcagaatta tatacagaat   9780
tggttgcttg aaagtggcct tttatagcag ctggatgtgt agcgtagttc ttactagata   9840
ttctgggagc tccatctgca tattccaatc tggaggaggg agaacctgta ttatggctcc   9900
agtgcttcca tgcattcata ggccctgtgt catcagactc agatactatc tgagaaacaa   9960
ggtgttcaaa gctctgtgaa tcattgaggg gtttgatttc ataggtaagg tcatctaact  10020
tcatgacccc tgacaggccc ccataacaag tatccacagt gaccatggat tgtgggatcc  10080
cctccaggta gccaatatag taacaatcta caggaaaaaa ggggtaatcc atctgtaagg  10140
ctccttggtc atcttgagtt gtcagcaaca agtgtctggg ccaaatgagt gtctttctcc  10200
gcaggtggat gatatgtctc tggccccgaa atgcaagct atatgagagc agtctttgtg   10260
cttgaagtcc tttggtatgg tagatctcct tccgaggaat aaccacctcc gatgagatgt  10320
aacgccaagt aggatggcct tgagaacacc agactggaac caggaggagc agccagagtg  10380
caaatagcaa gaggaggacc ctggggacca caggtctttc cactagcctc atgccccagg  10440
tcagagataa catcctgggt ggagctaaat ccctctgctg tggccactgc ctggtctaga  10500
aaatactgac agaggactaa aaacctcctc aggctcccaa cctaagtggt tacccagaca  10560
actggagtta ggtaacagtc actgggtgtg gcaggaattg agtctgaatg tgttagctga  10620
ggttgaggtt aaatattgtc aaaagggatg tctataaatg tgcctggaca agaaaagtca  10680
gaagcagcaa ggagtgtctc tgacaggctc aatcctttct tttctttttt tgaagttcaa  10740
aatatcattt ccacgtgaat gtatttggtt cccagtgtga ctctgggtct ctttctagga  10800
gtcaatattt ctttatatct tggctcatgt ttctcacagt tgttctaatt tcttgttttg  10860
ttttgtttgt ttgtttgaac gttagtagta aatactgtct atattagcct tttagctata  10920
aatgattgtt tttatttctt ctaatcatat tttgtttgag ttttggttaa actatttaca  10980
aatgagtttt tttttttttcc ttttgggtgt tgctcgaaag tttggagctt tctgttaata  11040
ttgtgttgtt attttttccaa tattattaga cctgagaatt ctatctgggt acctgtgaac  11100
tctagaattt ttaaaaattc catctcttgg gaacattacc tctgaccccg tctgaggccg  11160
aagtggctgt cccctccaa ccttagtat ctttctttcc tgactattgg gatttcttca    11220
agcaatcagg ctgatgggtt ctcagcagtg agaccagtag actgccggta tgaacgtcga  11280
agagactgcc acacactcca ggttcatcaa cagtgctttc gcgtctctta cttttgtaga  11340
aggaaaagca gcctctgagt tatctccaag aaatcattaa tgaaagagtt aaaagatggg  11400
tatcacccgg agttcatgac aagccctggc tcagacacgt gagcaaggtc tacagcccca  11460
aagataggct gccctgcaac atgtatttat aagatagaag aaaaaaatgg gtggttggag  11520
ggttgatcaa cttacttcct ctcaaacata tatatctcat ctaagtgtgc aggggaaaac  11580
tctgtaggac tactgggatt gttattatca ttattattat tattattatt attattatta  11640
```

```
ttattattat tattaactta aggcatttta ttagatattt tcttcattta gttttcaaat    11700
gttatccccg gaacctccta tactctctcc ctgccctgct ccccaaccca cccactccta    11760
catcctggcc ctggcattcc cctatactgt ggcagatgat cttcgtaaga ccaagagcct    11820
ttcctcccat tgatggccta ctaggctatc ctctttttaca tatgcaacta gagtcacagc   11880
tctggggagg tattgcttag ttcatattgt ttttcctcct atagggttgc agatcccttt    11940
agctccttgg gtactttctc tagctcctcc attgggggcc ctgtgttcca tccaatagat    12000
gactgtgagc atccacttct gtatttgcca ggtattggca tggatcttac tgcaccttct    12060
gaactctcta agcagctttc ctggtcacct ccaggagcct catgaataag tctctgcttc    12120
ccccttgtgg ctatgagcat tactgcacct gatacaccct gcagcttcct agggaagagg    12180
gaggaagtgg cttggcccct gtctggttaa ggtaagagga gataaatccc ttctcatgaa    12240
ttagggtgag aagggtcatg tgctctatca ttggtgacca acttgggac atgggcttat     12300
acagtcatca ctctgaggct ctgtgtacca ccagactgaa ctcccatatc ctacatgcac    12360
ataggacaac accaagtaga aggaggtttt aggactaaac tgaaggacag agatggggtt    12420
tctaaacaac tagggagtgc cagggccagc ctctctaacc actataggac actatggagt    12480
ctggttacaa agagagatta ctcaaggtcc ttagcactga ttacagagca tatctcagat    12540
gccttctgct gaccagatgt atctttgcat aatctgccta tccagattca gaaaattgat    12600
gccacatagc caagtggact ttcaggaaca gacgatttaa aaacaggcag agagatgtga    12660
gagaaaggag aaggagagag agaagggaga gggagagaag agagagggag acggagaagg    12720
aaagagggag aaggagaagg agagaagggg catggacaga gggagggaca gaaggagaga    12780
ggagatagag aggggataa ggaagaaagg agggagggag agagagagaa ggctaagtct     12840
ttccatacct gggtcccaat acctcttata acccaagcac atggtttcag atatcacaat    12900
gcggttggga tatagataac tgtaaatact tgtgaaaata atggggctga gatctggggt    12960
tttcatgata gtttcaaagt cactgtactg actaaaacct tccactggcc catctccagc    13020
ttgttaatct gagggtatca aatttcccac taagtgtgtt tagaaagatc tccaccttt     13080
tgccctagtc ttccagtgcc ccacctacgt tctggtctcc cacatctgat gtcttctcag    13140
tgattctggc cctgcctgct ccacagctac aaaccccttc ctataatgag ctctgtgctg    13200
agccatcatc ctgaatcaat ccaccttaag cagatgttt gcttattttt cctgtgtcca    13260
tactacagag gaagggtagg catgtagaag ctgaggcatc tcatctcact ctaagcaccc    13320
tcagtctcta aatgtgcccc tttgtttcca gcagttcagc ctcaagcatc ttttattcac    13380
tcgtcttaga gggacacatg tgctgtagtg ttataagatg aaatttaaag cattagttat    13440
tcccaacaag ccaattaaac aagccaaaaa cattcatcag tcattcccat ggaacctctg    13500
aagcatcttc ctgctctaac cttgagtttc ctagggctgc tgtgggatca caggagctgt    13560
cctgtttacc agcctatcct gtcccacggg attcagttat tagtgggtgc gaggggacc     13620
gcaaacctgg aagaaaatgg gattggaaga gaaagagaa acgaagacca agtagatctt     13680
ttcctatcaa ggtcttcgtt tattaggctg aggtgcctgg tgtaaagcat gcatcgcggg    13740
gaataggaag gggtcgaggg ggaattttac aaagaacaaa gaagcgggca tctgctgaca    13800
tgagggccga agtcaggctc caggcagcgg gagctccacc gcggtggcgc catttcatta    13860
cctctttctc cgcacccgac atagataaag ctta                                13894
```

<210> SEQ ID NO 4

```
<211> LENGTH: 251
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ccagcttcat tagtaatcgt tcatctgtgg taaaaaggca ggatttgaag cgatggaaga      60
tgggagtacg gggcgttgga agacaaagtg ccacacagcg cagccttcgt ctagacccc     120 gggctaacta taacggtcct aaggtagcga ggggatgaca gattctctgt tcagtgcact    180
cagggtctgc ctccacgaga atcaccatgc cctttctcaa gactgtgttc tgtgcagtgc    240
cctgtcagtg g                                                          251

<210> SEQ ID NO 5
<211> LENGTH: 245
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
aggggtcgag ggggaatttt acaaagaaca aagaagcggg catctgctga catgagggcc      60
gaagtcaggc tccaggcagc gggagctcca ccgcggtggc gccatttcat tacctctttc    120
tccgcacccg acatagataa agcttatccc ccaccaagca aatccccta cctggggccg     180 agcttcccgt atgtgggaaa atgaatccct gaggtcgatt gctgcatgca atgaaattca    240
actag                                                                 245

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caggtacagc tgcagcagtc a                                                21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ggagatggca caggtgagtg a                                                21

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tccaggactg gtgaagc                                                     17
```

```
<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tagtcccagt gatgagaaag agat                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gagaacacag aagtggatga gatc                                          24

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgagtccagt ccaggga                                                  17

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
aaaaattgag tgtgaatgga taagagtg                                      28

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
aaccctggtc agaaactgcc a                                             21

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
agagaaacag tggatacgt                                                19
```

```
<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aactacgcac agaagttcca gg                                              22

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gctcgtggat ttgtccgc                                                   18

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cagagtcacg attacc                                                     16

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tgagcagcac cctcacgtt                                                  19

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gtggcctcac aggtatagct gtt                                             23

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
accaaggacg agtatgaa                                                   18

<210> SEQ ID NO 21
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gctagtagtg gggcctacag gcctttgat atc                                    33

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gcaaaagccc aggggagtgg gagctactac acctatgctt ttgatatc                    48

<210> SEQ ID NO 23
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcgagagagg gtatagtggg aactactgag gactttgatt ac                          42

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcgagaggga cagtgggagc cctctttgac tac                                    33

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcgaaaccta gtgggagcta ctcctggttc gacccc                                 36

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcgagaggag gagggtataa ctggaactcg aatgcttttg atatc                       45

<210> SEQ ID NO 27
<211> LENGTH: 33
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcgagaggat ataactggaa ctactttgac tac                                33

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcgaaagagt ataactggaa ccactggtac tttgactac                          39

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gcgagagaga taactggaac cccctttgac tac                                33

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gcgaggggat ataactggaa cttttctttt tttgactac                          39

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
gcgagaggta actggaactc tctgggcttt gactac                             36

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcgaaaaggg ctactatggt tcggggagct cttgactac                          39

<210> SEQ ID NO 33
<211> LENGTH: 60
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 33
gcgagagata ttactatggt tcggggagtt attataacga aggtctacgg tatggacgtc     60

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gcgagagagt atagcagctt tgactac                                         27

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gcgagagaga gtatagcagc tcgttgtgac tac                                  33

<210> SEQ ID NO 36
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gcaagagagg ataggagctc gcccctcggg tactttgact ac                        42

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gcgagagatc ttggggaagg ctac                                            24

<210> SEQ ID NO 38
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
accacccata actggggagg gtttgactac                                      30

<210> SEQ ID NO 39
<211> LENGTH: 18
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 39
gcgagagata ggggaccg                                                        18

<210> SEQ ID NO 40
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
caacagagtt atagtaccccc tccggagacg                                          30

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
caacagctta atagttaccc tcggacg                                              27

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
caacagctta atagttacca ttcact                                               26

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43 caacattttta atagttaccc gctcact                                             27

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cagcagtata ataactggcc tctcact                                              27

<210> SEQ ID NO 45
<211> LENGTH: 27
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 45
ctacagcata atagttaccc gtggacg                                              27

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ctacagcata atagttaccc tcggacg                                              27

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cagcagtatg gtagctcacc tcggacg                                              27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
atgcaaggta cacactggcc gtggacg                                              27

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
atgcaaggtt cacactggcc gtacact                                              27

<210> SEQ ID NO 50
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atgcaaggta cacactggcc gctcact                                              27

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 51
caacagtatg ataatctccc tcccact                                              27

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
caacagtatg ataatctccc attcact                                              27

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
caacagtatg ataatctccc cgtcact                                              27

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
caacagtatg ataatctccc gatcacc                                              27

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
caacggattt acaatgccga cacc                                                 24

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
caacagagtt acagtacccc catgtacact                                           30

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
caacagagtt acagtacccc tctcact 27

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
caacagagtt acagtactcc tcccact 27

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ggtatagtgg gagctactac 20

<210> SEQ ID NO 60
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ggtataactg gaactac 17

<210> SEQ ID NO 61
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gtattactat ggttcgggga gttattataa c 31

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gagtatagca gctcgtcc 18

```
<210> SEQ ID NO 63
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ctaactgggg a                                                          11
```

ADAM6 MICE

SEQUENCE LISTING

The instant application contains a Sequence Listing that has been submitted electronically in ASCII format and is hereby incorporated by reference in its entirety. The ASCII copy, created on Dec. 22, 2020, is named 2010794_2162_ST25.TXT and is 46,485 bytes in size.

CROSS-REFERENCE TO RELATED APPLICATIONS

This application is a divisional of U.S. Non-Provisional application Ser. No. 16/059,821, filed Aug. 9, 2018, which is a continuation of U.S. Non-Provisional application Ser. No. 14/600,829, filed Jan. 20, 2015, which is a continuation of U.S. Non-Provisional application Ser. No. 14/192,051, filed Feb. 27, 2014, which is a continuation of U.S. Non-Provisional application Ser. No. 13/890,519, filed May 9, 2013, now U.S. Pat. No. 8,697,940, which is a continuation of U.S. Non-Provisional application Ser. No. 13/404,075, filed Feb. 24, 2012, now U.S. Pat. No. 8,642,835, which application claims the benefit under 35 USC § 119 (e) of U.S. Provisional Application Ser. No. 61/595,200, filed Feb. 6, 2012, U.S. Provisional Application Ser. No. 61/497,650, filed Jun. 16, 2011, and U.S. Provisional Application Ser. No. 61/446,895, filed Feb. 25, 2011, which applications are hereby incorporated by reference in their entireties.

FIELD OF INVENTION

Genetically modified mice, cells, embryos, and tissues that comprise a nucleic acid sequence encoding a functional ADAM6 locus are described. Modifications include human and/or humanized immunoglobulin loci. Mice that lack a functional endogenous ADAM6 gene but that comprise ADAM6 function are described, including mice that comprise an ectopic nucleic acid sequence that encodes an ADAM6 protein. Genetically modified male mice that comprise a modification of an endogenous immunoglobulin $V_H$ locus that renders the mouse incapable of making a functional ADAM6 protein and results in a loss in fertility, and that further comprise ADAM6 function in the male mice are described, including mice that comprise an ectopic nucleic acid sequence that restores fertility to the male mouse.

BACKGROUND OF INVENTION

Mice that contain human antibody genes are known in the art. Pharmaceutical applications for antibodies in the last two decades have fueled a great deal of research into making antibodies that are suitable for use as human therapeutics. Early antibody therapeutics, which were based on mouse antibodies, were not ideal as human therapeutics because repeated administration of mouse antibodies to humans results in immunogenicity that can confound long-term treatment regimens. Solutions based on humanizing mouse antibodies to make them appear more human and less mouse-like were developed. Methods for expressing human immunoglobulin sequences for use in antibodies followed, mostly based on in vitro expression of human immunoglobulin libraries in phage, bacteria, or yeast. Finally, attempts were made to make useful human antibodies from human lymphocytes in vitro, in mice engrafted with human hematopoietic cells, and in transchromosomal or transgenic mice with disabled endogenous immunoglobulin loci. In the transgenic mice, it was necessary to disable the endogenous mouse immunoglobulin genes so that the randomly integrated fully human transgenes would function as the source of immunoglobulin sequences expressed in the mouse. Such mice can make human antibodies suitable for use as human therapeutics, but these mice display substantial problems with their immune systems. These problems (1) make the mice impractical for generating a sufficiently diverse antibody repertoire, (2) require the use of extensive re-engineering fixes, (3) provide a suboptimal clonal selection process likely due to incompatibility between human and mouse elements, and (4) render these mice an unreliable source of large and diverse populations of human variable sequences needed to be truly useful for making human therapeutics.

There remains a need in the art for making improved genetically modified mice that are useful in generating immunoglobulin sequences, including human antibody sequences. There also remains a need for mice that are capable of rearranging immunoglobulin gene segments to form useful rearranged immunoglobulin genes, or capable of making proteins from altered immunoglobulin loci, while at the same time reducing or eliminating deleterious changes that might result from the genetic modifications.

SUMMARY OF INVENTION

In one aspect, nucleic acid constructs, cells, embryos, mice, and methods are provided for making mice that comprise a modification that results in a nonfunctional endogenous mouse ADAM6 protein or ADAM6 gene (e.g., a knockout of or a deletion in an endogenous ADAM6 gene), wherein the mice comprise a nucleic acid sequence that encodes an ADAM6 protein or ortholog or homolog or fragment thereof that is functional in a male mouse.

In one aspect, nucleic acid constructs, cells, embryos, mice, and methods are provided for making mice that comprise a modification of an endogenous mouse immunoglobulin locus, wherein the mice comprise an ADAM6 protein or ortholog or homolog or fragment thereof that is functional in a male mouse. In one embodiment, the endogenous mouse immunoglobulin locus is an immunoglobulin heavy chain locus, and the modification reduces or eliminates ADAM6 activity of a cell or tissue of a male mouse.

In one aspect, mice are provided that comprise an ectopic nucleotide sequence encoding a mouse ADAM6 or ortholog or homolog or functional fragment thereof; mice are also provided that comprise an endogenous nucleotide sequence encoding a mouse ADAM6 or ortholog or homolog or fragment thereof, and at least one genetic modification of a heavy chain immunoglobulin locus.

In one aspect, methods are provided for making mice that comprise a modification of an endogenous mouse immunoglobulin locus, wherein the mice comprise an ADAM6 protein or ortholog or homolog or fragment thereof that is functional in a male mouse.

In one aspect, methods are provided for making mice that comprise a genetic modification of an immunoglobulin heavy chain locus, wherein application of the methods result in male mice that comprise a modified immunoglobulin heavy chain locus (or a deletion thereof), and the male mice are capable of generating offspring by mating. In one embodiment, the male mice are capable of producing sperm that can transit from a mouse uterus through a mouse oviduct to fertilize a mouse egg.

In one aspect, methods are provided for making mice that comprise a genetic modification of an immunoglobulin heavy chain locus, wherein application of the methods result in male mice that comprise a modified immunoglobulin heavy chain locus (or a deletion thereof), and the male mice exhibit a reduction in fertility, and the mice comprise a genetic modification that restores in whole or in part the reduction in fertility. In various embodiments, the reduction in fertility is characterized by an inability of the sperm of the male mice to migrate from a mouse uterus through a mouse oviduct to fertilize a mouse egg. In various embodiments, the reduction in fertility is characterized by sperm that exhibit an in vivo migration defect. In various embodiments, the genetic modification that restores in whole or in part the reduction in fertility is a nucleic acid sequence encoding a mouse ADAM6 gene or ortholog or homolog or fragment thereof that is functional in a male mouse.

In one embodiment, the genetic modification comprises replacing endogenous immunoglobulin heavy chain variable loci with immunoglobulin heavy chain variable loci of another species (e.g., a non-mouse species). In one embodiment, the genetic modification comprises insertion of orthologous immunoglobulin heavy chain variable loci into endogenous immunoglobulin heavy chain variable loci. In a specific embodiment, the species is human. In one embodiment, the genetic modification comprises deletion of an endogenous immunoglobulin heavy chain variable locus in whole or in part, wherein the deletion results in a loss of endogenous ADAM6 function. In a specific embodiment, the loss of endogenous ADAM6 function is associated with a reduction in fertility in male mice.

In one aspect, mice are provided that comprise a modification that reduces or eliminates mouse ADAM6 expression from an endogenous ADAM6 allele such that a male mouse having the modification exhibits a reduced fertility (e.g., a highly reduced ability to generate offspring by mating), or is essentially infertile, due to the reduction or elimination of endogenous ADAM6 function, wherein the mice further comprise an ectopic ADAM6 sequence or homolog or ortholog or functional fragment thereof. In one aspect, the modification that reduces or eliminates mouse ADAM6 expression is a modification (e.g., an insertion, a deletion, a replacement, etc.) in a mouse immunoglobulin locus.

In one embodiment, the reduction or loss of ADAM6 function comprises an inability or substantial inability of the mouse to produce sperm that can travel from a mouse uterus through a mouse oviduct to fertilize a mouse egg. In a specific embodiment, at least about 95%, 96%, 97%, 98%, or 99% of the sperm cells produced in an ejaculate volume of the mouse are incapable of traversing through an oviduct in vivo following copulation and fertilizing a mouse ovum.

In one embodiment, the reduction or loss of ADAM6 function comprises an inability to form or substantial inability to form a complex of ADAM2 and/or ADAM3 and/or ADAM6 on a surface of a sperm cell of the mouse. In one embodiment, the loss of ADAM6 function comprises a substantial inability to fertilize a mouse egg by copulation with a female mouse.

In one aspect, a mouse is provided that lacks a functional endogenous ADAM6 gene, and comprises a protein (or an ectopic nucleotide sequence that encodes a protein) that confers ADAM6 functionality on the mouse. In one embodiment, the mouse is a male mouse and the functionality comprises enhanced fertility as compared with a mouse that lacks a functional endogenous ADAM6 gene.

In one embodiment, the protein is encoded by a genomic sequence located within an immunoglobulin locus in the germline of the mouse. In a specific embodiment, the immunoglobulin locus is a heavy chain locus. In another specific embodiment, the heavy chain locus comprises at least one human $V_H$, at least one human $D_H$ and at least one human $J_H$ gene segment. In one embodiment, the ectopic protein is encoded by a genomic sequence located within a non-immunoglobulin locus in the germline of the mouse. In one embodiment, the non-immunoglobulin locus is a transcriptionally active locus. In a specific embodiment, the transcriptionally active locus is the ROSA26 locus. In a specific embodiment, the transcriptionally active locus is associated with tissue-specific expression. In one embodiment, the tissue-specific expression is present in reproductive tissues. In one embodiment, the protein is encoded by a genomic sequence randomly inserted into the germline of the mouse.

In one embodiment, the mouse comprises a human or chimeric human/mouse or chimeric human/rat light chain (e.g., human variable, mouse or rat constant) and a chimeric human variable/mouse or rat constant heavy chain. In a specific embodiment, the mouse comprises a transgene that comprises a chimeric human variable/rat or mouse constant light chain gene operably linked to a transcriptionally active promoter, e.g., a ROSA26 promoter. In a further specific embodiment, the chimeric human/mouse or rat light chain transgene comprises a rearranged human light chain variable region sequence in the germline of the mouse.

In one embodiment, the ectopic nucleotide sequence is located within an immunoglobulin locus in the germline of the mouse. In a specific embodiment, the immunoglobulin locus is a heavy chain locus. In one embodiment, the heavy chain locus comprises at least one human $V_H$, at least one human $D_H$ and at least one human $J_H$ gene segment. In one embodiment, the ectopic nucleotide sequence is located within a non-immunoglobulin locus in the germline of the mouse. In one embodiment, the non-immunoglobulin locus is a transcriptionally active locus. In a specific embodiment, the transcriptionally active locus is the ROSA26 locus. In one embodiment, the ectopic nucleotide sequence is positioned randomly inserted into the germline of the mouse.

In one aspect, a mouse is provided that lacks a functional endogenous ADAM6 gene, wherein the mouse comprises an ectopic nucleotide sequence that complements the loss of mouse ADAM6 function. In one embodiment, the ectopic nucleotide sequence confers upon the mouse an ability to produce offspring that is comparable to a corresponding wild-type mouse that contains a functional endogenous ADAM6 gene. In one embodiment, the sequence confers upon the mouse an ability to form a complex of ADAM2 and/or ADAM3 and/or ADAM6 on the surface of sperm cell of the mouse. In one embodiment, the sequence confers upon the mouse an ability to travel from a mouse uterus through a mouse oviduct to a mouse ovum to fertilize the ovum.

In one embodiment, the mouse lacking the functional endogenous ADAM6 gene and comprising the ectopic nucleotide sequence produces at least about 50%, 60%, 70%, 80%, or 90% of the number of litters a wild-type mouse of the same age and strain produces in a six-month time period.

In one embodiment, the mouse lacking the functional endogenous ADAM6 gene and comprising the ectopic nucleotide sequence produces at least about 1.5-fold, about 2-fold, about 2.5-fold, about 3-fold, about 4-fold, about 6-fold, about 7-fold, about 8-fold, or about 10-fold or more progeny when bred over a six-month time period than a mouse of the same age and the same or similar strain that lacks the functional endogenous ADAM6 gene and that lacks the ectopic nucleotide sequence that is bred over substantially the same time period and under substantially the same conditions.

In one embodiment, the mouse lacking the functional endogenous ADAM6 gene and comprising the ectopic nucleotide sequence produces an average of at least about 2-fold, 3-fold, or 4-fold higher number of pups per litter in a 4- or 6-month breeding period than a mouse that lacks the functional endogenous ADAM6 gene and that lacks the ectopic nucleotide sequence, and that is bred for the same period of time.

In one embodiment, the mouse lacking the functional endogenous ADAM6 gene and comprising the ectopic nucleotide sequence is a male mouse, and the male mouse produces sperm that when recovered from oviducts at about 5-6 hours post-copulation reflects an oviduct migration that is at least 10-fold, at least 20-fold, at least 30-fold, at least 40-fold, at least 50-fold, at least 60-fold, at least 70-fold, at least 80-fold, at least 90-fold, 100-fold, 110-fold, or 120-fold or higher than a mouse that lacks the functional endogenous ADAM6 gene and that lacks the ectopic nucleotide sequence.

In one embodiment, the mouse lacking the functional endogenous ADAM6 gene and comprising the ectopic nucleotide sequence when copulated with a female mouse generates sperm that is capable of traversing the uterus and entering and traversing the oviduct within about 6 hours at an efficiency that is about equal to sperm from a wild-type mouse.

In one embodiment, the mouse lacking the functional endogenous ADAM6 gene and comprising the ectopic nucleotide sequence produces about 1.5-fold, about 2-fold, about 3-fold, or about 4-fold or more litters in a comparable period of time than a mouse that lacks the functional ADAM6 gene and that lacks the ectopic nucleotide sequence.

In one aspect, a mouse comprising in its germline a non-mouse nucleic acid sequence that encodes an immunoglobulin protein is provided, wherein the non-mouse immunoglobulin sequence comprises an insertion of a mouse ADAM6 gene or homolog or ortholog or functional fragment thereof. In one embodiment, the non-mouse immunoglobulin sequence comprises a human immunoglobulin sequence. In one embodiment, the sequence comprises a human immunoglobulin heavy chain sequence. In one embodiment, the sequence comprises a human immunoglobulin light chain sequence. In one embodiment, the sequence comprises one or more V gene segments, one or more D gene segments, and one or more J gene segments; in one embodiment, the sequence comprises one or more V gene segments and one or more J gene segments. In one embodiment, the one or more V, D, and J gene segments, or one or more V and J gene segments, are not rearranged. In one embodiment, the one or more V, D, and J gene segments, or one or more V and J gene segments, are rearranged. In one embodiment, following rearrangement of the one or more V, D, and J gene segments, or one or more V and J gene segments, the mouse comprises in its genome at least one nucleic acid sequence encoding a mouse ADAM6 gene or homolog or ortholog or functional fragment thereof. In one embodiment, following rearrangement the mouse comprises in its genome at least two nucleic acid sequences encoding a mouse ADAM6 gene or homolog or ortholog or functional fragment thereof. In one embodiment, following rearrangement the mouse comprises in its genome at least one nucleic acid sequence encoding a mouse ADAM6 gene or homolog or ortholog or functional fragment thereof. In one embodiment, the mouse comprises the ADAM6 gene or homolog or ortholog or functional fragment thereof in a B cell. In one embodiment, the mouse comprises the ADAM6 gene or homolog or ortholog or functional fragment thereof in a non-B cell.

In one aspect, mice are provided that express a human immunoglobulin heavy chain variable region or functional fragment thereof from an endogenous mouse immunoglobulin heavy chain locus, wherein the mice comprise an ADAM6 activity that is functional in a male mouse.

In one embodiment, the male mice comprise a single unmodified endogenous ADAM6 allele or ortholog of homolog or functional fragment thereof at an endogenous ADAM6 locus.

In one embodiment, the male mice comprise an ectopic mouse ADAM6 sequence or homolog or ortholog or functional fragment thereof that encodes a protein that confers ADAM6 function.

In one embodiment, the male mice comprise an ADAM6 sequence or homolog or ortholog or functional fragment thereof at a location in the mouse genome that approximates the location of the endogenous mouse ADAM6 allele, e.g., 3' of a final V gene segment sequence and 5' of an initial D gene segment.

In one embodiment, the male mice comprise an ADAM6 sequence or homolog or ortholog or functional fragment thereof flanked upstream, downstream, or upstream and downstream (with respect to the direction of transcription of the ADAM6 sequence) of a nucleic acid sequence encoding an immunoglobulin variable gene segment. In a specific embodiment, the immunoglobulin variable gene segment is a human gene segment. In one embodiment, the immunoglobulin variable gene segment is a human gene segment, and the sequence encoding the mouse ADAM6 or ortholog or homolog or fragment thereof functional in a mouse is between human V gene segments; in one embodiment, the mouse comprises two or more human V gene segments, and the sequence is at a position between the final V gene segment and the penultimate V gene segment; in one embodiment, the sequence is at a position following the final V gene segment and the first D gene segment.

In one aspect, a male mouse is provided that comprises a nonfunctional endogenous ADAM6 gene, or a deletion of an endogenous ADAM6 gene, in its germline; wherein sperm cells of the mouse are capable of transiting an oviduct of a female mouse and fertilizing an egg. In one embodiment, the mice comprise an extrachromosomal copy of a mouse ADAM6 gene or ortholog or homolog or functional fragment thereof that is functional in a male mouse. In one embodiment, the mice comprise an ectopic mouse ADAM6 gene or ortholog or homolog or functional fragment thereof that is functional in a male mouse.

In one aspect, mice are provided that comprise a genetic modification that reduces endogenous mouse ADAM6 function, wherein the mouse comprises at least some ADAM6 functionality provided either by an endogenous unmodified allele that is functional in whole or in part (e.g., a heterozygote), or by expression from an ectopic sequence that encodes an ADAM6 or an ortholog or homolog or functional fragment thereof that is functional in a male mouse.

In one embodiment, the mice comprise ADAM6 function sufficient to confer upon male mice the ability to generate offspring by mating, as compared with male mice that lack a functional ADAM6. In one embodiment, the ADAM6 function is conferred by the presence of an ectopic nucleotide sequence that encodes a mouse ADAM6 or a homolog or ortholog or functional fragment thereof. ADAM6 homologs or orthologs or fragments thereof that are functional in a male mouse include those that restore, in whole or in part, the loss of ability to generate offspring observed in a male mouse that lacks sufficient endogenous mouse ADAM6 activity, e.g., the loss in ability observed in an ADAM6 knockout mouse. In this sense ADAM6 knockout mice include mice that comprise an endogenous locus or fragment thereof, but that is not functional, i.e., that does not express ADAM6 (ADAM6a and/or ADAM6b) at all, or that expresses ADAM6 (ADAM6a and/or ADAM6b) at a level that is insufficient to support an essentially normal ability to generate offspring of a wild-type male mouse. The loss of function can be due, e.g., to a modification in a structural gene of the locus (i.e., in an ADAM6a or ADAM6b coding region) or in a regulatory region of the locus (e.g., in a sequence 5' to the ADAM6a gene, or 3' of the ADAM6a or ADAM6b coding region, wherein the sequence controls, in whole or in part, transcription of an ADAM6 gene, expression of an ADAM6 RNA, or expression of an ADAM6 protein). In various embodiments, orthologs or homologs or fragments thereof that are functional in a male mouse are those that enable a sperm of a male mouse (or a majority of sperm cells in the ejaculate of a male mouse) to transit a mouse oviduct and fertilize a mouse ovum.

In one embodiment, male mice that express the human immunoglobulin variable region or functional fragment thereof comprise sufficient ADAM6 activity to confer upon the male mice the ability to generate offspring by mating with female mice and, in one embodiment, the male mice exhibit an ability to generate offspring when mating with female mice that is in one embodiment at least 25%, in one embodiment, at least 30%, in one embodiment at least 40%, in one embodiment at least 50%, in one embodiment at least 60%, in one embodiment at least 70%, in one embodiment at least 80%, in one embodiment at least 90%, and in one embodiment about the same as, that of mice with one or two endogenous unmodified ADAM6 alleles.

In one embodiment male mice express sufficient ADAM6 (or an ortholog or homolog or functional fragment thereof) to enable a sperm cell from the male mice to traverse a female mouse oviduct and fertilize a mouse egg.

In one embodiment, the ADAM6 functionality is conferred by a nucleic acid sequence that is contiguous with a mouse chromosomal sequence (e.g., the nucleic acid is randomly integrated into a mouse chromosome; or placed at a specific location, e.g., by targeting the nucleic acid to a specific location, e.g., by site-specific recombinase-mediated (e.g., Cre-mediated) insertion or homologous recombination). In one embodiment, the ADAM6 sequence is present on a nucleic acid that is distinct from a chromosome of the mouse (e.g., the ADAM6 sequence is present on an episome, i.e., extrachromosomally, e.g., in an expression construct, a vector, a YAC, a transchromosome, etc.).

In one aspect, genetically modified mice and cells are provided that comprise a modification of an endogenous immunoglobulin heavy chain locus, wherein the mice express at least a portion of an immunoglobulin heavy chain sequence, e.g., at least a portion of a human sequence, wherein the mice comprise an ADAM6 activity that is functional in a male mouse. In one embodiment, the modification reduces or eradicates ADAM6 activity of the mouse. In one embodiment, the mouse is modified such that both alleles that encode ADAM6 activity are either absent or express an ADAM6 that does not substantially function to support normal mating in a male mouse. In one embodiment, the mouse further comprises an ectopic nucleic acid sequence encoding a mouse ADAM6 or ortholog or homolog or functional fragment thereof.

In one aspect, genetically modified mice and cells are provided that comprise a modification of an endogenous immunoglobulin heavy chain locus, wherein the modification reduces or eliminates ADAM6 activity expressed from an ADAM6 sequence of the locus, and wherein the mice comprise an ADAM6 protein or ortholog or homolog or functional fragment thereof. In various embodiments, the ADAM6 protein or fragment thereof is encoded by an ectopic ADAM6 sequence. In various embodiments, the ADAM6 protein or fragment thereof is expressed from an endogenous ADAM6 allele. In various embodiments, the mouse comprises a first immunoglobulin heavy chain allele comprises a first modification that reduces or eliminates expression of a functional ADAM6 from the first immunoglobulin heavy chain allele, and the mouse comprises a second immunoglobulin heavy chain allele that comprises a second modification that does not substantially reduce or does not eliminate expression of a functional ADAM6 from the second immunoglobulin heavy chain allele.

In one embodiment, the second modification is located 3' (with respect to the transcriptional directionality of the mouse V gene segment) of a final mouse V gene segment and located 5' (with respect to the transcriptional directionality of the constant sequence) of a mouse (or chimeric human/mouse) immunoglobulin heavy chain constant gene or fragment thereof (e.g., a nucleic acid sequence encoding a human and/or mouse: $C_H1$ and/or hinge and/or $C_H2$ and/or $C_H3$).

In one embodiment, the modification is at a first immunoglobulin heavy chain allele at a first locus that encodes a first ADAM6 allele, and the ADAM6 function results from expression of an endogenous ADAM6 at a second immunoglobulin heavy chain allele at a second locus that encodes a functional ADAM6, wherein the second immunoglobulin heavy chain allele comprises at least one modification of a V, D, and/or J gene segment. In a specific embodiment, the at least one modification of the V, D, and or J gene segment is a deletion, a replacement with a human V, D, and/or J gene segment, a replacement with a camelid V, D, and/or J gene segment, a replacement with a humanized or camelized V, D, and/or J gene segment, a replacement of a heavy chain sequence with a light chain sequence, and a combination thereof. In one embodiment, the at least one modification is the deletion of one or more heavy chain V, D, and/or J gene segments and a replacement with one or more light chain V and/or J gene segments (e.g., a human light chain V and/or J gene segment) at the heavy chain locus.

In one embodiment, the modification is at a first immunoglobulin heavy chain allele at a first locus and a second immunoglobulin heavy chain allele at a second locus, and the ADAM6 function results from expression of an ectopic ADAM6 at a non-immunoglobulin locus in the germline of the mouse. In a specific embodiment, the non-immunoglobulin locus is the ROSA26 locus. In a specific embodiment, the non-immunoglobulin locus is transcriptionally active in reproductive tissue.

In one aspect, a mouse comprising a heterozygous or a homozygous knockout of ADAM6 is provided. In one embodiment, the mouse further comprises a modified immunoglobulin sequence that is a human or a humanized immunoglobulin sequence, or a camelid or camelized human or mouse immunoglobulin sequence. In one embodiment, the modified immunoglobulin sequence is present at the endogenous mouse heavy chain immunoglobulin locus. In one embodiment, the modified immunoglobulin sequence comprises a human heavy chain variable gene sequence at an endogenous mouse immunoglobulin heavy chain locus. In one embodiment, the human heavy chain variable gene sequence replaces an endogenous mouse heavy chain variable gene sequence at the endogenous mouse immunoglobulin heavy chain locus.

In one aspect, a mouse incapable of expressing a functional endogenous mouse ADAM6 from an endogenous mouse ADAM6 locus is provided. In one embodiment, the mouse comprises an ectopic nucleic acid sequence that encodes an ADAM6, or functional fragment thereof, that is functional in the mouse. In a specific embodiment, the ectopic nucleic acid sequence encodes a protein that rescues a loss in the ability to generate offspring exhibited by a male mouse that is homozygous for an ADAM6 knockout. In a specific embodiment, the ectopic nucleic acid sequence encodes a mouse ADAM6 protein.

In one aspect, a mouse is provided that lacks a functional endogenous ADAM6 locus, and that comprises an ectopic nucleic acid sequence that confers upon the mouse ADAM6 function. In one embodiment, the nucleic acid sequence comprises an endogenous mouse ADAM6 sequence or functional fragment thereof. In one embodiment, the endogenous mouse ADAM6 sequence comprises ADAM6a- and ADAM6b-encoding sequence located in a wild-type mouse between the 3'-most mouse immunoglobulin heavy chain V gene segment ($V_H$) and the 5'-most mouse immunoglobulin heavy chain D gene segment ($D_H$).

In one embodiment, the nucleic acid sequence comprises a sequence encoding mouse ADAM6a or functional fragment thereof and/or a sequence encoding mouse ADAM6b or functional fragment thereof, wherein the ADAM6a and/or ADAM6b or functional fragment(s) thereof is operably linked to a promoter. In one embodiment, the promoter is a human promoter. In one embodiment, the promoter is the mouse ADAM6 promoter. In a specific embodiment, the ADAM6 promoter comprises sequence located between the first codon of the first ADAM6 gene closest to the mouse 5'-most $D_H$ gene segment and the recombination signal sequence of the 5'-most $D_H$ gene segment, wherein 5' is indicated with respect to direction of transcription of the mouse immunoglobulin genes. In one embodiment, the promoter is a viral promoter. In a specific embodiment, the viral promoter is a cytomegalovirus (CMV) promoter. In one embodiment, the promoter is a ubiquitin promoter.

In one embodiment, the promoter is an inducible promoter. In one embodiment, the inducible promoter regulates expression in non-reproductive tissues. In one embodiment, the inducible promoter regulates expression in reproductive tissues. In a specific embodiment, the expression of the mouse ADAM6a and/or ADAM6b sequences or functional fragments(s) thereof is developmentally regulated by the inducible promoter in reproductive tissues.

In one embodiment, the mouse ADAM6a and/or ADAM6b are selected from the ADAM6a of SEQ ID NO:1 and/or ADAM6b of sequence SEQ ID NO:2. In one embodiment, the mouse ADAM6 promoter is a promoter of SEQ ID NO:3. In a specific embodiment, the mouse ADAM6 promoter comprises the nucleic acid sequence of SEQ ID NO:3 directly upstream (with respect to the direction of transcription of ADAM6a) of the first codon of ADAM6a and extending to the end of SEQ ID NO:3 upstream of the ADAM6 coding region. In another specific embodiment, the ADAM6 promoter is a fragment extending from within about 5 to about 20 nucleotides upstream of the start codon of ADAM6a to about 0.5 kb, 1 kb, 2 kb, or 3 kb or more upstream of the start codon of ADAM6a.

In one embodiment, the nucleic acid sequence comprises SEQ ID NO:3 or a fragment thereof that when placed into a mouse that is infertile or that has low fertility due to a lack of ADAM6, improves fertility or restores fertility to about a wild-type fertility. In one embodiment, SEQ ID NO:3 or a fragment thereof confers upon a male mouse the ability to produce a sperm cell that is capable of traversing a female mouse oviduct in order to fertilize a mouse egg.

In one aspect, a mouse is provided that comprises a deletion of an endogenous nucleotide sequence that encodes an ADAM6 protein, a replacement of an endogenous mouse $V_H$ gene segment with a human $V_H$ gene segment, and an ectopic nucleotide sequence that encodes a mouse ADAM6 protein or ortholog or homolog or fragment thereof that is functional in a male mouse.

In one embodiment, the mouse comprises an immunoglobulin heavy chain locus that comprises a deletion of an endogenous immunoglobulin locus nucleotide sequence that comprises an endogenous ADAM6 gene, comprises a nucleotide sequence encoding one or more human immunoglobulin gene segments, and wherein the ectopic nucleotide sequence encoding the mouse ADAM6 protein is within or directly adjacent to the nucleotide sequence encoding the one or more human immunoglobulin gene segments.

In one embodiment, the mouse comprises a replacement of all or substantially all endogenous $V_H$ gene segments with a nucleotide sequence encoding one or more human $V_H$ gene segments, and the ectopic nucleotide sequence encoding the mouse ADAM6 protein is within, or directly adjacent to, the nucleotide sequence encoding the one or more human $V_H$ gene segments. In one embodiment, the mouse further comprises a replacement of one or more endogenous $D_H$ gene segments with one or more human $D_H$ gene segments at the endogenous $D_H$ gene locus. In one embodiment, the mouse further comprises a replacement of one or more endogenous $J_H$ gene segments with one or more human $J_H$ gene segments at the endogenous $J_H$ gene locus. In one embodiment, the mouse comprises a replacement of all or substantially all endogenous $V_H$, $D_H$, and $J_H$ gene segments and a replacement at the endogenous $V_H$, $D_H$, and $J_H$ gene loci with human $V_H$, $D_H$, and $J_H$ gene segments, wherein the mouse comprises an ectopic sequence encoding a mouse ADAM6 protein. In a specific embodiment, the ectopic sequence encoding the mouse ADAM6 protein is placed between the penultimate 3'-most $V_H$ gene segment of the human $V_H$ gene segments present, and the ultimate 3' $V_H$ gene segment of the human $V_H$ gene segments present. In a specific embodiment, the mouse comprises a deletion of all or substantially all mouse $V_H$ gene segments, and a replacement with all or substantially all human $V_H$ gene segments, and the ectopic nucleotide sequence encoding the mouse ADAM6 protein is placed downstream of human gene segment $V_H$1-2 and upstream of human gene segment $V_H$6-1.

In a specific embodiment, the mouse comprises a replacement of all or substantially all endogenous $V_H$ gene segments with a nucleotide sequence encoding one or more human $V_H$ gene segments, and the ectopic nucleotide sequence encoding the mouse ADAM6 protein is within, or directly adjacent to, the nucleotide sequence encoding the one or more human $V_H$ gene segments.

In one embodiment, the ectopic nucleotide sequence that encodes the mouse ADAM6 protein is present on a transgene in the genome of the mouse. In one embodiment, the ectopic nucleotide sequence that encodes the mouse ADAM6 protein is present extrachromosomally in the mouse.

In one aspect, a mouse is provided that comprises a modification of an endogenous immunoglobulin heavy chain locus, wherein the mouse expresses a B cell that comprises a rearranged immunoglobulin sequence operably linked to a heavy chain constant region gene sequence, and the B cell comprises in its genome (e.g., on a B cell chromosome) a gene encoding an ADAM6 or ortholog or homolog or fragment thereof that is functional in a male mouse. In one embodiment, the rearranged immunoglobulin sequence operably linked to the heavy chain constant region gene sequence comprises a human heavy chain V, D, and/or J sequence; a mouse heavy chain V, D, and/or J sequence; a human or mouse light chain V and/or J sequence. In one embodiment, the heavy chain constant region gene sequence comprises a human or a mouse heavy chain sequence selected from the group consisting of a $C_H1$, a hinge, a $C_H2$, a $C_H3$, and a combination thereof.

In one aspect, a genetically modified mouse is provided, wherein the mouse comprises a functionally silenced immunoglobulin light chain gene, and further comprises a replacement of one or more endogenous immunoglobulin heavy chain variable region gene segments with one or more human immunoglobulin heavy chain variable region gene segments, wherein the mouse lacks a functional endogenous ADAM6 locus, and wherein the mouse comprises an ectopic nucleotide sequence that expresses a mouse ADAM6 protein or an ortholog or homolog or fragment thereof that is functional in a male mouse.

In one aspect, a mouse is provided that lacks a functional endogenous mouse ADAM6 locus or sequence and that comprises an ectopic nucleotide sequence encoding a mouse ADAM6 locus or functional fragment of a mouse ADAM6 locus or sequence, wherein the mouse is capable of mating with a mouse of the opposite sex to produce a progeny that comprises the ectopic ADAM6 locus or sequence. In one embodiment, the mouse is male. In one embodiment, the mouse is female.

In one aspect, a genetically modified mouse is provided, wherein the mouse comprises a human immunoglobulin heavy chain variable region gene segment at an endogenous mouse immunoglobulin heavy chain variable region gene locus, the mouse lacks an endogenous functional ADAM6 sequence at the endogenous mouse immunoglobulin heavy chain variable region gene locus, and wherein the mouse comprises an ectopic nucleotide sequence that expresses a mouse ADAM6 protein or an ortholog or homolog or fragment thereof that is functional in a male mouse.

In one embodiment, the ectopic nucleotide sequence that expresses the mouse ADAM6 protein is extrachromosomal. In one embodiment, the ectopic nucleotide sequence that expresses the mouse ADAM6 protein is integrated at one or more loci in a genome of the mouse. In a specific embodiment, the one or more loci include an immunoglobulin locus.

In one aspect, a mouse is provided that expresses an immunoglobulin heavy chain sequence from a modified endogenous mouse immunoglobulin heavy chain locus, wherein the heavy chain is derived from a human V gene segment, a D gene segment, and a J gene segment, wherein the mouse comprises an ADAM6 activity that is functional in the mouse.

In one embodiment, the mouse comprises a plurality of human V gene segments, a plurality of D gene segments, and a plurality of J gene segments. In one embodiment, the D gene segments are human D gene segments. In one embodiment, the J gene segments are human J gene segments. In one embodiment, the mouse further comprises a humanized heavy chain constant region sequence, wherein the humanization comprises replacement of a sequence selected from a $C_H1$, hinge, $C_H2$, $C_H3$, and a combination thereof. In a specific embodiment, the heavy chain is derived from a human V gene segment, a human D gene segment, a human J gene segment, a human $C_H1$ sequence, a human or mouse hinge sequence, a mouse $C_H2$ sequence, and a mouse $C_H3$ sequence. In another specific embodiment, the mouse further comprises a human light chain constant sequence.

In one embodiment, the D gene segment is flanked 5' (with respect to transcriptional direction of the D gene segment) by a sequence encoding an ADAM6 activity that is functional in the mouse.

In one embodiment, the ADAM6 activity that is functional in the mouse results from expression of a nucleotide sequence located 5' of the 5'-most D gene segment and 3' of the 3'-most V gene segment (with respect to the direction of transcription of the V gene segment) of the modified endogenous mouse heavy chain immunoglobulin locus.

In one embodiment, the ADAM6 activity that is functional in the mouse results from expression of a nucleotide sequence located between two human V gene segments in the modified endogenous mouse heavy chain immunoglobulin locus. In one embodiment, the two human V segments are a human $V_H1$-2 gene segment and a $V_H6$-1 gene segment.

In one embodiment, the nucleotide sequence comprises a sequence selected from a mouse ADAM6b sequence or functional fragment thereof, a mouse ADAM6a sequence or functional fragment thereof, and a combination thereof.

In one embodiment, the nucleotide sequence between the two human V gene segments is placed in opposite transcription orientation with respect to the human V gene segments. In a specific embodiment, nucleotide sequence encodes, from 5' to 3' with respect to the direction of transcription of ADAM6 genes, and ADAM6a sequence followed by an ADAM6b sequence.

In one embodiment, the mouse comprises a replacement of a human ADAM6 pseudogene sequence between human V gene segments $V_H1$-2 and $V_H6$-1 with a mouse ADAM6 sequence or a functional fragment thereof.

In one embodiment, the sequence encoding the ADAM6 activity that is functional in the mouse is a mouse ADAM6 sequence or functional fragment thereof.

In one embodiment, the mouse comprises an endogenous mouse DFL16.1 gene segment (e.g., in a mouse heterozygous for the modified endogenous mouse immunoglobulin heavy chain locus), or a human $D_H1$-1 gene segment. In one embodiment, the D gene segment of the immunoglobulin heavy chain expressed by the mouse is derived from an endogenous mouse DFL16.1 gene segment or a human $D_H1$-1 gene segment.

In one aspect, a mouse is provided that comprises a nucleic acid sequence encoding a mouse ADAM6 (or homolog or ortholog or functional fragment thereof) in a DNA-bearing cell of non-rearranged B cell lineage, but does not comprise the nucleic acid sequence encoding the mouse ADAM6 (or homolog or ortholog or functional fragment thereof) in a B cell that comprise rearranged immunoglobulin loci, wherein the nucleic acid sequence encoding the mouse ADAM6 (or homolog or ortholog or functional fragment thereof) occurs in the genome at a position that is different from a position in which a mouse ADAM6 gene appears in a wild-type mouse. In one embodiment, the nucleic acid sequence encoding the mouse ADAM6 (or homolog or ortholog or functional fragment thereof) is present in all or substantially all DNA-bearing cells that are not of rearranged B cell lineage; in one embodiment, the nucleic acid sequence is present in germline cells of the mouse, but not in a chromosome of a rearranged B cell.

In one aspect, a mouse is provided that comprises a nucleic acid sequence encoding a mouse ADAM6 (or homolog or ortholog or functional fragment thereof) in all or substantially all DNA-bearing cells, including B cells that comprise rearranged immunoglobulin loci, wherein the nucleic acid sequence encoding the mouse ADAM6 (or homolog or ortholog or functional fragment thereof) occurs in the genome at a position that is different from a position in which a mouse ADAM6 gene appears in a wild-type mouse. In one embodiment, the nucleic acid sequence encoding the mouse ADAM6 (or homolog or ortholog or functional fragment thereof) is on a nucleic acid that is contiguous with the rearranged immunoglobulin locus. In one embodiment, the nucleic acid that is contiguous with the rearranged immunoglobulin locus is a chromosome. In one embodiment, the chromosome is a chromosome that is found in a wild-type mouse and the chromosome comprises a modification of a mouse immunoglobulin locus.

In one aspect, a genetically modified mouse is provided, wherein the mouse comprises a B cell that comprises in its genome an ADAM6 sequence or ortholog or homolog thereof. In one embodiment, the ADAM6 sequence or ortholog or homolog thereof is at an immunoglobulin heavy chain locus. In one embodiment, the ADAM6 sequence or ortholog or homolog thereof is at a locus that is not an immunoglobulin locus. In one embodiment, the ADAM6 sequence is on a transgene driven by a heterologous promoter. In a specific embodiment, the heterologous promoter is a non-immunoglobulin promoter. In a specific embodiment, B cell expresses an ADAM6 protein or ortholog or homolog thereof.

In one embodiment, 90% or more of the B cells of the mouse comprise a gene encoding an ADAM6 protein or an ortholog thereof or a homolog thereof or a fragment thereof that is functional in the mouse. In a specific embodiment, the mouse is a male mouse.

In one embodiment, the B cell genome comprises a first allele and a second allele comprising the ADAM6 sequence or ortholog or homolog thereof. In one embodiment, the B cell genome comprises a first allele but not a second allele comprising the ADAM6 sequence or ortholog or homolog thereof.

In one aspect, a mouse is provided that comprises a modification at one or more endogenous ADAM6 alleles.

In one embodiment, the modification renders the mouse incapable of expressing a functional ADAM6 protein from at least one of the one or more endogenous ADAM6 alleles. In a specific embodiment, the mouse is incapable of expressing a functional ADAM6 protein from each of the endogenous ADAM6 alleles.

In one embodiment, the mice are incapable of expressing a functional ADAM6 protein from each endogenous ADAM6 allele, and the mice comprise an ectopic ADAM6 sequence.

In one embodiment, the mice are incapable of expressing a functional ADAM6 protein from each endogenous ADAM6 allele, and the mice comprise an ectopic ADAM6 sequence located within 1, 2, 3, 4, 5, 10, 20, 30, 40, 50, 60, 70, 80, 90, 100, 110, or 120 or more kb upstream (with respect to the direction of transcription of the mouse heavy chain locus) of a mouse immunoglobulin heavy chain constant region sequence. In a specific embodiment, the ectopic ADAM6 sequence is at the endogenous immunoglobulin heavy chain locus (e.g., in an intergenic V-D region, between two V gene segments, between a V and a D gene segment, between a D and a J gene segment, etc.). In a specific embodiment, the ectopic ADAM6 sequence is located within a 90 to 100 kb intergenic sequence between the final mouse V gene segment and the first mouse D gene segment. In another specific embodiment, the endogenous 90 to 100 kb intergenic V-D sequence is removed, and the ectopic ADAM6 sequence is placed between the final V and the first D gene segment.

In one aspect, an infertile male mouse is provided, wherein the mouse comprises a deletion of two or more endogenous ADAM6 alleles. In one aspect, a female mouse is provided that is a carrier of a male infertility trait, wherein the female mouse comprises in its germline a nonfunctional ADAM6 allele or a knockout of an endogenous ADAM6 allele.

In one aspect, a mouse that lacks an endogenous immunoglobulin heavy chain V, D, and J gene segment is provided, wherein a majority of the B cells of the mouse comprise an ADAM6 sequence or ortholog or homolog thereof.

In one embodiment, the mouse lacks endogenous immunoglobulin heavy chain gene segments selected from two or more V gene segments, two or more D gene segments, two or more J gene segments, and a combination thereof. In one embodiment, the mouse lacks immunoglobulin heavy chain gene segments selected from at least one and up to 89 V gene segments, at least one and up to 13 D gene segments, at least one and up to four J gene segments, and a combination thereof. In one embodiment, the mouse lacks a genomic DNA fragment from chromosome 12 comprising about three megabases of the endogenous immunoglobulin heavy chain locus. In a specific embodiment, the mouse lacks all functional endogenous heavy chain V, D, and J gene segments. In a specific embodiment, the mouse lacks 89 $V_H$ gene segments, 13 $D_H$ gene segments and four $J_H$ gene segments.

In one aspect, a mouse is provided, wherein the mouse has a genome in the germline comprising a modification of an immunoglobulin heavy chain locus, wherein the modification to the immunoglobulin heavy chain locus comprises the replacement of one or more mouse immunoglobulin variable region sequences with one or more non-mouse immunoglobulin variable region sequences, and wherein the mouse comprises a nucleic acid sequence encoding a mouse ADAM6 protein. In a preferred embodiment, the $D_H$ and $J_H$ sequences and at least 3, at least 10, at least 20, at least 40, at least 60, or at least 80 $V_H$ sequences of the immunoglobulin heavy chain locus are replaced by non-mouse immunoglobulin variable region sequences. In a further preferred embodiment, the $D_H$, $J_H$, and all $V_H$ sequences of the immunoglobulin heavy chain locus are replaced by non-mouse immunoglobulin variable region sequences. The non-mouse immunoglobulin variable region sequences can be non-rearranged. In a preferred embodiment, the non-mouse immunoglobulin variable region sequences comprise complete non-rearranged $D_H$ and $J_H$ regions and at least 3, at least 10, at least 20, at least 40, at least 60, or at least 80 non-rearranged $V_H$ sequences of the non-mouse species. In a further preferred embodiment, the non-mouse immunoglobulin variable region sequences comprise the complete variable region, including all $V_H$, $D_R$, and $J_H$ regions, of the non-mouse species. The non-mouse species can be *Homo sapiens* and the non-mouse immunoglobulin variable region sequences can be human sequences.

In one aspect, a mouse that expresses an antibody that comprises at least one human variable domain/non-human constant domain immunoglobulin polypeptide is provided, wherein the mouse expresses a mouse ADAM6 protein or ortholog or homolog thereof from a locus other than an immunoglobulin locus.

In one embodiment, the ADAM6 protein or ortholog or homolog thereof is expressed in a B cell of the mouse, wherein the B cell comprises a rearranged immunoglobulin sequence that comprises a human variable sequence and a non-human constant sequence.

In one embodiment, the non-human constant sequence is a rodent sequence. In one embodiment, the rodent is selected from a mouse, a rat, and a hamster.

In one aspect, a method is provided for making an infertile male mouse, comprising rendering an endogenous ADAM6 allele of a donor ES cell nonfunctional (or knocking out said allele), introducing the donor ES cell into a host embryo, gestating the host embryo in a surrogate mother, and allowing the surrogate mother to give birth to progeny derived in whole or in part from the donor ES cell. In one embodiment, the method further comprises breeding progeny to obtain an infertile male mouse.

In one aspect, a method is provided for making a mouse with a genetic modification of interest, wherein the mouse is infertile, the method comprising the steps of (a) making a genetic modification of interest in a genome; (b) modifying the genome to knockout an endogenous ADAM6 allele, or render an endogenous ADAM6 allele nonfunctional; and, (c) employing the genome in making a mouse. In various embodiments, the genome is from an ES cell or used in a nuclear transfer experiment.

In one aspect, a mouse made using a targeting vector, nucleotide construct, or cell as described herein is provided.

In one aspect, a progeny of a mating of a mouse as described herein with a second mouse that is a wild-type mouse or genetically modified is provided.

In one aspect, a method for maintaining a mouse strain is provided, wherein the mouse strain comprises a replacement of a mouse immunoglobulin heavy chain sequence with one or more heterologous immunoglobulin heavy chain sequences. In one embodiment, the one or more heterologous immunoglobulin heavy chain sequences are human immunoglobulin heavy chain sequences.

In one embodiment, the mouse strain comprises a deletion of one or more mouse $V_H$, $D_H$, and/or $J_H$ gene segments. In one embodiment, the mouse further comprises one or more human $V_H$ gene segments, one or more human $D_H$ gene segments, and/or one or more human $J_H$ gene segments. In one embodiment, the mouse comprises at least 3, at least 10, at least 20, at least 40, at least 60, or at least 80 human $V_H$ segments, at least 27 human $D_H$ gene segments, and at least six $J_H$ gene segments. In a specific embodiment, the mouse comprises at least 3, at least 10, at least 20, at least 40, at least 60, or at least 80 human $V_H$ segments, the at least 27 human $D_R$ gene segments, and the at least six $J_H$ gene segments are operably linked to a constant region gene. In one embodiment, the constant region gene is a mouse constant region gene. In one embodiment, the constant region gene comprises a mouse constant region gene sequence selected from a $C_H1$, a hinge, a $C_H2$, a $C_H3$, and/or a $C_H4$ or a combination thereof.

In one embodiment, the method comprises generating a male mouse heterozygous for the replacement of the mouse immunoglobulin heavy chain sequence, and breeding the heterozygous male mouse with a wild-type female mouse or a female mouse that is homozygous or heterozygous for the human heavy chain sequence. In one embodiment, the method comprises maintaining the strain by repeatedly breeding heterozygous males with females that are wild type or homozygous or heterozygous for the human heavy chain sequence.

In one embodiment, the method comprises obtaining cells from male or female mice homozygous or heterozygous for the human heavy chain sequence, and employing those cells as donor cells or nuclei therefrom as donor nuclei, and using the cells or nuclei to make genetically modified animals using host cells and/or gestating the cells and/or nuclei in surrogate mothers.

In one embodiment, only male mice that are heterozygous for the replacement at the heavy chain locus are bred to female mice. In a specific embodiment, the female mice are homozygous, heterozygous, or wild type with respect to a replaced heavy chain locus.

In one embodiment, the mouse further comprises a replacement of λ and/or κ light chain variable sequences at an endogenous immunoglobulin light chain locus with heterologous immunoglobulin light chain sequences. In one embodiment, the heterologous immunoglobulin light chain sequences are human immunoglobulin λ and/or κ light chain variable sequences.

In one embodiment, the mouse further comprises a transgene at a locus other than an endogenous immunoglobulin locus, wherein the transgene comprises a sequence encoding a rearranged or unrearranged heterologous λ or κ light chain sequence (e.g., unrearranged $V_L$ and unrearranged $J_L$, or rearranged VJ) operably linked (for unrearranged) or fused (for rearranged) to an immunoglobulin light chain constant region sequence. In one embodiment, the heterologous λ or κ light chain sequence is human. In one embodiment, the constant region sequence is selected from rodent, human, and non-human primate. In one embodiment, the constant region sequence is selected from mouse, rat, and hamster. In one embodiment, the transgene comprises a non-immunoglobulin promoter that drives expression of the light chain sequences. In a specific embodiment, the promoter is a transcriptionally active promoter. In a specific embodiment, the promoter is a ROSA26 promoter.

In one aspect, a nucleic acid construct is provided, comprising an upstream homology arm and a downstream homology arm, wherein the upstream homology arm comprises a sequence that is identical or substantially identical to a human immunoglobulin heavy chain variable region sequence, the downstream homology arm comprises a sequence that is identical or substantially identical to a human or mouse immunoglobulin variable region sequence, and disposed between the upstream and downstream homology arms is a sequence that comprises a nucleotide sequence encoding a mouse ADAM6 protein. In a specific embodiment, the sequence encoding the mouse ADAM6 gene is operably linked with a mouse promoter with which the mouse ADAM6 is linked in a wild type mouse.

In one aspect, a targeting vector is provided, comprising (a) a nucleotide sequence that is identical or substantially identical to a human variable region gene segment nucleotide sequence; and, (b) a nucleotide sequence encoding a mouse ADAM6 or ortholog or homolog or fragment thereof that is functional in a mouse.

In one embodiment, the targeting vector further comprises a promoter operably linked to the sequence encoding the mouse ADAM6. In a specific embodiment, the promoter is a mouse ADAM6 promoter.

In one aspect, a nucleotide construct for modifying a mouse immunoglobulin heavy chain variable locus is provided, wherein the construct comprises at least one site-specific recombinase recognition site and a sequence encoding an ADAM6 protein or ortholog or homolog or fragment thereof that is functional in a mouse.

In one aspect, mouse cells and mouse embryos are provided, including but not limited to ES cells, pluripotent cells, and induced pluripotent cells, that comprise genetic modifications as described herein. Cells that are XX and cells that are XY are provided. Cells that comprise a nucleus containing a modification as described herein are also provided, e.g., a modification introduced into a cell by pronuclear injection. Cells, embryos, and mice that comprise a virally introduced ADAM6 gene are also provided, e.g., cells, embryos, and mice comprising a transduction construct comprising an ADAM6 gene that is functional in the mouse.

In one aspect, a genetically modified mouse cell is provided, wherein the cell lacks a functional endogenous mouse ADAM6 locus, and the cell comprises an ectopic nucleotide sequence that encodes a mouse ADAM6 protein or functional fragment thereof. In one embodiment, the cell further comprises a modification of an endogenous immunoglobulin heavy chain variable gene sequence. In a specific embodiment, the modification of the endogenous immunoglobulin heavy chain variable gene sequence comprises a deletion selected from a deletion of a mouse $V_H$ gene segment, a deletion of a mouse $D_H$ gene segment, a deletion of a mouse $J_H$ gene segment, and a combination thereof. In a specific embodiment, the mouse comprises a replacement of one or more mouse immunoglobulin $V_H$, $D_H$, and/or $J_H$ sequences with a human immunoglobulin sequence. In a specific embodiment, the human immunoglobulin sequence is selected from a human $V_H$, a human $V_L$, a human $D_H$, a human $J_H$, a human $J_L$, and a combination thereof.

In one embodiment, the cell is a totipotent cell, a pluripotent cell, or an induced pluripotent cell. In a specific embodiment, the cell is a mouse ES cell.

In one aspect, a mouse B cell is provided, wherein the mouse B cell comprises a rearranged immunoglobulin heavy chain gene, wherein the B cell comprises on a chromosome of the B cell a nucleic acid sequence encoding an ADAM6 protein or ortholog or homolog or fragment thereof that is functional in a male mouse. In one embodiment, the mouse B cell comprises two alleles of the nucleic acid sequence.

In one embodiment, the nucleic acid sequence is on a nucleic acid molecule (e.g., a B cell chromosome) that is contiguous with the rearranged mouse immunoglobulin heavy chain locus.

In one embodiment, the nucleic acid sequence is on a nucleic acid molecule (e.g., a B cell chromosome) that is distinct from the nucleic acid molecule that comprises the rearranged mouse immunoglobulin heavy chain locus.

In one embodiment, the mouse B cell comprises a rearranged non-mouse immunoglobulin variable gene sequence operably linked to a mouse or human immunoglobulin constant region gene, wherein the B cell comprises a nucleic acid sequence that encodes an ADAM6 protein or ortholog or homolog or fragment thereof that is functional in a male mouse.

In one aspect, a somatic mouse cell is provided, comprising a chromosome that comprises a modified immunoglobulin heavy chain locus, and a nucleic acid sequence encoding a mouse ADAM6 or ortholog or homolog or fragment thereof that is functional in a male mouse. In one embodiment, the nucleic acid sequence is on the same chromosome as the modified immunoglobulin heavy chain locus. In one embodiment, the nucleic acid is on a different chromosome than the modified immunoglobulin heavy chain locus. In one embodiment, the somatic cell comprises a single copy of the nucleic acid sequence. In one embodiment, the somatic cell comprises at least two copies of the nucleic acid sequence. In a specific embodiment, the somatic cell is a B cell. In a specific embodiment, the cell is a germ cell. In a specific embodiment, the cell is a stem cell.

In one aspect, a mouse germ cell is provided, comprising a nucleic acid sequence encoding a mouse ADAM6 (or homolog or ortholog or functional fragment thereof) on a chromosome of the germ cell, wherein the nucleic acid sequence encoding the mouse ADAM6 (or homolog or ortholog or functional fragment thereof) is at a position in the chromosome that is different from a position in a chromosome of a wild-type mouse germ cell. In one embodiment, the nucleic acid sequence is at a mouse immunoglobulin locus. In one embodiment, the nucleic acid sequence is on the same chromosome of the germ cell as a mouse immunoglobulin locus. In one embodiment, the nucleic acid sequence is on a different chromosome of the germ cell than the mouse immunoglobulin locus. In one embodiment, the mouse immunoglobulin locus comprises a replacement of at least one mouse immunoglobulin sequence with at least one non-mouse immunoglobulin sequence. In a specific embodiment, the at least one non-mouse immunoglobulin sequence is a human immunoglobulin sequence.

In one aspect, a pluripotent, induced pluripotent, or totipotent cell derived from a mouse as described herein is provided. In a specific embodiment, the cell is a mouse embryonic stem (ES) cell.

In one aspect, a tissue derived from a mouse as described herein is provided. In one embodiment, the tissue is derived from spleen, lymph node or bone marrow of a mouse as described herein.

In one aspect, a nucleus derived from a mouse as described herein is provided. In one embodiment, the nucleus is from a diploid cell that is not a B cell.

In one aspect, a nucleotide sequence encoding an immunoglobulin variable region made in a mouse as described herein is provided.

In one aspect, an immunoglobulin heavy chain or immunoglobulin light chain variable region amino acid sequence of an antibody made in a mouse as described herein is provided.

In one aspect, an immunoglobulin heavy chain or immunoglobulin light chain variable region nucleotide sequence encoding a variable region of an antibody made in a mouse as described herein is provided.

In one aspect, an antibody or antigen-binding fragment thereof (e.g., Fab, F(ab)$_2$, scFv) made in a mouse as described herein is provided. In one aspect, a method for making a genetically modified mouse is provided, comprising replacing one or more immunoglobulin heavy chain gene segments upstream (with respect to transcription of the immunoglobulin heavy chain gene segments) of an endogenous ADAM6 locus of the mouse with one or more human immunoglobulin heavy chain gene segments, and replacing one or more immunoglobulin gene segments downstream (with respect to transcription of the immunoglobulin heavy chain gene segments) of the ADAM6 locus of the mouse with one or more human immunoglobulin heavy chain or light chain gene segments. In one embodiment, the one or more human immunoglobulin gene segments replacing one or more endogenous immunoglobulin gene segments upstream of an endogenous ADAM6 locus of the mouse include V gene segments. In one embodiment, the human immunoglobulin gene segments replacing one or more endogenous immunoglobulin gene segments upstream of an endogenous ADAM6 locus of the mouse include V and D gene segments. In one embodiment, the one or more human immunoglobulin gene segments replacing one or more endogenous immunoglobulin gene segments downstream of an endogenous ADAM6 locus of the mouse include J gene segments. In one embodiment, the one or more human immunoglobulin gene segments replacing one or more endogenous immunoglobulin gene segments downstream of an endogenous ADAM6 locus of the mouse include D and J gene segments. In one embodiment, the one or more human immunoglobulin gene segments replacing one or more endogenous immunoglobulin gene segments downstream of an endogenous ADAM6 locus of the mouse include V, D and J gene segments.

In one embodiment, the one or more immunoglobulin heavy chain gene segments upstream and/or downstream of the ADAM6 gene are replaced in a pluripotent, induced pluripotent, or totipotent cell to form a genetically modified progenitor cell; the genetically modified progenitor cell is introduced into a host; and, the host comprising the genetically modified progenitor cell is gestated to form a mouse comprising a genome derived from the genetically modified progenitor cell. In one embodiment, the host is an embryo. In a specific embodiment, the host is selected from a mouse pre-morula (e.g., 8- or 4-cell stage), a tetraploid embryo, an aggregate of embryonic cells, or a blastocyst.

In one aspect, a method for making a genetically modified mouse is provided, comprising replacing a mouse nucleotide sequence that comprises a mouse immunoglobulin gene segment and a mouse ADAM6 (or ortholog or homolog or fragment thereof functional in a male mouse) nucleotide sequence with a sequence comprising a human immunoglobulin gene segment to form a first chimeric locus, then inserting a sequence comprising a mouse ADAM6-encoding sequence (or a sequence encoding an ortholog or homolog or functional fragment thereof) into the sequence comprising the human immunoglobulin gene segment to form a second chimeric locus.

In one embodiment, the second chimeric locus comprises a human immunoglobulin heavy chain variable ($V_H$) gene segment. In one embodiment, the second chimeric locus comprises a human immunoglobulin light chain variable ($V_L$) gene segment. In a specific embodiment, the second chimeric locus comprises a human $V_H$ gene segment or a human $V_L$ gene segment operably linked to a human $D_R$ gene segment and a human $J_R$ gene segment. In a further specific embodiment, the second chimeric locus is operably linked to a third chimeric locus that comprises a human $C_H1$ sequence, or a human $C_H1$ and human hinge sequence, fused with a mouse $C_H2+C_H3$ sequence.

In one aspect, use of a mouse that comprises an ectopic nucleotide sequence comprising a mouse ADAM6 locus or sequence to make a fertile male mouse is provided, wherein the use comprises mating the mouse comprising the ectopic nucleotide sequence that comprises the mouse ADAM6 locus or sequence to a mouse that lacks a functional endogenous mouse ADAM6 locus or sequence, and obtaining a progeny that is a female capable of producing progeny having the ectopic ADAM6 locus or sequence or that is a male that comprises the ectopic ADAM6 locus or sequence, and the male exhibits a fertility that is approximately the same as a fertility exhibited by a wild-type male mouse.

In one aspect, use of a mouse as described herein to make an immunoglobulin variable region nucleotide sequence is provided.

In one aspect, use of a mouse as described herein to make a fully human Fab or a fully human $F(ab)_2$ is provided.

In one aspect, use of a mouse as described herein to make an immortalized cell line is provided.

In one aspect, use of a mouse as described herein to make a hybridoma or quadroma is provided.

In one aspect, use of a mouse as described herein to make a phage library containing human heavy chain variable regions and human light chain variable regions is provided.

In one aspect, use of a mouse as described herein to generate a variable region sequence for making a human antibody is provided, comprising (a) immunizing a mouse as described herein with an antigen of interest, (b) isolating a lymphocyte from the immunized mouse of (a), (c) exposing the lymphocyte to one or more labeled antibodies, (d) identifying a lymphocyte that is capable of binding to the antigen of interest, and (e) amplifying one or more variable region nucleic acid sequence from the lymphocyte thereby generating a variable region sequence.

In one embodiment, the lymphocyte is derived from the spleen of the mouse. In one embodiment, the lymphocyte is derived from a lymph node of the mouse. In one embodiment, the lymphocyte is derived from the bone marrow of the mouse.

In one embodiment, the labeled antibody is a fluorophore-conjugated antibody. In one embodiment, the one or more fluorophore-conjugated antibodies are selected from an IgM, an IgG, and/or a combination thereof.

In one embodiment, the lymphocyte is a B cell.

In one embodiment, the one or more variable region nucleic acid sequence comprises a heavy chain variable region sequence. In one embodiment, the one or more variable region nucleic acid sequence comprises a light chain variable region sequence. In a specific embodiment, the light chain variable region sequence is an immunoglobulin κ light chain variable region sequence. In one embodiment, the one or more variable region nucleic acid sequence comprises a heavy chain and a κ light chain variable region sequence.

In one embodiment, use of a mouse as described herein to generate a heavy and a κ light chain variable region sequence for making a human antibody is provided, comprising (a) immunizing a mouse as described herein with an antigen of interest, (b) isolating the spleen from the immunized mouse of (a), (c) exposing B lymphocytes from the spleen to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and κ light chain variable region sequences.

In one embodiment, use of a mouse as described herein to generate a heavy and a κ light chain variable region sequence for making a human antibody is provided, comprising (a) immunizing a mouse as described herein with an antigen of interest, (b) isolating one or more lymph nodes from the immunized mouse of (a), (c) exposing B lymphocytes from the one or more lymph nodes to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and κ light chain variable region sequences.

In one embodiment, use of a mouse as described herein to generate a heavy and a κ light chain variable region sequence for making a human antibody is provided, comprising (a) immunizing a mouse as described herein with an antigen of interest, (b) isolating bone marrow from the immunized mouse of (a), (c) exposing B lymphocytes from the bone marrow to one or more labeled antibodies, (d) identifying a B lymphocyte of (c) that is capable of binding to the antigen of interest, and (e) amplifying a heavy chain variable region nucleic acid sequence and a κ light chain variable region nucleic acid sequence from the B lymphocyte thereby generating the heavy chain and κ light chain variable region sequences. In various embodiments, the one or more labeled antibodies are selected from an IgM, an IgG, and/or a combination thereof.

In various embodiments, use of a mouse as described herein to generate a heavy and κ light chain variable region sequence for making a human antibody is provided, further comprising fusing the amplified heavy and light chain variable region sequences to human heavy and light chain constant region sequences, expressing the fused heavy and light chain sequences in a cell, and recovering the expressed heavy and light chain sequences thereby generating a human antibody.

In various embodiments, the human heavy chain constant regions are selected from IgM, IgD, IgA, IgE and IgG. In various specific embodiments, the IgG is selected from an IgG1, an IgG2, an IgG3 and an IgG4. In various embodiments, the human heavy chain constant region comprises a $C_H1$, a hinge, a $C_H2$, a $C_H3$, a $C_H4$, or a combination thereof. In various embodiments, the light chain constant region is an immunoglobulin κ constant region. In various embodiments, the cell is selected from a HeLa cell, a DU145 cell, a Lncap cell, a MCF-7 cell, a MDA-MB-438 cell, a PC3 cell, a T47D cell, a THP-1 cell, a U87 cell, a SHSY5Y (human neuroblastoma) cell, a Saos-2 cell, a Vero cell, a CHO cell, a GH3 cell, a PC12 cell, a human retinal cell (e.g., a PER.C6™ cell), and a MC3T3 cell. In a specific embodiment, the cell is a CHO cell.

In one aspect, a method for generating a reverse-chimeric rodent-human antibody specific against an antigen of interest is provided, comprising the steps of immunizing a mouse as described herein with the antigen, isolating at least one cell from the mouse producing a reverse-chimeric mouse-human antibody specific against the antigen, culturing at least one cell producing the reverse-chimeric mouse-human antibody specific against the antigen, and obtaining said antibody.

In one embodiment, the reverse-chimeric mouse-human antibody comprises a human heavy chain variable domain fused with a mouse or rat heavy chain constant gene, and a human light chain variable domain fused with a mouse or rat or human light chain constant gene.

In one embodiment, culturing at least one cell producing the reverse-chimeric rodent-human antibody specific against the antigen is performed on at least one hybridoma cell generated from the at least one cell isolated from the mouse.

In one aspect, a method for generating a fully human antibody specific against an antigen of interest is provided, comprising the steps of immunizing a mouse as described herein with the antigen, isolating at least one cell from the mouse producing a reverse-chimeric rodent-human antibody specific against the antigen, generating at least one cell producing a fully human antibody derived from the reverse-chimeric rodent-human antibody specific against the antigen, and culturing at least one cell producing the fully human antibody, and obtaining said fully human antibody.

In various embodiments, the at least one cell isolated from the mouse producing a reverse-chimeric rodent-human antibody specific against the antigen is a splenocyte or a B cell.

In various embodiments, the antibody is a monoclonal antibody.

In various embodiments, immunization with the antigen of interest is carried out with protein, DNA, a combination of DNA and protein, or cells expressing the antigen.

In one aspect, use of a mouse as described herein to make a nucleic acid sequence encoding an immunoglobulin variable region or fragment thereof is provided. In one embodiment, the nucleic acid sequence is used to make a human antibody or antigen-binding fragment thereof. In one embodiment, the mouse is used to make an antigen-binding protein selected from an antibody, a multi-specific antibody (e.g., a bi-specific antibody), an scFv, a bi-specific scFv, a diabody, a triabody, a tetrabody, a V-NAR, a $V_{HH}$, a $V_L$, a F(ab), a F(ab)$_2$, a DVD (i.e., dual variable domain antigen-binding protein), a an SVD (i.e., single variable domain antigen-binding protein), or a bispecific T-cell engager (BiTE).

In one aspect, use of a mouse as described herein to introduce an ectopic ADAM6 sequence into a mouse that lacks a functional endogenous mouse ADAM6 sequence is provided, wherein the use comprises mating a mouse as described herein with the mouse that lacks the functional endogenous mouse ADAM6 sequence.

In one aspect, use of genetic material from a mouse as described herein to make a mouse having an ectopic ADAM6 sequence is provided. In one embodiment, the use comprises nuclear transfer using a nucleus of a cell of a mouse as described herein. In one embodiment, the use comprises cloning a cell of a mouse as described herein to produce an animal derived from the cell. In one embodiment, the use comprises employing a sperm or an egg of a mouse as described herein in a process for making a mouse comprising the ectopic ADAM6 sequence.

In one aspect, a method for making a fertile male mouse comprising a modified immunoglobulin heavy chain locus is provided, comprising fertilizing a first mouse germ cell that comprises a modification of an endogenous immunoglobulin heavy chain locus with a second mouse germ cell that comprises an ADAM6 gene or ortholog or homolog or fragment thereof that is functional in a male mouse; forming a fertilized cell; allowing the fertilized cell to develop into an embryo; and, gestating the embryo in a surrogate to obtain a mouse.

In one embodiment, the fertilization is achieved by mating a male mouse and a female mouse. In one embodiment, the female mouse comprises the ADAM6 gene or ortholog or homolog or fragment thereof. In one embodiment, the male mouse comprises the ADAM6 gene or ortholog or homolog or fragment thereof.

In one aspect, use of a nucleic acid sequence encoding a mouse ADAM6 protein or an ortholog or homolog thereof or a functional fragment of the corresponding ADAM6 protein for restoring or enhancing the fertility of a mouse having a genome comprising a modification of an immunoglobulin heavy chain locus is provided, wherein the modification reduces or eliminates endogenous ADAM6 function.

In one embodiment, the nucleic acid sequence is integrated into the genome of the mouse at an ectopic position. In one embodiment, the nucleic acid sequence is integrated into the genome of the mouse at an endogenous immunoglobulin locus. In a specific embodiment, the endogenous immunoglobulin locus is a heavy chain locus. In one embodiment, the nucleic acid sequence is integrated into the genome of the mouse at a position other than an endogenous immunoglobulin locus.

In one aspect, use of the mouse as described herein for the manufacture of a medicament (e.g., an antigen-binding protein), or for the manufacture of a sequence encoding a variable sequence of a medicament (e.g., an antigen-binding protein), for the treatment of a human disease or disorder is provided.

BRIEF DESCRIPTION OF FIGURES

FIG. 3B shows a representative calculation of observed probe copy number in parental and modified ES cells for a first insertion of human immunoglobulin heavy chain gene segments. Observed probe copy number for probes A through F were calculated as $2/2^{\Delta\Delta Ct}$. $\Delta\Delta Ct$ is calculated as ave[$\Delta Ct$(sample)−med$\Delta Ct$(control)] where $\Delta Ct$ is the difference in Ct between test and reference probes (between 4 and 6 reference probes depending on the assay). The term med$\Delta Ct$(control) is the median $\Delta Ct$ of multiple (>60) non-targeted DNA samples from parental ES cells. Each modified ES cell clone was assayed in sextuplicate. To calculate copy numbers of IgH probes G and H in parental ES cells, these probes were assumed to have copy number of 1 in modified ES cells and a maximum Ct of 35 was used even though no amplification was observed.

FIG. 3C shows a representative calculation of copy numbers for four mice of each genotype calculated using only probes D and H. Wild-type mice: WT Mice; Mice heterozygous for a first insertion of human immunoglobulin gene segments: HET Mice; Mice homozygous for a first insertion of human immunoglobulin gene segments: Homo Mice.

FIG. 7A shows representative heavy chain CDR3 sequences of randomly selected VELOCIMMUNE® antibodies around the $V_H$-$D_H$-$J_H$ (CDR3) junction, demonstrating junctional diversity and nucleotide additions. Heavy chain CDR3 sequences are grouped according to $D_H$ gene segment usage, the germline of which is provided above each group in bold. $V_H$ gene segments for each heavy chain CDR3 sequence are noted within parenthesis at the 5' end of each sequence (e.g., 3-72 is human $V_H$3-72). $J_H$ gene segments for each heavy chain CDR3 are noted within parenthesis at the 3' end of each sequence (e.g., 3 is human 43). SEQ ID NOs for each sequence shown are as follows proceeding from top to bottom: SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39.

FIG. 7B shows representative light chain CDR3 sequences of randomly selected VELOCIMMUNE® antibodies around the Vκ-Jκ (CDR3) junction, demonstrating junctional diversity and nucleotide additions. Vκ gene segments for each light chain CDR3 sequence are noted within parenthesis at the 5' end of each sequence (e.g., 1-6 is human Vκ1-6). Jκ gene segments for each light chain CDR3 are noted within parenthesis at the 3' end of each sequence (e.g., 1 is human Jκ1). SEQ ID NOs for each sequence shown are as follows proceeding from top to bottom: SEQ ID NO:40; SEQ ID NO:41; SEQ ID NO:42; SEQ ID NO:43; SEQ ID NO:44; SEQ ID NO:45; SEQ ID NO:46; SEQ ID NO:47; SEQ ID NO:48; SEQ ID NO:49; SEQ ID NO:50; SEQ ID NO:51; SEQ ID NO:52; SEQ ID NO:53; SEQ ID NO:54; SEQ ID NO:55; SEQ ID NO:56; SEQ ID NO:57; SEQ ID NO:58.

DETAILED DESCRIPTION OF INVENTION

Figure 1A:
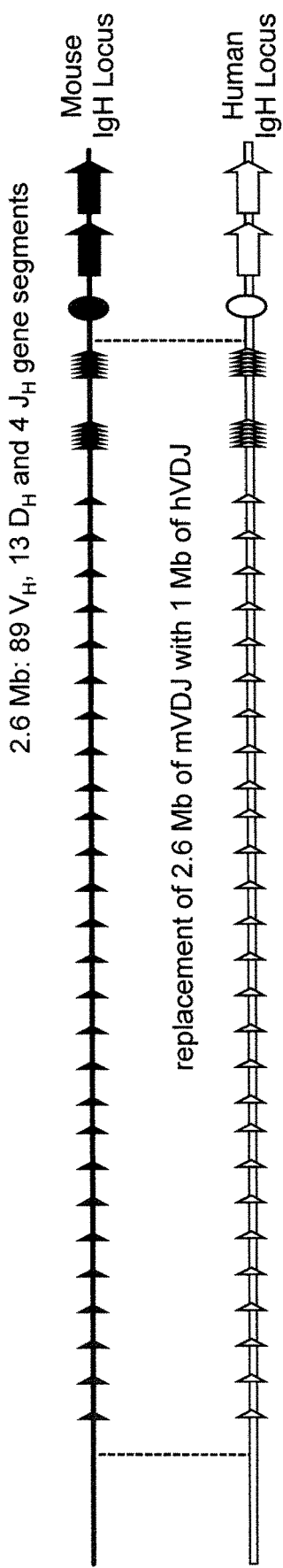
FIG. 1A shows a general illustration, not to scale, of direct genomic replacement of about three megabases (Mb) of a mouse immunoglobulin heavy chain variable gene locus (closed symbols) with about one megabase (Mb) of the human immunoglobulin heavy chain variable gene locus (open symbols).

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

The phrase "substantial" or "substantially" when used to refer to an amount of gene segments (e.g., "substantially all" V gene segments) includes both functional and non functional gene segments and include, in various embodiments, e.g., 80% or more, 85% or more, 90% or more, 95% or more 96% or more, 97% or more, 98% or more, or 99% or more of all gene segments; in various embodiments, "substantially all" gene segments includes, e.g., at least 95%, 96%, 97%, 98%, or 99% of functional (i.e., non-pseudogene) gene segments.

The term "replacement" includes wherein a DNA sequence is placed into a genome of a cell in such a way as to replace a sequence within the genome with a heterologous sequence (e.g., a human sequence in a mouse), at the locus of the genomic sequence. The DNA sequence so placed may include one or more regulatory sequences that are part of source DNA used to obtain the sequence so placed (e.g., promoters, enhancers, 5'- or 3'-untranslated regions, appropriate recombination signal sequences, etc.). For example, in various embodiments, the replacement is a substitution of an endogenous sequence for a heterologous sequence that results in the production of a gene product from the DNA sequence so placed (comprising the heterologous sequence), but not expression of the endogenous sequence; the replacement is of an endogenous genomic sequence with a DNA sequence that encodes a protein that has a similar function as a protein encoded by the endogenous genomic sequence (e.g., the endogenous genomic sequence encodes an immunoglobulin gene or domain, and the DNA fragment encodes one or more human immunoglobulin genes or domains). In various embodiments, an endogenous gene or fragment thereof is replaced with a corresponding human gene or fragment thereof. A corresponding human gene or fragment thereof is a human gene or fragment that is an ortholog of, a homolog of, or is substantially identical or the same in structure and/or function, as the endogenous gene or fragment thereof that is replaced.

The mouse as a genetic model has been greatly enhanced by transgenic and knockout technologies, which have allowed for the study of the effects of the directed overexpression or deletion of specific genes. Despite all of its advantages, the mouse still presents genetic obstacles that render it an imperfect model for human diseases and an imperfect platform to test human therapeutics or make them. First, although about 99% of human genes have a mouse homolog (Waterston et al. 2002, Initial sequencing and comparative analysis of the mouse genome, *Nature* 420: 520-562), potential therapeutics often fail to cross-react, or cross-react inadequately, with mouse orthologs of the intended human targets. To obviate this problem, selected target genes can be "humanized," that is, the mouse gene can be eliminated and replaced by the corresponding human orthologous gene sequence (e.g., U.S. Pat. Nos. 6,586,251, 6,596,541 and 7,105,348, incorporated herein by reference). Initially, efforts to humanize mouse genes by a "knockout-plus-transgenic humanization" strategy entailed crossing a mouse carrying a deletion (i.e., knockout) of the endogenous gene with a mouse carrying a randomly integrated human transgene (see, e.g., Bril et al., 2006, Tolerance to factor VIII in a transgenic mouse expressing human factor VIII cDNA carrying an Arg(593) to Cys substitution, *Thromb Haemost* 95:341-347; Homanics et al., 2006, Production and characterization of murine models of classic and intermediate maple syrup urine disease, *BMC Med Genet* 7:33; Jamsai et al., 2006, A humanized BAC transgenic/knockout mouse model for HbE/beta-thalassemia, *Genomics* 88(3):309-15; Pan et al., 2006, Different role for mouse and human CD3delta/epsilon heterodimer in preT cell receptor (preTCR) function:human CD3delta/epsilon heterodimer restores the defective preTCR function in CD3gamma- and CD3gammadelta-deficient mice, *Mol Immunol* 43:1741-1750). But those efforts were hampered by size limitations; conventional knockout technologies were not sufficient to directly replace large mouse genes with their large human genomic counterparts. A straightforward approach of direct homologous replacement, in which an endogenous mouse gene is directly replaced by the human counterpart gene at the same precise genetic location of the mouse gene (i.e., at the endogenous mouse locus), is rarely attempted because of technical difficulties. Until now, efforts at direct replacement involved elaborate and burdensome procedures, thus limiting the length of genetic material that could be handled and the precision with which it could be manipulated.

Exogenously introduced human immunoglobulin transgenes rearrange in precursor B cells in mice (Alt et al., 1985, Immunoglobulin genes in transgenic mice, *Trends Genet* 1:231-236). This finding was exploited by engineering mice using the knockout-plus-transgenic approach to express human antibodies (Green et al., 1994, Antigen-specific human monoclonal antibodies from mice engineered with human Ig heavy and light chain YACs, *Nat Genet* 7:13-21; Lonberg et al., 1994, Antigen-specific human antibodies from mice comprising four distinct genetic modifications, *Nature* 368:856-859; Jakobovits et al., 2007, From Xeno-Mouse technology to panitumumab, the first fully human antibody product from transgenic mice, *Nat Biotechnol* 25:1134-1143). The mouse immunoglobulin heavy chain and κ light chain loci were inactivated in these mice by targeted deletion of small but critical portions of each endogenous locus, followed by introducing human immunoglobulin gene loci as randomly integrated large transgenes, as described above, or minichromosomes (Tomizuka et al., 2000, Double trans-chromosomic mice: maintenance of two individual human chromosome fragments containing Ig heavy and kappa loci and expression of fully human antibodies, *PNAS USA* 97:722-727). Such mice represented an important advance in genetic engineering; fully human monoclonal antibodies isolated from them yielded promising therapeutic potential for treating a variety of human diseases (Gibson et al., 2006, Randomized phase III trial results of panitumumab, a fully human anti-epidermal growth factor receptor monoclonal antibody, in metastatic colorectal cancer, *Clin Colorectal Cancer* 6:29-31; Jakobovits et al., 2007; Kim et al., 2007, Clinical efficacy of zanolimumab (HuMax-CD4): two Phase II studies in refractory cutaneous T-cell lymphoma, *Blood* 109(11):4655-62; Lonberg, 2005, Human antibodies from transgenic animals, *Nat Biotechnol* 23:1117-1125; Maker et al., 2005, Tumor regression and autoimmunity in patients treated with cytotoxic T lymphocyte-associated antigen 4 blockade and interleukin 2: a phase study, *Ann Surg Oncol* 12:1005-1016; McClung et al., 2006, Denosumab in postmenopausal women with low bone mineral density, *New Engl J Med* 354:821-831). But, as discussed above, these mice exhibit compromised B cell development and immune deficiencies when compared to wild type mice. Such problems potentially limit the ability of the mice to support a vigorous humoral response and, consequently, generate fully human antibodies against some antigens. The deficiencies may be due to: (1) inefficient functionality due to the random introduction of the human immunoglobulin transgenes and resulting incorrect expression due to a lack of upstream and downstream control elements (Garrett et al., 2005, Chromatin architecture near a potential 3' end of the IgH locus involves modular regulation of histone modifications during B-Cell development and in vivo occupancy at CTCF sites, *Mol Cell Biol* 25:1511-1525; Manis et al., 2003, Elucidation of a downstream boundary of the 3' IgH regulatory region, *Mol Immunol* 39:753-760; Pawlitzky et al., 2006, Identification of a candidate regulatory element within the 5' flanking region of the mouse IgH locus defined by pro-B cell-specific hypersensitivity associated with binding of PU.1, Pax5, and E2A, *J Immunol* 176:6839-6851); (2) inefficient interspecies interactions between human constant domains and mouse components of the B-cell receptor signaling complex on the cell surface, which may impair signaling processes required for normal maturation, proliferation, and survival of B cells (Hombach et al., 1990, Molecular components of the B-cell antigen receptor complex of the IgM class, *Nature* 343:760-762); and (3) inefficient interspecies interactions between soluble human immunoglobulins and mouse Fc receptors that might reduce affinity selection (Rao et al., 2002, Differential expression of the inhibitory IgG Fc receptor FcgammaRIIB on germinal center cells: implications for selection of high-affinity B cells, *J Immunol* 169:1859-1868) and immunoglobulin serum concentrations (Brambell et al., 1964, A Theoretical Model of Gamma-Globulin Catabolism, *Nature* 203:1352-1354; Junghans and Anderson, 1996, The protection receptor for IgG catabolism is the beta2-microglobulin-containing neonatal intestinal transport receptor, *PNAS USA* 93:5512-5516; Rao et al., 2002; Hjelm et al., 2006, Antibody-mediated regulation of the immune response, *Scand J Immunol* 64:177-184; Nimmerjahn and Ravetch, 2007, Fc-receptors as regulators of immunity, *Adv Immunol* 96:179-204). These deficiencies can be corrected by in situ humanization of only the variable regions of the mouse immunoglobulin loci within their natural locations at the endogenous heavy and light chain loci. This would effectively result in mice that make "reverse chimeric" (i.e., human V:mouse C) antibodies which would be capable of normal interactions and selection with the mouse environment based on retaining mouse constant regions. Further such reverse chimeric antibodies may be readily reformatted into fully human antibodies for therapeutic purposes.

Genetically modified animals that comprise a replacement at the endogenous immunoglobulin heavy chain locus with heterologous (e.g., from another species) immunoglobulin sequences can be made in conjunction with replacements at endogenous immunoglobulin light chain loci or in conjunction with immunoglobulin light chain transgenes (e.g., chimeric immunoglobulin light chain transgenes or fully human fully mouse, etc.). The species from which the heterologous immunoglobulin heavy chain sequences are derived can vary widely; as with immunoglobulin light chain sequences employed in immunoglobulin light chain sequence replacements or immunoglobulin light chain transgenes.

Immunoglobulin variable region nucleic acid sequences, e.g., V, D, and/or J segments, are in various embodiments obtained from a human or a non-human animal. Non-human animals suitable for providing V, D, and/or J segments include, for example bony fish, cartilaginous fish such as sharks and rays, amphibians, reptiles, mammals, birds (e.g., chickens). Non-human animals include, for example, mammals. Mammals include, for example, non-human primates, goats, sheep, pigs, dogs, bovine (e.g., cow, bull, buffalo), deer, camels, ferrets and rodents and non-human primates (e.g., chimpanzees, orangutans, gorillas, marmosets, rhesus monkeys baboons). Suitable non-human animals are selected from the rodent family including rats, mice, and hamsters. In one embodiment, the non-human animals are mice. As clear from the context, various non-human animals can be used as sources of variable domains or variable region gene segments (e.g., sharks, rays, mammals (e.g., camels, rodents such as mice and rats).

According to the context, non-human animals are also used as sources of constant region sequences to be used in connection with variable sequences or segments, for example, rodent constant sequences can be used in transgenes operably linked to human or non-human variable sequences (e.g., human or non-human primate variable sequences operably linked to, e.g., rodent, e.g., mouse or rat or hamster, constant sequences). Thus, in various embodiments, human V, D, and/or J segments are operably linked to rodent (e.g., mouse or rat or hamster) constant region gene sequences. In some embodiments, the human V, D, and/or J segments (or one or more rearranged VDJ or VJ genes) are operably linked or fused to a mouse, rat, or hamster constant region gene sequence in, e.g., a transgene integrated at a locus that is not an endogenous immunoglobulin locus.

In a specific embodiment, a mouse is provided that comprises a replacement of $V_H$, $D_H$, and $J_H$ segments at an endogenous immunoglobulin heavy chain locus with one or more human $V_H$, $D_H$, and $J_H$ segments, wherein the one or more human $V_H$, $D_H$, and $J_H$ segments are operably linked to an endogenous immunoglobulin heavy chain gene; wherein the mouse comprises a transgene at a locus other than an endogenous immunoglobulin locus, wherein the transgene comprises an unrearranged or rearranged human $V_L$ and human $J_L$ segment operably linked to a mouse or rat or human constant region.

A method for a large in situ genetic replacement of the mouse germline immunoglobulin variable gene loci with human germline immunoglobulin variable gene loci while maintaining the ability of the mice to generate offspring is described. Specifically, the precise replacement of six megabases of both the mouse heavy chain and κ light chain immunoglobulin variable gene loci with their human counterparts while leaving the mouse constant regions intact is described. As a result, mice have been created that have a precise replacement of their entire germline immunoglobulin variable repertoire with equivalent human germline immunoglobulin variable sequences, while maintaining mouse constant regions. The human variable regions are linked to mouse constant regions to form chimeric human-mouse immunoglobulin loci that rearrange and express at physiologically appropriate levels. The antibodies expressed are "reverse chimeras," i.e., they comprise human variable region sequences and mouse constant region sequences. These mice having humanized immunoglobulin variable regions that express antibodies having human variable regions and mouse constant regions are called VELCOIMMUNE® mice.

VELOCIMMUNE® humanized mice exhibit a fully functional humoral immune system that is essentially indistinguishable from that of wild-type mice. They display normal cell populations at all stages of B cell development. They exhibit normal lymphoid organ morphology. Antibody sequences of VELOCIMMUNE® mice exhibit normal V(D)J rearrangement and normal somatic hypermutation frequencies. Antibody populations in these mice reflect isotype distributions that result from normal class switching (e.g., normal isotype cis-switching). Immunizing VELOCIMMUNE® mice results in robust humoral immune responses that generate a large, diverse antibody repertoires having human immunoglobulin variable domains suitable for use as therapeutic candidates. This platform provides a plentiful source of naturally affinity-matured human immunoglobulin variable region sequences for making pharmaceutically acceptable antibodies and other antigen-binding proteins.

It is the precise replacement of mouse immunoglobulin variable sequences with human immunoglobulin variable sequences that allows for making VELOCIMMUNE® mice. Yet even a precise replacement of endogenous mouse immunoglobulin sequences at heavy and light chain loci with equivalent human immunoglobulin sequences, by sequential recombineering of very large spans of human immunoglobulin sequences, may present certain challenges due to divergent evolution of the immunoglobulin loci between mouse and man. For example, intergenic sequences interspersed within the immunoglobulin loci are not identical between mice and humans and, in some circumstances, may not be functionally equivalent. Differences between mice and humans in their immunoglobulin loci can still result in abnormalities in humanized mice, particularly when humanizing or manipulating certain portions of endogenous mouse immunoglobulin heavy chain loci. Some modifications at mouse immunoglobulin heavy chain loci are deleterious. Deleterious modifications can include, for example, loss of the ability of the modified mice to mate and produce offspring.

Figure 1B:
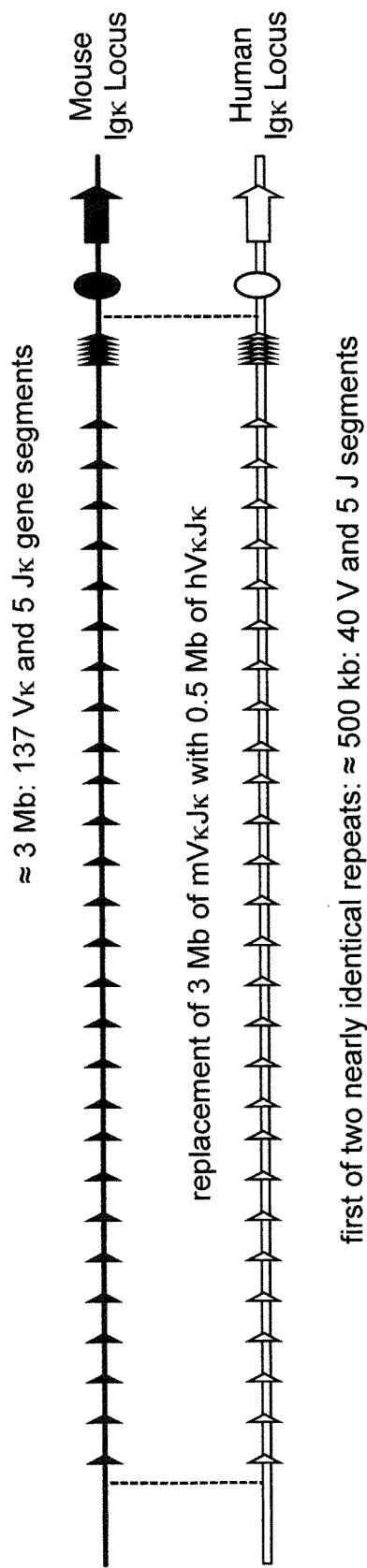
FIG. 1B shows a general illustration, not to scale, of direct genomic replacement of about three megabases (Mb) of a mouse immunoglobulin κ light chain variable gene locus (closed symbols) with about 0.5 megabases (Mb) of the first, or proximal, of two nearly identical repeats of a human immunoglobulin κ light chain variable gene locus (open symbols).

A precise, large-scale, in situ replacement of six megabases of the variable regions of the mouse heavy and light chain immunoglobulin loci ($V_H$-$D_H$-$J_H$ and Vκ-Jκ) with the corresponding 1.4 megabases human genomic sequences was performed, while leaving the flanking mouse sequences intact and functional within the hybrid loci, including all mouse constant chain genes and locus transcriptional control regions (FIG. 1A and FIG. 1B). Specifically, the human $V_H$, $D_H$, $J_H$, Vκ and Jκ gene sequences were introduced through stepwise insertion of 13 chimeric BAC targeting vectors bearing overlapping fragments of the human germline variable loci into mouse ES cells using VELOCIGENE® genetic engineering technology (see, e.g., U.S. Pat. No. 6,586,251 and Valenzuela et al., 2003, High-throughput engineering of the mouse genome coupled with high-resolution expression analysis, *Nat Biotechnol* 21:652-659).

Humanization of the mouse immunoglobulin genes represents the largest genetic modification to the mouse genome to date. While previous efforts with randomly integrated human immunoglobulin transgenes have met with some success (discussed above), direct replacement of the mouse immunoglobulin genes with their human counterparts dramatically increases the efficiency with which fully-human antibodies can be efficiently generated in otherwise normal mice. Further, such mice exhibit a dramatically increased diversity of fully human antibodies that can be obtained after immunization with virtually any antigen, as compared with mice bearing disabled endogenous loci and fully human antibody transgenes. Multiple versions of replaced, humanized loci exhibit completely normal levels of mature and immature B cells, in contrast to mice with randomly integrated human transgenes, which exhibit significantly reduced B cell populations at various stages of differentiation. While efforts to increase the number of human gene segments in human transgenic mice have reduced such defects, the expanded immunoglobulin repertoires have not altogether corrected reductions in B cell populations as compared to wild-type mice.

Notwithstanding the near wild-type humoral immune function observed in mice with replaced immunoglobulin loci (i.e., VELOCIMMUNE® mice), there are other challenges encountered when employing a direct replacement of the immunoglobulin that is not encountered in some approaches that employ randomly integrated transgenes. Differences in the genetic composition of the immunoglobulin loci between mice and humans has lead to the discovery of sequences beneficial for the propagation of mice with replaced immunoglobulin gene segments. Specifically, mouse ADAM genes located within the endogenous immunoglobulin locus are optimally present in mice with replaced immunoglobulin loci, due to their role in fertility.

Genomic Location and Function of Mouse ADAM6

Male mice that lack the ability to express any functional ADAM6 protein surprisingly exhibit a defect in the ability of the mice to mate and to generate offspring. The mice lack the ability to express a functional ADAM6 protein by virtue of a replacement of all or substantially all mouse immunoglobulin variable region gene segments with human variable region gene segments. The loss of ADAM6 function results because the ADAM6 locus is located within a region of the endogenous mouse immunoglobulin heavy chain variable region gene locus, proximal to the 3' end of the $V_H$ gene segment locus that is upstream of the $D_H$ gene segments. In order to breed mice that are homozygous for a replacement of all or substantially all endogenous mouse heavy chain variable gene segments with human heavy chain variable gene segments, it is generally a cumbersome approach to set up males and females that are each homozygous for the replacement and await a productive mating. Successful litters are low in frequency and size. Instead, males heterozygous for the replacement have been employed to mate with females homozygous for the replacement to generate progeny that are heterozygous for the replacement, then breed a homozygous mouse therefrom. The inventors have determined that the likely cause of the loss in fertility in the male mice is the absence in homozygous male mice of a functional ADAM6 protein.

In various aspects, male mice that comprise a damaged (i.e., nonfunctional or marginally functional) ADAM6 gene exhibit a reduction or elimination of fertility. Because in mice (and other rodents) the ADAM6 gene is located in the immunoglobulin heavy chain locus, the inventors have determined that in order to propagate mice, or create and maintain a strain of mice, that comprise a replaced immunoglobulin heavy chain locus, various modified breeding or propagation schemes are employed. The low fertility, or infertility, of male mice homozygous for a replacement of the endogenous immunoglobulin heavy chain variable gene locus renders maintaining such a modification in a mouse strain difficult. In various embodiments, maintaining the strain comprises avoiding infertility problems exhibited by male mice homozygous for the replacement.

In one aspect, a method for maintaining a strain of mouse as described herein is provided. The strain of mouse need not comprise an ectopic ADAM6 sequence, and in various embodiments the strain of mouse is homozygous or heterozygous for a knockout (e.g., a functional knockout) of ADAM6.

The mouse strain comprises a modification of an endogenous immunoglobulin heavy chain locus that results in a reduction or loss in fertility in a male mouse. In one embodiment, the modification comprises a deletion of a regulatory region and/or a coding region of an ADAM6 gene. In a specific embodiment, the modification comprises a modification of an endogenous ADAM6 gene (regulatory and/or coding region) that reduces or eliminates fertility of a male mouse that comprises the modification; in a specific embodiment, the modification reduces or eliminates fertility of a male mouse that is homozygous for the modification.

In one embodiment, the mouse strain is homozygous or heterozygous for a knockout (e.g., a functional knockout) or a deletion of an ADAM6 gene.

In one embodiment, the mouse strain is maintained by isolating from a mouse that is homozygous or heterozygous for the modification a cell, and employing the donor cell in host embryo, and gestating the host embryo and donor cell in a surrogate mother, and obtaining from the surrogate mother a progeny that comprises the genetic modification. In one embodiment, the donor cell is an ES cell. In one embodiment, the donor cell is a pluripotent cell, e.g., an induced pluripotent cell.

In one embodiment, the mouse strain is maintained by isolating from a mouse that is homozygous or heterozygous for the modification a nucleic acid sequence comprising the modification, and introducing the nucleic acid sequence into a host nucleus, and gestating a cell comprising the nucleic acid sequence and the host nucleus in a suitable animal. In one embodiment, the nucleic acid sequence is introduced into a host oocyte embryo.

In one embodiment, the mouse strain is maintained by isolating from a mouse that is homozygous or heterozygous for the modification a nucleus, and introducing the nucleus into a host cell, and gestating the nucleus and host cell in a suitable animal to obtain a progeny that is homozygous or heterozygous for the modification.

In one embodiment, the mouse strain is maintained by employing in vitro fertilization (IVF) of a female mouse (wild-type, homozygous for the modification, or heterozygous for the modification) employing a sperm from a male mouse comprising the genetic modification. In one embodiment, the male mouse is heterozygous for the genetic modification. In one embodiment, the male mouse is homozygous for the genetic modification.

In one embodiment, the mouse strain is maintained by breeding a male mouse that is heterozygous for the genetic modification with a female mouse to obtain progeny that comprises the genetic modification, identifying a male and a female progeny comprising the genetic modification, and employing a male that is heterozygous for the genetic modification in a breeding with a female that is wild-type, homozygous, or heterozygous for the genetic modification to obtain progeny comprising the genetic modification. In one embodiment, the step of breeding a male heterozygous for the genetic modification with a wild-type female, a female heterozygous for the genetic modification, or a female homozygous for the genetic modification is repeated in order to maintain the genetic modification in the mouse strain.

In one aspect, a method is provided for maintaining a mouse strain that comprises a replacement of an endogenous immunoglobulin heavy chain variable gene locus with one or more human immunoglobulin heavy chain sequences, comprising breeding the mouse strain so as to generate heterozygous male mice, wherein the heterozygous male mice are bred to maintain the genetic modification in the strain. In a specific embodiment, the strain is not maintained by any breeding of a homozygous male with a wild-type female, or a female homozygous or heterozygous for the genetic modification.

Figure 12:
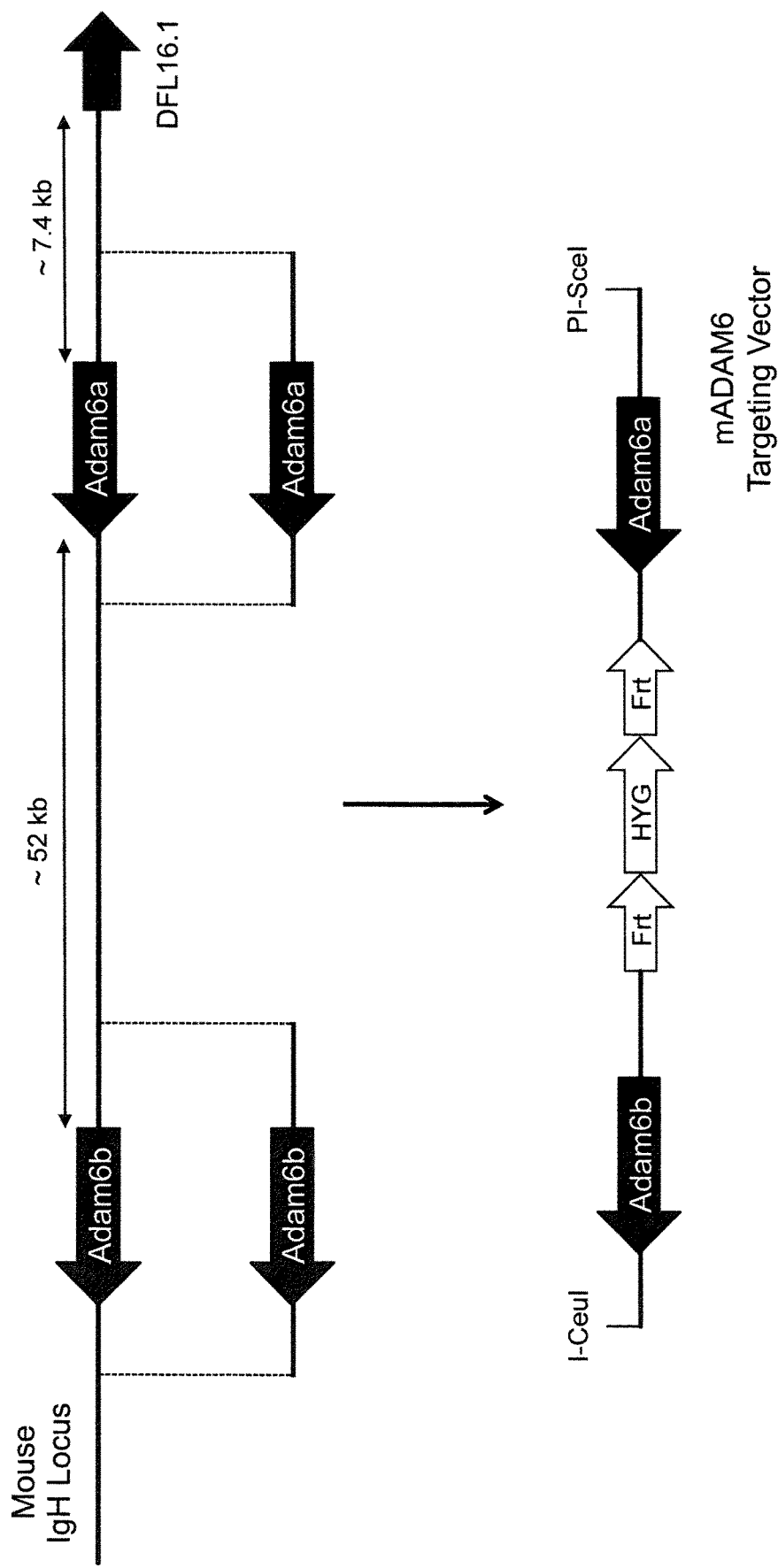
FIG. 12 shows a schematic illustration, not to scale, of mouse ADAM6a and ADAM6b genes in a mouse immunoglobulin heavy chain locus. A targeting vector (mADAM6 Targeting Vector) used for insertion of mouse ADAM6a and ADAM6b into a humanized endogenous heavy chain locus is shown with a selection cassette (HYG: hygromycin) flanked by site-specific recombination sites (Frt) including engineered restriction sites on the 5' and 3' ends.

The ADAM6 protein is a member of the ADAM family of proteins, where ADAM is an acronym for A Disintegrin And Metalloprotease. The ADAM family of proteins is large and diverse, with diverse functions including cell adhesion. Some members of the ADAM family are implicated in spermatogenesis and fertilization. For example, ADAM2 encodes a subunit of the protein fertilin, which is implicated in sperm-egg interactions. ADAM3, or cyritestin, appears necessary for sperm binding to the zona pellucida. The absence of either ADAM2 or ADAM3 results in infertility. It has been postulated that ADAM2, ADAM3, and ADAM6 form a complex on the surface of mouse sperm cells. The human ADAM6 gene, normally found between human $V_H$ gene segments $V_H1$-2 and $V_H6$-1, appears to be a pseudogene (FIG. 12). In mice, there are two ADAM6 genes—ADAM6a and ADAM6b—that are found in an intergenic region between mouse $V_H$ and $D_H$ gene segments, and in the mouse the ADAM6a and ADAM6b genes are oriented in opposite transcriptional orientation to that of the surrounding immunoglobulin gene segments (FIG. 12). In mice, a functional ADAM6 locus is apparently required for normal fertilization. A functional ADAM6 locus or sequence, then, refers to an ADAM6 locus or sequence that can complement, or rescue, the drastically reduced fertilization exhibited in male mice with missing or nonfunctional endogenous ADAM6 loci.

The position of the intergenic sequence in mice that encodes ADAM6a and ADAM6b renders the intergenic sequence susceptible to modification when modifying an endogenous mouse heavy chain. When $V_H$ gene segments are deleted or replaced, or when $D_H$ gene segments are deleted or replaced, there is a high probability that a resulting mouse will exhibit a severe deficit in fertility. In order to compensate for the deficit, the mouse is modified to include a nucleotide sequence that encodes a protein that will complement the loss in ADAM6 activity due to a modification of the endogenous mouse ADAM6 locus. In various embodiments, the complementing nucleotide sequence is one that encodes a mouse ADAM6a, a mouse ADAM6b, or a homolog or ortholog or functional fragment thereof that rescues the fertility deficit.

The nucleotide sequence that rescues fertility can be placed at any suitable position. It can be placed in the intergenic region, or in any suitable position in the genome (i.e., ectopically). In one embodiment, the nucleotide sequence can be introduced into a transgene that randomly integrates into the mouse genome. In one embodiment, the sequence can be maintained episomally, that is, on a separate nucleic acid rather than on a mouse chromosome. Suitable positions include positions that are transcriptionally permissive or active, e.g., a ROSA26 locus (Zambrowicz et al., 1997, *PNAS USA* 94:3789-3794), a BT-5 locus (Michael et al., 1999, *Mech. Dev.* 85:35-47), or an Oct4 locus (Wallace et al., 2000, *Nucleic Acids Res.* 28:1455-1464). Targeting nucleotide sequences to transcriptionally active loci are described, e.g., in U.S. Pat. No. 7,473,557, herein incorporated by reference.

Alternatively, the nucleotide sequence that rescues fertility can be coupled with an inducible promoter so as to facilitate optimal expression in the appropriate cells and/or tissues, e.g., reproductive tissues. Exemplary inducible promoters include promoters activated by physical (e.g., heat shock promoter) and/or chemical means (e.g., IPTG or Tetracycline).

Further, expression of the nucleotide sequence can be linked to other genes so as to achieve expression at specific stages of development or within specific tissues. Such expression can be achieved by placing the nucleotide sequence in operable linkage with the promoter of a gene expressed at a specific stage of development. For example, immunoglobulin sequences from one species engineered into the genome of a host species are place in operable linkage with a promoter sequence of a CD19 gene (a B cell specific gene) from the host species. B cell-specific expression at precise developmental stages when immunoglobulins are expressed is achieved.

Yet another method to achieve robust expression of an inserted nucleotide sequence is to employ a constitutive promoter. Exemplary constitutive promoters include SV40, CMV, UBC, EF1A, PGK and CAGG. In a similar fashion, the desired nucleotide sequence is placed in operable linkage with a selected constitutive promoter, which provides high level of expression of the protein(s) encoded by the nucleotide sequence.

The term "ectopic" is intended to include a displacement, or a placement at a position that is not normally encountered in nature (e.g., placement of a nucleic acid sequence at a position that is not the same position as the nucleic acid sequence is found in a wild-type mouse). The term, in various embodiments, is used in the sense of its object being out of its normal, or proper, position. For example, the phrase "an ectopic nucleotide sequence encoding . . . " refers to a nucleotide sequence that appears at a position at which it is not normally encountered in the mouse. For example, in the case of an ectopic nucleotide sequence encoding a mouse ADAM6 protein (or an ortholog or homolog or fragment thereof that provides the same or similar fertility benefit on male mice), the sequence can be placed at a different position in the mouse's genome than is normally found in a wild-type mouse. In such cases, novel sequence junctions of mouse sequence will be created by placing the sequence at a different position in the mouse's genome than in a wild-type mouse. A functional homolog or ortholog of mouse ADAM6 is a sequence that confers a rescue of fertility loss (e.g., loss of the ability of a male mouse to generate offspring by mating) that is observed in an ADAM6$^{-/-}$ mouse. Functional homologs or orthologs include proteins that have at least about 89% identity or more, e.g., up to 99% identity, to the amino acid sequence of ADAM6a and/or to the amino acid sequence of ADAM6b, and that can complement, or rescue ability to successfully mate, of a mouse that has a genotype that includes a deletion or knockout of ADAM6a and/or ADAM6b.

The ectopic position can be anywhere (e.g., as with random insertion of a transgene containing a mouse ADAM6 sequence), or can be, e.g., at a position that approximates (but is not precisely the same as) its location in a wild-type mouse (e.g., in a modified endogenous mouse immunoglobulin locus, but either upstream or downstream of its natural position, e.g., within a modified immunoglobulin locus but between different gene segments, or at a different position in a mouse V-D intergenic sequence). One example of an ectopic placement is placement within a humanized immunoglobulin heavy chain locus. For example, a mouse comprising a replacement of one or more endogenous $V_H$ gene segments with human $V_H$ gene segments, wherein the replacement removes an endogenous ADAM6 sequence, can be engineered to have a mouse ADAM6 sequence located within a sequence that contains the human $V_H$ gene segments. The resulting modification would generate a (ectopic) mouse ADAM6 sequence within a human gene sequence, and the (ectopic) placement of the mouse ADAM6 sequence within the human gene sequence can approximate the position of the human ADAM6 pseudogene (i.e., between two V segments) or can approximate the position of the mouse ADAM6 sequence (i.e., within the V-D intergenic region). The resulting sequence junctions created by the joining of a (ectopic) mouse ADAM6 sequence within or adjacent to a human gene sequence (e.g., an immunoglobulin gene sequence) within the germline of the mouse would be novel as compared to the same or similar position in the genome of a wild-type mouse.

In various embodiments, non-human animals are provided that lack an ADAM6 or ortholog or homolog thereof, wherein the lack renders the non-human animal infertile, or substantially reduces fertility of the non-human animal. In various embodiments, the lack of ADAM6 or ortholog or homolog thereof is due to a modification of an endogenous immunoglobulin heavy chain locus. A substantial reduction in fertility is, e.g., a reduction in fertility (e.g., breeding frequency, pups per litter, litters per year, etc.) of about 50%, 60%, 70%, 80%, 90%, or 95% or more. In various embodiments, the non-human animals are supplemented with a mouse ADAM6 gene or ortholog or homolog or functional fragment thereof that is functional in a male of the non-human animal, wherein the supplemented ADAM6 gene or ortholog or homolog or functional fragment thereof rescues the reduction in fertility in whole or in substantial part. A rescue of fertility in substantial part is, e.g., a restoration of fertility such that the non-human animal exhibits a fertility that is at least 70%, 80%, or 90% or more as compared with an unmodified (i.e., an animal without a modification to the ADAM6 gene or ortholog or homolog thereof) heavy chain locus.

The sequence that confers upon the genetically modified animal (i.e., the animal that lacks a functional ADAM6 or ortholog or homolog thereof, due to, e.g., a modification of a immunoglobulin heavy chain locus) is, in various embodiments, selected from an ADAM6 gene or ortholog or homolog thereof. For example, in a mouse, the loss of ADAM6 function is rescued by adding, in one embodiment, a mouse ADAM6 gene. In one embodiment, the loss of ADAM6 function in the mouse is rescued by adding an ortholog or homolog of a closely related specie with respect to the mouse, e.g., a rodent, e.g., a mouse of a different strain or species, a rat of any species, a rodent; wherein the addition of the ortholog or homolog to the mouse rescues the loss of fertility due to loss of ADAM6 function or loss of an ADAM6 gene. Orthologs and homologs from other species, in various embodiments, are selected from a phylogenetically related species and, in various embodiments, exhibit a percent identity with the endogenous ADAM6 (or ortholog) that is about 80% or more, 85% or more, 90% or more, 95% or more, 96% or more, or 97% or more; and that rescue ADAM6-related or (in a non-mouse) ADAM6 ortholog-related loss of fertility. For example, in a genetically modified male rat that lacks ADAM6 function (e.g., a rat with an endogenous immunoglobulin heavy chain variable region replaced with a human immunoglobulin heavy chain variable region, or a knockout in the rat immunoglobulin heavy chain region), loss of fertility in the rat is rescued by addition of a rat ADAM6 or, in some embodiments, an ortholog of a rat ADAM6 (e.g., an ADAM6 ortholog from another rat strain or species, or, in one embodiment, from a mouse).

Thus, in various embodiments, genetically modified animals that exhibit no fertility or a reduction in fertility due to modification of a nucleic acid sequence encoding an ADAM6 protein (or ortholog or homolog thereof) or a regulatory region operably linked with the nucleic acid sequence, comprise a nucleic acid sequence that complements, or restores, the loss in fertility where the nucleic acid sequence that complements or restores the loss in fertility is from a different strain of the same species or from a phylogenetically related species. In various embodiments, the complementing nucleic acid sequence is an ADAM6 ortholog or homolog or functional fragment thereof. In various embodiments, the complementing ADAM6 ortholog or homolog or functional fragment thereof is from a non-human animal that is closely related to the genetically modified animal having the fertility defect. For example, where the genetically modified animal is a mouse of a particular strain, an ADAM6 ortholog or homolog or functional fragment thereof can be obtained from a mouse of another strain, or a mouse of a related species. In one embodiment, where the genetically modified animal comprising the fertility defect is of the order Rodentia, the ADAM6 ortholog or homolog or functional fragment thereof is from another animal of the order Rodentia. In one embodiment, the genetically modified animal comprising the fertility defect is of a suborder Myomoropha (e.g., jerboas, jumping mice, mouse-like hamsters, hamsters, New World rats and mice, voles, true mice and rats, gerbils, spiny mice, crested rats, climbing mice, rock mice, white-tailed rats, malagasy rats and mice, spiny dormice, mole rats, bamboo rats, zokors), and the ADAM6 ortholog or homolog or functional fragment thereof is selected from an animal of order Rodentia, or of the suborder Myomorpha.

In one embodiment, the genetically modified animal is from the superfamily Dipodoidea, and the ADAM6 ortholog or homolog or functional fragment thereof is from the superfamily Muroidea. In one embodiment, the genetically modified animal is from the superfamily Muroidea, and the ADAM6 ortholog or homolog or functional fragment thereof is from the superfamily Dipodoidea.

In one embodiment, the genetically modified animal is a rodent. In one embodiment, the rodent is selected from the superfamily Muroidea, and the ADAM6 ortholog or homolog is from a different species within the superfamily Muroidea. In one embodiment, the genetically modified animal is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors); and the ADAM6 ortholog or homolog is selected from a different species of the same family. In a specific embodiment, the genetically modified rodent is selected from a true mouse or rat (family Muridae), and the ADAM6 ortholog or homolog is from a species selected from a gerbil, spiny mouse, or crested rat. In one embodiment, the genetically modified mouse is from a member of the family Muridae, and the ADAM6 ortholog or homolog is from a different species of the family Muridae. In a specific embodiment, the genetically modified rodent is a mouse of the family Muridae, and the ADAM6 ortholog or homolog is from a rat, gerbil, spiny mouse, or crested rat of the family Muridae.

In various embodiments, one or more rodent ADAM6 orthologs or homologs or functional fragments thereof of a rodent in a family restores fertility to a genetically modified rodent of the same family that lacks an ADAM6 ortholog or homolog (e.g., Cricetidae (e.g., hamsters, New World rats and mice, voles); Muridae (e.g., true mice and rats, gerbils, spiny mice, crested rats)).

In various embodiments, ADAM6 orthologs, homologs, and fragments thereof are assessed for functionality by ascertaining whether the ortholog, homolog, or fragment restores fertility to a genetically modified male non-human animal that lacks ADAM6 activity (e.g., a rodent, e.g., a mouse or rat, that comprises a knockout of ADAM6 or its ortholog). In various embodiments, functionality is defined as the ability of a sperm of a genetically modified animal lacking an endogenous ADAM6 or ortholog or homolog thereof to migrate an oviduct and fertilize an ovum of the same specie of genetically modified animal.

In various aspects, mice that comprise deletions or replacements of the endogenous heavy chain variable region locus or portions thereof can be made that contain an ectopic nucleotide sequence that encodes a protein that confers similar fertility benefits to mouse ADAM6 (e.g., an ortholog or a homolog or a fragment thereof that is functional in a male mouse). The ectopic nucleotide sequence can include a nucleotide sequence that encodes a protein that is an ADAM6 homolog or ortholog (or fragment thereof) of a different mouse strain or a different species, e.g., a different rodent species, and that confers a benefit in fertility, e.g., increased number of litters over a specified time period, and/or increased number of pups per litter, and/or the ability of a sperm cell of a male mouse to traverse through a mouse oviduct to fertilize a mouse egg.

In one embodiment, the ADAM6 is a homolog or ortholog that is at least 89% to 99% identical to a mouse ADAM6 protein (e.g., at least 89% to 99% identical to mouse ADAM6a or mouse ADAM6b). In one embodiment, the ectopic nucleotide sequence encodes one or more proteins independently selected from a protein at least 89% identical to mouse ADAM6a, a protein at least 89% identical to mouse ADAM6b, and a combination thereof. In one embodiment, the homolog or ortholog is a rat, hamster, mouse, or guinea pig protein that is or is modified to be about 89% or more identical to mouse ADAM6a and/or mouse ADAM6b. In one embodiment, the homolog or ortholog is or is at least 90%, 91%, 92%, 93%, 94%, 95%, 96%, 97%, 98%, or 99% identical to a mouse ADAM6a and/or mouse ADAM6b.

Ectopic ADAM6 in Humanized Heavy Chain Mice

Developments in gene targeting, e.g., the development of bacterial artificial chromosomes (BACs), now enable the recombination of relatively large genomic fragments. BAC engineering has allowed for the ability to make large deletions, and large insertions, into mouse ES cells.

Mice that make human antibodies have been available for some time now. Although they represent an important advance in the development of human therapeutic antibodies, these mice display a number of significant abnormalities that limit their usefulness. For example, they display compromised B cell development. The compromised development may be due to a variety of differences between the transgenic mice and wild-type mice.

Human antibodies might not optimally interact with mouse pre B cell or B cell receptors on the surface of mouse cells that signal for maturation, proliferation, or survival during clonal selection. Fully human antibodies might not optimally interact with a mouse Fc receptor system; mice express Fc receptors that do not display a one-to-one correspondence with human Fc receptors. Finally, various mice that make fully human antibodies do not include all genuine mouse sequences, e.g., downstream enhancer elements and other locus control elements, which may be required for wild-type B cell development.

Mice that make fully human antibodies generally comprise endogenous immunoglobulin loci that are disabled in some way, and human transgenes that comprise variable and constant immunoglobulin gene segments are introduced into a random location in the mouse genome. As long as the endogenous locus is sufficiently disabled so as not to rearrange gene segments to form a functional immunoglobulin gene, the goal of making fully human antibodies in such a mouse can be achieved—albeit with compromised B cell development.

Although compelled to make fully human antibodies from the human transgene locus, generating human antibodies in a mouse is apparently an unfavored process. In some mice, the process is so unfavored as to result in formation of chimeric human variable/mouse constant heavy chains (but not light chains) through the mechanism of trans-switching. By this mechanism, transcripts that encode fully human antibodies undergo isotype switching in trans from the human isotype to a mouse isotype. The process is in trans, because the fully human transgene is located apart from the endogenous locus that retains an undamaged copy of a mouse heavy chain constant region gene. Although in such mice trans-switching is readily apparent the phenomenon is still insufficient to rescue B cell development, which remains frankly impaired. In any event, trans-switched antibodies made in such mice retain fully human light chains, since the phenomenon of trans-switching apparently does not occur with respect to light chains; trans-switching presumably relies on switch sequences in endogenous loci used (albeit differently) in normal isotype switching in cis. Thus, even when mice engineered to make fully human antibodies select a trans-switching mechanism to make antibodies with mouse constant regions, the strategy is still insufficient to rescue normal B cell development.

A primary concern in making antibody-based human therapeutics is making a sufficiently large diversity of human immunoglobulin variable region sequences to identify useful variable domains that specifically recognize particular epitopes and bind them with a desirable affinity, usually—but not always—with high affinity. Prior to the development of VELOCIMMUNE® mice (described herein), there was no indication that mice expressing human variable regions with mouse constant regions would exhibit any significant differences from mice that made human antibodies from a transgene. That supposition, however, was incorrect.

VELOCIMMUNE® mice, which contain a precise replacement of mouse immunoglobulin variable regions with human immunoglobulin variable regions at the endogenous mouse loci, display a surprising and remarkable similarity to wild-type mice with respect to B cell development. In a surprising and stunning development, VELOCIMMUNE® mice displayed an essentially normal, wild-type response to immunization that differed only in one significant respect from wild-type mice—the variable regions generated in response to immunization are fully human.

VELOCIMMUNE® mice contain a precise, large-scale replacement of germline variable regions of mouse immunoglobulin heavy chain (IgH) and immunoglobulin light chain (e.g., κ light chain, Igκ) with corresponding human immunoglobulin variable regions, at the endogenous loci. In total, about six megabases of mouse loci are replaced with about 1.5 megabases of human genomic sequence. This precise replacement results in a mouse with hybrid immunoglobulin loci that make heavy and light chains that have a human variable regions and a mouse constant region. The precise replacement of mouse $V_H$-$D_H$-$J_H$ and Vκ-Jκ segments leave flanking mouse sequences intact and functional at the hybrid immunoglobulin loci. The humoral immune system of the mouse functions like that of a wild-type mouse. B cell development is unhindered in any significant respect and a rich diversity of human variable regions is generated in the mouse upon antigen challenge.

VELOCIMMUNE® mice are possible because immunoglobulin gene segments for heavy and κ light chains rearrange similarly in humans and mice, which is not to say that their loci are the same or even nearly so—clearly they are not. However, the loci are similar enough that humanization of the heavy chain variable gene locus can be accomplished by replacing about three million base pairs of contiguous mouse sequence that contains all the $V_H$, $D_H$, and $J_H$ gene segments with about one million bases of contiguous human genomic sequence covering basically the equivalent sequence from a human immunoglobulin locus.

In some embodiments, further replacement of certain mouse constant region gene sequences with human gene sequences (e.g., replacement of mouse $C_H1$ sequence with human $C_H1$ sequence, and replacement of mouse $C_L$ sequence with human $C_L$ sequence) results in mice with hybrid immunoglobulin loci that make antibodies that have human variable regions and partly human constant regions, suitable for, e.g., making fully human antibody fragments, e.g., fully human Fab's. Mice with hybrid immunoglobulin loci exhibit normal variable gene segment rearrangement, normal somatic hypermutation frequencies, and normal class switching. These mice exhibit a humoral immune system that is indistinguishable from wild type mice, and display normal cell populations at all stages of B cell development and normal lymphoid organ structures—even where the mice lack a full repertoire of human variable region gene segments. Immunizing these mice results in robust humoral responses that display a wide diversity of variable gene segment usage.

The precise replacement of mouse germline variable region gene segments allows for making mice that have partly human immunoglobulin loci. Because the partly human immunoglobulin loci rearrange, hypermutate, and class switch normally, the partly human immunoglobulin loci generate antibodies in a mouse that comprise human variable regions. Nucleotide sequences that encode the variable regions can be identified and cloned, then fused (e.g., in an in vitro system) with any sequences of choice, e.g., any immunoglobulin isotype suitable for a particular use, resulting in an antibody or antigen-binding protein derived wholly from human sequences.

Large-scale humanization by recombineering methods were used to modify mouse embryonic stem (ES) cells to precisely replace up to three megabases of the mouse heavy chain immunoglobulin locus that included essentially all of the mouse $V_H$, $D_H$, and $J_H$ gene segments with equivalent human gene segments with up to a one megabase human genomic sequence containing some or essentially all human $V_H$, $D_H$, and $J_H$ gene segments. Up to a one-half megabase segment of the human genome comprising one of two repeats encoding essentially all human Vκ and Jκ gene segments was used to replace a three megabase segment of the mouse immunoglobulin κ light chain locus containing essentially all of the mouse Vκ and Jκ gene segments.

Mice with such replaced immunoglobulin loci can comprise a disruption or deletion of the endogenous mouse ADAM6 locus, which is normally found between the 3'-most $V_H$ gene segment and the 5'-most $D_H$ gene segment at the mouse immunoglobulin heavy chain locus. Disruption in this region can lead to reduction or elimination of functionality of the endogenous mouse ADAM6 locus. If the 3'-most $V_H$ gene segments of the human heavy chain repertoire are used in a replacement, an intergenic region containing a pseudogene that appears to be a human ADAM6 pseudogene is present between these $V_H$ gene segments, i.e., between human $V_H$1-2 and $V_H$1-6. However, male mice that comprise this human intergenic sequence exhibit a reduction in fertility.

Mice are described that comprise the replaced loci as described above, and that also comprise an ectopic nucleic acid sequence encoding a mouse ADAM6, where the mice exhibit essentially normal fertility. In one embodiment, the ectopic nucleic acid sequence comprises a mouse ADAM6a and/or a mouse ADAM6b sequence or functional fragments thereof placed between a human $V_H$1-2 and a human $V_H$6-1 at a modified endogenous heavy chain locus. In one embodiment, the ectopic nucleic acid sequence is SEQ ID NO:3, placed between a human $V_H$1-2 and a human $V_H$6-1 at a modified endogenous heavy chain locus. The direction of transcription of the ADAM6 genes of SEQ ID NO:3 are opposite with respect to the direction of transcription of the surrounding human $V_H$ gene segments. Although examples herein show rescue of fertility by placing the ectopic sequence between the indicated human $V_H$ gene segments, skilled persons will recognize that placement of the ectopic sequence at any suitable transcriptionally-permissive locus in the mouse genome (or even extrachromosomally) will be expected to similarly rescue fertility in a male mouse.

The phenomenon of complementing a mouse that lacks a functional ADAM6 locus with an ectopic sequence that comprises a mouse ADAM6 gene or ortholog or homolog or functional fragment thereof is a general method that is applicable to rescuing any mice with nonfunctional or minimally functional endogenous ADAM6 loci. Thus, a great many mice that comprise an ADAM6-disrupting modification of the immunoglobulin heavy chain locus can be rescued with the compositions and methods of the invention. Accordingly, the invention comprises mice with a wide variety of modifications of immunoglobulin heavy chain loci that compromise endogenous ADAM6 function. Some (non-limiting) examples are provided in this description. In addition to the VELOCIMMUNE® mice described, the compositions and methods related to ADAM6 can be used in a great many applications, e.g., when modifying a heavy chain locus in a wide variety of ways.

In one aspect, a mouse is provided that comprises an ectopic ADAM6 sequence that encodes a functional ADAM6 protein (or ortholog or homolog or functional fragment thereof), a replacement of all or substantially all mouse $V_H$ gene segments with one or more human $V_H$ gene segments, a replacement of all or substantially all mouse $D_R$ gene segments and $J_H$ gene segments with human $D_H$ and human $J_H$ gene segments; wherein the mouse lacks a $C_H1$ and/or hinge region. In one embodiment, the mouse makes a single variable domain binding protein that is a dimer of immunoglobulin chains selected from: (a) human $V_H$-mouse $C_H1$-mouse $C_H2$-mouse $C_H3$; (b) human $V_H$-mouse hinge-mouse $C_H2$-mouse $C_H3$; and, (c) human $V_H$-mouse $C_H2$-mouse $C_H3$.

In one aspect, the nucleotide sequence that rescues fertility is placed within a human immunoglobulin heavy chain variable region sequence (e.g., between human $V_H1$-2 and $V_H1$-6 gene segments) in a mouse that has a replacement of one or more mouse immunoglobulin heavy chain variable gene segments (m$V_H$'s, m$D_H$'s, and/or m$J_H$'s) with one or more human immunoglobulin heavy chain variable gene segments (h$V_H$'s, h$D_H$'s, and/or h$J_H$'s), and the mouse further comprises a replacement of one or more mouse immunoglobulin κ light chain variable gene segments (m$V_κ$'s and/or m$J_κ$'s) with one or more human immunoglobulin κ light chain variable gene segments (h$V_κ$'s and/or h$J_κ$'s).

In one embodiment, the one or more mouse immunoglobulin heavy chain variable gene segments comprises about three megabases of the mouse immunoglobulin heavy chain locus. In one embodiment, the one or more mouse immunoglobulin heavy chain variable gene segments comprises at least 89 $V_H$ gene segments, at least 13 $D_H$ gene segments, at least four $J_H$ gene segments or a combination thereof of the mouse immunoglobulin heavy chain locus. In one embodiment, the one or more human immunoglobulin heavy chain variable gene segments comprises about one megabase of a human immunoglobulin heavy chain locus. In one embodiment, the one or more human immunoglobulin heavy chain variable gene segments comprises at least 80 $V_H$ gene segments, at least 27 $D_H$ gene segments, at least six $J_H$ gene segments or a combination thereof of a human immunoglobulin heavy chain locus.

In one embodiment, the one or more mouse immunoglobulin κ light chain variable gene segments comprises about three megabases of the mouse immunoglobulin κ light chain locus. In one embodiment, the one or more mouse immunoglobulin κ light chain variable gene segments comprises at least 137 Vκ gene segments, at least five Jκ gene segments or a combination thereof of the mouse immunoglobulin κ light chain locus. In one embodiment, the one or more human immunoglobulin κ light chain variable gene segments comprises about one-half megabase of a human immunoglobulin κ light chain locus. In a specific embodiment, the one or more human immunoglobulin κ light chain variable gene segments comprises the proximal repeat (with respect to the immunoglobulin κ constant region) of a human immunoglobulin κ light chain locus. In one embodiment, the one or more human immunoglobulin κ light chain variable gene segments comprises at least 40Vκ gene segments, at least five Jκ gene segments or a combination thereof of a human immunoglobulin κ light chain locus.

In one embodiment, the nucleotide sequence is place between two human immunoglobulin gene segments. In a specific embodiment, the two human immunoglobulin gene segments are heavy chain gene segments. In one embodiment, the nucleotide sequence is placed between a human $V_H1$-2 gene segment and a human $V_H1$-6 gene segment in a VELOCIMMUNE® mouse (U.S. Pat. Nos. 6,596,541 and 7,105,348, incorporated herein by reference). In one embodiment, the VELOCIMMUNE® mouse so modified comprises a replacement of mouse immunoglobulin heavy chain variable gene segments with at least 80 human $V_H$ gene segments, 27 human $D_H$ gene segments and six human $J_H$ gene segments, and a replacement of mouse immunoglobulin κ light chain variable gene segments with at least 40 human Vκ gene segments and five human Jκ gene segments.

In one aspect, a functional mouse ADAM6 locus (or ortholog or homolog or functional fragment thereof) is present in the midst of human $V_H$ gene segments that replace endogenous mouse $V_H$ gene segments. In one embodiment, at least 89 mouse $V_H$ gene segments are removed and replaced with one or more human $V_H$ gene segments, and the mouse ADAM6 locus is present immediately adjacent to the 3' end of the human $V_H$ gene segments, or between two human $V_H$ gene segments. In a specific embodiment, the mouse ADAM6 locus is present between two $V_H$ gene segments within about 20 kilo bases (kb) to about 40 kilo bases (kb) of the 3' terminus of the inserted human $V_H$ gene segments. In a specific embodiment, the mouse ADAM6 locus is present between two $V_H$ gene segments within about 29 kb to about 31 kb of the 3' terminus of the inserted human $V_H$ gene segments. In a specific embodiment, the mouse ADAM6 locus is present within about 30 kb of the 3' terminus of the inserted human $V_H$ gene segments. In a specific embodiment, the mouse ADAM6 locus is present within about 30,184 bp of the 3' terminus of the inserted human VH gene segments. In a specific embodiment, the replacement includes human $V_H$ gene segments $V_H1$-2 and $V_H6$-1, and the mouse ADAM6 locus is present downstream of the $V_H1$-2 gene segment and upstream of the $V_H6$-1 gene segment. In a specific embodiment, the mouse ADAM6 locus is present between a human $V_H1$-2 gene segment and a human $V_H6$-1 gene segment, wherein the 5' end of the mouse ADAM6 locus is about 13,848 bp from the 3' terminus of the human $V_H1$-2 gene segment and the 3' end of the ADAM6 locus is about 29,737 bp 5' of the human $V_H6$-1 gene segment. In a specific embodiment, the mouse ADAM6 locus comprises SEQ ID NO:3 or a fragment thereof that confers ADAM6 function within cells of the mouse. In a specific embodiment, the arrangement of human $V_H$ gene segments is then the following (from upstream to downstream with respect to direction of transcription of the human $V_H$ gene segments): human $V_H1$-2-mouse ADAM6 locus-human $V_H6$-1. In a specific embodiment, the ADAM6 pseudogene between human $V_H1$-2 and human $V_H6$-1 is replaced with the mouse ADAM6 locus. In one embodiment, the orientation of one or more of mouse ADAM6a and mouse ADAM6b of the mouse ADAM6 locus is opposite with respect to direction of transcription as compared with the orientation of the human $V_H$ gene segments. Alternatively, the mouse ADAM6 locus is present in the intergenic region between the 3'-most human $V_H$ gene segment and the 5'-most $D_H$ gene segment. This can be the case whether the 5'-most $D_H$ segment is mouse or human.

Similarly, a mouse modified with one or more human $V_L$ gene segments (e.g., Vκ or Vλ segments) replacing all or substantially all endogenous mouse $V_H$ gene segments can be modified so as to either maintain the endogenous mouse ADAM6 locus, as described above, e.g., by employing a targeting vector having a downstream homology arm that includes a mouse ADAM6 locus or functional fragment thereof, or to replace a damaged mouse ADAM6 locus with an ectopic sequence positioned between two human $V_L$ gene segments or between the human $V_L$ gene segments and a $D_H$ gene segment (whether human or mouse, e.g., Vλ+m/h$D_H$), or a J gene segment (whether human or mouse, e.g., Vκ+$J_H$). In one embodiment, the replacement includes two or more human $V_L$ gene segments, and the mouse ADAM6 locus or functional fragment thereof is present between the two 3'-most $V_L$ gene segments. In a specific embodiment, the arrangement of human $V_L$ gene segments is then the following (from upstream to downstream with respect to direction of transcription of the human gene segments): human $V_L$3'-1-mouse ADAM6 locus-human $V_L$3'. In one embodiment, the orientation of one or more of mouse ADAM6a and mouse ADAM6b of the mouse ADAM6 locus is opposite with respect to direction of transcription as compared with the orientation of the human $V_L$ gene segments. Alternatively, the mouse ADAM6 locus is present in the intergenic region between the 3'-most human $V_L$ gene segment and the 5'-most $D_H$ gene segment. This can be the case whether the 5'-most $D_H$ segment is mouse or human.

In one aspect, a mouse is provided with a replacement of one or more endogenous mouse $V_H$ gene segments, and that comprises at least one endogenous mouse $D_H$ gene segment. In such a mouse, the modification of the endogenous mouse $V_H$ gene segments can comprise a modification of one or more of the 3'-most $V_H$ gene segments, but not the 5'-most $D_H$ gene segment, where care is taken so that the modification of the one or more 3'-most $V_H$ gene segments does not disrupt or render the endogenous mouse ADAM6 locus nonfunctional. For example, in one embodiment the mouse comprises a replacement of all or substantially all endogenous mouse $V_H$ gene segments with one or more human $V_H$ gene segments, and the mouse comprises one or more endogenous $D_H$ gene segments and a functional endogenous mouse ADAM6 locus.

In another embodiment, the mouse comprises the modification of endogenous mouse 3'-most $V_H$ gene segments, and a modification of one or more endogenous mouse $D_H$ gene segments, and the modification is carried out so as to maintain the integrity of the endogenous mouse ADAM6 locus to the extent that the endogenous ADAM6 locus remains functional. In one example, such a modification is done in two steps: (1) replacing the 3'-most endogenous mouse $V_H$ gene segments with one or more human $V_H$ gene segments employing a targeting vector with an upstream homology arm and a downstream homology arm wherein the downstream homology arm includes all or a portion of a functional mouse ADAM6 locus; (2) then replacing endogenous mouse $D_H$ gene segment with a targeting vector having an upstream homology arm that includes a all or a functional portion of a mouse ADAM6 locus.

In various aspects, employing mice that contain an ectopic sequence that encodes a mouse ADAM6 protein or an ortholog or homolog or functional homolog thereof are useful where modifications disrupt the function of endogenous mouse ADAM6. The probability of disrupting endogenous mouse ADAM6 function is high when making modifications to mouse immunoglobulin loci, in particular when modifying mouse immunoglobulin heavy chain variable regions and surrounding sequences. Therefore, such mice provide particular benefit when making mice with immunoglobulin heavy chain loci that are deleted in whole or in part, are humanized in whole or in part, or are replaced (e.g., with Vκ or Vλ sequences) in whole or in part. Methods for making the genetic modifications described for the mice described below are known to those skilled in the art.

Mice containing an ectopic sequence encoding a mouse ADAM6 protein, or a substantially identical or similar protein that confers the fertility benefits of a mouse ADAM6 protein, are particularly useful in conjunction with modifications to a mouse immunoglobulin heavy chain variable gene locus that disrupt or delete the endogenous mouse ADAM6 sequence. Although primarily described in connection with mice that express antibodies with human variable regions and mouse constant regions, such mice are useful in connection with any genetic modifications that disrupt endogenous mouse ADAM6 genes. Persons of skill will recognize that this encompasses a wide variety of genetically modified mice that contain modifications of mouse immunoglobulin heavy chain variable gene loci. These include, for example, mice with a deletion or a replacement of all or a portion of mouse immunoglobulin heavy chain gene segments, regardless of other modifications. Non-limiting examples are described below.

In some aspects, genetically modified mice are provided that comprise an ectopic mouse, rodent, or other ADAM6 gene (or ortholog or homolog or fragment) functional in a mouse, and one or more human immunoglobulin variable and/or constant region gene segments. In various embodiments, other ADAM6 gene orthologs or homologs or fragments functional in a mouse may include sequences from bovine, canine, primate, rabbit or other non-human sequences.

In one aspect, a mouse is provided that comprises an ectopic ADAM6 sequence that encodes a functional ADAM6 protein, a replacement of all or substantially all mouse $V_H$ gene segments with one or more human $V_H$ gene segments; a replacement of all or substantially all mouse $D_H$ gene segments with one or more human $D_H$ gene segments; and a replacement of all or substantially all mouse $J_H$ gene segments with one or more human $J_H$ gene segments.

In one embodiment, the mouse further comprises a replacement of a mouse $C_H1$ nucleotide sequence with a human $C_H1$ nucleotide sequence. In one embodiment, the mouse further comprises a replacement of a mouse hinge nucleotide sequence with a human hinge nucleotide sequence. In one embodiment, the mouse further comprises a replacement of an immunoglobulin light chain variable locus ($V_L$ and $J_L$) with a human immunoglobulin light chain variable locus. In one embodiment, the mouse further comprises a replacement of a mouse immunoglobulin light chain constant region nucleotide sequence with a human immunoglobulin light chain constant region nucleotide sequence. In a specific embodiment, the $V_L$, $J_L$, and $C_L$ are immunoglobulin κ light chain sequences. In a specific embodiment, the mouse comprises a mouse $C_H2$ and a mouse $C_H3$ immunoglobulin constant region sequence fused with a human hinge and a human $C_H1$ sequence, such that the mouse immunoglobulin loci rearrange to form a gene that encodes a binding protein comprising (a) a heavy chain that has a human variable region, a human $C_H1$ region, a human hinge region, and a mouse $C_H2$ and a mouse $C_H3$ region; and (b) a gene that encodes an immunoglobulin light chain that comprises a human variable domain and a human constant region.

In one aspect, a mouse is provided that comprises an ectopic ADAM6 sequence that encodes a functional ADAM6 protein, a replacement of all or substantially all mouse $V_H$ gene segments with one or more human $V_L$ gene segments, and optionally a replacement of all or substantially all $D_H$ gene segments and/or $J_H$ gene segments with one or more human $D_H$ gene segments and/or human $J_H$ gene segments, or optionally a replacement of all or substantially all $D_H$ gene segments and $J_H$ gene segments with one or more human $J_L$ gene segments.

In one embodiment, the mouse comprises a replacement of all or substantially all mouse $V_H$, $D_H$, and $J_H$ gene segments with one or more $V_L$, one or more $D_H$, and one or more J gene segments (e.g., Jκ or Jλ), wherein the gene segments are operably linked to an endogenous mouse hinge region, wherein the mouse forms a rearranged immunoglobulin chain gene that contains, from 5' to 3' in the direction of transcription, human $V_L$-human or mouse $D_H$-human or mouse J-mouse hinge-mouse $C_H2$-mouse $C_H3$. In one embodiment, the J region is a human Jκ region. In one embodiment, the J region is a human $J_H$ region. In one embodiment, the J region is a human Jλ region. In one embodiment, the human $V_L$ region is selected from a human Vλ region and a human Vκ region.

In specific embodiments, the mouse expresses a single variable domain antibody having a mouse or human constant region and a variable region derived from a human Vκ, a human $D_H$ and a human Jκ; a human Vκ, a human $D_H$, and a human $J_H$; a human Vλ, a human $D_H$, and a human Jλ; a human Vλ, a human $D_H$, and a human $J_H$; a human Vκ, a human $D_H$, and a human Jλ; a human Vλ, a human $D_H$, and a human Jκ. In specific embodiment, recombination recognition sequences are modified so as to allow for productive rearrangements to occur between recited V, D, and J gene segments or between recited V and J gene segments.

In one aspect, a mouse is provided that comprises an ectopic ADAM6 sequence that encodes a functional ADAM6 protein (or ortholog or homolog or functional fragment thereof), a replacement of all or substantially all mouse $V_H$ gene segments with one or more human $V_L$ gene segments, a replacement of all or substantially all mouse $D_H$ gene segment and $J_H$ gene segments with human $J_L$ gene segments; wherein the mouse lacks a $C_H1$ and/or hinge region.

In one embodiment, the mouse lacks a sequence encoding a $C_H1$ domain. In one embodiment, the mouse lacks a sequence encoding a hinge region. In one embodiment, the mouse lacks a sequence encoding a $C_H1$ domain and a hinge region.

In a specific embodiment, the mouse expresses a binding protein that comprises a human immunoglobulin light chain variable domain (λ or κ) fused to a mouse $C_H2$ domain that is attached to a mouse $C_H3$ domain.

In one aspect, a mouse is provided that comprises an ectopic ADAM6 sequence that encodes a functional ADAM6 protein (or ortholog or homolog or functional fragment thereof), a replacement of all or substantially all mouse $V_H$ gene segments with one or more human $V_L$ gene segments, a replacement of all or substantially all mouse $D_H$ and $J_H$ gene segments with human $J_L$ gene segments.

In one embodiment, the mouse comprises a deletion of an immunoglobulin heavy chain constant region gene sequence encoding a $C_H1$ region, a hinge region, a $C_H1$ and a hinge region, or a $C_H1$ region and a hinge region and a $C_H2$ region.

In one embodiment, the mouse makes a single variable domain binding protein comprising a homodimer selected from the following: (a) human $V_L$-mouse $C_H1$-mouse $C_H2$-mouse $C_H3$; (b) human $V_L$-mouse hinge-mouse $C_H2$-mouse $C_H3$; (c) human $V_L$-mouse $C_H2$-mouse $C_H3$.

In one aspect, a mouse is provided with a disabled endogenous heavy chain immunoglobulin locus, comprising a disabled or deleted endogenous mouse ADAM6 locus, wherein the mouse comprises a nucleic acid sequence that expresses a human or mouse or human/mouse or other chimeric antibody. In one embodiment, the nucleic acid sequence is present on a transgene integrated that is randomly integrated into the mouse genome. In one embodiment, the nucleic acid sequence is on an episome (e.g., a chromosome) not found in a wild-type mouse.

In one embodiment, the mouse further comprises a disabled endogenous immunoglobulin light chain locus. In a specific embodiment, the endogenous immunoglobulin light chain locus is selected from a kappa (κ) and a lambda (λ) light chain locus. In a specific embodiment, the mouse comprises a disabled endogenous κ light chain locus and a disabled λ, light chain locus, wherein the mouse expresses an antibody that comprises a human immunoglobulin heavy chain variable domain and a human immunoglobulin light chain domain. In one embodiment, the human immunoglobulin light chain domain is selected from a human κ light chain domain and a human λ light chain domain.

In one aspect, a genetically modified animal is provided that expresses a chimeric antibody and expresses an ADAM6 protein or ortholog or homolog thereof that is functional in the genetically modified animal.

In one embodiment, the genetically modified animal is selected from a mouse and a rat. In one embodiment, the genetically modified animal is a mouse, and the ADAM6 protein or ortholog or homolog thereof is from a mouse strain that is a different strain than the genetically modified animal. In one embodiment, the genetically modified animal is a rodent of family Cricetidae (e.g., a hamster, a New World rat or mouse, a vole), and the ADAM6 protein ortholog or homolog is from a rodent of family Muridae (e.g., true mouse or rat, gerbil, spiny mouse, crested rat). In one embodiment, the genetically modified animal is a rodent of the family Muridae, and the ADAM6 protein ortholog or homolog is from a rodent of family Cricetidae.

In one embodiment, the chimeric antibody comprises a human variable domain and a constant region sequence of a rodent. In one embodiment, the rodent is selected from a rodent of the family Cricetidae and a rodent of family Muridae, In a specific embodiment, the rodent of the family Cricetidae and of the family Muridae is a mouse. In a specific embodiment, the rodent of the family Cricetidae and of the family Muridae is a rat. In one embodiment, the chimeric antibody comprises a human variable domain and a constant domain from an animal selected from a mouse or rat; in a specific embodiment, the mouse or rat is selected from the family Cricetidae and the family Muridae. In one embodiment, the chimeric antibody comprises a human heavy chain variable domain, a human light chain variable domain and a constant region sequence derived from a rodent selected from mouse and rat, wherein the human heavy chain variable domain and the human light chain are cognate. In a specific embodiment, cognate includes that the human heavy chain and the human light chain variable domains are from a single B cell that expresses the human light chain variable domain and the human heavy chain variable domain together and present the variable domains together on the surface of an individual B cell.

In one embodiment, the chimeric antibody is expressed from an immunoglobulin locus. In one embodiment, the heavy chain variable domain of the chimeric antibody is expressed from a rearranged endogenous immunoglobulin heavy chain locus. In one embodiment, the light chain variable domain of the chimeric antibody is expressed from a rearranged endogenous immunoglobulin light chain locus. In one embodiment, the heavy chain variable domain of the chimeric antibody and/or the light chain variable domain of the chimeric antibody is expressed from a rearranged transgene (e.g., a rearranged nucleic acid sequence derived from an unrearranged nucleic acid sequence integrated into the animal's genome at a locus other than an endogenous immunoglobulin locus). In one embodiment, the light chain variable domain of the chimeric antibody is expressed from a rearranged transgene (e.g., a rearranged nucleic acid sequence derived from an unrearranged nucleic acid sequence integrated into the animal's genome at a locus other than an endogenous immunoglobulin locus).

In a specific embodiment, the transgene is expressed from a transcriptionally active locus, e.g., a ROSA26 locus, e.g., a murine (e.g., mouse) ROSA26 locus.

In one aspect, a non-human animal is provided, comprising a humanized immunoglobulin heavy chain locus, wherein the humanized immunoglobulin heavy chain locus comprises a non-human ADAM6 sequence or ortholog or homolog thereof.

In one embodiment, the non-human animal is a rodent selected from a mouse, a rat, and a hamster.

In one embodiment, the non-human ADAM6 ortholog or homolog is a sequence that is orthologous and/or homologous to a mouse ADAM6 sequence, wherein the ortholog or homolog is functional in the non-human animal.

In one embodiment, the non-human animal is selected from a mouse, a rat, and a hamster and the ADAM6 ortholog or homolog is from a non-human animal selected from a mouse, a rat, and a hamster. In a specific embodiment, the non-human animal is a mouse and the ADAM6 ortholog or homolog is from an animal that is selected from a different mouse species, a rat, and a hamster. In specific embodiment, the non-human animal is a rat, and the ADAM6 ortholog or homolog is from a rodent that is selected from a different rat species, a mouse, and a hamster. In a specific embodiment, the non-human animal is a hamster, and the ADAM6 ortholog or homolog is form a rodent that is selected from a different hamster species, a mouse, and a rat.

In a specific embodiment, the non-human animal is from the suborder Myomorpha, and the ADAM6 sequence is from an animal selected from a rodent of superfamily Dipodoidea and a rodent of the superfamily Muroidea. In a specific embodiment, the rodent is a mouse of superfamily Muroidea, and the ADAM6 ortholog or homolog is from a mouse or a rat or a hamster of superfamily Muroidea.

In one embodiment, the humanized heavy chain locus comprises one or more human $V_H$ gene segments, one or more human $D_H$ gene segments and one or more human $J_H$ gene segments. In a specific embodiment, the one or more human $V_H$ gene segments, one or more human $D_H$ gene segments and one or more human $J_H$ gene segments are operably linked to one or more human, chimeric and/or rodent (e.g., mouse or rat) constant region genes. In one embodiment, the constant region genes are mouse. In one embodiment, the constant region genes are rat. In one embodiment, the constant region genes are hamster. In one embodiment, the constant region genes comprise a sequence selected from a hinge, a $C_H2$, a $C_H3$, and a combination thereof. In specific embodiment, the constant region genes comprise a hinge, a $C_H2$, and a $C_H3$ sequence.

In one embodiment, the non-human ADAM6 sequence is contiguous with a human immunoglobulin heavy chain sequence. In one embodiment, the non-human ADAM6 sequence is positioned within a human immunoglobulin heavy chain sequence. In a specific embodiment, the human immunoglobulin heavy chain sequence comprises a V, D and/or J gene segment.

In one embodiment, the non-human ADAM6 sequence is positioned between two V gene segments. In one embodiment, the non-human ADAM6 sequence is juxtaposed between a V and a D gene segment. In one embodiment, the mouse ADAM6 sequence is positioned between a V and a J gene segment. In one embodiment, the mouse ADAM6 sequence is juxtaposed between a D and a J gene segment.

In one aspect, a genetically modified non-human animal is provided, comprising a B cell that expresses a human $V_H$ domain cognate with a human $V_L$ domain from an immunoglobulin locus, wherein the non-human animal expresses a non-immunoglobulin non-human protein from the immunoglobulin locus. In one embodiment, the non-immunoglobulin non-human protein is an ADAM protein. In a specific embodiment, the ADAM protein is an ADAM6 protein or homolog or ortholog or functional fragment thereof.

In one embodiment the non-human animal is a rodent (e.g., mouse or rat). In one embodiment, the rodent is of family Muridae. In one embodiment, the rodent is of subfamily Murinae. In a specific embodiment, the rodent of subfamily Murinae is selected from a mouse and a rat.

In one embodiment, the non-immunoglobulin non-human protein is a rodent protein. In one embodiment, the rodent is of family Muridae. In one embodiment, the rodent is of subfamily Murinae. In a specific embodiment, the rodent is selected from a mouse, a rat, and a hamster.

In one embodiment, the human $V_H$ and $V_L$ domains are attached directly or through a linker to an immunoglobulin constant domain sequence. In a specific embodiment, the constant domain sequence comprises a sequence selected from a hinge, a $C_H2$ a $C_H3$, and a combination thereof. In a specific embodiment, the human $V_L$ domain is selected from a Vκ or a Vλ domain.

In one aspect, a genetically modified non-human animal is provided, comprising in its germline a human immunoglobulin sequence, wherein the sperm of a male non-human animal is characterized by an in vivo migration defect. In one embodiment, the in vivo migration defect comprises an inability of the sperm of the male non-human animal to migrate from a uterus through an oviduct of a female non-human animal of the same species. In one embodiment, the non-human animal lacks a nucleotide sequence that encodes and ADAM6 protein or functional fragment thereof. In a specific embodiment, the ADAM6 protein or functional fragment thereof includes an ADAM6a and/or an ADAM6b protein or functional fragments thereof. In one embodiment, the non-human animal is a rodent. In a specific embodiment, the rodent is selected from a mouse, a rat, and a hamster.

In one aspect, a non-human animal is provided, comprising a human immunoglobulin sequence contiguous with a non-human sequence that encodes an ADAM6 protein or ortholog or homolog or functional fragment thereof. In one embodiment, the non-human animal is a rodent. In a specific embodiment, the rodent is selected from a mouse, a rat, and a hamster.

In one embodiment, the human immunoglobulin sequence is an immunoglobulin heavy chain sequence. In one embodiment, the immunoglobulin sequence comprises one or more $V_H$ gene segments. In one embodiment, the human immunoglobulin sequence comprises one or more $D_H$ gene segments. In one embodiment, the human immunoglobulin sequence comprises one or more $J_H$ gene segments. In one embodiment, the human immunoglobulin sequence comprises one or more $V_H$ gene segments, one or more $D_H$ gene segments and one or more $J_H$ gene segments.

In one embodiment, the immunoglobulin sequence comprises one or more $V_H$ gene segments have a high frequency in natural human repertoires. In a specific embodiment, the one or more $V_H$ gene segments comprise no more than two $V_H$ gene segments, no more than three $V_H$ gene segments, no more than four $V_H$ gene segments, no more than five $V_H$ gene segments, no more than six $V_H$ gene segments, no more than seven VH gene segments, no more than eight $V_H$ gene segments, no more than nine $V_H$ gene segments, no more than 10 $V_H$ gene segments, no more than 11 $V_H$ gene segments, no more than 12 $V_H$ gene segments, no more than 13 $V_H$ gene segments, no more than 14 $V_H$ gene segments, no more than 15 $V_H$ gene segments, no more than 16, $V_H$ gene segments, no more than 17 $V_H$ gene segments, no more than 18 $V_H$ gene segments, no more than 19 $V_H$ gene segments, no more than 20 $V_H$ gene segments, no more than 21 $V_H$ gene segments, no more than 22 $V_H$ gene segments or no more than 23 $V_H$ gene segments.

In a specific embodiment, the one or more $V_H$ gene segments comprise five $V_H$ gene segments. In a specific embodiment, the one or more $V_H$ gene segments comprise 10 $V_H$ gene segments. In a specific embodiment, the one or more $V_H$ gene segments comprise 15 $V_H$ gene segments. In a specific embodiment, the one or more $V_H$ gene segments comprise 20 $V_H$ gene segments.

In various embodiments, the $V_H$ gene segments are selected from $V_H6$-1, $V_H1$-2, $V_H1$-3, $V_H2$-5, $V_H3$-7, $V_H1$-8, $V_H3$-9, $V_H3$-11, $V_H3$-13, $V_H3$-15, $V_H3$-16, $V_H1$-18, $V_H3$-20, $V_H3$-21, $V_H3$-23, $V_H1$-24, $V_H2$-26, $V_H4$-28, $V_H3$-30, $V_H4$-31, $V_H3$-33, $V_H4$-34, $V_H3$-35, $V_H3$-38, $V_H4$-39, $V_H3$-43, $V_H1$-45, $V_H1$-46, $V_H3$-48, $V_H3$-49, $V_H5$-51, $V_H3$-53, $V_H1$-58, $V_H4$-59, $V_H4$-61, $V_H3$-64, $V_H3$-66, $V_H1$-69, $V_H2$-70, $V_H3$-72, $V_H3$-73 and $V_H3$-74.

In various embodiments, the $V_H$ gene segments are selected from $V_H1$-2, $V_H1$-8, $V_H1$-18, $V_H1$-46, $V_H1$-69, $V_H3$-7, $V_H3$-9, $V_H3$-11, $V_H3$-13, $V_H3$-15, $V_H3$-21, $V_H3$-23, $V_H3$-30, $V_H3$-33, $V_H3$-43, $V_H3$-48, $V_H4$-31, $V_H4$-34, $V_H4$-39, $V_H4$-59, $V_H5$-51 and $V_H6$-1.

In various embodiments, the $V_H$ gene segments are selected from $V_H1$-18, $V_H1$-46, $V_H1$-69, $V_H3$-7, $V_H3$-11, $V_H3$-15, $V_H3$-21, $V_H3$-23, $V_H3$-30, $V_H3$-33, $V_H3$-48, $V_H4$-34, $V_H4$-39, $V_H4$-59 and $V_H5$-51.

In various embodiments, the $V_H$ gene segments are selected from $V_H1$-18, $V_H1$-69, $V_H3$-7, $V_H3$-11, $V_H3$-15, $V_H3$-21, $V_H3$-23, $V_H3$-30, $V_H3$-43, $V_H3$-48, $V_H4$-39, $V_H4$-59 and $V_H5$-51.

In various embodiments, the $V_H$ gene segments are selected from $V_H1$-18, $V_H3$-11, $V_H3$-21, $V_H3$-23, $V_H3$-30, $V_H4$-39 and $V_H4$-59.

In various embodiments, the $V_H$ gene segments are selected from $V_H1$-18, $V_H3$-21, $V_H3$-23, $V_H3$-30 and $V_H4$-39.

In various embodiments, the $V_H$ gene segments are selected from $V_H1$-18, $V_H3$-23 and $V_H4$-39.

In various embodiments, the $V_H$ gene segments are selected from $V_H3$-21, $V_H3$-23 and $V_H3$-30.

In various embodiments, the $V_H$ gene segments are selected from $V_H3$-23, $V_H3$-30 and $V_H4$-39.

In a specific embodiment, human immunoglobulin sequence comprises at least 18 $V_H$ gene segments, 27 $D_H$ gene segments and six $J_H$ gene segments. In a specific embodiment, the human immunoglobulin sequence comprises at least 39 $V_H$ gene segments, 27 $D_H$ gene segments and six $J_H$ gene segments. In a specific embodiment, the human immunoglobulin sequence comprises at least 80 $V_H$ gene segments, 27 $D_H$ gene segments and six $J_H$ gene segments.

In one embodiment, the non-human animal is a mouse, and the mouse comprises a replacement of endogenous mouse $V_H$ gene segments with one or more human $V_H$ gene segments, wherein the human $V_H$ gene segments are operably linked to a mouse $C_H$ region gene, such that the mouse rearranges the human $V_H$ gene segments and expresses a reverse chimeric immunoglobulin heavy chain that comprises a human $V_H$ domain and a mouse $C_H$. In one embodiment, 90-100% of unrearranged mouse $V_H$ gene segments are replaced with at least one unrearranged human $V_H$ gene segment. In a specific embodiment, all or substantially all of the endogenous mouse $V_H$ gene segments are replaced with at least one unrearranged human $V_H$ gene segment. In one embodiment, the replacement is with at least 19, at least 39, or at least 80 or 81 unrearranged human $V_H$ gene segments. In one embodiment, the replacement is with at least 12 functional unrearranged human $V_H$ gene segments, at least 25 functional unrearranged human $V_H$ gene segments, or at least 43 functional unrearranged human $V_H$ gene segments. In one embodiment, the mouse comprises a replacement of all mouse $D_H$ and $J_H$ segments with at least one unrearranged human $D_H$ segment and at least one unrearranged human $J_H$ segment. In one embodiment, the at least one unrearranged human $D_H$ segment is selected from 1-1, 1-7, 1-26, 2-8, 2-15, 3-3, 3-10, 3-16, 3-22, 5-5, 5-12, 6-6, 6-13, 7-27, and a combination thereof. In one embodiment, the at least one unrearranged human $J_H$ segment is selected from 1, 2, 3, 4, 5, 6, and a combination thereof. In a specific embodiment, the one or more human $V_H$ gene segment is selected from a 1-2, 1-8, 1-24, 1-69, 2-5, 3-7, 3-9, 3-11, 3-13, 3-15, 3-20, 3-23, 3-30, 3-33, 3-48, 3-53, 4-31, 4-39, 4-59, 5-51, a 6-1 human $V_H$ gene segment, and a combination thereof.

In various embodiments, the human immunoglobulin sequence is in operable linkage with a constant region in the germline of the non-human animal (e.g., the rodent, e.g., the mouse, rat, or hamster). In one embodiment, the constant region is a human, chimeric human/mouse or chimeric human/rat or chimeric human/hamster, a mouse, a rat, or a hamster constant region. In one embodiment, the constant region is a rodent (e.g., mouse or rat or hamster) constant region. In a specific embodiment, the rodent is a mouse or rat. In various embodiments, the constant region comprises at least a $C_H2$ domain and a $C_H3$ domain.

In one embodiment, the human immunoglobulin heavy chain sequence is located at an immunoglobulin heavy chain locus in the germline of the non-human animal (e.g., the rodent, e.g., the mouse, rat or hamster). In one embodiment, the human immunoglobulin heavy chain sequence is located at a non-immunoglobulin heavy chain locus in the germline of the non-human animal, wherein the non-heavy chain locus is a transcriptionally active locus. In a specific embodiment, the non-heavy chain locus is a ROSA26 locus.

In various aspects, the non-human animal further comprises a human immunoglobulin light chain sequence (e.g., one or more unrearranged light chain V and J sequences, or one or more rearranged VJ sequences) in the germline of the non-human animal. In a specific embodiment, the immunoglobulin light chain sequence is an immunoglobulin κ light chain sequence. In one embodiment, the human immunoglobulin light chain sequence comprises one or more $V_L$ gene segments. In one embodiment, the human immunoglobulin light chain sequence comprises one or more $J_L$ gene segments. In one embodiment, the human immunoglobulin light chain sequence comprises one or more $V_L$ gene segments and one or more $J_L$ gene segments. In a specific embodiment, the human immunoglobulin light chain sequence comprises at least 16 Vκ gene segments and five Jκ gene segments. In a specific embodiment, the human immunoglobulin light chain sequence comprises at least 30 Vκ gene segments and five Jκ gene segments. In a specific embodiment, the human immunoglobulin light chain sequence comprises at least 40 Vκ gene segments and five Jκ gene segments. In various embodiments, the human immunoglobulin light chain sequence is in operable linkage with a constant region in the germline of the non-human animal (e.g., rodent, e.g., mouse or rat or hamster). In one embodiment, the constant region is a human, chimeric human/rodent, mouse, rat, or hamster constant region. In a specific embodiment, the constant region is a mouse or rat constant region. In a specific embodiment, the constant region is a mouse κ constant (mCκ) region or a rat κ constant (rCκ) region.

In one embodiment, the non-human animal is a mouse and the mouse comprises a replacement of all or substantially all Vκ and Jκ gene segments with at least six human Vκ gene segments and at least one Jκ gene segment. In one embodiment, all or substantially all Vκ and Jκ gene segments are replaced with at least 16 human Vκ gene segments (human Vκ) and at least one Jκ gene segment. In one embodiment, all or substantially all Vκ and Jκ gene segments are replaced with at least 30 human Vκ gene segments and at least one Jκ gene segment. In one embodiment, all or substantially all Vκ and Jκ gene segments are replaced with at least 40 human Vκ gene segments and at least one Jκ gene segment. In one embodiment, the at least one Jκ gene segment comprises two, three, four, or five human Jκ gene segments.

In one embodiment, the human Vκ gene segments comprise Vκ4-1, Vκ5-2, Vκ7-3, Vκ2-4, Vκ1-5, and Vκ1-6. In one embodiment, the Vκ gene segments comprise Vκ3-7, Vκ1-8, Vκ1-9, Vκ2-10, Vκ3-11, Vκ1-12, Vκ1-13, Vκ2-14, Vκ3-15 and Vκ1-16. In one embodiment, the human Vκ gene segments comprise Vκ1-17, Vκ2-18, Vκ2-19, Vκ3-20, Vκ6-21, Vκ1-22, Vκ1-23, Vκ2-24, Vκ3-25, Vκ2-26, Vκ1-27, Vκ2-28, Vκ2-29, and Vκ2-30. In one embodiment, the human Vκ gene segments comprise Vκ3-31, Vκ1-32, Vκ1-33, Vκ3-34, Vκ1-35, Vκ2-36, Vκ1-37, Vκ2-38, Vκ1-39, and Vκ2-40.

In a specific embodiment, the Vκ gene segments comprise contiguous human immunoglobulin κ gene segments spanning the human immunoglobulin κ light chain locus from Vκ4-1 through Vκ2-40, and the Jκ gene segments comprise contiguous gene segments spanning the human immunoglobulin κ light chain locus from Jκ1 through Jκ5.

In one embodiment, the human immunoglobulin light chain sequence is located at an immunoglobulin light chain locus in the germline of the non-human animal. In a specific embodiment, the immunoglobulin light chain locus in the germline of the non-human animal is an immunoglobulin κ light chain locus. In one embodiment, the human immunoglobulin light chain sequence is located at a non-immunoglobulin light chain locus in the germline of the non-human animal that is transcriptionally active. In a specific embodiment, the non-immunoglobulin locus is a ROSA26 locus.

In one aspect, a method of making a human antibody is provided, wherein the human antibody comprises variable domains derived from one or more variable region nucleic acid sequences encoded in a cell of a non-human animal as described herein.

In one aspect, a pharmaceutical composition is provided, comprising a polypeptide that comprises antibody or antibody fragment that is derived from one or more variable region nucleic acid sequences isolated from a non-human animal as described herein. In one embodiment, the polypeptide is an antibody. In one embodiment, the polypeptide is a heavy chain only antibody. In one embodiment, the polypeptide is a single chain variable fragment (e.g., an scFv).

In one aspect, use of a non-human animal as described herein to make an antibody is provided. In various embodiments, the antibody comprises one or more variable domains that are derived from one or more variable region nucleic acid sequences isolated from the non-human animal. In a specific embodiment, the variable region nucleic acid sequences comprise immunoglobulin heavy chain gene segments. In a specific embodiment, the variable region nucleic acid sequences comprise immunoglobulin light chain gene segments.

EXAMPLES

The following examples are provided so as to describe how to make and use methods and compositions of the invention, and are not intended to limit the scope of what the inventors regard as their invention. Unless indicated otherwise, temperature is indicated in Celsius, and pressure is at or near atmospheric.

Example 1

Humanization of Mouse Immunoglobulin Genes

Human and mouse bacterial artificial chromosomes (BACs) were used to engineer 13 different BAC targeting vectors (BACvecs) for humanization of the mouse immunoglobulin heavy chain and κ light chain loci. Tables 1 and 2 set forth descriptions of the steps performed for construction of all BACvecs employed for the humanization of mouse immunoglobulin heavy chain and κ light chain loci, respectively.

Identification of human and mouse BACs. Mouse BACs that span the 5' and 3' ends of the immunoglobulin heavy chain and κ light chain loci were identified by hybridization of filters spotted with BAC library or by PCR screening mouse BAC library DNA pools. Filters were hybridized under standard conditions using probes that corresponded to the regions of interest. Library pools were screened by PCR using unique primer pairs that flank the targeted region of interest. Additional PCR using the same primers was performed to deconvolute a given well and isolate the corresponding BAC of interest. Both BAC filters and library pools were generated from 129 SvJ mouse ES cells (Incyte Genomics/Invitrogen). Human BACs that cover the entire immunoglobulin heavy chain and κ light chain loci were identified either by hybridization of filters spotted with BAC library (Caltech B, C, or D libraries & RPCI-11 library, Research Genetics/Invitrogen) through screening human BAC library pools (Caltech library, Invitrogen) by a PCR-based method or by using a BAC end sequence database (Caltech D library, TIGR).

Construction of BACvecs by bacterial homologous recombination and ligation. Bacterial homologous recombination (BHR) was performed as described (Valenzuela et al., 2003; Zhang et al., 1998, A new logic for DNA engineering using recombination in *Escherichia coli*, *Nat Genet* 20:123-128). In most cases, linear fragments were generated by ligating PCR-generated homology boxes to cloned cassettes followed by gel isolation of ligation products and electroporation into BHR-competent bacteria harboring the target BAC. After selection on appropriate antibiotic petri dishes, correctly recombined BACs were identified by PCR across both novel junctions followed by restriction analysis on pulsed-field gels (Schwartz and Cantor, 1984, Separation of yeast chromosome-sized DNAs by pulsed field gradient gel electrophoresis, *Cell* 37:67-75) and spot-checking by PCR using primers distributed across the human sequences.

Figure 4A:
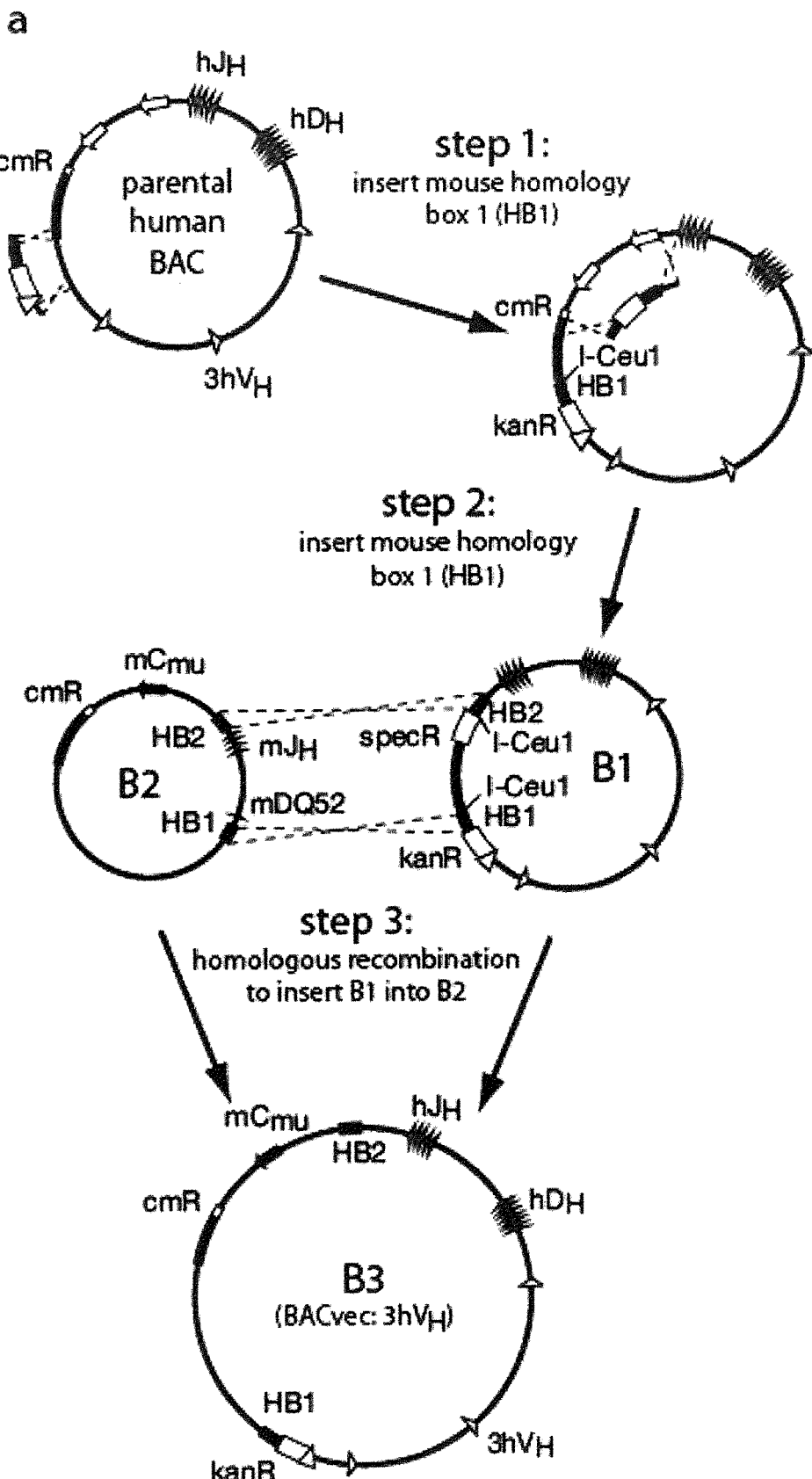
FIG. 4A shows a detailed illustration, not to scale, of the three steps employed for construction of a 3hV$_H$ BACvec by bacterial homologous recombination (BHR). Human (open symbols) and mouse (closed symbols) immunoglobulin gene segments, selection cassettes (open rectangles) and site-specific recombination sites (open triangles) inserted from targeting vectors are shown.
Figure 4B:
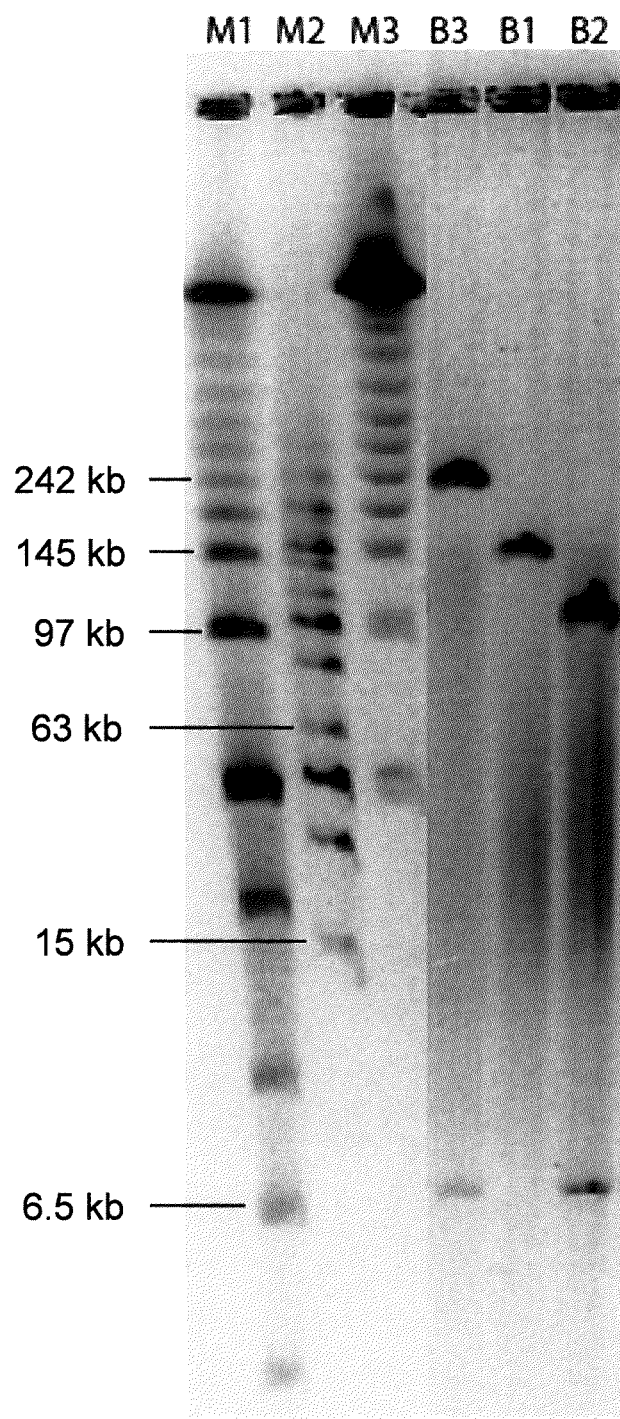
FIG. 4B shows pulse-field gel electrophoresis (PFGE) of three BAC clones (B1, B2 and B3) after NotI digestion. Markers M1, M2 and M3 are low range, mid range and lambda ladder PFG markers, respectively (New England BioLabs, Ipswich, MA).

A $3hV_H$ BACvec was constructed using three sequential BHR steps for the initial step of humanization of the immunoglobulin heavy chain locus (FIG. 4A and Table 1). In the first step (Step 1), a cassette was introduced into a human parental BAC upstream from the human $V_H$1-3 gene segment that contains a region of homology to the mouse immunoglobulin heavy chain locus (HB1), a gene that confers kanamycin resistance in bacteria and G418 resistance in animals cells (kanR) and a site-specific recombination site (e.g., loxP). In the second step (Step 2), a second cassette was introduced just downstream from the last $J_H$ segment that contains a second region of homology to the mouse immunoglobulin heavy chain locus (HB2) and a gene that confers resistance in bacteria to spectinomycin (specR). This second step included deleting human immunoglobulin heavy chain locus sequences downstream from $J_H6$ and the BAC vector chloramphenicol resistance gene (cmR). In the third step (Step 3), the doubly modified human BAC (B1) was then linearized using I-CeuI sites that had been added during the first two steps and integrated into a mouse BAC (B2) by BHR through the two regions of homology (HB1 and HB2). The drug selections for first (cm/kan), second (spec/kan) and third (cm/kan) steps were designed to be specific for the desired products. Modified BAC clones were analyzed by pulse-filed gel electrophoresis (PFGE) after digestion with restriction enzymes to determine appropriate construction (FIG. 4B).

In a similar fashion, 12 additional BACvecs were engineered for humanization of the heavy chain and κ light chain loci. In some instances, BAC ligation was performed in lieu of BHR to conjoin two large BACs through introduction of rare restriction sites into both parental BACvecs by BHR along with careful placement of selectable markers. This allowed for the survival of the desired ligation product upon selection with specific drug marker combinations. Recombinant BACs obtained by ligation after digestion with rare restriction enzymes were identified and screened in a similar fashion to those obtained by BHR (as described above).

TABLE 1

| BACvec | Step | Description | Process |
|---|---|---|---|
| $3hV_H$ | 1 | Insert upstream mouse homology box into human proximal BAC CTD-2572o2 | BHR |
| | 2 | Insert downstream mouse homology box into human proximal BAC CTD-2572o2 | BHR |
| | 3 | Insert $3hV_H/27hD_H/9hJ_H$ into mouse proximal BAC CT7-302a07 to create $3hV_H$ BACvec | BHR |
| DC | 1 | Insert cassette at distal end of mouse IgH locus using mouse BAC CT7-253i20 | BHR |
| $18hV_H$ | 1 | Insert specR marker at downstream end of $3hV_H$ insertion using human BAC CTD-2572o2 | BHR |
| | 2 | Insert I-CeuI and Not sites flanking puroR at upstream end of $3hV_H$ insertion | BHR |
| | 3 | Insert Not site at downstream end of Rel2-408p02 BAC (≈10 kb downstream of $V_H2$-5) | BHR |
| | 4 | Insert I-CeuI site at upstream end of Rel2-408p02 BAC (≈23 kb upstream of $V_H1$-18) | BHR |
| | 5 | Ligate 184 kb fragment from step 4 into 153 kb vector from step 2 | Ligation |
| | 6 | Trim human homology from CTD-2572o2 BAC deleting ≈85 kb and leaving 65 kb homology to $3hV_H$ | BHR |
| | 7 | Insert cassette and Not site at distal end of mouse IgH locus in CT7-253i20 BAC | BHR |
| | 8 | Subclone mouse distal homology arm for insertion upstream from human BACs | Ligation |
| | 9 | Insert 20 kb mouse arm upstream of Rel2-408p02 | BHR |
| | 10 | Swap selection cassette from hygR to neoR to create $18hV_H$ BACvec | BHR |
| $39hV_H$ | 1 | Insert I-CeuI and PI-SceI sites flanking hygR into distal end of human BAC CTD-2534n10 | BHR |
| | 2 | Insert CmR at proximal end of CTD-2534n10 BAC to allow for selection for ligation to RP11-72n10 BAC | BHR |
| | 3 | Insert PI-SceI site into RP11-72n10 BAC for ligation to CTD-2534n10 BAC | BHR |
| | 4 | Insert I-CeuI and AscI sites flanking puroR at distal end of RP11-72n10 BAC | BHR |
| | 5 | Ligate 161 kb fragment from construct of step 4 into construct of step 2 replacing hygR | Ligation |
| | 6 | Insert neoR and AscI site at proximal end of mouse distal homology arm using CT7-253i20 BAC | BHR |
| | 7 | Insert specR and I-CeuI site at distal end of mouse distal homology arm | BHR |

TABLE 1-continued

| BACvec | Step | Description | Process |
|---|---|---|---|
| | 8 | Ligate mouse distal homology arm onto human insert from step 5 | Ligation |
| | 9 | Swap selection cassette from neo to hyg using UbCp and pA as homology boxes to create 39hV$_H$ BACvec | BHR |
| 53hV$_H$ | 1 | Insert specR at proximal end of human CTD-3074b5 BAC | BHR |
| | 2 | Insert AscI site at distal end of human CTD-3074b5 BAC | BHR |
| | 3 | Insert hygR and AscI site at proximal end of mouse distal homology arm using CT7-253i20 BAC | BHR |
| | 4 | Ligate mouse distal homology arm onto construct from step 2 | Ligation |
| | 5 | Swap selection cassette from hyg to neo using UbCp and pA as homology boxes to create 53hV$_H$ BACvec | BHR |
| 70hV$_H$ | 1 | Insert PI-SceI and I-CeuI sites flanking spec at distal end of human CTD-2195p5 BAC | BHR |
| | 2 | Insert I-CeuI site at proximal end of RP11-926p12 BAC for ligation to CTD-2195p5 BAC | BHR |
| | 3 | Insert PI-SceI and AscI sites at distal end of RP11-926p12 BAC for ligation of mouse arm | BHR |
| | 4 | Ligate mouse distal homology arm onto construct from step 3 | Ligation |
| | 5 | Ligate mouse distal homology arm and hIgH fragment from RP11-926p12 BAC onto CTD-2195p5 BAC to create 70 hV$_H$ BACvec | Ligation |
| 80hV$_H$ | 1 | Insert I-CeuI and AscI sites flanking hygR at distal end of CTD-2313e3 BAC | BHR |
| | 2 | Ligate mouse distal homology arm onto human CTD-2313e3 BAC from step 1 to create 80hV$_H$ BACvec | Ligation |

TABLE 2

| BACvec | Step | Description | Process |
|---|---|---|---|
| Igκ-PC | 1 | Insert loxP site within mouse J-C intron using CT7-254m04 BAC | BHR |
| Igκ-DC | 1 | Insert loxP site at distal end of mouse Igκ locus using CT7-302g12 BAC | BHR |
| 6hVκ | 1 | Insert PI-SceI site ≈400 bp downstream from hJκ5 in CTD-2366j12 BAC | BHR |
| | 2 | Insert I-CeuI and AscI sites flanking hygR at distal end of CTD-2366j12 BAC | BHR |
| | 3 | Insert I-CeuI and PI-SceI sites flanking puroR downstream from mJκ using CT7-254m04 BAC | BHR |
| | 4 | Insert hIgVκ/Jκ upstream from mouse Enhκ/Cκ using construct from step 3 | Ligation |
| | 5 | Replace cmR in construct of step 4 with specR | BHR |
| | 6 | Insert Neo selection cassette at distal end of mouse Igκ locus using CT7-302g12 BAC | BHR |
| | 7 | Ligate mouse distal homology arm upstream of human insert in construct of step 6 to create 6hVκ BACvec | Ligation |
| 16hVκ | 1 | Insert NeoR at distal end of RP11-1061b13 BAC | BHR |
| | 2 | Replace cmR in construct of step 1 with specR | BHR |
| | 3 | Insert Hyg selection cassette at distal end of mouse Igκ locus using CT7-302g12 BAC | BHR |
| | 4 | Ligate mouse distal homology arm upstream of human insert from construct of step 2 to create 16hVκ BACvec | Ligation |
| 30hVκ | 1 | Insert HygR at distal end of RP11-99g6 BAC | BHR |
| | 2 | Replace cmR in construct of step 1 with specR | BHR |
| | 3 | Insert Neo selection cassette at distal end of mouse Igκ locus using CT7-302g12 BAC | BHR |
| | 4 | Ligate mouse distal homology arm upstream of human insert from construct of step 2 to create 30hVκ BACvec | Ligation |
| 40hVκ | 1 | Insert NeoR at distal end of hIgH locus in CTD-2559d6 BAC | BHR |
| | 2 | Replace cmR in construct of step 1 with specR | BHR |
| | 3 | Ligate mouse distal homology arm upstream of human insert in construct of step 2 to create 40hVκ BACvec | Ligation |

Modification of embryonic stem (ES) cells and generation of mice. ES cell (F1H4) targeting was performed using the VELOCIGENE® genetic engineering method as described (Valenzuela et al., 2003). Derivation of mice from modified ES cells by either blastocyst (Valenzuela et al., 2003) or 8-cell injection (Poueymirou et al., 2007, F0 generation mice fully derived from gene-targeted embryonic stem cells allowing immediate phenotypic analyses, *Nat Biotechnol* 25:91-99) was as described. Targeted ES cells and mice were confirmed by screening DNA from ES cells or mice with unique sets of probes and primers in a PCR based assay (e.g., FIGS. 3A, 3B and 3C). All mouse studies were overseen and approved by Regeneron's Institutional Animal Care and Use Committee (IACUC).

Karyotype Analysis and Fluorescent in situ Hybridization (FISH). Karyotype Analysis was performed by Coriell Cell Repositories (Coriell Institute for Medical Research, Camden, NJ). FISH was performed on targeted ES cells as described (Valenzuela et al., 2003). Probes corresponding to either mouse BAC DNA or human BAC DNA were labeled by nick translation (Invitrogen) with the fluorescently labeled dUTP nucleotides spectrum orange or spectrum green (Vysis).

Immunoglobulin Heavy Chain Variable Gene Locus. Humanization of the variable region of the heavy chain locus was achieved in nine sequential steps by the direct replacement of about three million base pairs (Mb) of contiguous mouse genomic sequence containing all $V_H$, $D_H$ and $J_H$ gene segments with about one Mb of contiguous human genomic sequence containing the equivalent human gene segments (FIG. 1A and Table 1) using VELOCI-GENE® genetic engineering technology (see, e.g., U.S. Pat. No. 6,586,251 and Valenzuela et al., 2003).

The intron between $J_H$ gene segments and constant region genes (the J-C intron) contains a transcriptional enhancer (Neuberger, 1983, Expression and regulation of immunoglobulin heavy chain gene transfected into lymphoid cells, *EMBO J* 2:1373-1378) followed by a region of simple repeats required for recombination during isotype switching (Kataoka et al., 1980, Rearrangement of immunoglobulin gamma 1-chain gene and mechanism for heavy-chain class switch, *PNAS USA* 77:919-923). The junction between human $V_H$-$D_H$-$J_H$ region and the mouse $C_H$ region (the proximal junction) was chosen to maintain the mouse heavy chain intronic enhancer and switch domain in order preserve both efficient expression and class switching of the humanized heavy chain locus within the mouse. The exact nucleotide position of this and subsequent junctions in all the replacements was possible by use of the VELOCIGENE® genetic engineering method (supra), which employed bacterial homologous recombination driven by synthesized oligonucleotides. Thus, the proximal junction was placed about 200 bp downstream from the last $J_H$ gene segment and the distal junction was placed several hundred upstream of the most 5' $V_H$ gene segment of the human locus and about 9 kb downstream from the mouse $V_H$1-86 gene segment, also known as J558.55. The mouse $V_H$1-86 (J558.55) gene segment is the most distal heavy chain variable gene segment, reported to be a pseudogene in C57BL/6 mice, but potentially active, albeit with a poor RSS sequence, in the targeted 129 allele. The distal end of the mouse heavy chain locus reportedly may contain control elements that regulate locus expression and/or rearrangement (Pawlitzky et al., 2006).

Figure 2A:
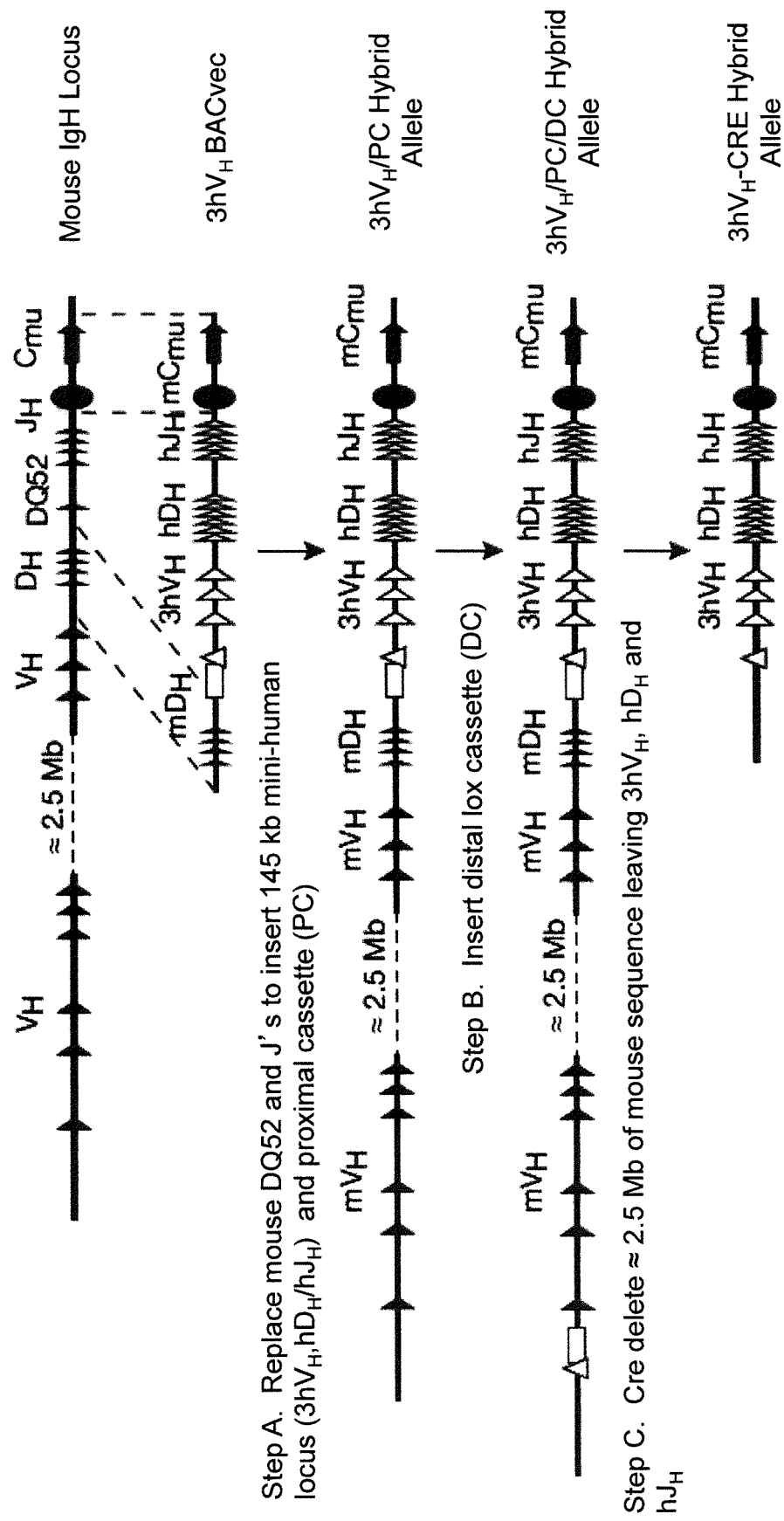
FIG. 2A shows a detailed illustration, not to scale, of three initial steps (A-C) for direct genomic replacement of a mouse immunoglobulin heavy chain variable gene locus that results in deletion of all mouse $V_H$, $D_H$ and $J_H$ gene segments and replacement with three human $V_H$, all human $D_H$ and $J_H$ gene segments. A targeting vector for a first insertion of human immunoglobulin heavy chain gene segments is shown (3hV$_H$ BACvec) with a 67 kb 5' mouse homology arm, a selection cassette (open rectangle), a site-specific recombination site (open triangle), a 145 kb human genomic fragment and an 8 kb 3' mouse homology arm. Human (open symbols) and mouse (closed symbols) immunoglobulin gene segments, additional selection cassettes (open rectangles) and site-specific recombination sites (open triangles) inserted from subsequent targeting vectors are shown.
Figure 3A:
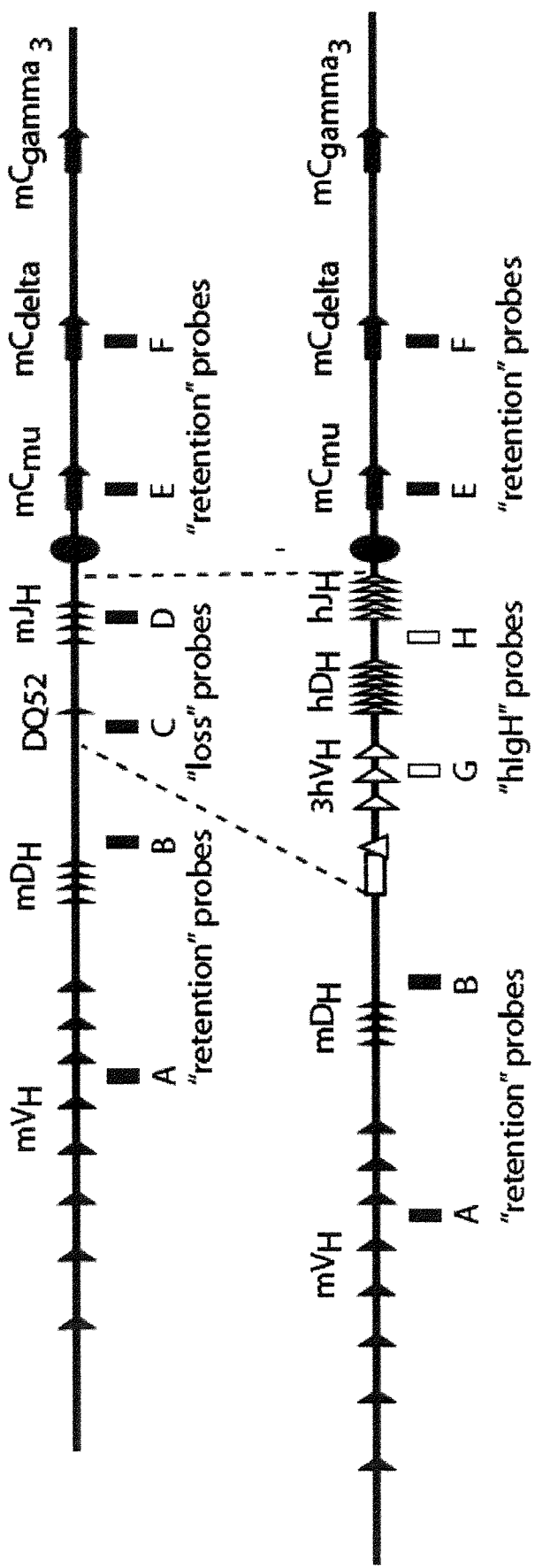
FIG. 3A shows a general illustration, not to scale, of a screening strategy including the locations of quantitative PCR (qPCR) primer/probe sets to detect insertion of human heavy chain gene sequences and loss of mouse heavy chain gene sequences in targeted embryonic stem (ES) cells. The screening strategy in ES cells and mice for a first human heavy gene insertion is shown with qPCR primer/probe sets for the deleted region ("loss" probes C and D), the region inserted ("hIgH" probes G and H) and flanking regions ("retention" probes A, B, E and F) on an unmodified mouse chromosome (top) and a correctly targeted chromosome (bottom).

A first insertion of human immunoglobulin DNA sequence into the mouse was achieved using 144 kb of the proximal end of the human heavy chain locus containing 3 $V_H$, all 27 $D_H$ and 9 $J_H$ human gene segments inserted into the proximal end of the mouse IgH locus, with a concomitant 16.6 kb deletion of mouse genomic sequence, using about 75 kb of mouse homology arms (Step A, FIG. 2A; Tables 1 and 3, $3hV_H$). This large 144 kb insertion and accompanying 16.6 kb deletion was performed in a single step (Step A) that occurred with a frequency of 0.2% (Table 3). Correctly targeted ES cells were scored by a loss-of-native-allele (LONA) assay (Valenzuela et al., 2003) using probes within and flanking the deleted mouse sequence and within the inserted human sequence, and the integrity of the large human insert was verified using multiple probes spanning the entire insertion (FIGS. 3A, 3B and 3C). Because many rounds of sequential ES cell targeting were anticipated, targeted ES cell clones at this, and all subsequent, steps were subjected to karyotypic analysis (supra) and only those clones showing normal karyotypes in at least 17 of 20 spreads were utilized for subsequent steps.

Targeted ES cells from Step A were re-targeted with a BACvec that produced a 19 kb deletion at the distal end of the heavy chain locus (Step B, FIG. 2A). The Step B BACvec contained a hygromycin resistance gene (hyg) in contrast to the neomycin resistance gene (neo) contained on the BACvec of Step A. The resistance genes from the two BACvecs were designed such that, upon successful targeting to the same chromosome, approximately three Mb of the mouse heavy chain variable gene locus containing all of the mouse $V_H$ gene segments other than $V_H$1-86 and all of the $D_H$ gene segments other than DQ52, as well as the two resistance genes, were flanked by loxP sites; DQ52 and all of the mouse $J_H$ chain gene segments were deleted in Step A. ES cell clones doubly targeted on the same chromosome were identified by driving the $3hV_H$ proximal cassette to homozygosity in high G418 (Mortensen et al., 1992, Production of homozygous mutant ES cells with a single targeting construct, *Mol Cell Biol* 12:2391-2395) and following the fate of the distal hyg cassette. Mouse segments up to four Mb in size, having been modified in a manner to be flanked by loxP sites, have been successfully deleted in ES cells by transient expression of CRE recombinase with high efficiencies (up to =11%) even in the absence of drug selection (Zheng et al., 2000, Engineering mouse chromosomes with Cre-loxP: range, efficiency, and somatic applications, *Mol Cell Biol* 20:648-655). In a similar manner, the inventors achieved a three Mb deletion in 8% of ES cell clones following transient CRE expression (Step C, FIG. 2A; Table 3). The deletion was scored by the LONA assay using probes at either end of the deleted mouse sequence, as well as the loss of neo and hyg and the appearance of a PCR product across the deletion point containing the sole remaining loxP site. Further, the deletion was confirmed by fluorescence in situ hybridization (data not shown).

Figure 2B:
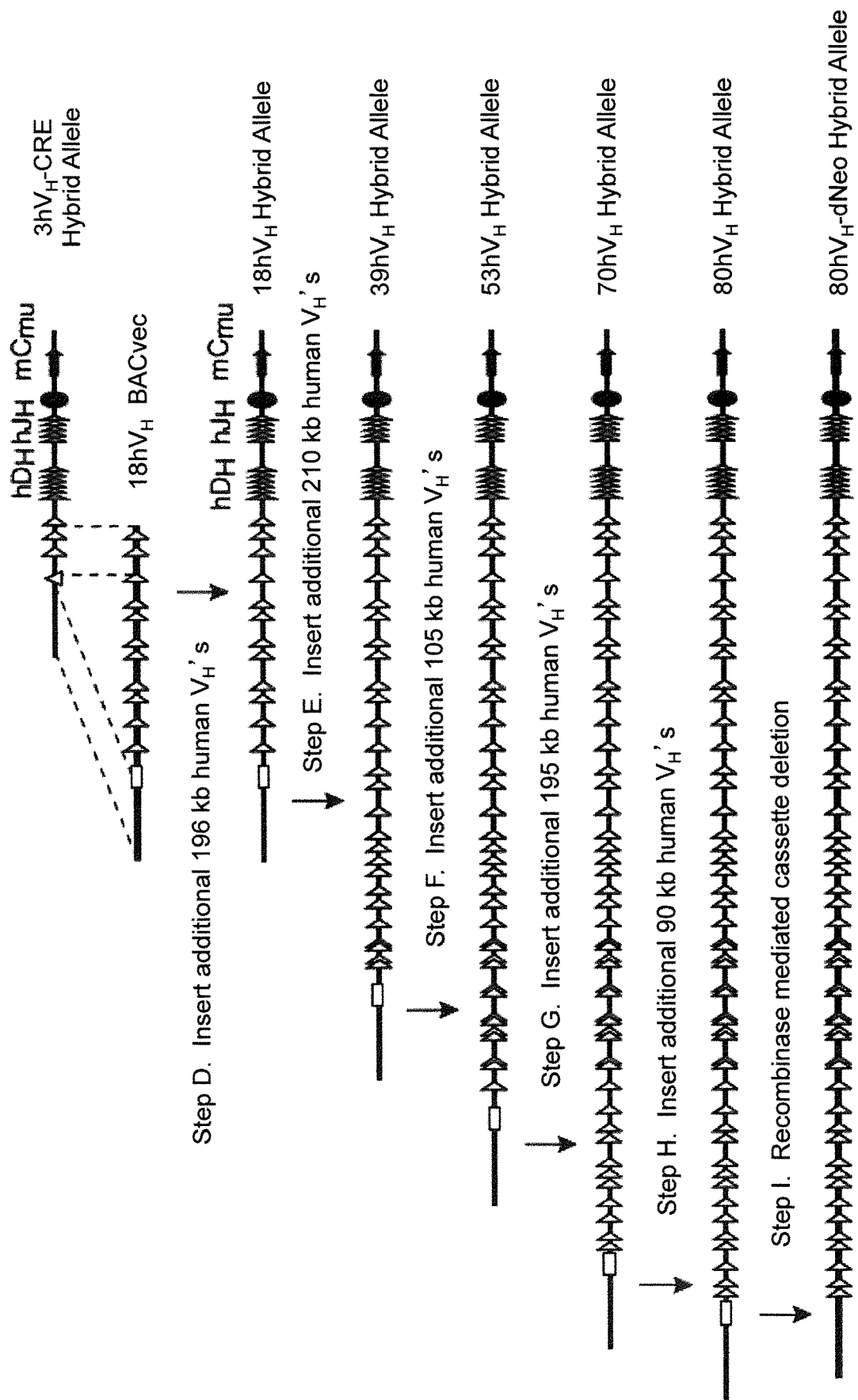
FIG. 2B shows a detailed illustration, not to scale, of six additional steps (D-I) for direct genomic replacement of a mouse immunoglobulin heavy chain variable gene locus that results in the insertion of 77 additional human $V_H$ gene segments and removal of a final selection cassette. A targeting vector for insertion of additional human $V_H$ gene segments (18hV$_H$ BACvec) to the initial insertion of human heavy chain gene segments (3hV$_H$-CRE Hybrid Allele) is shown with a 20 kb 5' mouse homology arm, a selection cassette (open rectangle), a 196 kb human genomic fragment and a 62 kb human homology arm that overlaps with the 5' end of the initial insertion of human heavy chain gene segments which is shown with a site-specific recombination site (open triangle) located 5' to the human gene segments. Human (open symbols) and mouse (closed symbols) immunoglobulin gene segments and additional selection cassettes (open rectangles) inserted by subsequent targeting vectors are shown.

The remainder of the human heavy chain variable region was added to the $3hV_H$ allele in a series of 5 steps using the VELOCIGENE® genetic engineering method (Steps E-H, FIG. 2B), with each step involving precise insertion of up to 210 kb of human gene sequences. For each step, the proximal end of each new BACvec was designed to overlap the most distal human sequences of the previous step and the distal end of each new BACvec contained the same distal region of mouse homology as used in Step A. The BACvecs of steps D, F and H contained neo selection cassettes, whereas those of steps E and G contained hyg selection cassettes, thus selections were alternated between G418 and hygromycin. Targeting in Step D was assayed by the loss of the unique PCR product across the distal loxP site of $3hV_H$ Hybrid Allele. Targeting for Steps E through I was assayed by loss of the previous selection cassette. In the final step (Step I, FIG. 2B), the neo selection cassette, flanked by Frt sites (McLeod et al., 1986, Identification of the crossover site during FLP-mediated recombination in the *Saccharomyces cerevisiae* plasmid 2 microns circle, *Mol Cell Biol* 6:3357-3367), was removed by transient FLPe expression (Buchholz et al., 1998, Improved properties of FLP recombinase evolved by cycling mutagenesis, *Nat Biotechnol* 16:657-662). The human sequences of the BACvecs for Steps D, E and G were derived from two parental human BACs each, whereas those from Steps F and H were from single BACs. Retention of human sequences was confirmed at every step using multiple probes spanning the inserted human sequences (as described above, e.g., FIGS. 3A, 3B and 3C). Only those clones with normal karyotype and germline potential were carried forward in each step. ES cells from the final step were still able to contribute to the germline after nine sequential manipulations (Table 3). Mice homozygous for each of the heavy chain alleles were viable, appeared healthy and demonstrated an essentially wild-type humoral immune system (see Example 3).

TABLE 3

| Hybrid Allele | Human sequence | Targeting construct | Targeting efficiency | % usage | Total $V_H$ | Functional $V_H$ |
|---|---|---|---|---|---|---|
| 3h$V_H$ | 144 kb | 240 kb | 0.2% | 5 | 3 | 3 |
| 3h$V_H$/DC | 144 kb | 110 kb | 0.1% | 5 | 3 | 3 |
| 3h$V_H$-CRE | 144 kb | — | 8% | 5 | 3 | 3 |
| 18h$V_H$ | 340 kb | 272 kb | 0.1% | 25 | 18 | 12 |
| 39h$V_H$ | 550 kb | 282 kb | 0.2% | 60 | 39 | 25 |
| 53h$V_H$ | 655 kb | 186 kb | 0.4% | 65 | 53 | 29 |
| 70h$V_H$ | 850 kb | 238 kb | 0.5% | 90 | 70 | 39 |
| 80h$V_H$ | 940 kb | 124 kb | 0.2% | 100 | 80 | 43 |
| 80h$V_H$dNeo | 940 kb | — | 2.6% | 100 | 80 | 43 |

Immunoglobulin κ Light Chain Variable Gene Locus. The κ light chain variable region was humanized in eight sequential steps by the direct replacement of about three Mb of mouse sequence containing all Vκ and Jκ gene segments with about 0.5 Mb of human sequence containing the proximal human Vκ and Jκ gene segments in a manner similar to that of the heavy chain (FIG. 1B; Tables 2 and 4).

Figure 2C:
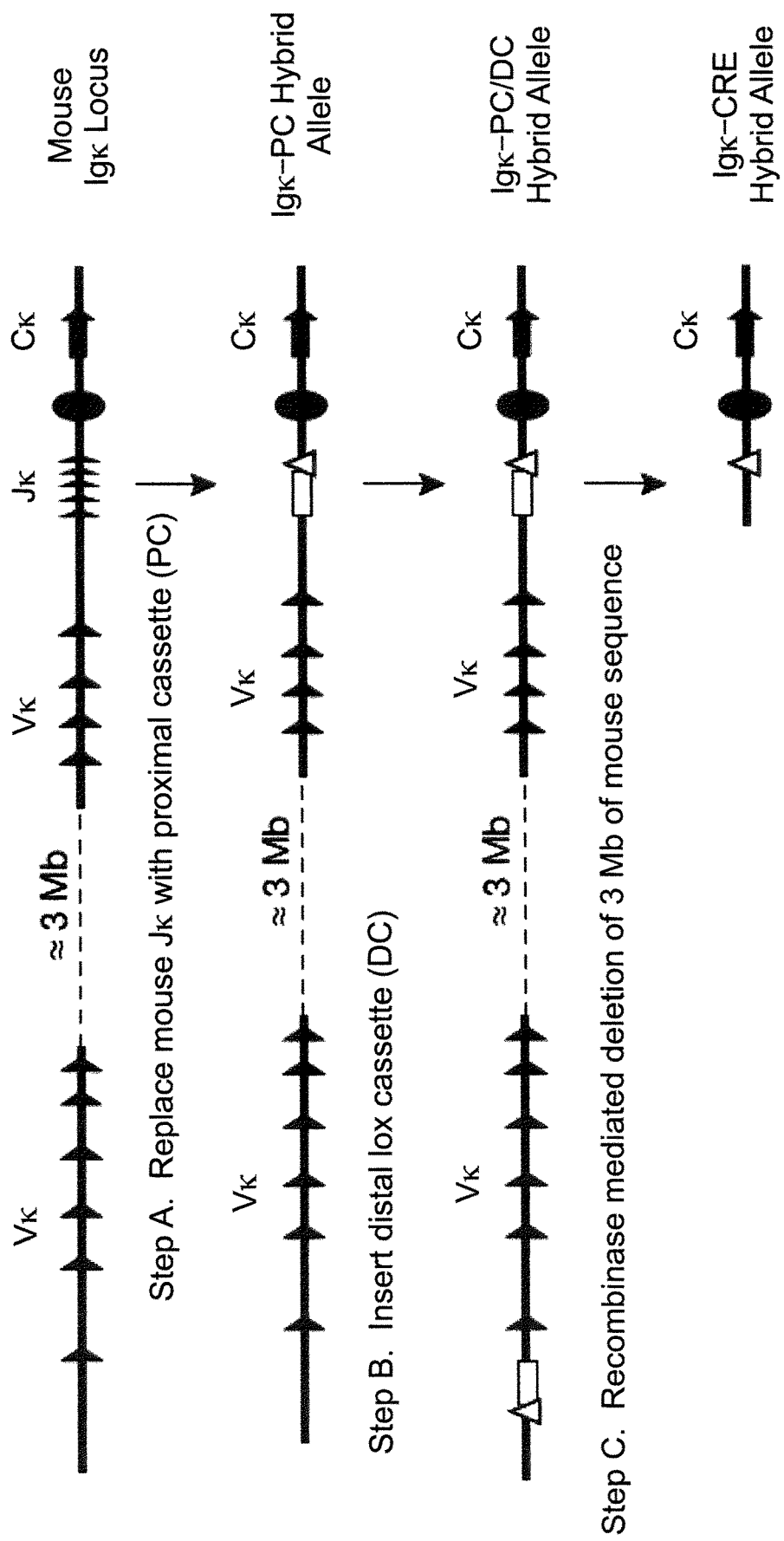
FIG. 2C shows a detailed illustration, not to scale, of three initial steps (A-C) for direct genomic replacement of a mouse immunoglobulin κ light chain variable gene locus that results in deletion of all mouse Vκ, and Jκ gene segments (Igκ-CRE Hybrid Allele). Selection cassettes (open rectangles) and site-specific recombination sites (open triangles) inserted from the targeting vectors are shown.

The variable region of the human κ light chain locus contains two nearly identical 400 kb repeats separated by an 800 kb spacer (Weichhold et al., 1993, The human immunoglobulin kappa locus consists of two copies that are organized in opposite polarity, *Genomics* 16:503-511). Because the repeats are so similar, nearly all of the locus diversity can be reproduced in mice by using the proximal repeat. Further, a natural human allele of the κ light chain locus missing the distal repeat has been reported (Schaible et al., 1993, The immunoglobulin kappa locus: polymorphism and haplotypes of Caucasoid and non-Caucasoid individuals, *Hum Genet* 91:261-267). The inventors replaced about three Mb of mouse κ light chain variable gene sequence with about 0.5 Mb of human κ light chain variable gene sequence to effectively replace all of the mouse Vκ and Jκ gene segments with the proximal human Vκ and all of the human Jκ gene segments (FIGS. 2C and 2D; Tables 2 and 4). In contrast to the method described in Example 1 for the heavy chain locus, the entire mouse Vκ gene region, containing all Vκ and Jκ gene segments, was deleted in a three-step process before any human sequence was added. First, a neo cassette was introduced at the proximal end of the variable region (Step A, FIG. 2C). Next, a hyg cassette was inserted at the distal end of the κ locus (Step B, FIG. 2C). Recombinase recognition sites (e.g., loxP) were again situated within each selection cassette such that CRE treatment induced deletion of the remaining 3 Mb of the mouse Vκ region along with both resistance genes (Step C, FIG. 2C).

Figure 2D:
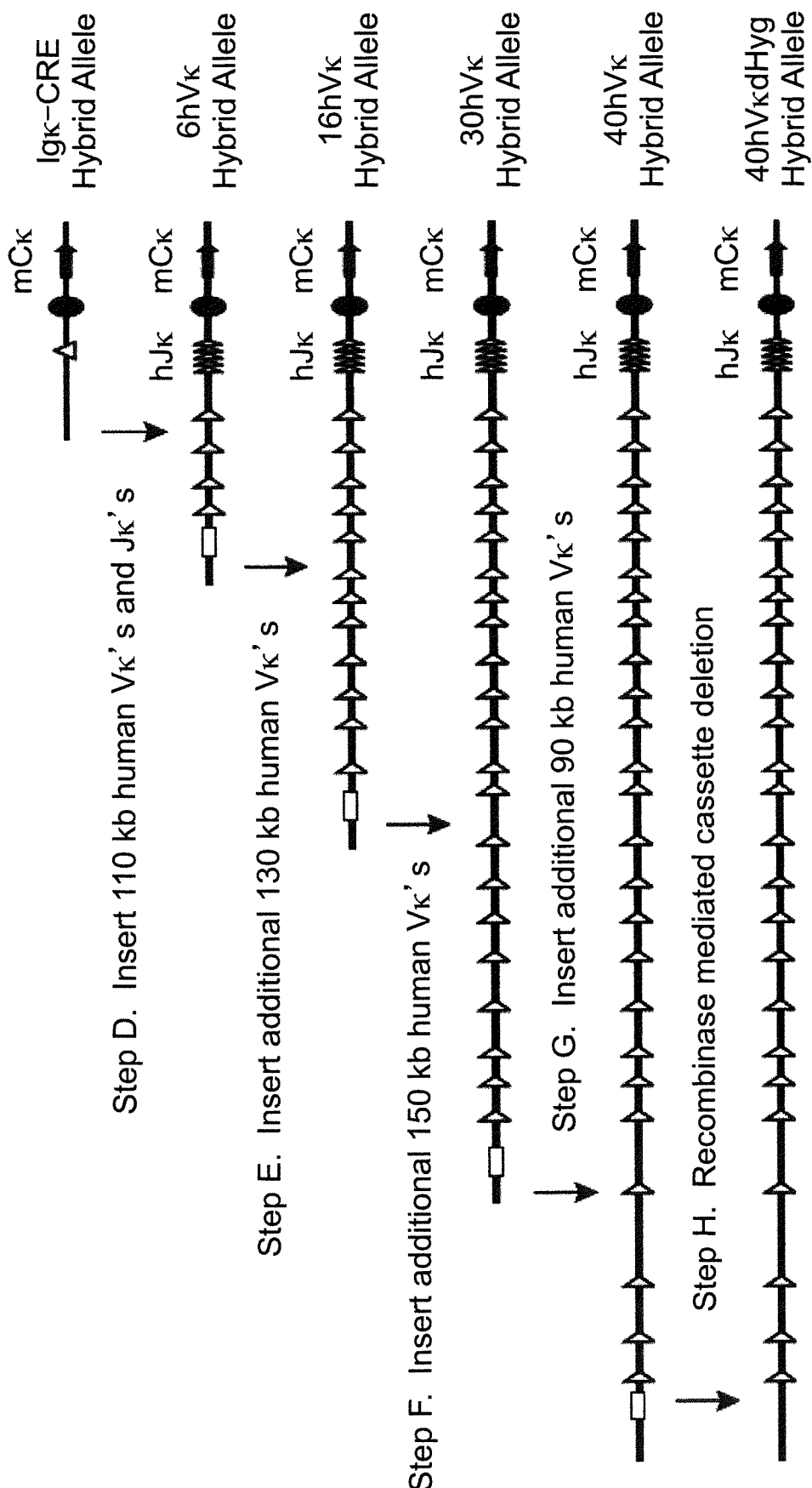
FIG. 2D shows a detailed illustration, not to scale, of five additional steps (D-H) for direct genomic replacement of a mouse immunoglobulin κ light chain variable gene locus that results in the insertion of all human Vκ and Jκ gene segments of the proximal repeat and deletion of a final selection cassette (40hVκdHyg Hybrid Allele). Human (open symbols) and mouse (closed symbols) immunoglobulin gene segments and additional selection cassettes (open rectangles) inserted by subsequent targeting vectors are shown.

A human genomic fragment of about 480 kb in size containing the entire immunoglobulin κ light chain variable region was inserted in four sequential steps (FIG. 2D; Tables 2 and 4), with up to 150 kb of human immunoglobulin κ light chain sequence inserted in a single step, using methods similar to those employed for the heavy chain (see Example 1). The final hygromycin resistance gene was removed by transient FLPe expression. As with the heavy chain, targeted ES cell clones were evaluated for integrity of the entire human insert, normal karyotype and germ-line potential after every step. Mice homozygous for each of the κ light chain alleles were generated and found to be healthy and of normal appearance.

TABLE 4

| Hybrid Allele | Human sequence | Targeting construct | Targeting efficiency | % usage | Total Vκ | Functional Vκ |
|---|---|---|---|---|---|---|
| Igκ-PC | 0 | 132 kb | 1.1% | — | — | — |
| Igκ-PC/DC | 0 | 90 kb | 0.4% | — | — | — |
| Igκ-CRE | 0 | — | 1% | — | — | — |
| 6hVκ | 110 kb | 122 kb | 0.3% | 14 | 6 | 4 |
| 16hVκ | 240 kb | 203 kb | 0.4% | 47 | 16 | 11 |
| 30hVκ | 390 kb | 193 kb | 0.1% | 70 | 30 | 18 |
| 40hVκ | 480 kb | 185 kb | 0.2% | 100 | 40 | 25 |
| 40hVκdHyg | 480 kb | — | 0.7% | 100 | 40 | 25 |

Example 2

Figure 5A:
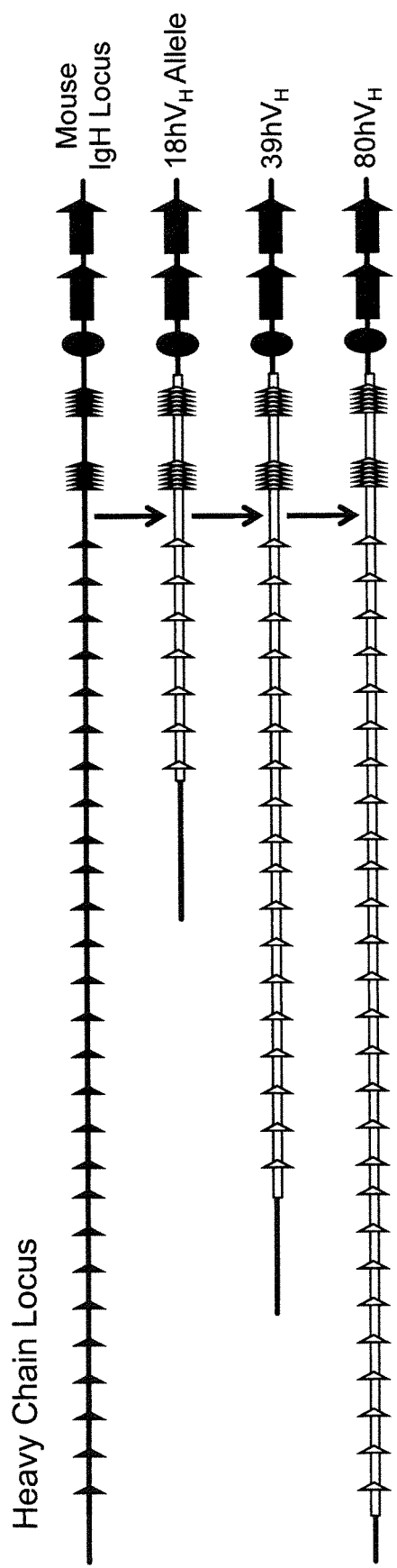
FIG. 5A shows a schematic illustration, not to scale, of sequential modifications of a mouse immunoglobulin heavy chain locus with increasing amounts of human immunoglobulin heavy chain gene segments. Homozygous mice were made from each of the three different stages of heavy chain humanization. Open symbols indicate human sequence; closed symbols indicate mouse sequence.
Figure 5B:
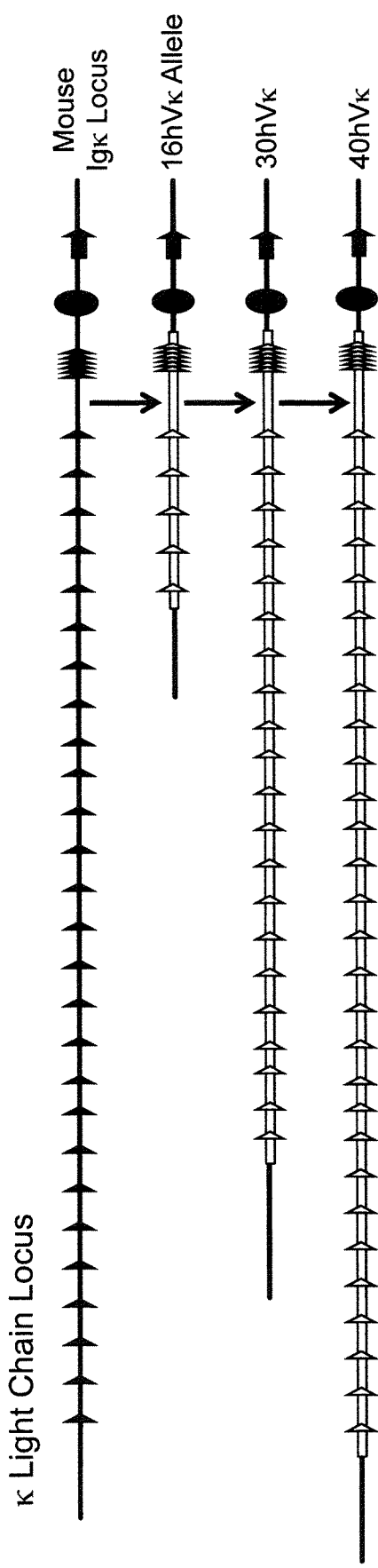
FIG. 5B shows a schematic illustration, not to scale, of sequential modifications of a mouse immunoglobulin κ light chain locus with increasing amounts of human immunoglobulin κ light chain gene segments. Homozygous mice were made from each of the three different stages of κ light chain humanization. Open symbols indicate human sequence; closed symbols indicate mouse sequence.

Generation of Fully Humanized Mice by Combination of Multiple Humanized Immunoglobulin Alleles At several points, ES cells bearing a portion of the human immunoglobulin heavy chain or κ light chain variable repertoires as described in Example 1 were microinjected and the resulting mice bred to create multiple versions of VELOCIMMUNE® mice with progressively larger fractions of the human germline immunoglobulin repertoires (Table 5; FIGS. 5A and 5B). VELOCIMMUNE® 1 (V1) mice possess eighteen human $V_H$ gene segments and all of the human $D_H$ and $J_H$ gene segments combined with sixteen human Vκ gene segments and all the human Jκ gene segments. VELOCIMMUNE® 2 (V2) and VELOCIMMUNE® (V3) mice have increased variable repertoires bearing a total of thirty-nine $V_H$ and thirty Vκ, and eighty $V_H$ and forty Vκ, respectively. Since the genomic regions encoding the mouse $V_H$, $D_H$ and $J_H$ gene segments, and Vκ and Jκ gene segments, have been completely replaced, antibodies produced by all versions of VELOCIMMUNE® mice contain human variable regions linked to mouse constant regions. The mouse λ light chain loci remain intact in various embodiments of the VELOCIMMUNE® mice and serve as a comparator for efficiency of expression of the various VELOCIMMUNE® κ light chain loci.

Mice doubly homozygous for both immunoglobulin heavy chain and κ light chain humanizations were generated from a subset of the alleles described in Example 1. All genotypes observed during the course of breeding to generate the doubly homozygous mice occurred in roughly Mendelian proportions. Male progeny homozygous for each of the human heavy chain alleles demonstrated reduced fertility, which resulted from loss of mouse ADAM6 activity. The mouse heavy chain variable gene locus contains two embedded functional ADAM6 genes (ADAM6a and ADAM6b). During humanization of the mouse heavy chain variable gene locus, the inserted human genomic sequence contained an ADAM6 pseudogene. Mouse ADAM6 may be required for fertility, and thus lack of mouse ADAM6 genes in humanized heavy chain variable gene loci might lead to a reduction in fertility notwithstanding the presence of the human pseudogene. Examples 7-11 describe the reengineering of mouse ADAM6 genes into a humanized heavy chain variable gene locus, and restoration of wild-type level fertility in mice with a humanized heavy chain immunoglobulin locus.

VELOCIMMUNE® mice tested were virtually identical to those of wild type mice, regardless of the number of $V_H$ gene segments they contained. In addition, mice containing homozygous hybrid humanized immunoglobulin heavy chain loci, even those with only 3 $V_H$ gene segments but normal mouse immunoglobulin κ light chain loci or mice containing homozygous hybrid humanized κ light chain loci with normal mouse immunoglobulin heavy chain loci, also had normal numbers of B220$^+$ IgM$^+$ cells in their peripheral compartments (not shown). These results indicate that chimeric loci with human variable gene segments and mouse constant regions can fully populate the mature B cell compartment. Further, the number of variable gene segments at either the heavy chain or κ light chain loci, and thus the theoretical diversity of the antibody repertoire, does not

TABLE 5

| Version of VELOCIMMUNE® Mouse | Heavy Chain | | | κ Light Chain | | |
|---|---|---|---|---|---|---|
| | Human $V_H$ | Allele | 5' $V_H$ gene | Human Vκ | Allele | 5' Vκ gene |
| V1 | 18 | 18h$V_H$ | $V_H$1-18 | 16 | 16hVκ | Vκ1-16 |
| V2 | 39 | 39h$V_H$ | $V_H$4-39 | 30 | 30hVκ | Vκ2-29 |
| V3 | 80 | 80h$V_H$ | $V_H$3-74 | 40 | 40hVκ | Vκ2-40 |

Example 3

Lymphocyte Populations in Mice with Humanized Immunoglobulin Genes

Mature B cell populations in the three different versions of VELOCIMMUNE® mice were evaluated by flow cytometry.

Briefly, cell suspensions from bone marrow, spleen and thymus were made using standard methods. Cells were resuspended at 5×10$^5$ cells/mL in BD Pharmingen FACS staining buffer, blocked with anti-mouse CD16/32 (BD Pharmingen), stained with the appropriate cocktail of antibodies and fixed with BD CYTOFIX™ all according to the manufacturer's instructions. Final cell pellets were resuspended in 0.5 mL staining buffer and analyzed using a BD FACSCALIBUR™ and BD CELLQUEST PRO™ software. All antibodies (BD Pharmingen) were prepared in a mass dilution/cocktail and added to a final concentration of 0.5 mg/10$^5$ cells.

Antibody cocktails for bone marrow (A-D) staining were as follows: A: anti-mouse IgM$^b$-FITC, anti-mouse IgM$^a$-PE, anti-mouse CD45R(B220)-APC; B: anti-mouse CD43(S7)-PE, anti-mouse CD45R(B220)-APC; C: anti-mouse CD24 (HSA)-PE; anti-mouse CD45R(B220)-APC; D: anti-mouse BP-1-PE, anti-mouse CD45R(B220)-APC.

Antibody cocktails for spleen and inguinal lymph node (E-H) staining were as follows: E: anti-mouse IgM$^b$-FITC, anti-mouse IgM$^a$-PE, anti-mouse CD45R(B220)-APC; F: anti-mouse Ig, λ1, λ2, λ3 Light Chain-FITC, anti mouse Igκ Light Chain-PE, anti-mouse CD45R(B220)-APC; G: anti-mouse Ly6G/C-FITC, anti-mouse CD49b(DX5)-PE, anti-mouse CD11b-APC; H: anti-mouse CD4(L3T4)-FITC, anti-mouse CD45R(B220)-PE, anti-mouse CD8a-APC. Results are shown in FIG. 6.

Figure 6:
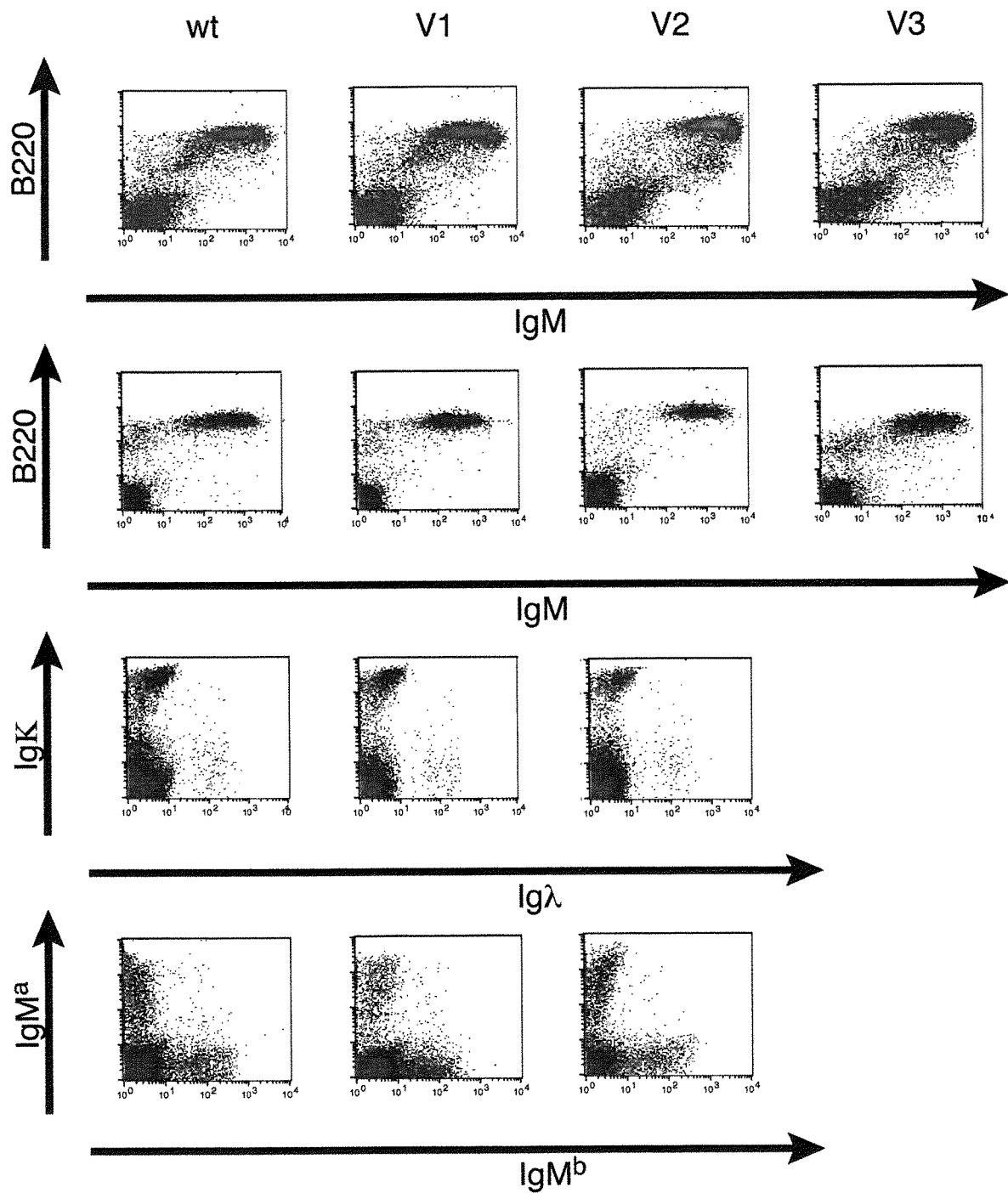
FIG. 6 shows FACS dot plots of B cell populations in wild type and VELOCIMMUNE® humanized mice. Cells from spleen (top row, third row from top and bottom row) or inguinal lymph node (second row from top) of wild type (wt), VELOCIMMUNE® 1 (V1), VELOCIMMUNE® 2 (V2) or VELOCIMMUNE® 3 (V3) mice were stained for surface IgM expressing B cells (top row, and second row from top), surface immunoglobulin containing either κ or λ light chains (third row from top) or surface IgM of specific haplotypes (bottom row), and populations separated by FACS.

Lymphocytes isolated from spleen or lymph node of homozygous VELOCIMMUNE® mice were stained for surface expression of the markers B220 and IgM and analyzed using flow cytometry (FIG. 6). The sizes of the B220$^+$ IgM$^+$ mature B cell populations in all versions of correlate with the ability to generate wild type populations of mature B cells. In contrast, mice with randomly integrated fully-human immunoglobulin transgenes and inactivated mouse immunoglobulin loci have reduced numbers of B cells in these compartments, with the severity of the deficit depending on the number of variable gene segments included in the transgene (Green and Jakobovits, 1998, Regulation of B cell development by variable gene complexity in mice reconstituted with human immunoglobulin yeast artificial chromosomes, *J Exp Med* 188:483-495). This demonstrates that the "in situ genetic humanization" strategy results in a fundamentally different functional outcome than the randomly integrated transgenes achieved in the "knock-out-plus-transgenic" approach.

Allelic Exclusion and Locus Choice. The ability to maintain allelic exclusion was examined in mice heterozygous for different versions of the humanized immunoglobulin heavy chain locus.

The humanization of the immunoglobulin loci was carried out in an F1 ES line (F1H4, Valenzuela et al., 2003), derived from 12956/SvEvTac and C57BL/6NTac heterozygous embryos. The human heavy chain germline variable gene sequences are targeted to the 129S6 allele, which carries the IgM$^a$ haplotype, whereas the unmodified mouse C576BL/6N allele bears the IgM$^b$ haplotype. These allelic forms of IgM can be distinguished by flow cytometry using antibodies specific to the polymorphisms found in the IgM$^a$ or IgM$^b$ alleles. As shown in FIG. 6 (bottom row), the B cells identified in mice heterozygous for each version of the humanized heavy chain locus only express a single allele, either IgM$^a$ (the humanized allele) or IgM$^b$ (the wild type allele). This demonstrates that the mechanisms involved in allelic exclusion are intact in VELOCIMMUNE® mice. In addition, the relative number of B cells positive for the humanized allele (IgM$^a$) is roughly proportional to the number of $V_H$ gene segments present. The humanized immunoglobulin locus is expressed in approximately 30% of the B cells in VELOCIMMUNE® 1 heterozygote mice, which have 18 human $V_H$ gene segments, and in 50% of the B cells in VELOCIMMUNE® 2 and 3 (not shown) heterozygote mice, with 39 and 80 human $V_H$ gene segments, respectively. Notably, the ratio of cells expressing the humanized versus wild type mouse allele (0.5 for VELOCIMMUNE® 1 mice and 0.9 for VELOCIMMUNE® 2 mice) is greater than the ratio of the number of variable gene segments contained in the humanized versus wild type loci (0.2 for VELOCIMMUNE® 1 mice and 0.4 for VELOCIMMUNE® 2 mice). This may indicate that the probability of allele choice is intermediate between a random choice of one or the other chromosome and a random choice of any particular V segment RSS. Further, there may be a fraction of B-cells, but not all, in which one allele becomes accessible for recombination, completes the process and shuts down recombination before the other allele becomes accessible. In addition, the even distribution of cells that have surface IgM (sIgM) derived from either the hybrid humanized heavy chain locus or the wild type mouse heavy chain locus is evidence that the hybrid locus is operating at a normal level. In contrast, randomly integrated human immunoglobulin transgenes compete poorly with wild type mouse immunoglobulin loci (Bruggemann et al., 1989, A repertoire of monoclonal antibodies with human heavy chains from transgenic mice, *PNAS* 86:6709-6713; Green et al., 1994; Tuaillon et al., 1993, Human immunoglobulin heavy-chain minilocus recombination in transgenic mice: gene-segment use in mu and gamma transcripts, *PNAS USA* 90:3720-3724). This further demonstrates the immunoglobulins produced by VELOCIMMUNE® mice are functionally different than those produced by randomly integrated transgenes in mice made by "knockout-plus-transgenic" approaches.

Polymorphisms of the Cκ regions are not available in 129S6 or C57BL/6N to examine allelic exclusion of humanized versus non-humanized κ light chain loci. However, VELOCIMMUNE® mice all possess wild type mouse 2 light chain loci, therefore, it is possible to observe whether rearrangement and expression of humanized κ light chain loci can prevent mouse λ light chain expression. The ratio of the number of cells expressing the humanized κ light chain relative to the number of cells expressing mouse λ light chain was relatively unchanged in VELOCIMMUNE® mice compared with wild type mice, regardless of the number of human Vκ gene segments inserted at the κ light chain locus (FIG. 6, third row from top). In addition there was no increase in the number of double positive (κ plus λ) cells, indicating that productive recombination at the hybrid κ light chain loci results in appropriate suppression of recombination of the mouse λ light chain loci. In contrast, mice containing randomly integrated κ light chain transgenes with inactivated mouse κ light chain loci—but wild type mouse λ light chain loci—exhibit dramatically increased λ/κ ratios (Jakobovits, 1998), implying that the introduced κ light chain transgenes do not function well in such mice. This further demonstrates the different functional outcome observed in immunoglobulins made by VELOCIMMUNE® mice as compared to those made by "knockout-plus-transgenic" mice.

B cell Development. Because the mature B cell populations in VELOCIMMUNE® mice resemble those of wild type mice (described above), it is possible that defects in early B cell differentiation are compensated for by the expansion of mature B cell populations. The various stages of B cell differentiation were examined by analysis of B cell populations using flow cytometry. Table 6 sets forth the ratio of the fraction of cells in each B cell lineage defined by FACs, using specific cell surface markers, in VELOCIMMUNE® mice compared to wild type littermates.

Early B cell development occurs in the bone marrow, and different stages of B cell differentiation are characterized by changes in the types and amounts of cell surface marker expression. These differences in surface expression correlate with the molecular changes occurring at the immunoglobulin loci inside the cell. The pro-B to pre-B cell transition requires the successful rearrangement and expression of functional heavy chain protein, while transition from the pre-B to mature B stage is governed by the correct rearrangement and expression of a κ or Δ light chain. Thus, inefficient transition between stages of B cell differentiation can be detected by changes in the relative populations of B cells at a given stage.

TABLE 6

| | Bone Marrow | | | | Spleen | |
|---|---|---|---|---|---|---|
| | | | | | Emerging | |
| Version of VELOCIMMUNE ® Mice | pro-B CD43$^{hi}$ B220$^{lo}$ | pre-B CD24$^{hi}$ B220$^{lo}$ | Immature B220$^{lo}$ IgM$^+$ | Mature B220$^{hi}$ IgM$^+$ | B220$^{hi}$ IgM$^+$ IgD$^+$ | Mature B220hi IgM$^+$ |
| V1 | 1.1 | 1.0 | 0.9 | 1.0 | 1.1 | 1.0 |
| V2 | 1.0 | 1.0 | 1.0 | 1.0 | 1.0 | 1.0 |
| V3 | 1.0 | 1.0 | 1.1 | 1.0 | 1.0 | 1.1 |

No major defects were observed in B cell differentiation in any of the VELOCIMMUNE® mice. The introduction of human heavy chain gene segments does not appear to affect the pro-B to pre-B transition, and introduction of human κ light chain gene segments does not affect the pre-B to B transition in VELOCIMMUNE® mice. This demonstrates that "reverse chimeric" immunoglobulin molecules possessing human variable regions and mouse constants function normally in the context of B cell signaling and co-receptor molecules leading to appropriate B cell differentiation in a mouse environment. In contrast, the balance between the different populations during B cell differentiation are perturbed to varying extents in mice that contain randomly integrated immunoglobulin transgenes and inactivated endogenous heavy chain or κ light chain loci (Green and Jakobovits, 1998).

Example 4

Variable Gene Repertoire in Humanized Immunoglobulin Mice

Usage of human variable gene segments in the humanized antibody repertoire of VELOCIMMUNE® mice was analyzed by reverse transcriptase-polymerase chain reaction (RT-PCR) of human variable regions from multiple sources including splenocytes and hybridoma cells. Variable region sequence, gene segment usage, somatic hypermutation, and junctional diversity of rearranged variable region gene segments were determined.

Briefly, total RNA was extracted from $1\times10^7$-$2\times10^7$ splenocytes or about $10^4$-$10^5$ hybridoma cells using TRIZOL™ (Invitrogen) or Qiagen RNEASY™ Mini Kit (Qiagen) and primed with mouse constant region specific primers using the SUPERSCRIPT™ III One-Step RT-PCR system (Invitrogen). Reactions were carried out with 2-5 µL of RNA from each sample using the aforementioned 3' constant specific primers paired with pooled leader primers for each family of human variable regions for both the heavy chain and κ light chain, separately. Volumes of reagents and primers, and RT-PCR/PCR conditions were performed according to the manufacturer's instructions. Primers sequences were based upon multiple sources (Wang and Stollar, 2000, Human immunoglobulin variable region gene analysis by single cell RT-PCR, *J Immunol Methods* 244:217-225; Ig-primer sets, Novagen). Where appropriate, nested secondary PCR reactions were carried out with pooled family-specific framework primers and the same mouse 3' immunoglobulin constant-specific primer used in the primary reaction. Aliquots (5 µL) from each reaction were analyzed by agarose electrophoresis and reaction products were purified from agarose using a MONTAGE™ Gel Extraction Kit (Millipore). Purified products were cloned using the TOPO™ TA Cloning System (Invitrogen) and transformed into DH10β *E. coli* cells by electroporation. Individual clones were selected from each transformation reaction and grown in 2 mL LB broth cultures with antibiotic selection overnight at 37° C. Plasmid DNA was purified from bacterial cultures by a kit-based approach (Qiagen).

Immunoglobulin Variable Gene Usage. Plasmid DNA of both heavy chain and κ light chain clones were sequenced with either T7 or M13 reverse primers on the ABI 3100 Genetic Analyzer (Applied Biosystems). Raw sequence data were imported into SEQUENCHER™ (v4.5, Gene Codes). Each sequence was assembled into contigs and aligned to human immunoglobulin sequences using IMGT V-Quest (Brochet et al., 2008, IMGT/V-QUEST: the highly customized and integrated system for IG and TR standardized V-J and V-D-J sequence analysis, *Nucleic Acids Res* 36:W503-508) search function to identify human $V_H$, $D_H$, $J_H$ and Vκ, Jκ segment usage. Sequences were compared to germline sequences for somatic hypermutation and recombination junction analysis.

Mice were generated from ES cells containing the initial heavy chain modification (3h$V_H$-CRE Hybrid Allele, bottom of FIG. 2A) by RAG complementation (Chen et al., 1993, RAG-2-deficient blastocyst complementation: an assay of gene function in lymphocyte development, *PNAS USA* 90:4528-4532), and cDNA was prepared from splenocyte RNA. The cDNA was amplified using primer sets (described above) specific for the predicted chimeric heavy chain mRNA that would arise by V(D)J recombination within the inserted human gene segments and subsequent splicing to either mouse IgM or IgG constant domains. Sequences derived from these cDNA clones (not shown) demonstrated that proper V(D)J recombination had occurred within the human variable gene sequences, that the rearranged human V(D)J gene segments were properly spliced in-frame to mouse constant domains, and that class-switch recombination had occurred. Further sequence analysis of mRNA products of subsequent hybrid immunoglobulin loci was performed.

In a similar experiment, B cells from non-immunized wild type and VELOCIMMUNE® mice were separated by flow cytometry based upon surface expression of B220 and IgM or IgG. The B220$^+$ IgM$^+$ or surface IgG$^+$ (sIgG$^+$) cells were pooled and $V_H$ and Vκ sequences were obtained following RT-PCR amplification and cloning (described above). Representative gene usage in a set of RT-PCR amplified cDNAs from unimmunized VELOCIMMUNE® 1 mice (Table 7) and VELOCIMMUNE® 3 mice (Table 8) was recorded (*defective RSS; †missing or pseudogene). Asterisk: gene segments with defective RSS. †: gene segment is missing or pseudogene.

TABLE 7

|  | Observed |
|---|---|
| $V_H$ | |
| 1-18 | 3 |
| 1-17P | 0 |
| 3-16* | 0 |
| 3-15 | 13 |
| 3-13 | 9 |
| 3-11 | 6 |
| 3-9 | 8 |
| 1-8 | 6 |
| 3-7 | 2 |
| 2-5 | 2 |
| 1-3 | 0 |
| 1-2 | 11 |
| 6-1 | 5 |
| $J_H$ | |
| 1 | 2 |
| 2 | 1 |
| 3 | 8 |
| 4 | 33 |
| 5 | 5 |
| 6 | 16 |
| $D_H$ | |
| 1-1 | 1 |
| 2-2 | 2 |
| 3-3 | 4 |
| 4-4 | 0 |
| 5-5 | 0 |
| 5-18 | 4 |
| 6-6 | 5 |
| 1-7 | 7 |
| 2-8 | 0 |
| 3-9 | 4 |
| 3-10 | 2 |
| 4-11 | 1 |
| 5-12 | 1 |
| 6-13 | 3 |
| 1-14 | 0 |
| 2-15 | 0 |
| 3-16 | 1 |
| 4-17 | 0 |
| 6-19 | 2 |
| 1-20 | 2 |
| 2-21 | 1 |
| 3-22 | 0 |
| 4-23 | 2 |
| 5-24 | 1 |
| 6-25 | 1 |
| 1-26 | 6 |
| 7-27 | 10 |
| Vκ | |
| 1-16 | 2 |
| 3-15 | 1 |
| 1-12 | 5 |
| 3-11 | 1 |
| 1-9 | 5 |
| 1-8 | 2 |
| 3-7* | 0 |
| 1-6 | 5 |

TABLE 7-continued

| | Observed |
|---|---|
| 1-5 | 8 |
| 5-2 | 6 |
| 4-1 | 8 |
| Jκ | |
| 1 | 12 |
| 2 | 10 |
| 3 | 5 |
| 4 | 10 |
| 5 | 0 |

TABLE 8

| | Observed |
|---|---|
| $V_H$ | |
| 7-81† | 0 |
| 3-74† | 0 |
| 3-73 | 1 |
| 3-72 | 2 |
| 2-70 | 2 |
| 1-69 | 3 |
| 3-66 | 1 |
| 3-64 | 1 |
| 4-61 | 1 |
| 4-59 | 10 |
| 1-58 | 0 |
| 3-53 | 0 |
| 5-51 | 5 |
| 3-49 | 2 |
| 3-48 | 7 |
| 1-46 | 1 |
| 1-45 | 0 |
| 3-43 | 10 |
| 4-39 | 4 |
| 3-38* | 0 |
| 3-35* | 0 |
| 4-34 | 8 |
| 3-33 | 14 |
| 4-31 | 4 |
| 3-30 | 13 |
| 4-28 | 0 |
| 2-26 | 0 |
| 1-24 | 3 |
| 3-23 | 18 |
| 3-21 | 0 |
| 3-20 | 0 |
| 1-18 | 4 |
| 1-17P | 1 |
| 3-16* | 0 |
| 3-15 | 13 |
| 3-13 | 6 |
| 3-11 | 5 |
| 3-9 | 31 |
| 1-8 | 7 |
| 3-7 | 11 |
| 2-5 | 1 |
| 1-3 | 0 |
| 1-2 | 6 |
| 6-1 | 9 |
| $D_H$ | |
| 1-1 | 7 |
| 2-2 | 8 |
| 3-3 | 9 |
| 4-4 | 4 |
| 5-5 | 6 |
| 5-18 | 6 |
| 6-6 | 29 |
| 1-7 | 30 |
| 2-8 | 4 |
| 3-9 | 8 |
| 3-10 | 10 |
| 4-11 | 4 |
| 5-12 | 5 |
| 6-13 | 17 |
| 1-14 | 2 |
| 2-15 | 3 |
| 3-16 | 4 |
| 4-17 | 3 |
| 6-19 | 8 |
| 1-20 | 3 |
| 2-21 | 1 |
| 3-22 | 5 |
| 4-23 | 2 |
| 5-24 | 2 |
| 6-25 | 2 |
| 1-26 | 17 |
| 7-27 | 7 |
| $J_H$ | |
| 1 | 2 |
| 2 | 8 |
| 3 | 26 |
| 4 | 95 |
| 5 | 11 |
| 6 | 58 |
| Vκ | |
| 2-40 | 1 |
| 1-39 | 34 |
| 1-37 | 2 |
| 1-33 | 35 |
| 2-30 | 8 |
| 2-29 | 2 |
| 2-28 | 7 |
| 1-27 | 5 |
| 2-24 | 7 |
| 6-21* | 3 |
| 3-20 | 10 |
| 1-17 | 13 |
| 1-16 | 10 |
| 3-15 | 13 |
| 1-12 | 13 |
| 3-11 | 13 |
| 1-9 | 11 |
| 1-8 | 1 |
| 3-7* | 0 |
| 1-6 | 6 |
| 1-5 | 7 |
| 5-2 | 0 |
| 4-1 | 21 |
| Jκ | |
| 1 | 50 |
| 2 | 37 |
| 3 | 28 |
| 4 | 64 |
| 5 | 22 |

As shown in Tables 7 and 8, nearly all of the functional human $V_H$, $D_H$, $J_H$, Vκ and Jκ gene segments are utilized. Of the functional variable gene segments described but not detected in the VELOCIMMUNE® mice of this experiment, several have been reported to possess defective recombination signal sequences (RSS) and, thus, would not be expected to be expressed (Feeney, 2000, Factors that influence formation of B cell repertoire, *Immunol Res* 21:195-202). Analysis of several other sets of immunoglobulin sequences from various VELOCIMMUNE® mice, isolated from both naïve and immunized repertoires, has shown usage of these gene segments, albeit at lower frequencies (data not shown). Aggregate gene usage data has shown that all functional human $V_H$, $D_H$, $J_H$, Vκ, and Jκ gene segments contained in VELOCIMMUNE® mice have been observed in various naïve and immunized repertoires (data not shown). Although the human $V_H$-81 gene segment has been identified in the analysis of human heavy chain locus sequences (Matsuda et al., 1998, The complete nucleotide sequence of the human immunoglobulin heavy chain variable region locus, *J Exp Med* 188:2151-2162), it is not present in the VELOCIMMUNE® mice as confirmed by re-sequencing of the entire VELOCIMMUNE® 3 mouse genome.

Sequences of heavy and light chains of antibodies are known to show exceptional variability, especially in short polypeptide segments within the rearranged variable domain. These regions, known as hypervariable regions or complementary determining regions (CDRs), create the binding site for antigen in the structure of the antibody molecule. The intervening polypeptide sequences are called framework regions (FRs). There are three CDRs (CDR1, CDR2, CDR3) and 4 FRs (FR1, FR2, FR3, FR4) in both heavy and light chains. One CDR, CDR3, is unique in that this CDR is created by recombination of both the $V_H$, $D_H$ and $J_H$ and Vκ and Jκ gene segments and generates a significant amount of repertoire diversity before antigen is encountered. This joining is imprecise due to both nucleotide deletions via exonuclease activity and non-template encoded additions via terminal deoxynucleotidyl transferase (TdT) and, thus, allows for novel sequences to result from the recombination process. Although FRs can show substantial somatic mutation due to the high mutability of the variable region as a whole, variability is not, however, distributed evenly across the variable region. CDRs are concentrated and localized regions of high variability in the surface of the antibody molecule that allow for antigen binding. Heavy chain and light chain sequences of selected antibodies from VELOCIMMUNE® mice around the CDR3 junction demonstrating junctional diversity are shown in FIGS. 7A and 7B, respectively.

As shown in FIG. 7A, non-template encoded nucleotide additions (N-additions) are observed at both the $V_H$-$D_H$ and $D_H$-$J_H$ joint in antibodies from VELOCIMMUNE® mice, indicating proper function of TdT with the human segments. The endpoints of the $V_H$, $D_H$ and $J_H$ segments relative to their germline counterparts indicate that exonuclease activity has also occurred. Unlike the heavy chain locus, the human κ light chain rearrangements exhibit little or no TdT additions at CDR3, which is formed by the recombination of the Vκ and Jκ segments (FIG. 7B). This is expected due to the lack of TdT expression in mice during light chain rearrangements at the pre-B to B cell transition. The diversity observed in the CDR3 of rearranged human Vκ regions is introduced predominantly through exonuclease activity during the recombination event.

Somatic hypermutation. Additional diversity is added to the variable regions of rearranged immunoglobulin genes during the germinal center reaction by a process termed somatic hypermutation. B cells expressing somatically mutated variable regions compete with other B cells for access to antigen presented by the follicular dendritic cells. Those B cells with higher affinity for the antigen will further expand and undergo class switching before exiting to the periphery. Thus, B cells expressing switched isotypes typically have encountered antigen and undergone germinal center reactions and will have increased numbers of mutations relative to naïve B cells. Further, variable region sequences from predominantly naïve sIgM⁺ B cells would be expected to have relatively fewer mutations than variable sequences from sIgG⁺ B cells which have undergone antigen selection.

Sequences from random $V_H$ or Vκ clones from sIgM⁺ or sIgG⁺ B cells from non-immunized VELOCIMMUNE® mice or sIgG⁺ B cells from immunized mice were compared with their germline variable gene segments and changes relative to the germline sequence annotated. The resulting nucleotide sequences were translated in silico and mutations leading to amino acid changes also annotated. The data were collated from all the variable regions and the percent change at a given position was calculated (FIG. 8).

Figure 8:
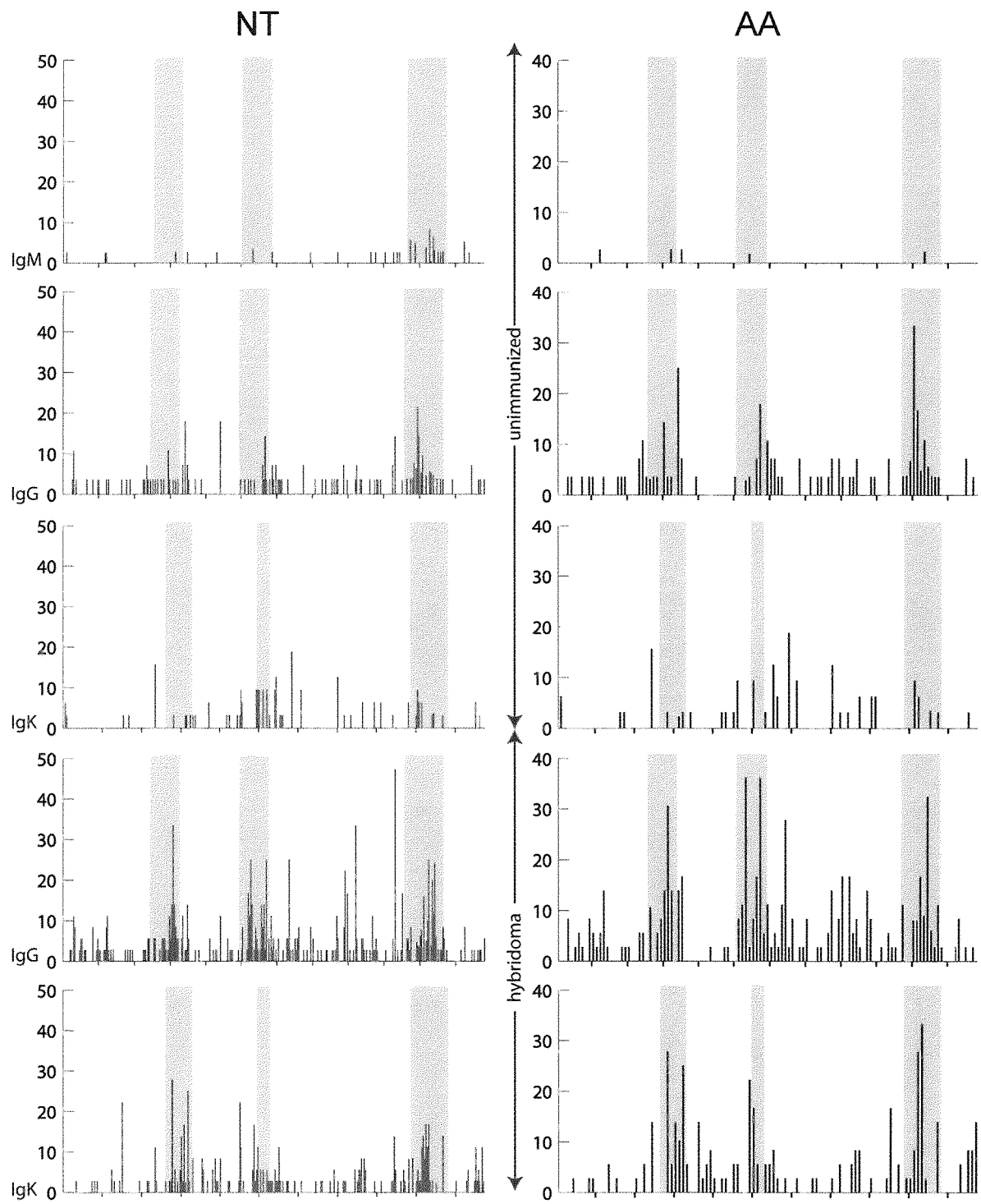
FIG. 8 shows somatic hypermutation frequencies of heavy and light chains of VELOCIMMUNE® antibodies scored (after alignment to matching germline sequences) as percent of sequences changed at each nucleotide (NT; left column) or amino acid (AA; right column) position among sets of 38 (unimmunized IgM), 28 (unimmunized IgG), 32 (unimmunized Igκ from IgG), 36 (immunized IgG) or 36 (immunized Igκ from IgG) sequences. Shaded bars indicate the locations of CDRs.

As shown in FIG. 8, human heavy chain variable regions derived from sIgG⁺ B cells from non-immunized VELOCIMMUNE® mice exhibit many more nucleotides relative to sIgM⁺ B cells from the same splenocyte pools, and heavy chain variable regions derived from immunized mice exhibit even more changes. The number of changes is increased in the complementarity-determining regions (CDRs) relative to the framework regions, indicating antigen selection. The corresponding amino acid sequences from the human heavy chain variable regions also exhibit significantly higher numbers of mutations in IgG versus IgM and even more in immunized IgG. These mutations again appear to be more frequent in the CDRs compared with the framework sequences, suggesting that the antibodies were antigen-selected in vivo. A similar increase in the number the nucleotide and amino acid mutations are seen in the Vκ sequences derived from IgG⁺ B cells from immunized mice.

The gene usage and somatic hypermutation frequency observed in VELOCIMMUNE® mice demonstrate that essentially all gene segments present are capable of rearrangement to form fully functionally reverse chimeric antibodies in these mice. Further, VELOCIMMUNE® antibodies fully participate within the mouse immune system to undergo affinity selection and maturation to create fully mature human antibodies that can effectively neutralize their target antigen. VELOCIMMUNE® mice are able to mount robust immune responses to multiple classes of antigens that result in usage of a wide range of human antibodies that are both high affinity and suitable for therapeutic use (data not shown).

Example 5

Analysis of Lymphoid Structure and Serum Isotypes

The gross structures of spleen, inguinal lymph nodes, Peyer's patches and thymus of tissue samples from wild type or VELOCIMMUNE® mice stained with H&E were examined by light microscopy. The levels of immunoglobulin isotypes in serum collected from wild type and VELOCIMMUNE® mice were analyzed using LUMINEX™ technology.

Lymphoid Organ Structure. The structure and function of the lymphoid tissues are in part dependent upon the proper development of hematopoietic cells. A defect in B cell development or function may be exhibited as an alteration in the structure of the lymphoid tissues. Upon analysis of stained tissue sections, no significant difference in appearance of secondary lymphoid organs between wild type and VELOCIMMUNE® mice was identified (data not shown).

Figure 9A:
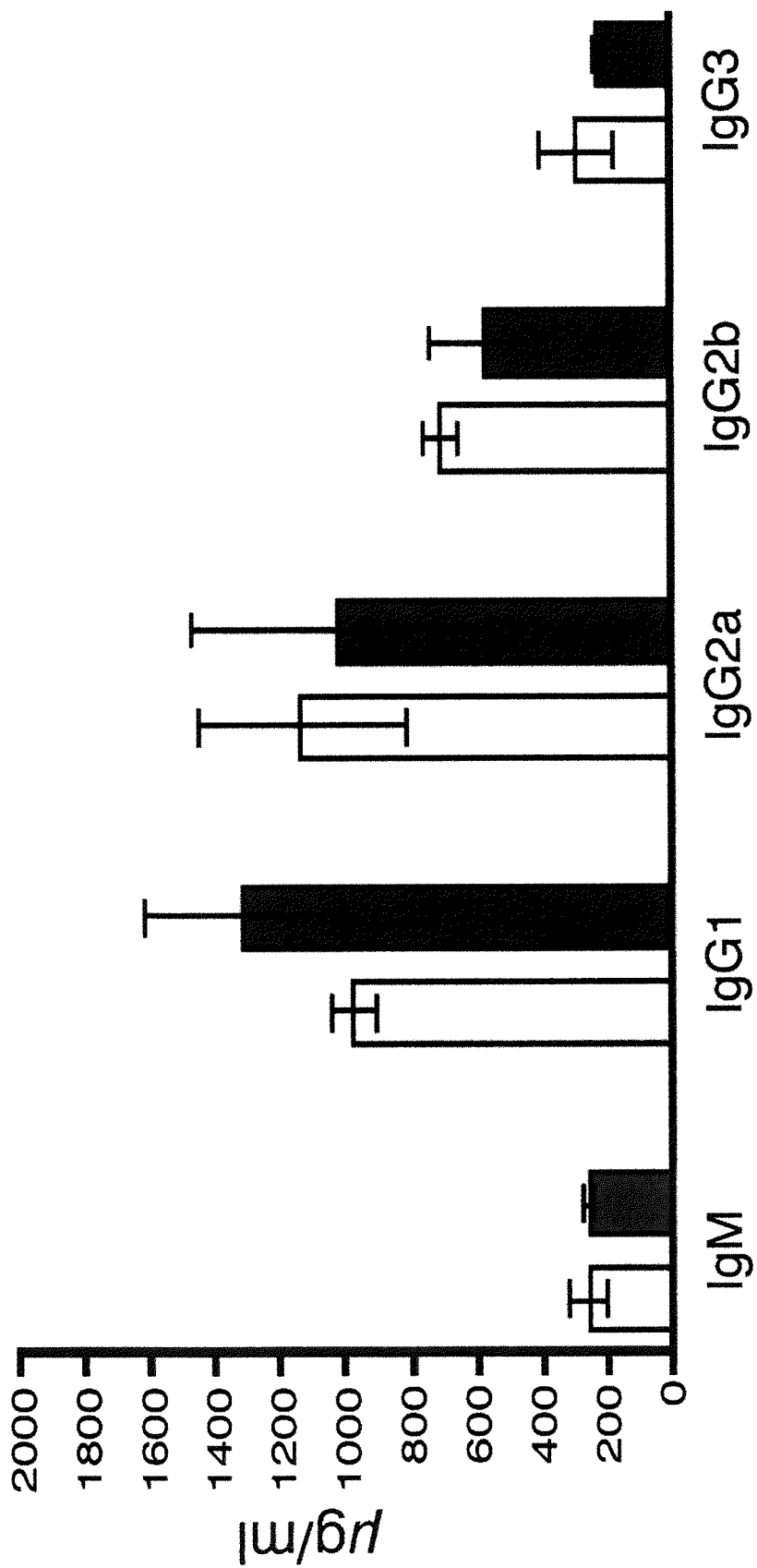
FIG. 9A shows levels of serum immunoglobulin for IgM and IgG isotypes in wild type (open bars) or VELOCIMMUNE® mice (closed bars).
Figure 9B:
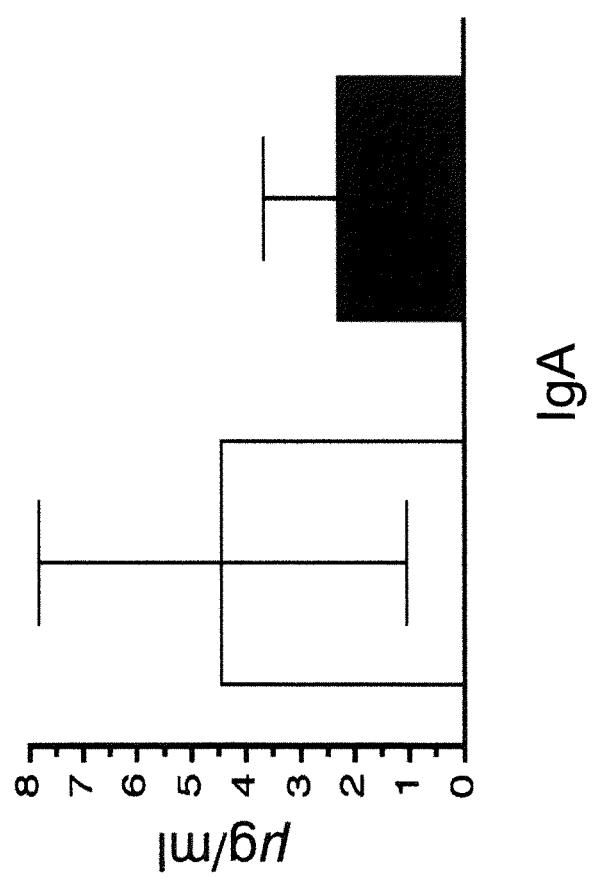
FIG. 9B shows levels of serum immunoglobulin for IgA isotype in wild type (open bars) or VELOCIMMUNE® mice (closed bars).
Figure 9C:
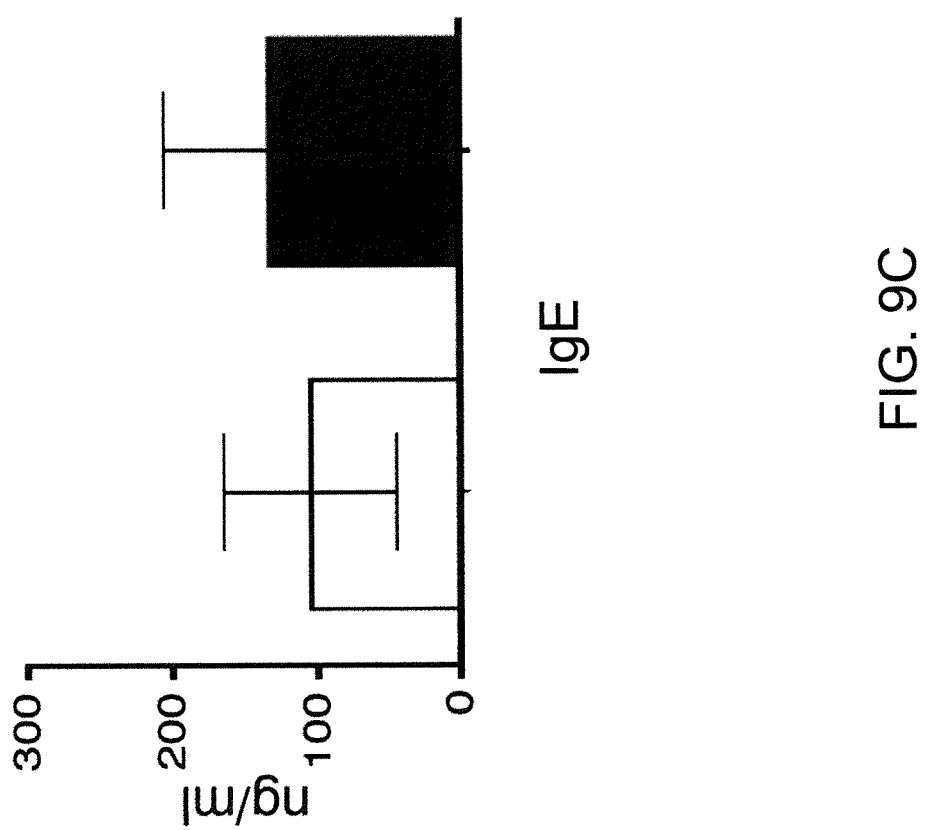
FIG. 9C shows levels of serum immunoglobulin for IgE isotype in wild type (open bars) or VELOCIMMUNE® mice (closed bars).

Serum Immunoglobulin Levels. The level of expression of each isotype is similar in wild type and VELOCIMMUNE® mice (FIGS. 9A, 9B and 9C). This demonstrates that humanization of the variable gene segments had no apparent adverse effect upon class switching or immunoglobulin expression and secretion and therefore apparently maintain all the endogenous mouse sequences necessary for these functions.

Example 6

Immunization and Antibody Production in Humanized Immunoglobulin Mice

Different versions of VELOCIMMUNE® mice were immunized with antigen to examine the humoral response to foreign antigen challenge.

Immunization and Hybridoma Development. VELOCIMMUNE® and wild-type mice can be immunized with an antigen in the form of protein, DNA, a combination of DNA and protein, or cells expressing the antigen. Animals are typically boosted every three weeks for a total of two to three times. Following each antigen boost, serum samples from each animal are collected and analyzed for antigen-specific antibody responses by serum titer determination. Prior to fusion, mice received a final pre-fusion boost of 5 µg protein or DNA, as desired, via intra-peritoneal and/or intravenous injections. Splenocytes are harvested and fused to Ag8.653 myeloma cells in an electrofusion chamber according to the manufacture's suggested protocol (Cyto Pulse Sciences Inc., Glen Burnie, MD). Ten days after culture, hybridomas are screened for antigen specificity using an ELISA assay (Harlow and Lane, 1988, Antibodies: A Laboratory Manual, Cold Spring Harbor Press, New York). Alternatively, antigen specific B cells are isolated directly from immunized VELOCIMMUNE® mice and screened using standard techniques, including those described here, to obtain human antibodies specific for an antigen of interest (e.g., see US 2007/0280945A1, herein incorporated by reference in its entirety).

Serum Titer Determination. To monitor animal anti-antigen serum response, serum samples are collected about 10 days after each boost and the titers are determined using antigen specific ELISA. Briefly, Nunc MAXISORP™ 96 well plates are coated with 2 µg/mL antigen overnight at 4° C. and blocked with bovine serum albumin (Sigma, St. Louis, MO). Serum samples in a serial 3 fold dilutions are allowed to bind to the plates for one hour at room temperature. The plates are then washed with PBS containing 0.05% Tween-20 and the bound IgG are detected using HRP-conjugated goat anti-mouse Fc (Jackson Immuno Research Laboratories, Inc., West Grove, PA) for total IgG titer, or biotin-labeled isotype specific or light chain specific polyclonal antibodies (Southern Biotech Inc.) for isotype specific titers, respectively. For biotin-labeled antibodies, following plate wash, HRP-conjugated streptavidin (Pierce, Rockford, IL) is added. All plates are developed using colorimetric substrates such as BD OPTEIA™ (BD Biosciences Pharmingen, San Diego, CA). After the reaction is stopped with 1 M phosphoric acid, optical absorptions at 450 nm are recorded and the data are analyzed using PRISM™ software from Graph Pad. Dilutions required to obtain two-fold of background signal are defined as titer.

In one experiment, VELOCIMMUNE® mice were immunized with human interleukin-6 receptor (hIL-6R). A representative set of serum titers for VELOCIMMUNE® and wild type mice immunized with hIL-6R is shown in FIGS. 10A and 10B.

Figure 10A:
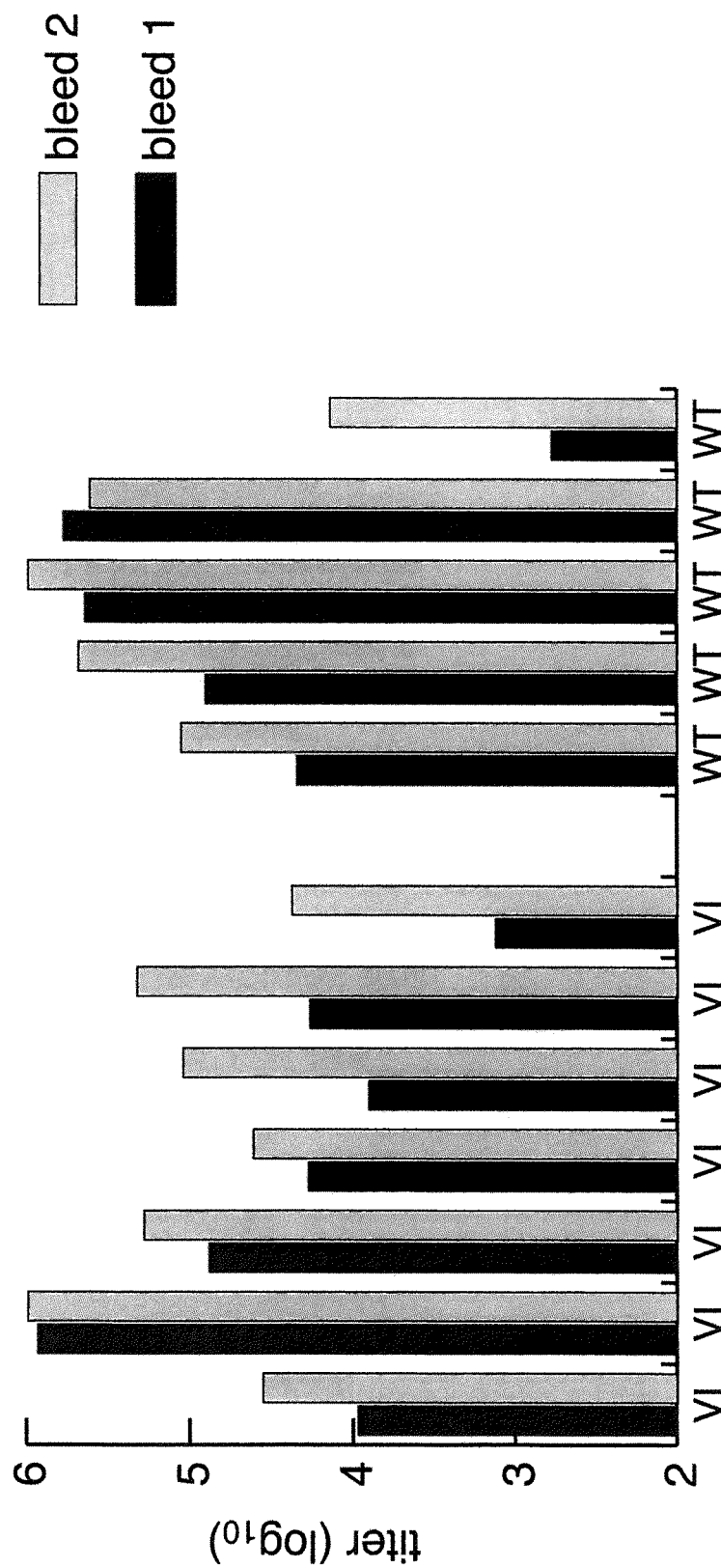
FIG. 10A shows antigen-specific IgG titers against interleukin-6 receptor (IL-6R) of serum from seven VELOCIMMUNE® (VI) and five wild type (WT) mice after two (bleed 1) or three (bleed 2) rounds of immunization with the ectodomain of IL-6R.
Figure 10B:
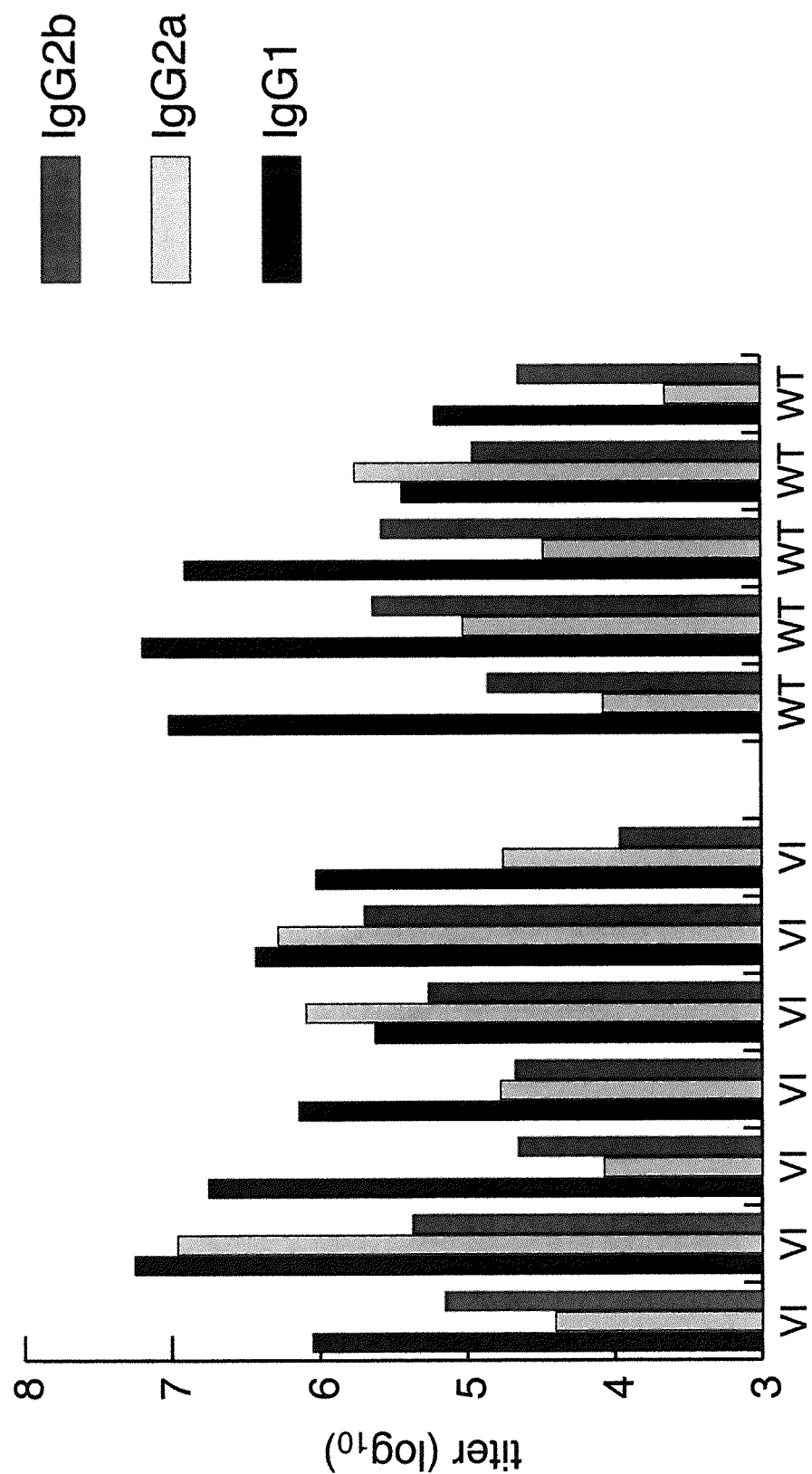
FIG. 10B shows anti-IL-6R-specific IgG isotype-specific titers from seven VELOCIMMUNE® (VI) and five wild type (WT) mice.

VELOCIMMUNE® and wild-type mice mounted strong responses towards IL-6R with similar titer ranges (FIG. 10A). Several mice from the VELOCIMMUNE® and wild-type cohorts reached a maximal response after a single antigen boost. These results indicate that the immune response strength and kinetics to this antigen were similar in the VELOCIMMUNE® and wild type mice. These antigen-specific antibody responses were further analyzed to examine the particular isotypes of the antigen-specific antibodies found in the sera. Both VELOCIMMUNE® and wild type groups predominantly elicited an IgG1 response (FIG. 10B), suggesting that class switching during the humoral response is similar in mice of each type.

Affinity Determination of Antibody Binding to Antigen in Solution. An ELISA-based solution competition assay is typically designed to determine antibody-binding affinity to the antigen.

Briefly, antibodies in conditioned medium are premixed with serial dilutions of antigen protein ranging from 0 to 10 mg/mL. The solutions of the antibody and antigen mixture are then incubated for two to four hours at room temperature to reach binding equilibria. The amounts of free antibody in the mixtures are then measured using a quantitative sandwich ELISA. Ninety-six well MAXISORB™ plates (VWR, West Chester, PA) are coated with 1 µg/mL antigen protein in PBS solution overnight at 4° C. followed by BSA nonspecific blocking. The antibody-antigen mixture solutions are then transferred to these plates followed by one-hour incubation. The plates are then washed with washing buffer and the plate-bound antibodies were detected with an HRP-conjugated goat anti-mouse IgG polyclonal antibody reagent (Jackson Immuno Research Lab) and developed using colorimetric substrates such as BD OPTEIA™ (BD Biosciences Pharmingen, San Diego, CA). After the reaction is stopped with 1 M phosphoric acid, optical absorptions at 450 nm are recorded and the data are analyzed using PRISM™ software from Graph Pad. The dependency of the signals on the concentrations of antigen in solution are analyzed with a 4 parameter fit analysis and reported as $IC_{50}$, the antigen concentration required to achieve 50% reduction of the signal from the antibody samples without the presence of antigen in solution.

Figure 11A:
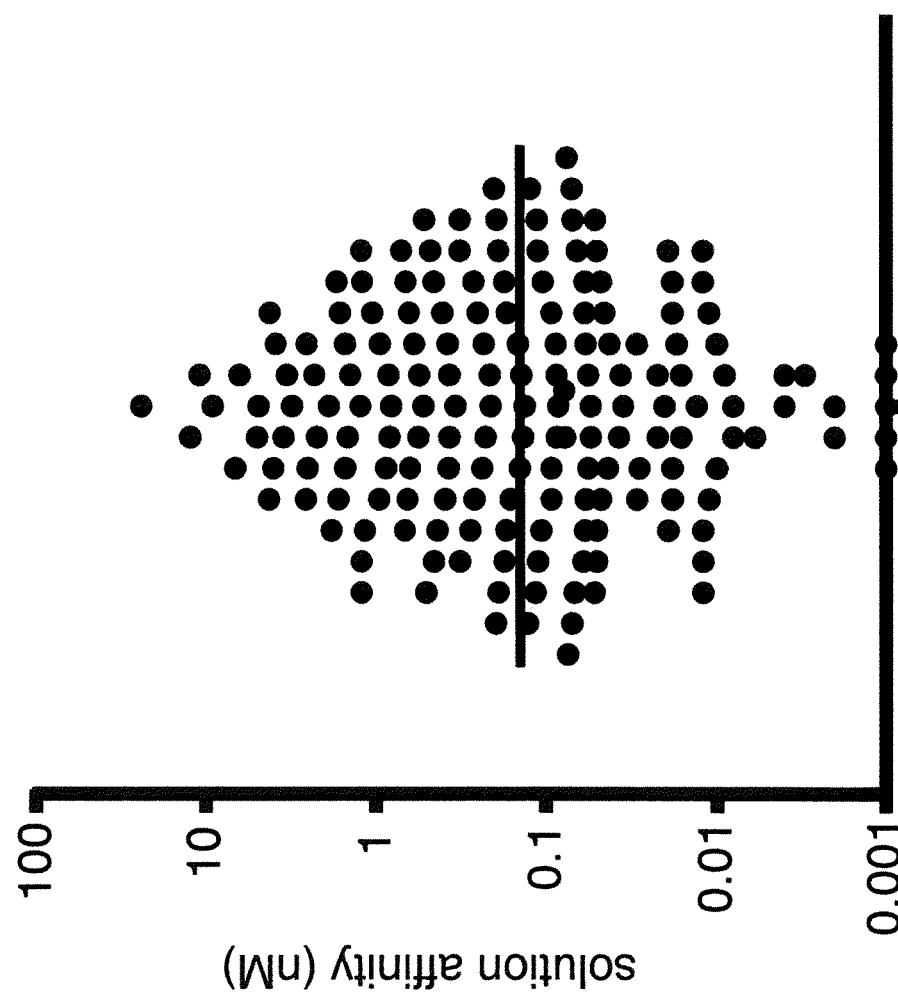
FIG. 11A shows the affinity distribution of anti-interleukin-6 receptor monoclonal antibodies generated in VELOCIMMUNE® mice.
Figure 11B:
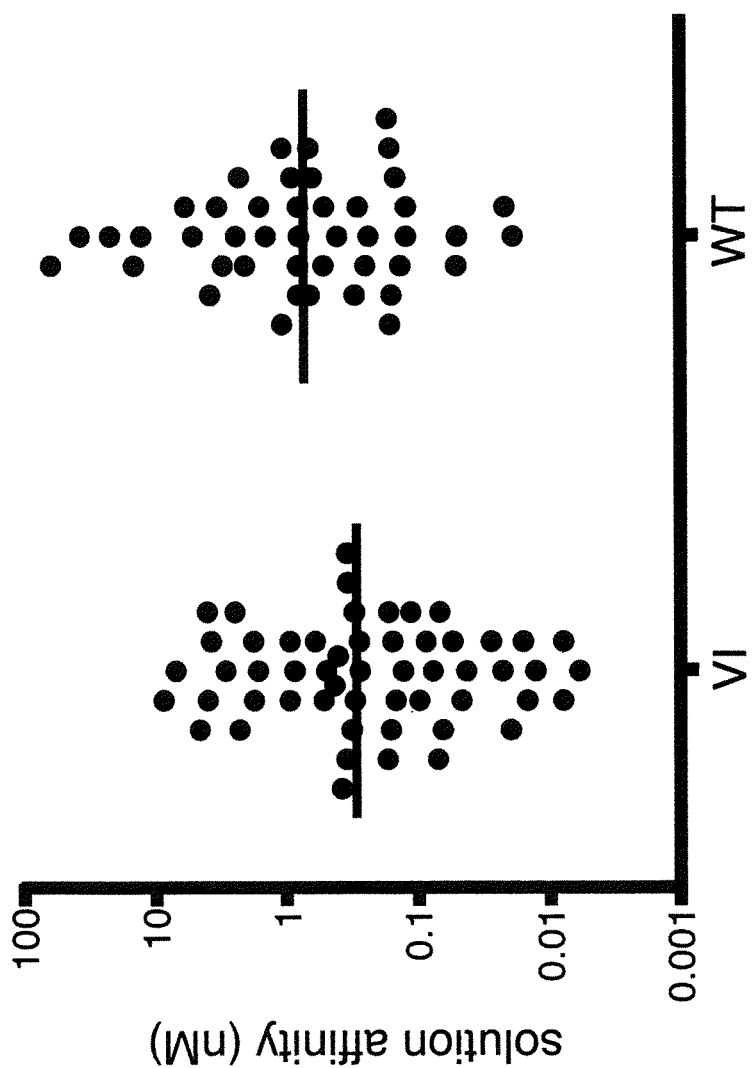
FIG. 11B shows the antigen-specific blocking of anti-interleukin-6 receptor monoclonal antibodies generated in VELOCIMMUNE® (VI) and wild type (WT) mice.

In one experiment, VELOCIMMUNE® mice were immunized with hIL-6R (as described above). FIGS. 11A and 11B show a representative set of affinity measurements for anti-hIL6R antibodies from VELOCIMMUNE® and wild-type mice.

After immunized mice receive a third antigen boost, serum titers are determined using an ELISA assay. Splenocytes are isolated from selected wild type and VELOCIMMUNE® mouse cohorts and fused with Ag8.653 myeloma cells to form hybridomas and grown under selection (as described above). Out of a total of 671 anti-IL-6R hybridomas produced, 236 were found to express antigen-specific antibodies. Media harvested from antigen positive wells was used to determine the antibody affinity of binding to antigen using a solution competition ELISA. Antibodies derived from VELOCIMMUNE® mice exhibit a wide range of affinity in binding to antigen in solution (FIG. 11A). Furthermore, 49 out of 236 anti-IL-6R hybridomas were found to block IL-6 from binding to the receptor in an in vitro bioassay (data not shown). Further, these 49 anti-IL-6R blocking antibodies exhibited a range of high solution affinities similar to that of blocking antibodies derived from the parallel immunization of wild type mice (FIG. 11B).

Example 7

Construction of a Mouse ADAM6 Targeting Vector

Due to replacement of mouse immunoglobulin heavy chain variable gene loci with human immunoglobulin heavy chain variable gene loci, early versions of VELOCIMMUNE® mice lack expression of mouse ADAM6 genes. In particular, male VELOCIMMUNE® mice demonstrate a reduction in fertility. Thus, the ability to express ADAM6 was reengineered into VELOCIMMUNE® mice to rescue the fertility defect.

A targeting vector for insertion of mouse ADAM6a and ADAM6b genes into a humanized heavy chain locus was constructed using VELOCIGENE® genetic engineering technology (supra) to modify a Bacterial Artificial Chromosome (BAC) 929d24, which was obtained from Dr. Frederick Alt (Harvard University). 929d24 BAC DNA was engineered to contain genomic fragments containing the mouse ADAM6a and ADAM6b genes and a hygromycin cassette for targeted deletion of a human ADAM6 pseudogene (hADAM6Ψ)) located between human $V_H$1-2 and $V_H$6-1 gene segments of a humanized heavy chain locus (FIG. 12).

First, a genomic fragment containing the mouse ADAM6b gene, ~800 bp of upstream (5') sequence and ~4800 bp of downstream (3') sequence was subcloned from the 929d24 BAC clone. A second genomic fragment containing the mouse ADAM6a gene, ~300 bp of upstream (5') sequence and ~3400 bp of downstream (3') sequence, was separately subcloned from the 929d24 BAC clone. The two genomic fragments containing the mouse ADAM6b and ADAM6a genes were ligated to a hygromycin cassette flanked by Frt recombination sites to create the targeting vector (Mouse ADAM6 Targeting Vector, FIG. 12; SEQ ID NO:3). Different restriction enzyme sites were engineered onto the 5' end of the targeting vector following the mouse ADAM6b gene and onto the 3' end following the mouse ADAM6a gene (bottom of FIG. 12) for ligation into the humanized heavy chain locus.

Figure 13:
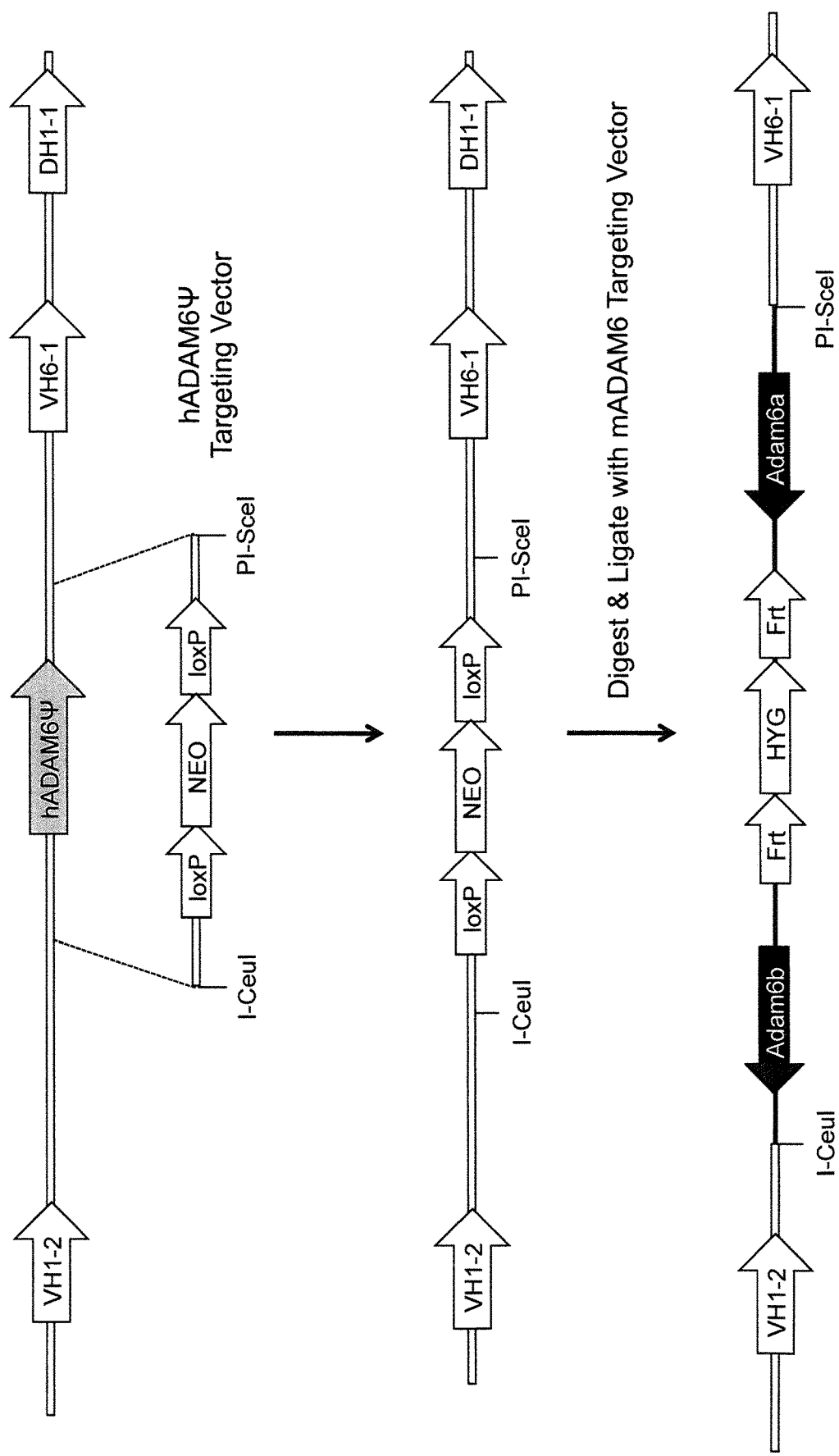
FIG. 13 shows a schematic illustration, not to scale, of a human ADAM6 pseudogene (hADAM6Ψ) located between human heavy chain variable gene segments 1-2 ($V_H$1-2) and 6-1 ($V_H$6-1). A targeting vector for bacterial homologous recombination (hADAM6Ψ Targeting Vector) to delete a human ADAM6 pseudogene and insert unique restriction sites into a human heavy chain locus is shown with a selection cassette (NEO: neomycin) flanked by site-specific recombination sites (loxP) including engineered restriction sites on the 5' and 3' ends. An illustration, not to scale, of the resulting targeted humanized heavy chain locus containing a genomic fragment that encodes for the mouse ADAM6a and ADAM6b genes including a selection cassette flanked by site-specific recombination sites is shown.
Figure 14A:
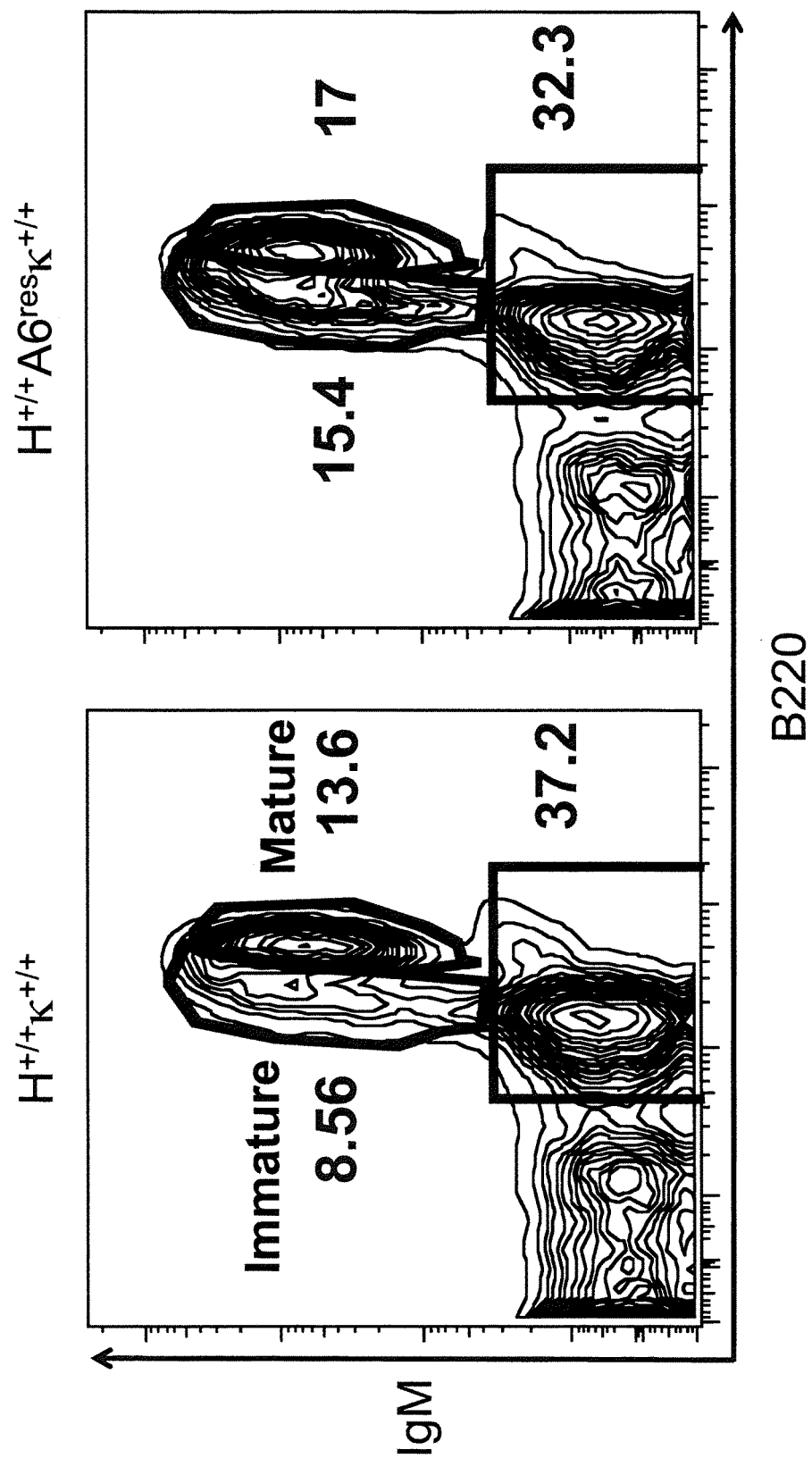
FIG. 14A shows FACS contour plots of lymphocytes gated on singlets for surface expression of IgM and B220 in the bone marrow for mice homozygous for human heavy and human κ light chain variable gene loci ($H^{+/+}κ^{+/+}$) and mice homozygous for human heavy and human κ light chain variable gene loci having an ectopic mouse genomic fragment encoding mouse ADAM6 genes ($H^{+/+}A6^{res}κ^{+/+}$). Percentage of immature ($B220^{int}IgM^+$) and mature ($B220^{high}IgM^+$) B cells is noted in each contour plot.
Figure 14B:
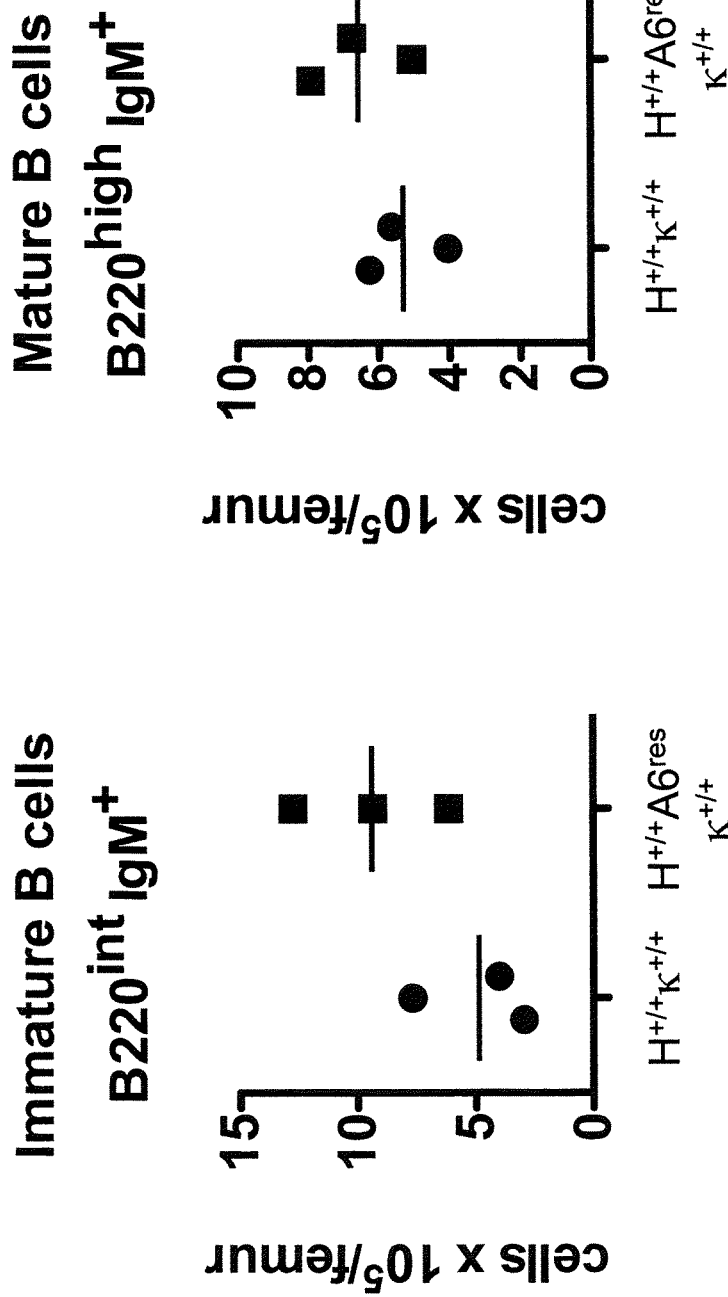
FIG. 14B shows the total number of immature ($B220^{int}IgM^+$) and mature ($B220^{high}IgM^+$) B cells in the bone marrow isolated from femurs of mice homozygous for human heavy and human κ light chain variable gene loci ($H^{+/+}κ^{+/+}$) and mice homozygous for human heavy and human κ light chain variable gene loci having an ectopic mouse genomic fragment encoding mouse ADAM6 genes ($H^{+/+}A6^{res}κ^{+/+}$).
Figure 15A:
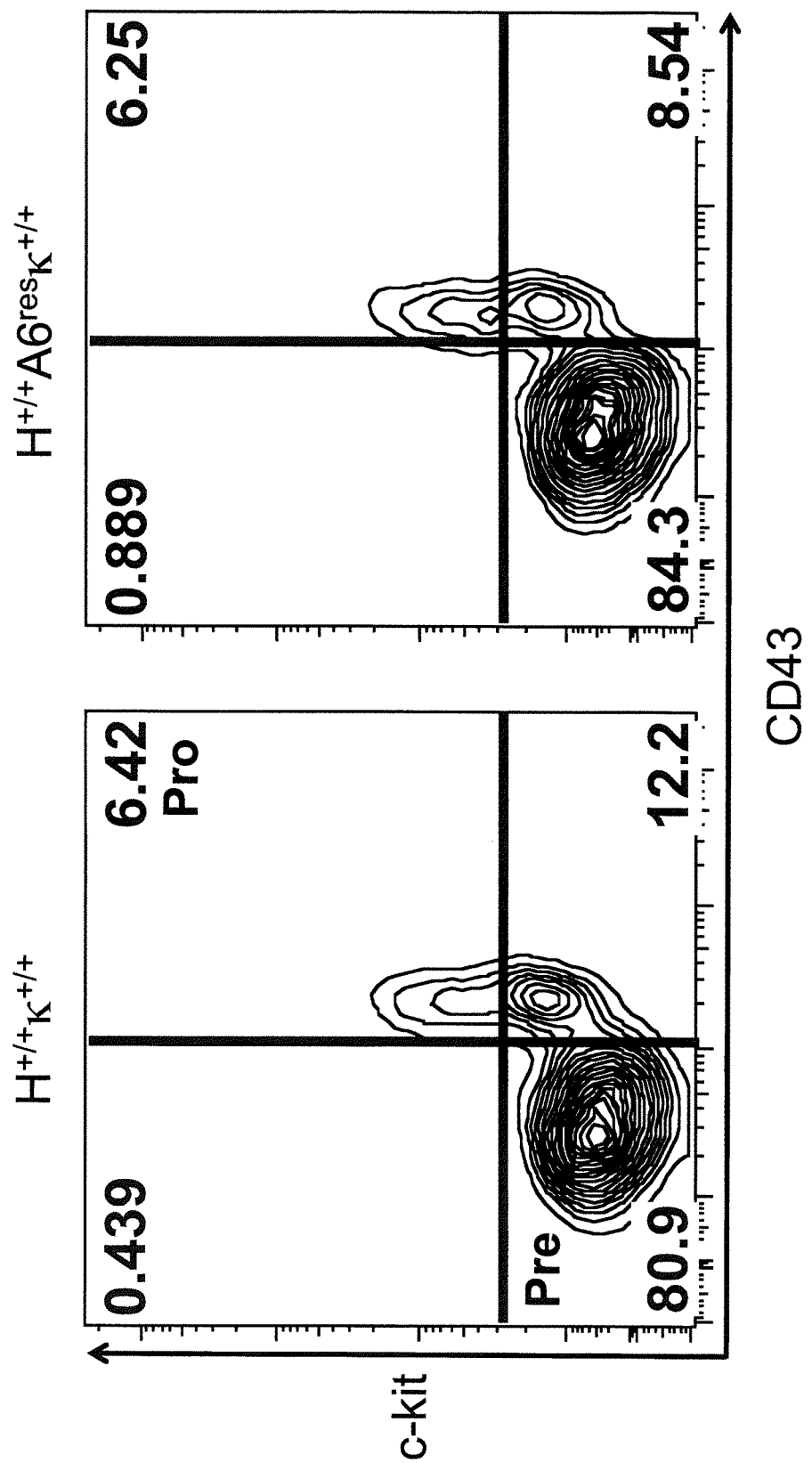
FIG. 15A shows FACS contour plots of $CD19^+$-gated B cells for surface expression of c-kit and CD43 in the bone marrow for mice homozygous for human heavy and human κ light chain variable gene loci ($H^{+/+}κ^{+/+}$) and mice homozygous for human heavy and human κ light chain variable gene loci having an ectopic mouse genomic fragment encoding mouse ADAM6 genes ($H^{+/+}A6^{res}κ^{+/+}$). Percentage of pro-B ($CD19^+CD43^+ckit^+$) and pre-B ($CD19^+CD43^-ckit^-$) cells is noted in the upper right and lower left quadrants, respectively, of each contour plot.
Figure 15B:
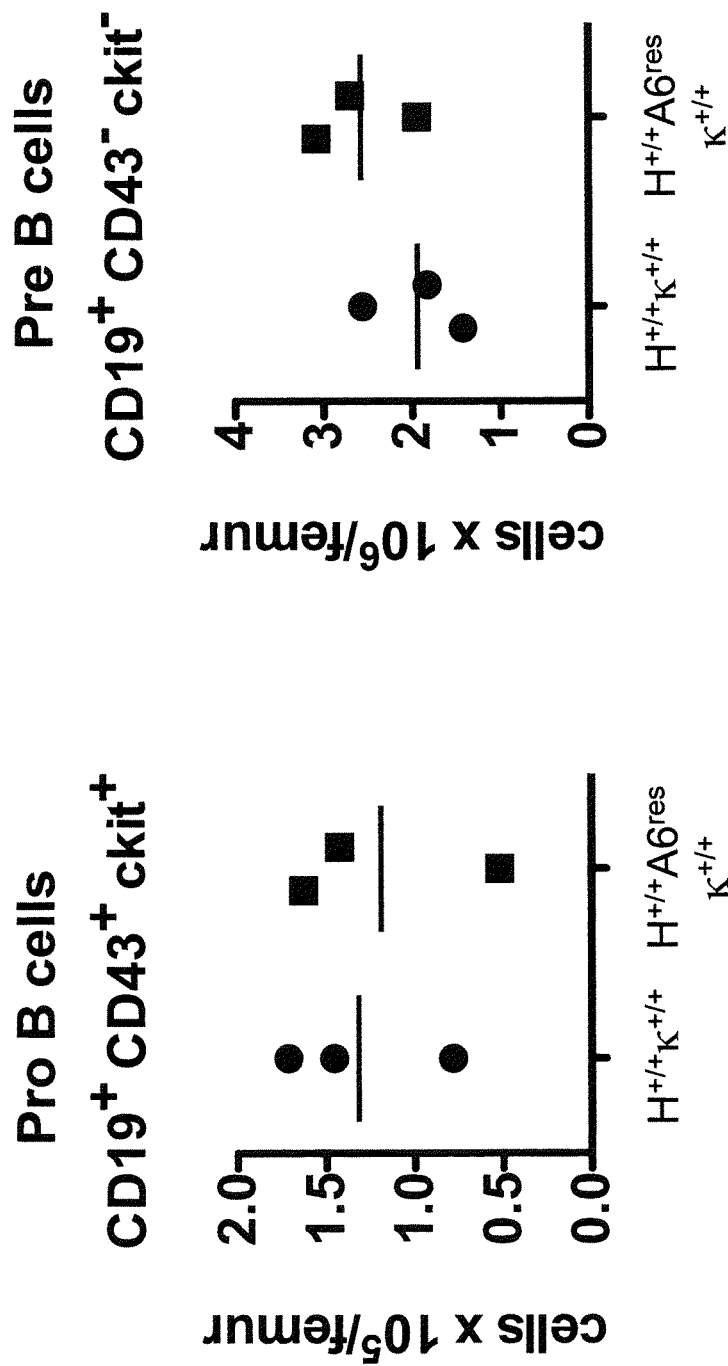
FIG. 15B shows the total number of pro-B cells ($CD19^+CD43^+ckit^+$) and pre-B cells ($CD19^+CD43^-ckit^-$) in the bone marrow isolated from femurs of mice homozygous for human heavy and human κ light chain variable gene loci ($H^{+/+}κ^{+/+}$) and mice homozygous for human heavy and human κ light chain variable gene loci having an ectopic mouse genomic fragment encoding mouse ADAM6 genes ($H^{+/+}A6^{res}κ^{+/+}$).

A separate modification was made to a BAC clone containing a replacement of mouse heavy chain variable gene loci with human heavy chain variable gene loci, including the human ADAM6 pseudogene (hADAM6Ψ) located between the human $V_H$1-2 and $V_H$6-1 gene segments of the humanized locus for the subsequent ligation of the mouse ADAM6 targeting vector (FIG. 13).

Briefly, a neomycin cassette flanked by loxP recombination sites was engineered to contain homology arms containing human genomic sequence at positions 3' of the human $V_H$1-2 gene segment (5' with respect to hADAM6Ψ) and 5' of human $V_H$6-1 gene segment (3' with respect to hADAM6Ψ; see middle of FIG. 13). The location of the insertion site of this targeting construct was about 1.3 kb 5' and ~350 bp 3' of the human ADAM6 pseudogene. The targeting construct also included the same restriction sites as the mouse ADAM6 targeting vector to allow for subsequent BAC ligation between the modified BAC clone containing the deletion of the human ADAM6 pseudogene and the mouse ADAM6 targeting vector.

Following digestion of BAC DNA derived from both constructs, the genomic fragments were ligated together to construct an engineered BAC clone containing a humanized heavy chain locus containing an ectopically placed genomic sequence comprising mouse ADAM6a and ADAM6b nucleotide sequences. The final targeting construct for the deletion of a human ADAM6 gene within a humanized heavy chain locus and insertion of mouse ADAM6a and ADAM6b sequences in ES cells contained, from 5' to 3', a 5' genomic fragment containing ~13 kb of human genomic sequence 3' of the human $V_H$1-2 gene segment, ~800 bp of mouse genomic sequence downstream of the mouse ADAM6b gene, the mouse ADAM6b gene, ~4800 bp of genomic sequence upstream of the mouse ADAM6b gene, a 5' Frt site, a hygromycin cassette, a 3' Frt site, ~300 bp of mouse genomic sequence downstream of the mouse ADAM6a gene, the mouse ADAM6a gene, ~3400 bp of mouse genomic sequence upstream of the mouse ADAM6a gene, and a 3' genomic fragment containing ~30 kb of human genomic sequence 5' of the human $V_H$6-1 gene segment (bottom of FIG. 13).

The engineered BAC clone (described above) was used to electroporate mouse ES cells that contained a humanized heavy chain locus to created modified ES cells comprising a mouse genomic sequence ectopically placed that comprises mouse ADAM6a and ADAM6b sequences within a humanized heavy chain locus. Positive ES cells containing the ectopic mouse genomic fragment within the humanized heavy chain locus were identified by a quantitative PCR assay using TAQMAN™ probes (Lie and Petropoulos, 1998, Advances in quantitative PCR technology: 5'nuclease assays, *Curr Opin Biotechnol* 9(1):43-48). The upstream and downstream regions outside of the modified portion of the humanized heavy chain locus were confirmed by PCR using primers and probes located within the modified region to confirm the presence of the ectopic mouse genomic sequence within the humanized heavy chain locus as well as the hygromycin cassette. The nucleotide sequence across the upstream insertion point included the following, which indicates human heavy chain genomic sequence upstream of the insertion point and an I-CeuI restriction site (contained within the parentheses below) linked contiguously to mouse genomic sequence present at the insertion point:

(SEQ ID NO: 4)
(CCAGCTTCAT TAGTAATCGT TCATCTGTGG

TAAAAAGGCA GGATTTGAAG CGATGGAAGA

TGGGAGTACG GGGCGTTGGA AGACAAAGTG

CCACACAGCG CAGCCTTCGT CTAGACCCCC

GGGCTAACTA TAACGGTCCT AAGGTAGCGA

G)

GGGATGACAG ATTCTCTGTT CAGTGCACTC

AGGGTCTGCC TCCACGAGAA TCACCATGCC

CTTTCTCAAG ACTGTGTTCT GTGCAGTGCC

CTGTCAGTGG.

The nucleotide sequence across the downstream insertion point at the 3' end of the targeted region included the following, which indicates mouse genomic sequence and a PI-SceI restriction site (contained within the parentheses below) linked contiguously with human heavy chain genomic sequence downstream of the insertion point:

(SEQ ID NO: 5)
(AGGGGTCGAG GGGGAATTTT ACAAAGAACA AAGAAGCGGG

CATCTGCTGA CATGAGGGCC GAAGTCAGGC TCCAGGCAGC

GGGAGCTCCA CCGCGGTGGC GCCATTTCAT TACCTCTTTC

TCCGCACCCG ACATAGATAAAGCTT) ATCCCCCACC

AAGCAAATCC CCCTACCTGG GGCCGAGCTT CCCGTATGTG

GGAAAATGAA TCCCTGAGGT CGATTGCTGC ATGCAATGAA

ATTCAACTAG.

Targeted ES cells described above were used as donor ES cells and introduced into an 8-cell stage mouse embryo by the VELOCIMOUSE® mouse engineering method (see, e.g., U.S. Pat. Nos. 7,659,442, 7,576,259, 7,294,754). Mice bearing a humanized heavy chain locus containing an ectopic mouse genomic sequence comprising mouse ADAM6a and ADAM6b sequences were identified by genotyping using a modification of allele assay (Valenzuela et al., 2003) that detected the presence of the mouse ADAM6a and ADAM6b genes within the humanized heavy chain locus.

Mice bearing a humanized heavy chain locus that contains mouse ADAM6a and ADAM6b genes are bred to a FLPe deleter mouse strain (see, e.g., Rodriguez et al., 2000, High-efficiency deleter mice show that FLPe is an alternative to Cre-loxP. *Nature Genetics* 25:139-140) in order to remove any Frt'ed hygromycin cassette introduced by the targeting vector that is not removed, e.g., at the ES cell stage or in the embryo. Optionally, the hygromycin cassette is retained in the mice.

Pups are genotyped and a pup heterozygous for a humanized heavy chain locus containing an ectopic mouse genomic fragment that comprises mouse ADAM6a and ADAM6b sequences is selected for characterizing mouse ADAM6 gene expression and fertility.

Example 8

Characterization of ADAM6 Rescue Mice

Flow Cytometry. Three mice at age 25 weeks homozygous for human heavy and human κ light chain variable gene loci ($H^{+/+}\kappa^{+/+}$) and three mice at age 18-20 weeks homozygous for human heavy and human κ light chain having the ectopic mouse genomic fragment encoding the mouse ADAM6a and ADAM6b genes within both alleles of the human heavy chain locus ($H^{+/+}A6^{res}\kappa^{+/+}$) were sacrificed for identification and analysis of lymphocyte cell populations by FACs on the BD LSR II System (BD Bioscience). Lymphocytes were gated for specific cell lineages and analyzed for progression through various stages of B cell development. Tissues collected from the animals included blood, spleen and bone marrow. Blood was collected into BD microtainer tubes with EDTA (BD Biosciences). Bone marrow was collected from femurs by flushing with complete RPMI medium supplemented with fetal calf serum, sodium pyruvate, HEPES, 2-mercaptoethanol, non-essential amino acids, and gentamycin. Red blood cells from blood, spleen and bone marrow preparations were lysed with an ammonium chloride-based lysis buffer (e.g., ACK lysis buffer), followed by washing with complete RPMI medium.

For staining of cell populations, $1 \times 10^6$ cells from the various tissue sources were incubated with anti-mouse CD16/CD32 (2.4G2, BD Biosciences) on ice for 10 minutes, followed by labeling with one or a combination of the following antibody cocktails for 30 minutes on ice.

Bone marrow: anti-mouse FITC-CD43 (1B11, BioLegend), PE-ckit (2B8, BioLegend), PeCy7-IgM (II/41, eBioscience), PerCP-Cy5.5-IgD (11-26c.2a, BioLegend), APC-eFluor780-B220 (RA3-6B2, eBioscience), A700-CD19 (1D3, BD Biosciences).

Peripheral blood and spleen: anti-mouse FITC-κ (187.1, BD Biosciences), PE-λ (RML-42, BioLegend), PeCy7-IgM (II/41, eBioscience), PerCP-Cy5.5-IgD (11-26c.2a, BioLegend), APC-CD3 (145-2C11, BD), A700-CD19 (1D3, BD), APC-eFluor780-6220 (RA3-6B2, eBioscience). Following incubation with the labeled antibodies, cells were washed and fixed in 2% formaldehyde. Data acquisition was performed on an LSRII flow cytometer and analyzed with FlowJo (Treestar, Inc.). Results from a representative $H^{+/+}\kappa^{+/+}$ and $H^{+/+}A6^{res}\kappa^{+/+}$ mouse are shown in FIGS. 14-18.

Figure 16A:
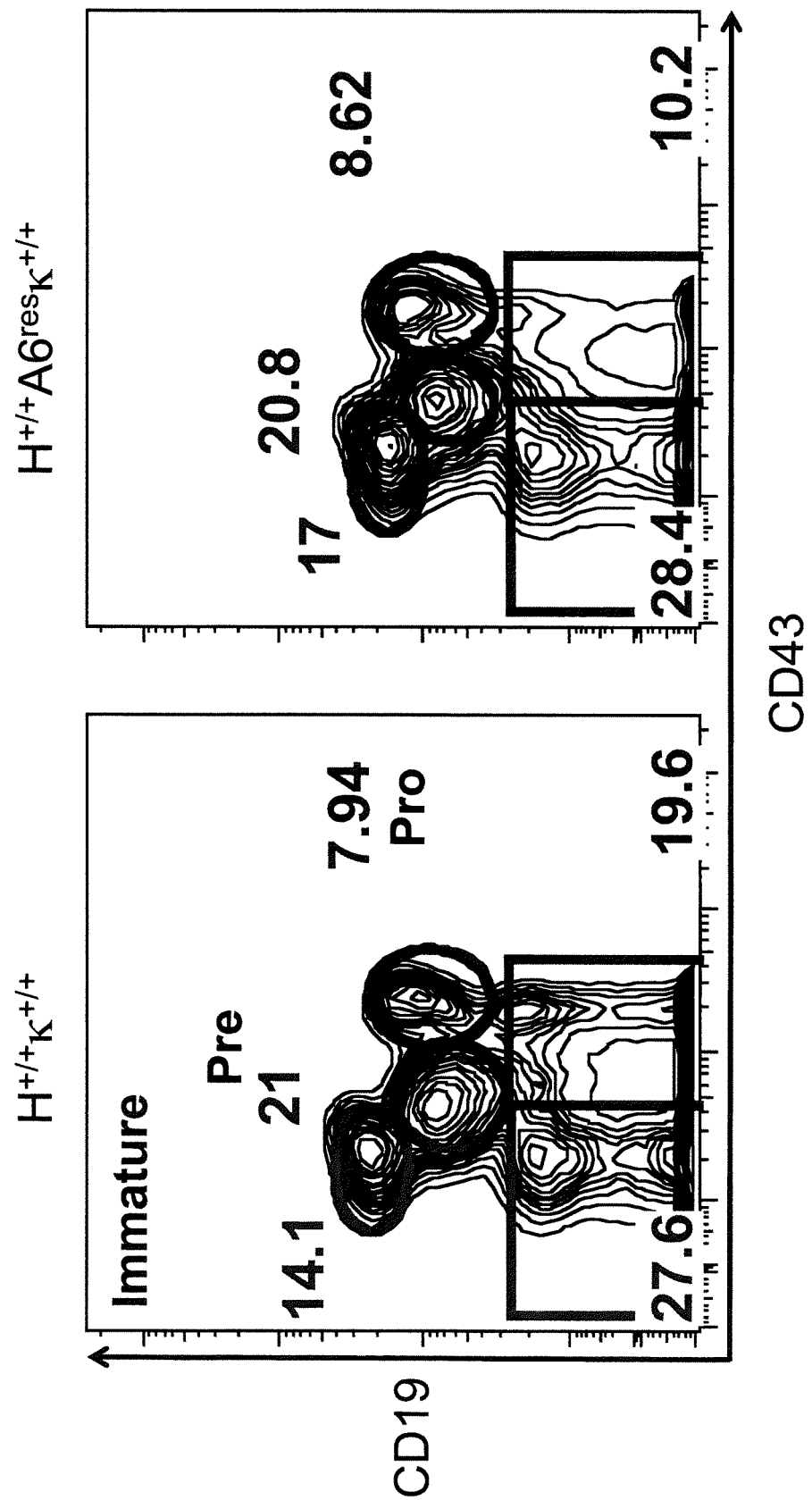
FIG. 16A shows FACS contour plots of lymphocytes gated on singlets for surface expression of CD19 and CD43 in the bone marrow for mice homozygous for human heavy and human κ light chain variable gene loci ($H^{+/+}\kappa^{+/+}$) and mice homozygous for human heavy and human κ light chain variable gene loci having an ectopic mouse genomic fragment encoding mouse ADAM6 genes ($H^{+/+}A6^{res}\kappa^{+/+}$). Percentage of immature B ($CD19^+CD43^-$), pre-B ($CD19^+CD43^{int}$) and pro-B ($CD19^+CD43^+$) cells is noted in each contour plot.
Figure 16B:
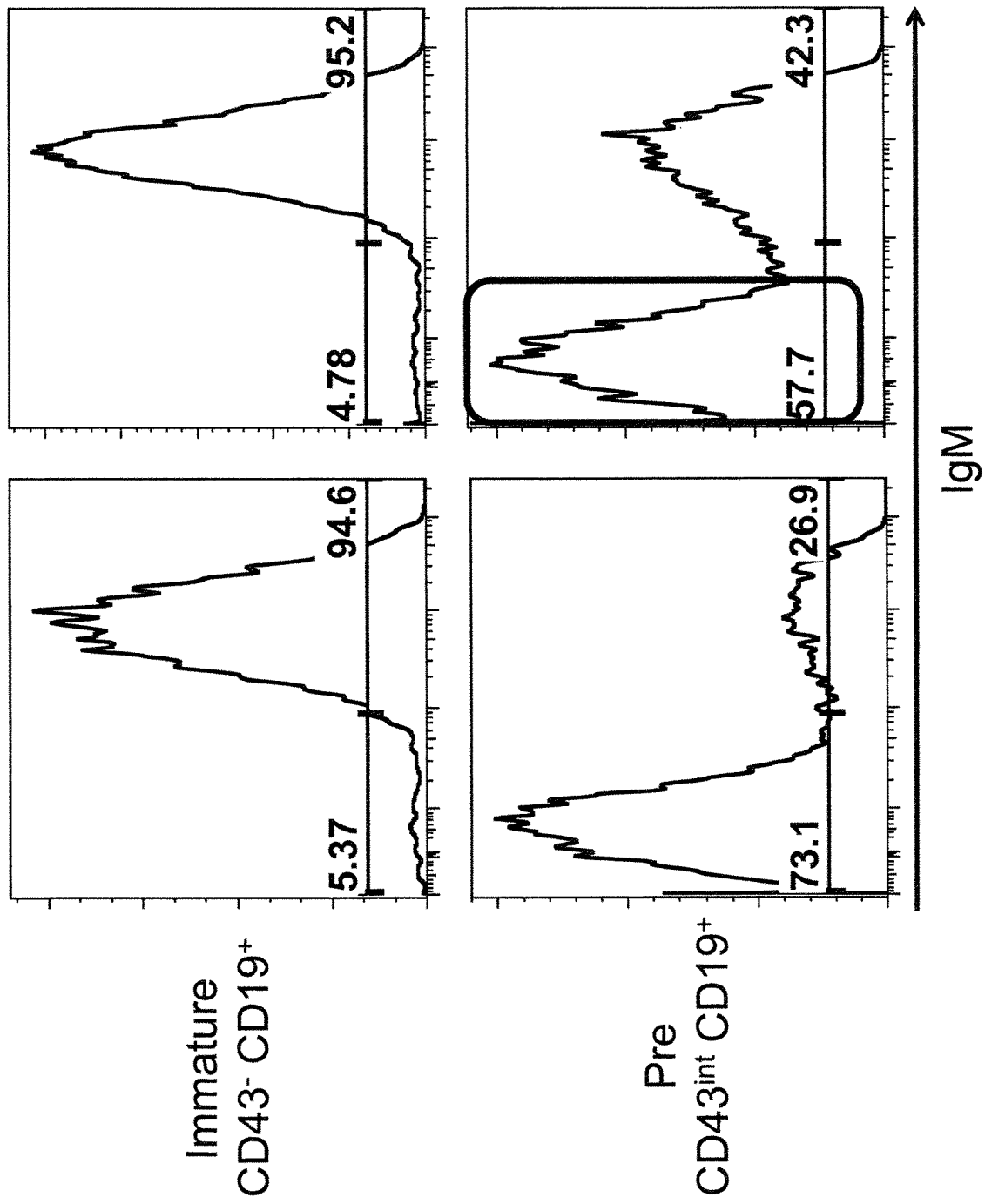
FIG. 16B shows histograms of immature B ($CD19^+CD43^-$) and pre-B ($CD19^+CD43^{int}$) cells in the bone marrow of mice homozygous for human heavy and human κ light chain variable gene loci ($H^{+/+}\kappa^{+/+}$) and mice homozygous for human heavy and human κ light chain variable gene loci having an ectopic mouse genomic fragment encoding mouse ADAM6 genes ($H^{+/+}A6^{res}\kappa^{+/+}$).
Figure 17A:
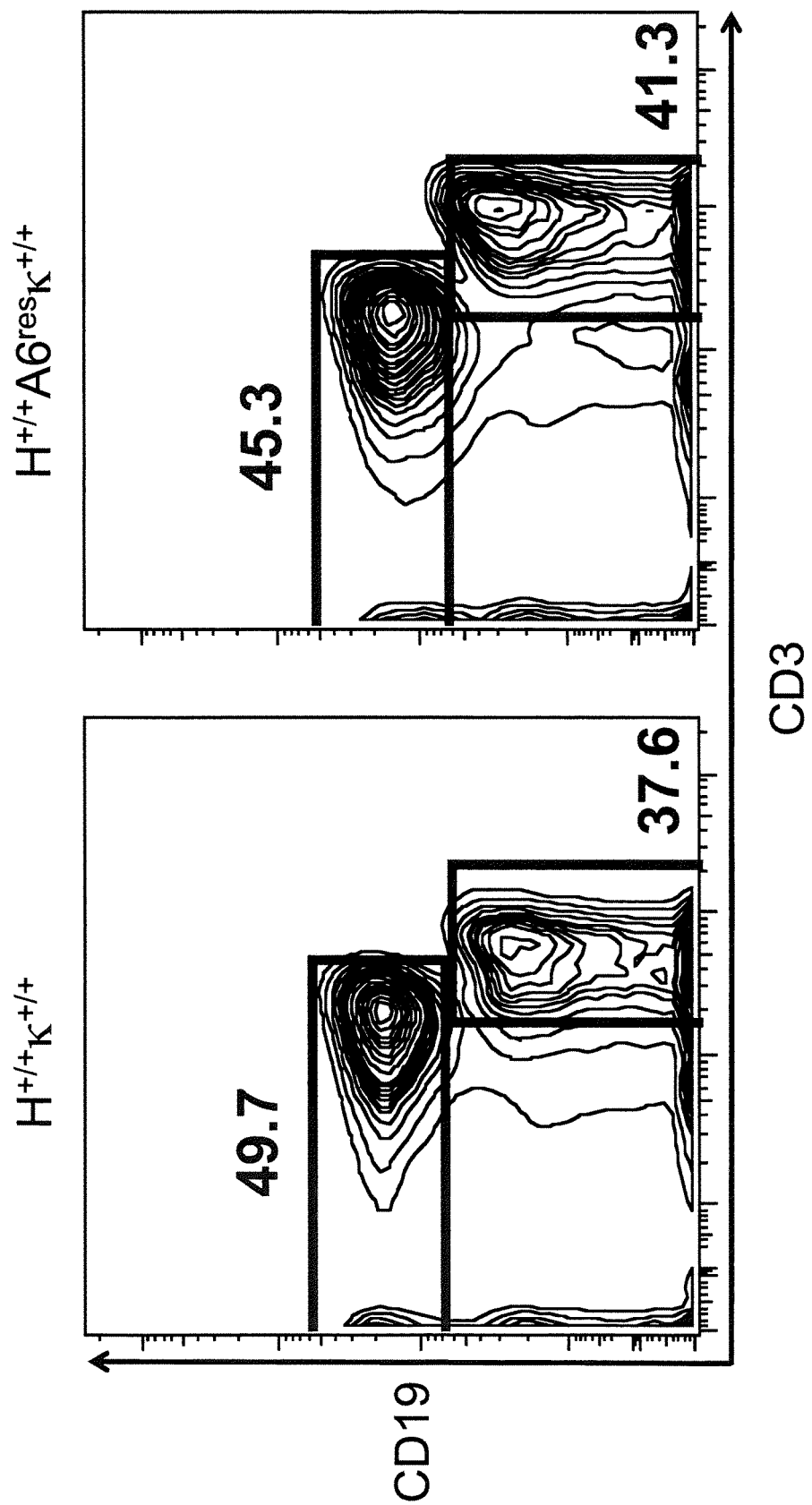
FIG. 17A shows FACS contour plots of lymphocytes gated on singlets for surface expression of CD19 and CD3 in splenocytes for mice homozygous for human heavy and human κ light chain variable gene loci ($H^{+/+}\kappa^{+/+}$) and mice homozygous for human heavy and human κ light chain variable gene loci having an ectopic mouse genomic fragment encoding mouse ADAM6 genes ($H^{+/+}A6^{res}\kappa^{+/+}$). Percentage of B ($CD19^+CD3^-$) and T ($CD19^-CD3^+$) cells is noted in each contour plot.
Figure 17B:
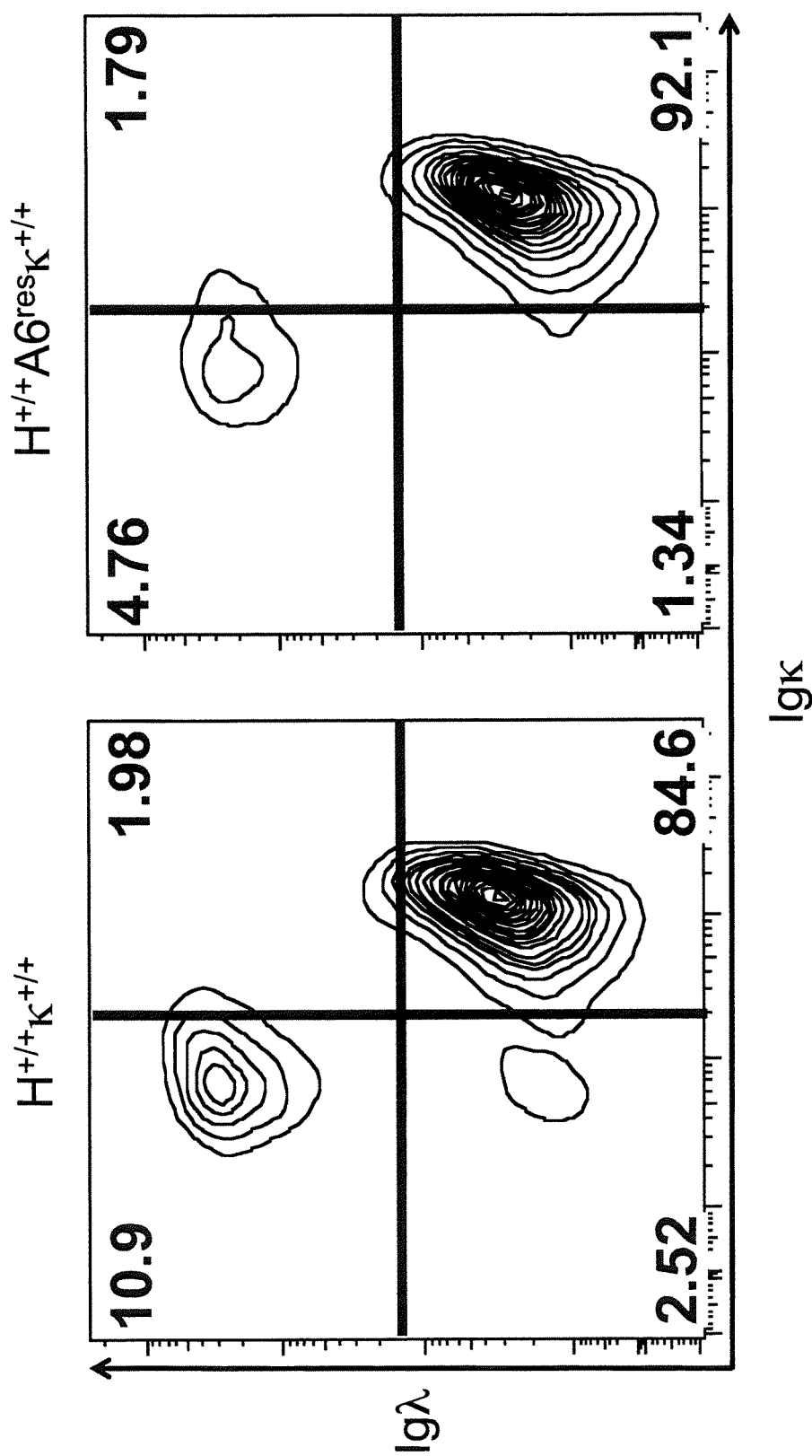
FIG. 17B shows FACs contour plots for $CD19^+$-gated B cells for surface expression of Igλ and Igκ light chain in the spleen of mice homozygous for human heavy and human κ light chain variable gene loci ($H^{+/+}\kappa^{+/+}$) and mice homozygous for human heavy and human κ light chain variable gene loci having an ectopic mouse genomic fragment encoding mouse ADAM6 genes ($H^{+/+}A6^{res}\kappa^{+/+}$). Percentage of Igλ$^+$ (upper left quadrant) and Igκ$^+$ (lower right quadrant) B cells is noted in each contour plot.
Figure 17C:
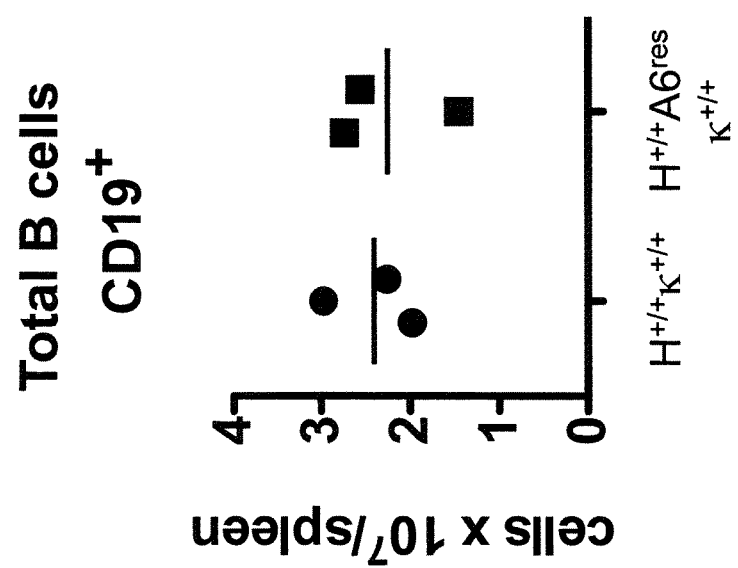
FIG. 17C shows the total number of $CD19^+$ B cells in the spleen of mice homozygous for human heavy and human κ light chain variable gene loci ($H^{+/+}\kappa^{+/+}$) and mice homozygous for human heavy and human κ light chain variable gene loci having an ectopic mouse genomic fragment encoding mouse ADAM6 genes ($H^{+/+}A6^{res}\kappa^{+/+}$).
Figure 18A:
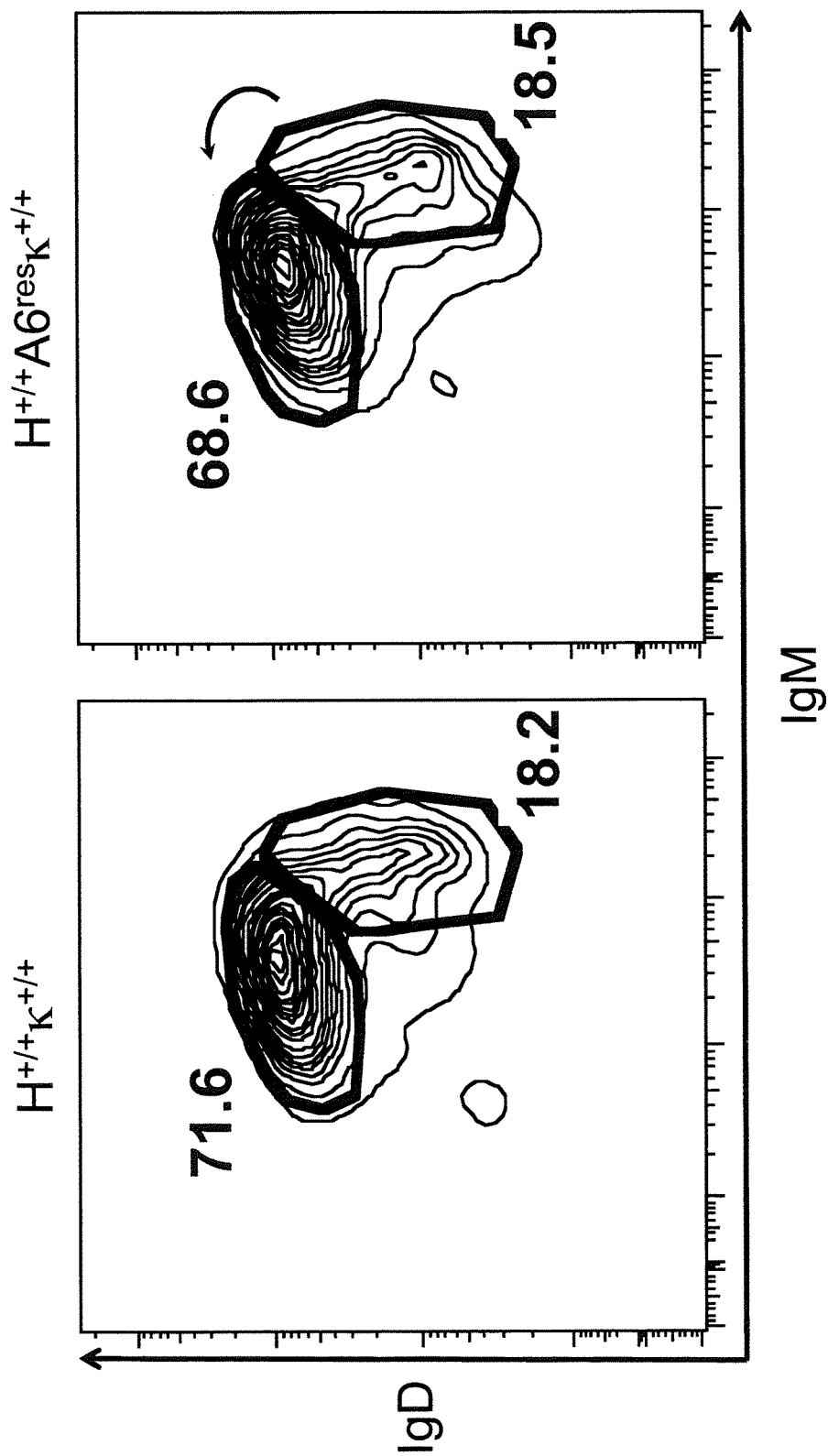
FIG. 18A shows FACs contour plots of $CD19^+$-gated B cells for surface expression of IgD and IgM in the spleen of mice homozygous for human heavy and human κ light chain variable gene loci ($H^{+/+}\kappa^{+/+}$) and mice homozygous for human heavy and human κ light chain variable gene loci having an ectopic mouse genomic fragment encoding mouse ADAM6 genes ($H^{+/+}A6^{res}\kappa^{+/+}$). Percentage of mature B cells ($CD19^+IgD^{high}IgM^{int}$) is noted for each contour plot. The arrow on the right contour plot illustrates the process of maturation for B cells in relation to IgM and IgD surface expression.
Figure 18B:
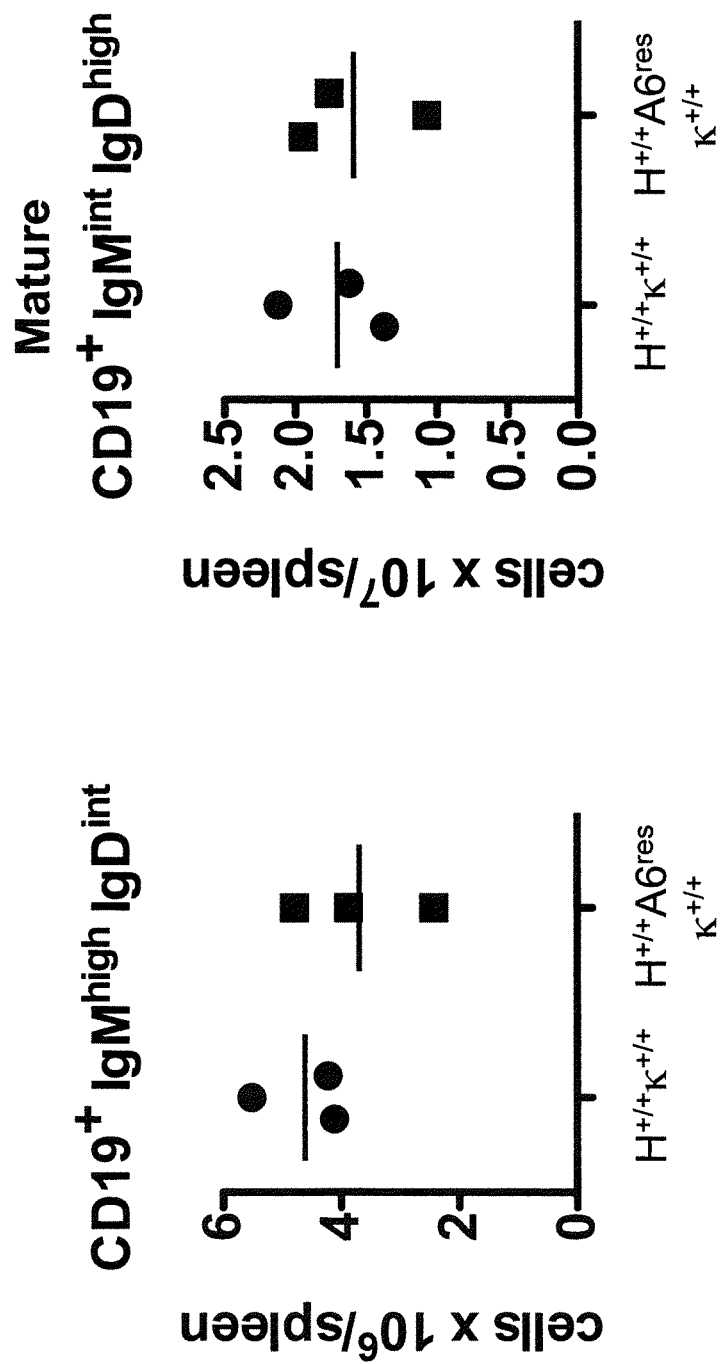
FIG. 18B shows the total number of B cells in the spleen of mice homozygous for human heavy and human κ light chain variable gene loci ($H^{+/+}\kappa^{+/+}$) and mice homozygous for human heavy and human κ light chain variable gene loci having an ectopic mouse genomic fragment encoding mouse ADAM6 genes ($H^{+/+}A6^{res}\kappa^{+/+}$) during maturation from $CD19^+IgM^{high}IgD^{int}$ to $CD19^+IgM^{int}IgD^{high}$.

The results demonstrate that B cells of $H^{+/+}A6^{res}\kappa^{+/+}$ mice progress through the stages of B cell development in a similar fashion to $H^{+/+}\kappa^{+/+}$ mice in the bone marrow and peripheral compartments, and show normal patterns of maturation once they enter the periphery. $H^{+/+}A6^{res}\kappa^{+/+}$ mice demonstrated an increased $CD43^{int}CD19^+$ cell population as compared to $H^{+/+}\kappa^{+/+}$ mice (FIG. 16B). This may indicate an accelerated IgM expression from the humanized heavy chain locus containing an ectopic mouse genomic fragment comprising the mouse ADAM6a and ADAM6b sequences in $H^{+/+}A6^{res}\kappa^{+/+}$ mice. In the periphery, B and T cell populations of $H^{+/+}A6^{res}\kappa^{+/+}$ mice appear normal and similar to $H^{+/+}\kappa^{+/+}$ mice.

Testis Morphology and Sperm Characterization. To determine if infertility in mice having humanized immunoglobulin heavy chain variable loci is due to testis and/or sperm production defects, testis morphology and sperm content of the epididymis was examined.

Briefly, testes from two groups (n=5 per group; group 1: mice homozygous for human heavy and κ light chain variable gene loci, $H^{+/+}\kappa^{+/+}$; group 2: mice heterozygous for human heavy chain variable gene loci and homozygous for κ light chain variable gene loci, $H^{+/-}\kappa^{+/+}$) were dissected with the epididymis intact and weighed. The specimens were then fixed, embedded in paraffin, sectioned and stained with hematoxylin and eosin (HE) stain. Testis sections (2 testes per mouse, for a total of 20) were examined for defects in morphology and evidence of sperm production, while epididymis sections were examined for presence of sperm.

In this experiment, no differences in testis weight or morphology was observed between $H^{+/+}\kappa^{+/+}$ mice and $H^{+/-}\kappa^{+/+}$ mice. Sperm was observed in both the testes and the epididymis of all genotypes. These results establish that the absence of mouse ADAM6a and ADAM6b genes does not lead to detectable changes in testis morphology, and that sperm is produced in mice in the presence and absence of these two genes. Defects in fertility of male $H^{+/+}\kappa^{+/+}$ mice are therefore not likely to be due to low sperm production.

Sperm Motility and Migration. Mice that lack other ADAM gene family members are infertile due to defects in sperm motility or migration. Sperm migration is defined as the ability of sperm to pass from the uterus into the oviduct, and is normally necessary for fertilization in mice. To determine if the deletion of mouse ADAM6a and ADAM6b affects this process, sperm migration and motility was evaluated in $H^{+/+}\kappa^{+/+}$ mice.

Briefly, sperm was obtained from testes of (1) mice heterozygous for human heavy chain variable gene loci and homozygous for human κ light chain variable gene loci ($H^{+/-}\kappa^{+/+}$); (2) mice homozygous for human heavy chain variable gene loci and homozygous for human κ light chain variable gene loci ($H^{+/+}\kappa^{+/+}$); (3) mice homozygous for human heavy chain variable gene loci and homozygous for wild-type κ light chain ($H^{+/+}$mκ); and, (4) wild-type C57 BL/6 mice (WT). No significant abnormalities were observed in sperm count or overall sperm motility by inspection. For all mice, cumulus dispersal was observed, indicating that each sperm sample was able to penetrate the cumulus cells and bind the zona pellucida in vitro. These results establish that $H^{+/+}\kappa^{+/+}$ mice have sperm that are capable of penetrating the cumulus and binding the zona pellucida.

Fertilization of mouse ova in vitro (IVF) was done using sperm from mice as described above. A slightly lower number of cleaved embryos were observed for $H^{+/+}\kappa^{+/+}$ mice the day following IVF, as well as a reduced number of sperm bound to the eggs. These results establish that sperm from $H^{+/+}\kappa^{+/+}$ mice, once exposed to an ovum, are capable of penetrating the cumulus and binding the zona pellucida.

In another experiment, the ability of sperm from $H^{+/+}\kappa^{+/+}$ mice to migrate from the uterus and through the oviduct was determined in a sperm migration assay.

Briefly, a first group of super-ovulated female mice (n=5) were set up with $H^{+/+}\kappa^{+/+}$ males (n=5) and a second group of super-ovulated female mice (n=5) were set up with $H^{+/-}\kappa^{+/+}$ males (n=5). The mating pairs were observed for copulation, and five to six hours post-copulation the uterus and attached oviduct from all females were removed and flushed for analysis. Flush solutions were checked for eggs to verify ovulation and obtain a sperm count. Sperm migration was evaluated in two different ways. First, both oviducts were removed from the uterus, flushed with saline, and any sperm identified were counted. The presence of eggs was also noted as evidence of ovulation. Second, oviducts were left attached to the uterus and both tissues were fixed, embedded in paraffin, sectioned and stained (as described above). Sections were examined for presence of sperm, in both the uterus and in both oviducts.

For the females mated with the five $H^{+/+}\kappa^{+/+}$ males, very little sperm was found in the flush solution from the oviduct. Flush solutions from oviducts of the females mated with the $H^{+/-}\kappa^{+/+}$ males exhibited a sperm level about 25- to 30-fold higher (avg, n=10 oviducts) than present in flush solutions from the oviducts of the females mated with the $H^{+/+}\kappa^{+/+}$ males. A representative breeding comparison of $H^{+/+}\kappa^{+/+}$ and $H^{+/+}A6^{res}\kappa^{+/+}$ mice is shown in Table 9.

Histological sections of uterus and oviduct were prepared. The sections were examined for sperm presence in the uterus and the oviduct (the colliculus tubarius). Inspection of histological sections of oviduct and uterus revealed that for female mice mated with $H^{+/+}\kappa^{+/+}$ mice, sperm was found in the uterus but not in the oviduct. Further, sections from females mated with $H^{+/+}\kappa^{+/+}$ mice revealed that sperm was not found at the uterotubal junction (UTJ). In sections from females mated with $H^{+/-}\kappa^{+/+}$ mice, sperm was identified in the UTJ and in the oviduct.

These results establish that mice lacking ADAM6a and ADAM6b genes make sperm that exhibit an in vivo migration defect. In all cases, sperm was observed within the uterus, indicating that copulation and sperm release apparently occur as normal, but little to no sperm was observed within the oviducts after copulation as measured either by sperm count or histological observation. These results establish that mice lacking ADAM6a and ADAM6b genes produce sperm that exhibit an inability to migrate from the uterus to the oviduct. This defect apparently leads to infertility because sperm are unable to cross the uterine-tubule junction into the oviduct, where eggs are fertilized. Taken together, all of these results converge to the support the hypothesis that mouse ADAM6 genes help direct sperm with normal motility to migrate out of the uterus, through the uterotubal junction and the oviduct, and thus approach an egg to achieve the fertilization event. The mechanism by which ADAM6 achieves this may be directed by one or both of the ADAM6 proteins, or through coordinate expression with other proteins, e.g., other ADAM proteins, in the sperm cell, as described below.

TABLE 9

| Male Genotype | Breeding Animals (Male/Female) | Duration of Breeding | Litters | Offspring |
|---|---|---|---|---|
| $H^{+/+}\kappa^{+/+}$ | 6/6 | 6 months | 2 | 25 |
| $H^{+/+}A6^{res}\kappa^{+/+}$ | 4/8 | 4 months | 4 | 198 |

ADAM Gene Family Expression. A complex of ADAM proteins are known to be present as a complex on the surface of maturing sperm. Mice lacking other ADAM gene family members lose this complex as sperm mature, and exhibit a reduction of multiple ADAM proteins in mature sperm. To determine if a lack of ADAM6a and ADAM6b genes affects other ADAM proteins in a similar manner, Western blots of protein extracts from testis (immature sperm) and epididymis (maturing sperm) were analyzed to determine the expression levels of other ADAM gene family members.

In this experiment, protein extracts were analyzed from groups (n=4 per group) of $H^{+/+}\kappa^{+/+}$ and $H^{+/-}\kappa^{+/+}$ mice. The results showed that expression of ADAM2 and ADAM3 were not affected in testis extracts. However, both ADAM2 and ADAM3 were dramatically reduced in epididymis extracts. This demonstrates that the absence of ADAM6a and ADAM6b in sperm of $H^{+/+}\kappa^{+/+}$ mice may have a direct affect on the expression and perhaps function of other ADAM proteins as sperm matures (e.g., ADAM2 and ADAM3). This suggests that ADAM6a and ADAM6b are part of an ADAM protein complex on the surface of sperm, which might be critical for proper sperm migration.

Example 9

Human Heavy Chain Variable Gene Utilization in ADAM6 Rescue Mice

Selected human heavy chain variable gene usage was determined for mice homozygous for human heavy and κ light chain variable gene loci either lacking mouse ADAM6a and ADAM6b genes ($H^{+/+}\kappa^{+/+}$) or containing an ectopic genomic fragment encoding for mouse ADAM6a and ADAM6b genes ($H^{+/+}A6^{res}\kappa^{+/+}$) by a quantitative PCR assay using TAQMAN™ probes (as described above).

Briefly, CD19+ B cells were purified from the spleens of $H^{+/+}\kappa^{+/+}$ and $H^{+/+}A6^{res}\kappa^{+/+}$ mice using mouse CD19 Microbeads (Miltenyi Biotec) and total RNA was purified using the RNEASY™ Mini kit (Qiagen). Genomic RNA was removed using an RNase-free DNase on-column treatment (Qiagen). About 200 ng mRNA was reverse-transcribed into cDNA using the First Stand cDNA Synthesis kit (Invitrogen) and then amplified with the TAQMAN™ Universal PCR Master Mix (Applied Biosystems) using the ABI 7900 Sequence Detection System (Applied Biosystems). Relative expression of each gene was normalized to the expression of mouse κ light chain constant region (mCκ). Table 10 sets forth the sense/antisense/TAQMAN™ MGB probe combinations used in this experiment.

TABLE 10

| Human $V_H$ | Sequence (5'-3') | SEQ ID NO: |
|---|---|---|
| $V_H6-1$ | Sense: CAGGTACAGCTGCAGCAGTCA | 6 |
| | Anti-sense: GGAGATGGCACAGGTGAGTGA | 7 |
| | Probe: TCCAGGACTGGTGAAGC | 8 |

TABLE 10-continued

| Human $V_H$ | Sequence (5'-3') | SEQ ID NO: |
|---|---|---|
| $V_H$1-2 | Sense: TAGTCCCAGTGATGAGAAAGAGAT | 9 |
| | Anti-sense: GAGAACACAGAAGTGGATGAGATC | 10 |
| | Probe: TGAGTCCAGTCCAGGGA | 11 |
| $V_H$3-23 | Sense: AAAAATTGAGTGTGAATGGATAAGAGTG | 12 |
| | Anti-sense: AACCCTGGTCAGAAACTGCCA | 13 |
| | Probe: AGAGAAACAGTGGATACGT | 14 |
| $V_H$1-69 | Sense: AACTACGCACAGAAGTTCCAGG | 15 |
| | Anti-sense: GCTCGTGGATTTGTCCGC | 16 |
| | Probe: CAGAGTCACGATTACC | 17 |
| mCκ | Sense: TGAGCAGCACCCTCACGTT | 18 |
| | Anti-sense: GTGGCCTCACAGGTATAGCTGTT | 19 |
| | Probe: ACCAAGGACGAGTATGAA | 20 |

In this experiment, expression of all four human $V_H$ genes was observed in the samples analyzed. Further, the expression levels were comparable between $H^{+/+}κ^{+/+}$ and $H^{+/+}A6^{res}κ^{+/+}$ mice. These results demonstrate that human $V_H$ genes that were both distal to the modification site ($V_H$3-23 and $V_H$1-69) and proximal to the modification site ($V_H$1-2 and $V_H$6-1) were all able to recombine to form a functionally expressed human heavy chain. These results demonstrate that the ectopic genomic fragment comprising mouse ADAM6a and ADAM6b sequences inserted into a human heavy chain genomic sequence did not affect V(D)J recombination of human heavy chain gene segments within the locus, and these mice are able to recombine human heavy chain gene segments in normal fashion to produce functional heavy chain immunoglobulin proteins.

Example 10

Humoral Immune Response in ADAM6 Rescue Mice

The humoral immune response was determined for mice homozygous for human heavy and κ light chain variable gene loci either lacking mouse ADAM6a and ADAM6b genes ($H^{+/+}κ^{+/+}$) or containing an ectopic genomic fragment encoding for mouse ADAM6a and ADAM6b genes ($H^{+/+}A6^{res}κ^{+/+}$) by a multi-antigen immunization scheme followed by antibody isolation and characterization. Results were compared for determination of any effect on V(D)J recombination involving the human immunoglobulin gene segments, assessment of serum titer progression, production of antibodies by hybridomas and affinity for antigen.

Immunization protocol. A human cell surface receptor (Antigen A), a human antibody specific for a human receptor tyrosine-protein kinase (Antigen B), a secreted human protein that functions in regulation of the TGF-β signaling pathway (Antigen C), and a human receptor tyrosine kinase (Antigen D) were employed for comparative immunizations in groups of mice. Serum was collected from groups of mice prior to immunization with the above antigens. Each antigen (2.3 μg each) was administered in an initial priming immunization mixed with 10 μg of CpG oligonucleotide as adjuvant (Invivogen). The immunogen was administered via footpad (f.p.) in a volume of 25 μl per mouse. Subsequently, mice were boosted via f.p. with 2.3 μg of antigen along with 10 μg CpG and 25 μg Adju-Phos (Brenntag) as adjuvants on days 3, 6, 11, 13, 17, and 20 for a total of six boosts. Mice were bled on days 15 and 22 after the fourth and sixth boosts, respectively, and antisera were assayed for antibody titer to each specific antigen.

Antibody titers were determined in sera of immunized mice using an ELISA assay. Ninety six-well microliter plates (Thermo Scientific) were coated with the respective antigen (2 μg/ml) in phosphate-buffered saline (PBS, Irvine Scientific) overnight at 4° C. The following day, plates were washed with phosphate-buffered saline containing 0.05% Tween 20 (PBS-T, Sigma-Aldrich) four times using a plate washer (Molecular Devices). Plates were then blocked with 250 μl of 0.5% bovine serum albumin (BSA, Sigma-Aldrich) in PBS and incubated for one hour at room temperature. The plates were then washed four times with PBS-T. Sera from immunized mice and pre-immune sera were serially diluted three-fold in 0.5% BSA-PBS starting at 1:300 or 1:1000 and added to the blocked plates in duplicate and incubated for one hour at room temperature. The last two wells were left blank to be used as secondary antibody control. The plates were again washed four times with PBS-T in a plate washer. A 1:5000/1:10,000 dilution of goat anti-mouse IgG-Fc-Horse Radish Peroxidase (HRP, Jackson Immunoresearch) or goat anti-mouse IgG-kappa-HRP (Southern Biotech) conjugated secondary antibody was added to the plates and incubated for one hour at room temperature. Plates were again washed eight times with PBS-T and developed using TMB/$H_2O_2$ as substrate. The substrate was incubated for twenty minutes and the reaction stopped with 2 N $H_2SO_4$ (VWR) or 1 N $H_3PO_4$ (JT Baker). Plates were read on a spectrophotometer (Victor, Perkin Elmer) at 450 nm. Antibody titers were calculated using Graphpad PRISM software.

Figure 19:
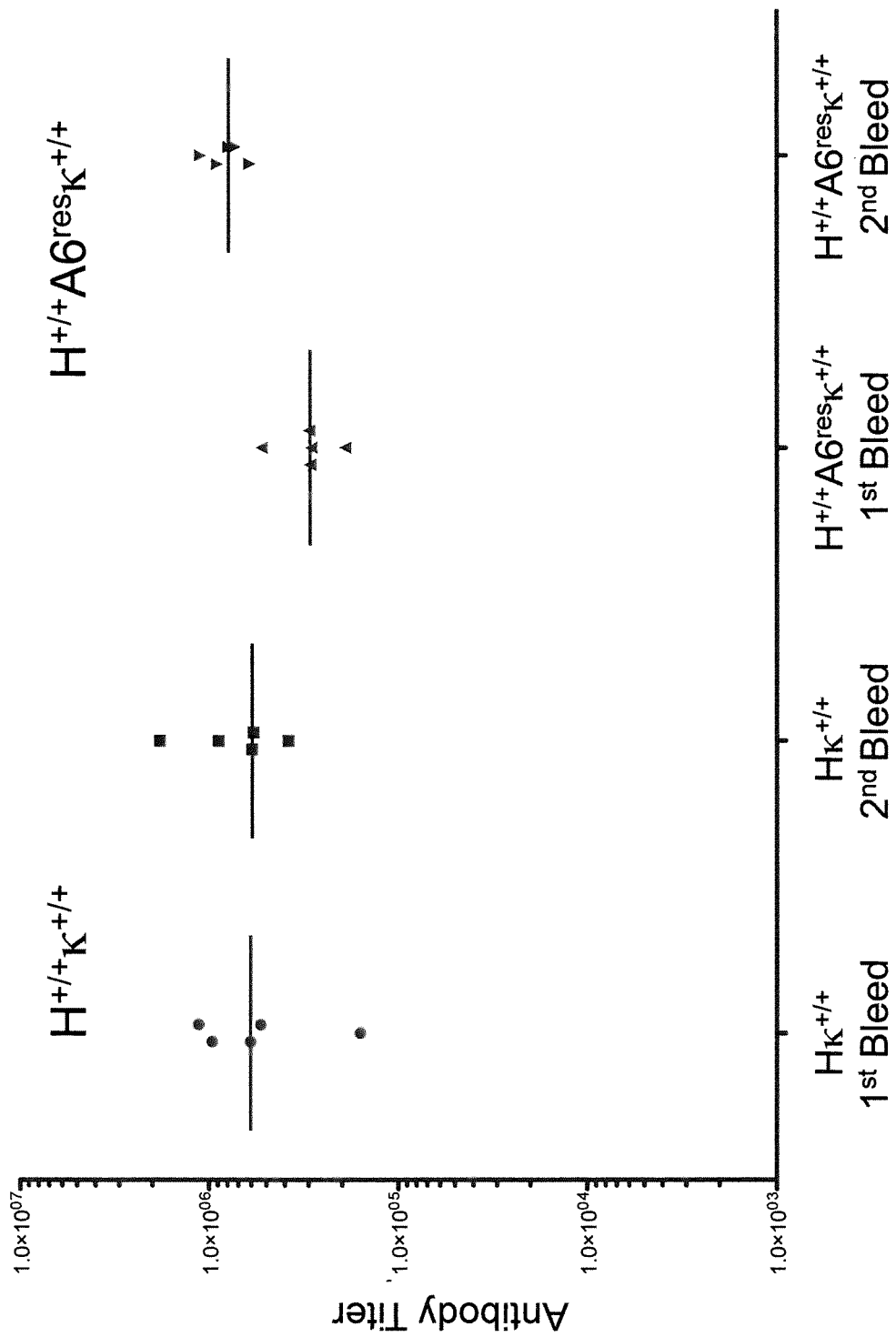
FIG. 19 shows the antibody titer for first and second bleeds from mice homozygous for human heavy and human κ light chain variable gene loci ($H^{+/+}\kappa^{+/+}$; n=5) and mice homozygous for human heavy and human κ light chain variable gene loci having an ectopic mouse genomic fragment encoding mouse ADAM6 genes ($H^{+/+}A6^{res}\kappa^{+/+}$; n=5) that were immunized with a human cell surface receptor (Antigen A).
Figure 20:
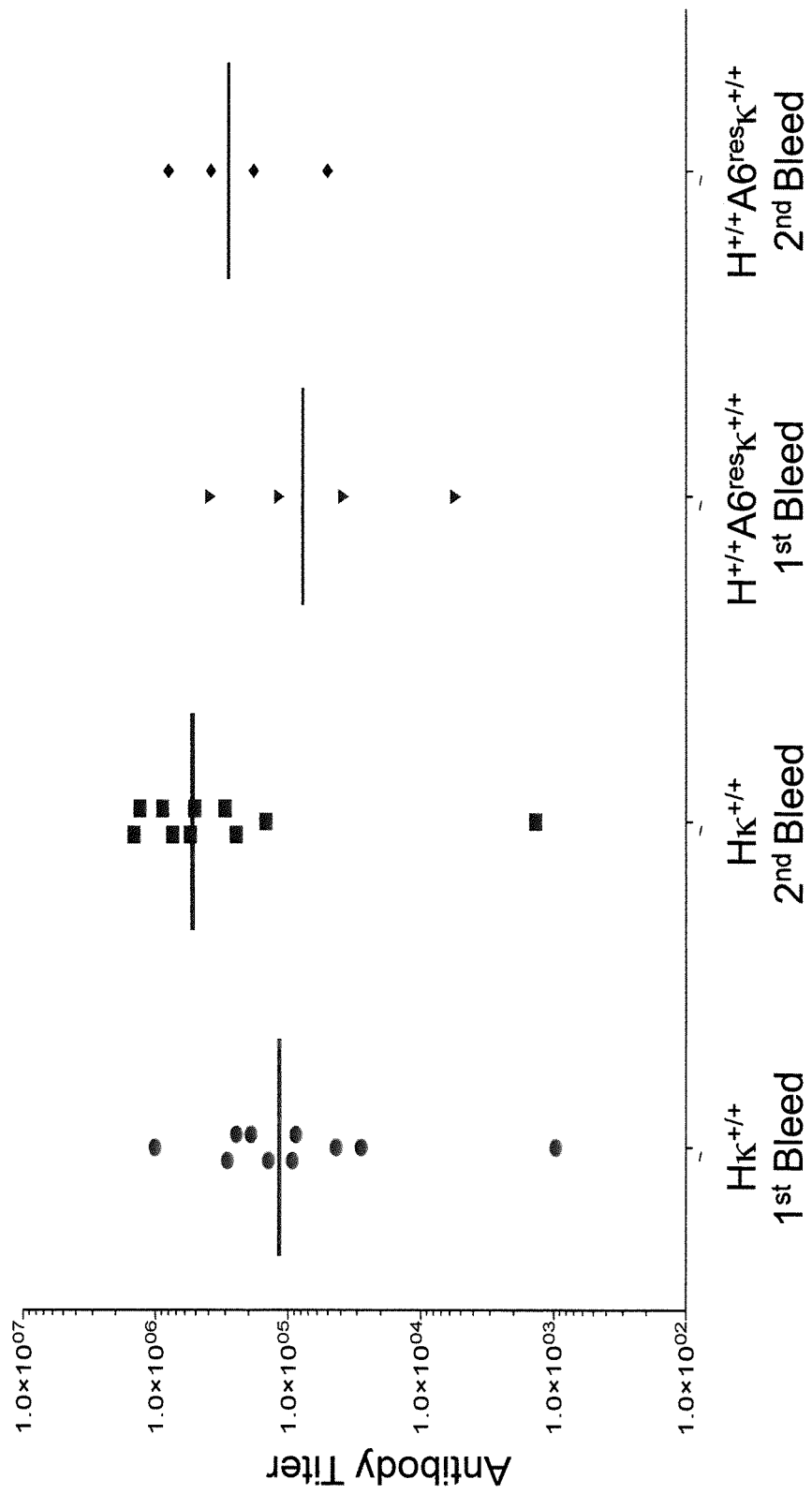
FIG. 20 shows the antibody titer for first and second bleeds from mice homozygous for human heavy and human κ light chain variable gene loci ($H^{+/+}\kappa^{+/+}$; n=5) and mice homozygous for human heavy and human κ light chain variable gene loci having an ectopic mouse genomic fragment encoding mouse ADAM6 genes ($H^{+/+}A6^{res}\kappa^{+/+}$; n=10) that were immunized with a human antibody specific for a human receptor tyrosine-protein kinase (Antigen B).
Figure 21:
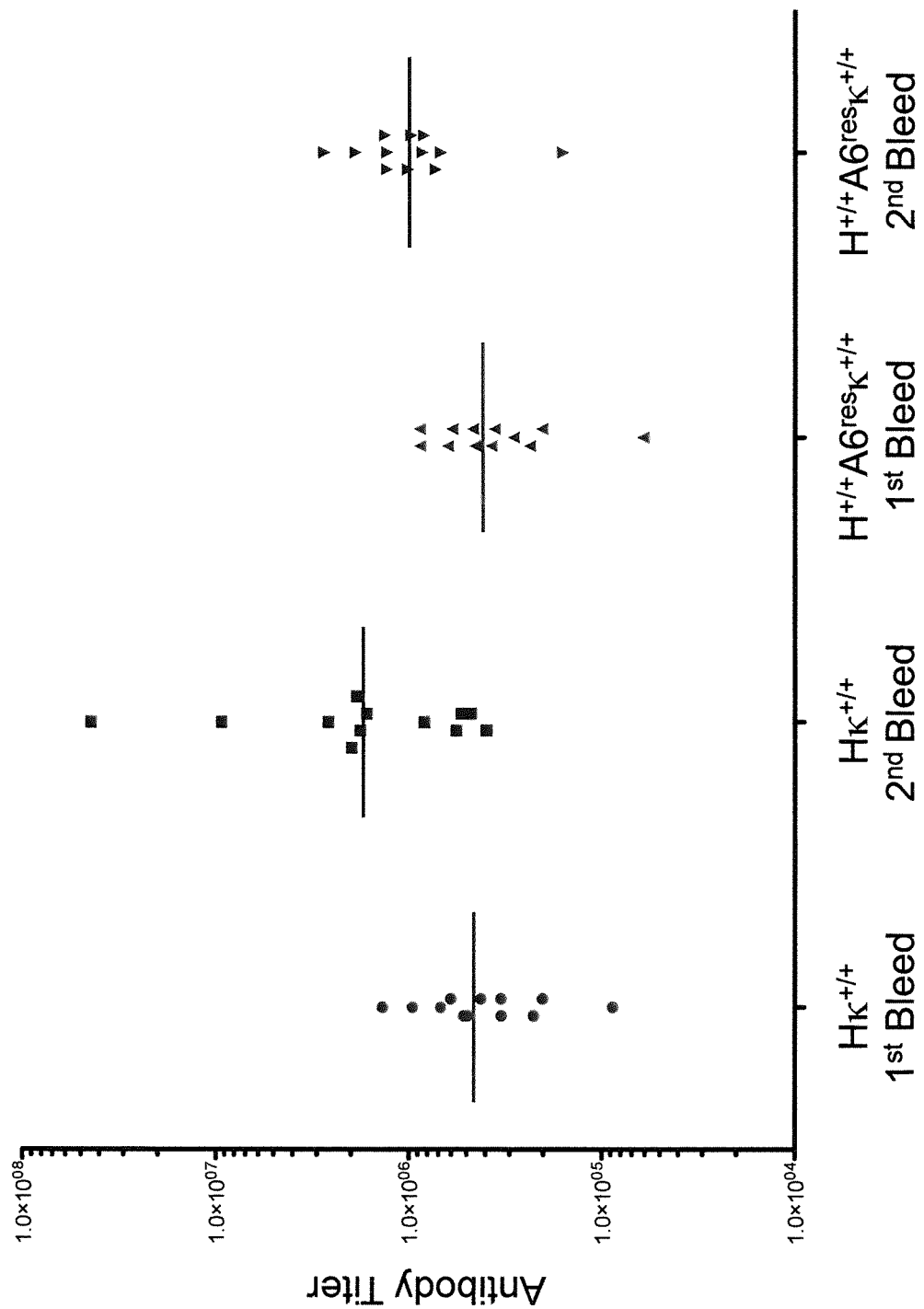
FIG. 21 shows the antibody titer for first and second bleeds from mice homozygous for human heavy and human κ light chain variable gene loci ($H^{+/+}\kappa^{+/+}$; n=12) and mice homozygous for human heavy and human κ light chain variable gene loci having an ectopic mouse genomic fragment encoding mouse ADAM6 genes ($H^{+/+}A6^{res}\kappa^{+/+}$; n=12) that were immunized with a secreted human protein that functions in regulation of the TGF-β signaling pathway (Antigen C).
Figure 22:
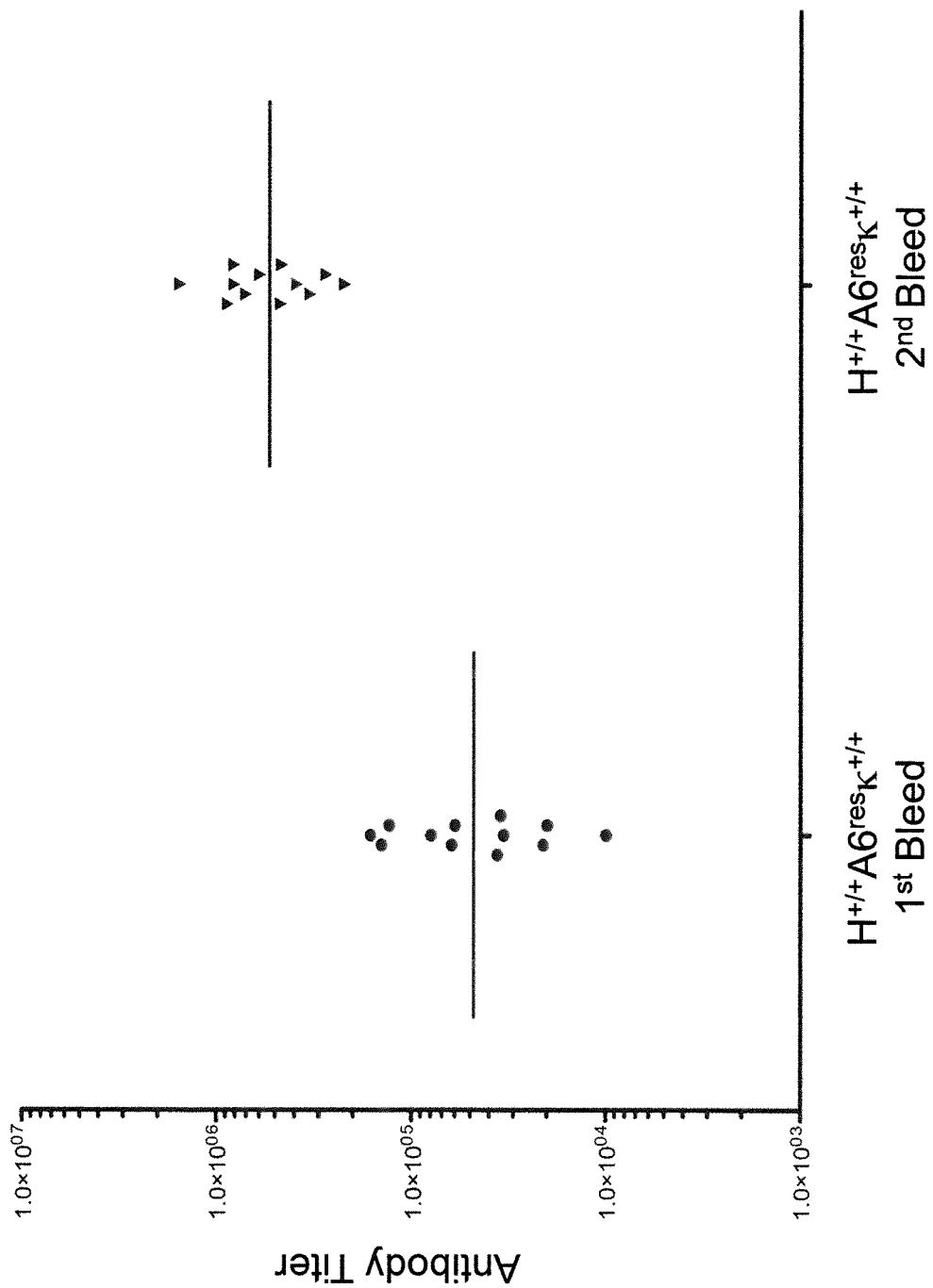
FIG. 22 shows the antibody titer for first and second bleeds from mice homozygous for human heavy and human κ light chain variable gene loci having an ectopic mouse genomic fragment encoding mouse ADAM6 genes ($H^{+/+}A6^{res}\kappa^{+/+}$; n=12) that were immunized with a human receptor tyrosine kinase (Antigen D).

Serum titer was calculated as serum dilution within experimental titration range at the signal of antigen binding equivalent to two times above background. Results for the humoral immune response are shown in FIG. 19 (Antigen A), FIG. 20 (Antigen B), FIG. 21 (Antigen C), and FIG. 22 (Antigen D). Antigen positive score of hybridomas made using two spleens isolated from mice from each group of selected immunizations is shown in Table 11 (Antigen score is equal to 2X/background).

As shown in this Example, antibody titers generated in Adam6 rescue mice ($H^{+/+}A6^{res}κ^{+/+}$) were comparable to those generated in mice lacking ADMA6a and ADAM6b and having humanized heavy chain ($H^{+/+}κ^{+/+}$). Further, spleens from $H^{+/+}A6^{res}κ^{+/+}$ mice yielded antigen-positive hybridomas for all antigens tested, including antibodies of high affinity, at levels comparable to $H^{+/+}κ^{+/+}$ mice. Thus, no impairment of V(D)J recombination of human immunoglobulin gene segments in Adam6 rescue mice is believed to exist given the production of antibodies with high affinity containing human immunoglobulin genes.

TABLE 11

| Antigen | Mouse Strain | Antigen Score |
|---|---|---|
| A | $H^{+/+}A6^{res}κ^{+/+}$ | 76 |
| A | $H^{+/+}A6^{res}κ^{+/+}$ | 32 |
| B | $H^{+/+}κ^{+/+}$ | 4 |
| B | $H^{+/+}κ^{+/+}$ | 12 |
| B | $H^{+/+}A6^{res}κ^{+/+}$ | 41 |
| B | $H^{+/+}A6^{res}κ^{+/+}$ | 95 |

Example 11

Antigen Binding Affinity Determination

Binding affinities of antibodies showing specific binding to Antigen B were screened using a real-time surface plasmon resonance biosensor (BIAcore 2000). Conditioned media from hybridomas isolated from two strains of mice immunized with Antigen B ($H^{+/+}\kappa^{+/+}$ and $H^{+/+}A6^{res}\kappa^{+/+}$) were used during BIAcore screening. BIAcore sensor surface was first derivatized with polyclonal rabbit anti-mouse antibody (GE) to capture anti-Antigen B antibodies from conditioned media. During the entire screening method, HBST (0.01M HEPES pH 7.4, 0.15M NaCl, 3 mM EDTA, 0.005% v/v Surfactant P20) was used as the running buffer. Fab fragment of Antigen B was injected over the anti-Antigen B antibody captured surface at a flow rate of 50 µl/minute at 100 nM concentration. Antibody-antigen association was monitored for three minutes while the dissociation of antigen from the captured antibody was monitored for five minutes in HBST running buffer. The experiment was performed at 25° C. Kinetic association (ka) and dissociation (kd) rate constants were determined by processing and fitting the data to a 1:1 binding model using Scrubber 2.0 curve fitting software. Binding dissociation equilibrium constants ($K_D$) and dissociative half-lives ($T_y$) were calculated from the kinetic rate constants as: $K_D$ (M)=kd/ka; and T½(min)=(ln 2/(60*kd). Results for selected anti-Antigen B antibodies are shown in Table 12.

TABLE 12

| Antibody | Mouse strain | $K_D$ (M) | $T_{1/2}$ (min) |
|---|---|---|---|
| 5D6 | $H^{+/+}\kappa^{+/+}$ | 1.62E-08 | 3 |
| 8G10 | $H^{+/+}\kappa^{+/+}$ | 1.20E-08 | 5 |
| 10F10 | $H^{+/+}\kappa^{+/+}$ | 1.09E-08 | 3 |
| 1F5 | $H^{+/+}\kappa^{+/+}$ | 1.00E-07 | 0.3 |
| 10G8 | $H^{+/+}\kappa^{+/+}$ | 1.47E-07 | 0.3 |
| 1B11 | $H^{+/+}A6^{res}\kappa^{+/+}$ | 1.98E-08 | 6 |
| 2D9 | $H^{+/+}A6^{res}\kappa^{+/+}$ | 9.40E-10 | 51 |
| 4D11 | $H^{+/+}A6^{res}\kappa^{+/+}$ | 5.60E-08 | 0.8 |
| 6C5 | $H^{+/+}A6^{res}\kappa^{+/+}$ | 1.10E-09 | 188 |
| 6F4 | $H^{+/+}A6^{res}\kappa^{+/+}$ | 1.35E-08 | 3 |
| 7C4 | $H^{+/+}A6^{res}\kappa^{+/+}$ | 2.00E-06 | 0.05 |
| 8G12 | $H^{+/+}A6^{res}\kappa^{+/+}$ | 2.31E-09 | 19 |
| 9B12 | $H^{+/+}A6^{res}\kappa^{+/+}$ | 3.47E-09 | 13 |
| 10B4 | $H^{+/+}A6^{res}\kappa^{+/+}$ | 3.60E-09 | 23 |
| 11E7 | $H^{+/+}A6^{res}\kappa^{+/+}$ | 3.06E-08 | 2 |
| 11E12 | $H^{+/+}A6^{res}\kappa^{+/+}$ | 2.70E-07 | 0.1 |
| 1E4 | $H^{+/+}A6^{res}\kappa^{+/+}$ | 7.00E-10 | 58 |
| 4D2 | $H^{+/+}A6^{res}\kappa^{+/+}$ | 5.80E-10 | 150 |
| 5H6 | $H^{+/+}A6^{res}\kappa^{+/+}$ | 2.60E-09 | 3 |
| 5H10 | $H^{+/+}A6^{res}\kappa^{+/+}$ | 6.00E-09 | 70 |
| 9A9 | $H^{+/+}A6^{res}\kappa^{+/+}$ | 3.80E-09 | 12 |
| 11C11 | $H^{+/+}A6^{res}\kappa^{+/+}$ | 1.55E-09 | 38 |
| 12C10 | $H^{+/+}A6^{res}\kappa^{+/+}$ | 5.90E-09 | 16 |
| 12G7 | $H^{+/+}A6^{res}\kappa^{+/+}$ | 9.00E-08 | 7 |
| 12G9 | $H^{+/+}A6^{res}\kappa^{+/+}$ | 3.32E-09 | 12 |

In a similar experiment, kinetics of different monoclonal antibodies present in hybridoma-conditioned media binding to Antigen A was determined using a real-time surface plasmon resonance biosensor (BIAcore 4000) assay. All hybridoma clones used in this assay were produced in $H^{+/+}A6^{res}\kappa^{+/+}$ mice.

Briefly, to capture the Antigen A-specific antibodies, polyclonal rabbit anti-mouse antibody (GE Catalog #BR-1008-38) was first immobilized on the sensor chip. BIAcore screening was performed in two different buffers—PBSP, pH7.2 and PBSP, pH6.0. Both the buffers were supplemented with 0.1 mg/ml BSA. Following the capture of anti-Antigen A antibodies from the conditioned media, 1 µM of Antigen A monomer (prepared in respective running buffer) was injected over the captured antibody surface for 1.5 minutes at 30 µl/minute and the dissociation of bound Antigen A monomer was monitored for 1.5 minutes in the respective running buffer at 25° C. Kinetic association (ka) and dissociation (kd) rate constants were determined by processing and fitting the data to a 1:1 binding model using Scrubber 2.0 curve fitting software. Binding dissociation equilibrium constants ($K_D$) and dissociative half-lives ($T_{1/2}$) were calculated from the kinetic rate constants as: $K_D$ (M)=kd/ka; and $T_{1/2}$(min)=(ln 2/(60*kd). Table 13 sets forth the binding kinetics parameters for selected anti-Antigen A antibody binding to Antigen A monomer at pH7.2 and pH6.0. NB: no binding detected under current experimental conditions.

TABLE 13

| | pH 7.2 | | pH 6.0 | |
|---|---|---|---|---|
| Antibody | $K_D$ (M) | $T_{1/2}$ (min) | $K_D$ (M) | $T_{1/2}$ (min) |
| 1D7 | 3.89E-10 | 25 | 9.45E-10 | 17 |
| 2B4 | NB | NB | NB | NB |
| 2B7 | 3.90E-09 | 1.2 | 2.98E-09 | 2 |
| 2F7 | 2.36E-10 | 144 | 2.06E-11 | 1882 |
| 3A7 | NB | NB | 6.42E-10 | 17 |
| 3F6 | NB | NB | NB | NB |
| 4A6 | 1.91E-09 | 2 | 2.12E-09 | 2 |
| 4C4 | NB | NB | NB | NB |
| 4E12 | 2.69E-10 | 16 | 2.03E-10 | 18 |
| 5C11 | 1.68E-09 | 3 | 2.31E-09 | 3 |
| 5D10 | NB | NB | 4.56E-09 | 2 |
| 5E7 | NB | NB | NB | NB |
| 5F10 | NB | NB | NB | NB |
| 5F11 | 8.18E-10 | 8 | 6.79E-10 | 7 |
| 5G4 | 3.55E-10 | 15 | 7.42E-11 | 53 |
| 5G9 | 6.39E-10 | 15 | 4.31E-10 | 21 |
| 5H8 | 4.73E-10 | 15 | NB | NB |
| 6D2 | NB | NB | NB | NB |
| 6D3 | 2.88E-10 | 14 | 8.82E-11 | 39 |
| 6E4 | NB | NB | 2.67E-09 | 4 |
| 6E6 | 1.37E-09 | 10 | 1.30E-09 | 14 |
| 6H6 | NB | NB | NB | NB |
| 7A12 | NB | NB | NB | NB |
| 7C3 | NB | NB | NB | NB |
| 7E8 | 4.38E-10 | 22 | 2.63E-10 | 34 |
| 7F10 | NB | NB | NB | NB |
| 7G9 | NB | NB | NB | NB |
| 8B8 | NB | NB | NB | NB |
| 8B11 | NB | NB | NB | NB |
| 8C3 | NB | NB | NB | NB |
| 8E9 | NB | NB | NB | NB |
| 8G3 | NB | NB | NB | NB |
| 8H3 | NB | NB | NB | NB |
| 8H4 | 3.70E-07 | 0.1 | NB | NB |
| 8H8 | NB | NB | NB | NB |
| 1A8 | 2.30E-09 | 4 | 7.40E-10 | 6 |
| 1B6 | NB | NB | NB | NB |
| 1C6 | NB | NB | NB | NB |
| 1C12 | NB | NB | NB | NB |
| 1D2 | NB | NB | NB | NB |
| 1E2 | 1.17E-09 | 42 | 3.08E-09 | 29 |
| 1E3 | 5.05E-10 | 89 | 8.10E-10 | 57 |
| 1E6 | 1.97E-08 | 3 | 1.84E-08 | 3 |
| 1E9 | 1.14E-09 | 30 | 1.14E-09 | 25 |
| 1H6 | 2.93E-09 | 14 | 9.87E-10 | 25 |
| 2H9 | 2.30E-08 | 2 | 1.91E-08 | 2 |
| 3A2 | 1.15E-10 | 44 | 1.25E-10 | 33 |
| 3A4 | 1.70E-10 | 31 | 1.44E-10 | 30 |
| 3D11 | NB | NB | 1.58E-08 | 1 |
| 3H10 | 2.82E-09 | 20 | 2.59E-09 | 15 |
| 4B6 | 7.79E-10 | 6 | 6.36E-10 | 7 |
| 4H6 | 9.18E-11 | 62 | 1.20E-10 | 43 |
| 5A2 | NB | NB | 7.04E-10 | 12 |
| 5C5 | 8.71E-11 | 49 | 7.02E-11 | 48 |
| 5F6 | 6.16E-11 | 114 | 5.46E-11 | 121 |

As shown above, high affinity antibodies were obtained from both $H^{+/+}A6^{res}\kappa^{+/+}$ and $H^{+/+}\kappa^{+/+}$ mice in a comparable manner. Among the twenty-five antibodies represented in Table 12, twenty produced in $H^{+/+}A6^{res}\kappa^{+/+}$ mice demonstrated an affinity range of 0.5 nM to 1 µM, while the five generated in H$^{+/+}$κ$^{+/+}$ mice demonstrated an affinity range of 10 nM to 150 nM. Further, the fifty-five antibodies shown in Table 13 demonstrated an affinity range of 20 pM to 350 nM for binding to Antigen A monomer.

As demonstrated in this Example, the reinsertion of mouse Adam6 genes into a humanized immunoglobulin heavy chain locus does not impair the ability of the mouse to mount a robust immunize response to multiple antigens characterized by repertoires of human antibodies having diverse affinities in the subnanomolar range, which are derived from human gene segments rearranged from a engineered germline.

---

We claim:

1. A method of making a fully human heavy chain or a fully human light chain comprising the steps of:
   (a) immunizing a genetically modified mouse with an antigen, wherein the mouse:
      (i) has a genome that comprises:
         (A) one or more human $V_H$ gene segments, one or more human $D_H$ gene segments, and one or more human $J_H$ gene segments operably linked to a mouse heavy chain constant region at an endogenous mouse immunoglobulin heavy chain locus,
         (B) one or more human $V_L$ gene segments and one or more human $J_L$ gene segments operably linked to a light chain constant region, and
         (C) a nucleotide sequence that encodes a mouse ADAM6 protein, which nucleotide sequence is integrated in the genome of the mouse, wherein the mouse ADAM6 protein is expressed in the genetically modified mouse;
      (ii) generates antibodies when immunized with the antigen, wherein the antibodies each comprise a human heavy chain variable domain operably linked to a mouse heavy chain constant domain; and
      (iii) is fertile;
   (b) allowing the genetically modified mouse to mount an immune response to the antigen;
   (c) isolating a B cell from the genetically modified mouse that expresses an antibody that specifically binds the antigen;
   (d) determining an amino acid sequence of a human heavy or light chain variable domain of an antibody that specifically binds the antigen and that was generated by the genetically modified mouse; and
   (e) operably linking the human heavy or light chain variable domain to a human heavy or light chain constant domain, respectively, to form a fully human heavy chain or a fully human light chain.

2. The method of claim 1, further comprising determining the amino acid sequence of the fully human heavy chain or a fully human light chain.

3. The method of claim 1, wherein operably linking the human heavy or light chain variable domain to the human heavy or light chain constant domain, respectively, comprises operably linking a nucleotide sequence encoding the human heavy or light chain variable domain to a nucleotide sequence encoding the human heavy or light chain constant domain, respectively.

4. The method of claim 1, wherein the one or more human $V_H$ gene segments comprise a $V_H6$-1, $V_H1$-2, $V_H1$-3, $V_H2$-5, $V_H3$-7, $V_H1$-8, $V_H3$-9, $V_H3$-11, $V_H3$-13, $V_H3$-15, $V_H3$-16, $V_H1$-18, $V_H3$-20, $V_H3$-21, $V_H3$-23, $V_H1$-24, $V_H2$-26, $V_H4$-28, $V_H3$-30, $V_H4$-31, $V_H3$-33, $V_H4$-34, $V_H3$-35, $V_H3$-38, $V_H4$-39, $V_H3$-43, $V_H1$-45, $V_H1$-46, $V_H3$-48, $V_H3$-49, $V_H5$-51, $V_H3$-53, $V_H1$-58, $V_H4$-59, $V_H4$-61, $V_H3$-64, $V_H3$-66, $V_H1$-69, $V_H2$-70, $V_H3$-72, $V_H3$-73, $V_H3$-74, or any combination thereof.

5. The method of claim 1, wherein the one or more human VL gene segments and one or more human JL gene segments are operably linked to a mouse light chain constant region at an endogenous mouse light chain locus.

6. The method of claim 1, wherein the one or more human VL gene segments comprise a $V_\kappa1$-5, $V_\kappa1$-6, $V_\kappa1$-8, $V_\kappa1$-9, $V_\kappa1$-12, $V_\kappa1$-16, $V_\kappa1$-17, $V_\kappa1$-27, $V_\kappa1$-33, $V_\kappa1$-37, $V_\kappa1$-39, $V_\kappa2$-24, $V_\kappa2$-28, $V_\kappa2$-29, $V_\kappa2$-30, $V_\kappa2$-40, $V_\kappa3$-11, $V_\kappa3$-15, $V_\kappa3$-20, $V_\kappa4$-1, $V_\kappa6$-21, or any combination thereof.

7. The method of claim 1, wherein the nucleotide sequence encoding the mouse ADAM6 protein:
   (a) is present on the same chromosome as the endogenous mouse immunoglobulin heavy chain locus; and/or
   (b) is present at an ectopic position.

8. The method of claim 1, wherein the mouse ADAM6 protein is a mouse ADAM6a protein or a mouse ADAM6b protein.

9. The method of claim 1, wherein the nucleotide sequence that encodes the mouse ADAM6 protein is contiguous with one or more human $V_H$ gene segments, one or more human $D_H$ gene segments, or one or more human $J_H$ gene segments.

10. The method of claim 1, wherein the one or more human $V_L$ gene segments are one or more human $V_\kappa$ gene segments and the one or more human $J_L$ gene segments are one or more human $J_\kappa$ gene segments.

11. The method of claim 10, wherein the one or more human $V_\kappa$ gene segments and one or more human $J_\kappa$ gene segments are operably linked to a mouse κ light chain constant region at an endogenous mouse κ light chain locus.

12. The method of claim 1, wherein the one or more human $V_L$ gene segments are one or more human Vλ gene segments and the one or more human $J_L$ gene segments are one or more human Jλ gene segments.

13. The method of claim 12, wherein the one or more human Vλ gene segments and one or more human Jλ gene segments are operably linked to a mouse λ light chain constant region at an endogenous mouse λ light chain locus.

* * * * *

UNITED STATES PATENT AND TRADEMARK OFFICE
CERTIFICATE OF CORRECTION

PATENT NO. : 12,207,628 B2
APPLICATION NO. : 17/129706
DATED : January 28, 2025
INVENTOR(S) : Lynn Macdonald et al.

Page 1 of 1

It is certified that error appears in the above-identified patent and that said Letters Patent is hereby corrected as shown below:

In the Claims

At Column 126, Claim number 10, Line number 46, please delete:
"Vκgene" and insert: --Vκ gene--

At Column 126, Claim number 10, Line number 48, please delete:
"Jκgene" and insert: --Jκ gene--

At Column 126, Claim number 11, Line number 50, please delete:
"Vκgene" and insert: --Vκ gene--

At Column 126, Claim number 11, Line number 50, please delete:
"Jκgene" and insert: --Jκ gene--

Signed and Sealed this
Twenty-second Day of April, 2025

Coke Morgan Stewart
*Acting Director of the United States Patent and Trademark Office*